US008217067B2

(12) United States Patent
Carroll et al.

(10) Patent No.: US 8,217,067 B2
(45) Date of Patent: Jul. 10, 2012

(54) AMINO-TETRAZOLES ANALOGUES AND METHODS OF USE

(75) Inventors: William A. Carroll, Evanston, IL (US); Arturo Perez-Medrano, Grayslake, IL (US); Alan S. Florjancic, Kenosha, WI (US); Derek W. Nelson, Highland Park, IL (US); Sridhar Peddi, Grayslake, IL (US); Tongmei Li, Lake Bluff, IL (US); Eric M. Bunnelle, Berkeley, CA (US); Gavin Hirst, Princeton, MA (US); Biqin C. Li, Northboro, MA (US)

(73) Assignee: Abbott Laboratories, Abbott Park, IL (US)

( * ) Notice: Subject to any disclaimer, the term of this patent is extended or adjusted under 35 U.S.C. 154(b) by 532 days.

(21) Appl. No.: 11/120,718

(22) Filed: Apr. 29, 2005

(65) Prior Publication Data

US 2007/0049584 A1 Mar. 1, 2007

Related U.S. Application Data

(60) Provisional application No. 60/566,238, filed on Apr. 29, 2004.

(51) Int. Cl.
  *A61K 31/41* (2006.01)
  *C07D 257/04* (2006.01)
(52) U.S. Cl. .......................... 514/381; 548/250
(58) Field of Classification Search .............. 548/250; 514/381
  See application file for complete search history.

(56) References Cited

U.S. PATENT DOCUMENTS

| 4,999,347 A | 3/1991 | Sorenson | |
| 6,310,095 B1 * | 10/2001 | Sebti et al. | ............... 514/539 |
| 2002/0143003 A1 | 10/2002 | Howard | |
| 2006/0052374 A1 * | 3/2006 | Carroll et al. | ............... 514/227.5 |

FOREIGN PATENT DOCUMENTS

| BE | 671 402 | 2/1966 |
| EP | 0 855 394 | 7/1998 |
| WO | 93/11106 | 6/1993 |
| WO | 96/25426 | 8/1996 |
| WO | 01/81347 | 1/2001 |
| WO | 01/58853 | 8/2001 |
| WO | 03/035615 | 5/2003 |
| WO | 2004/092134 | 10/2004 |

OTHER PUBLICATIONS

Atherton, et al., Tetrahedron (1983), 39(15), 2599-608 (See CAS RN 88104-43-2).*
Yu, et al, Tetrahedron Letters, 45, 2004, 7787-7789, especially p. 7788.*
Patani et al., Chem Rev, 1996, vol. 96 (8), especially p. 3147. See IDS submitted Dec. 17, 2009, cite No. 005.*
Patini, et al., Chem. Rev., 1996, 96, 3147-3176, esp. p. 3149.*
Adachi; et al., Daigaku Yakugakubu Kenkyo Nempo, vol. 7, p. 10; (1957).
Brigas, Amadeu F., et al., Metal-assisted reactions, Journal of the Chemical Society, Perkin Transactions 2, vol. 8, pp. 1315-1324, (2001).
Anderson, C., et al., Drug Dev. Res., vol. 50, p. 92, (2000).
Atherton, F.R., et al., Tetrahedron, vol. 39, Issue 15, pp. 2599-2608, (1983).
Batey, Robert. A. and Powell, David A., Org. Letters, vol. 2, pp. 3237-3240, (2000).
Breitmaier, et al., Tetrahedron, vol. 26, pp. 5907-5912, (1970).
Brough, et al., Molecular and Cellular Neuroscience, vol. 19, pp. 272-280, (2002).
Chessell, et al., Pain, vol. 114, Issue 3, pp. 386-396, (2005).
Collo, G., et al., Neuropharmacology, vol. 36, pp. 1277-1283, (1997).
Database-Accession No. 6427790(BRN) XP002350782 ,Beilstein Institut Zur Foederung Der Chemischen Wissenschaften; & Helv. Chim. Acta, vol. 71, pp. 33-46 (1988).
Database Crossfire Beilstein Institut Zur Foederung Der Chemischen Wissenschaften; Database Accession No. 338156(BRN) XP002350783 abstract & Journal FUR Praktische Chemie, vol. 134, pp. 282-309, (1932).
Database CA, Chemical Abstracts Service, Columbus, Ohio, U.S.; 1984, Svetlik J., et al., Preparation and spectral properties of tetrazoles, Database-Accession No. XP002350784.
Dell Antonio et al., Neuroscience Lett., vol. 327, pp. 87-90, (2002).
Deuchars, et al., J. Neuroscience, vol. 21, pp. 7143-7152, (2001).
Dixon, Ann. Rev. Pharmacol. Toxicol., vol. 20, pp. 441-462, (1980).
Djuric, S., J. Med. Chem., vol. 43, pp. 2975-2981, (2000).
Imhof, R.; et al., J. Org. Chem., vol. 42, pp. 3709-3713, (1977).
Kim and Chung, Pain, vol. 50, pp. 355-363, (1992).
Kuehle, et al, Angewandte Chemie, vol. 79 (15), pp. 663-680, (1967).
Lu, et al., Bioorg. Med. Chem. Lett., vol. 13, pp. 1821-1824, (2003).
Marsais, F., et al., J of Organomet. Chem., vol. 216, pp. 139-147, (1981).

(Continued)

*Primary Examiner* — Susannah Chung
(74) *Attorney, Agent, or Firm* — Lisa V. Mueller; Micheal Best & Friedrich LLP

(57) ABSTRACT

A compound having Formula (I) or Formula (II)

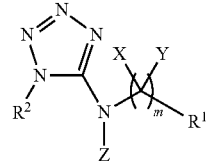

Formula (I)

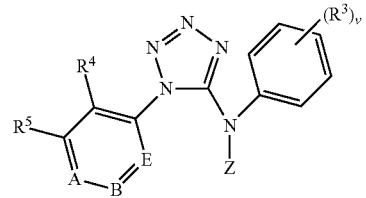

Formula (II)

is disclosed as an $P2X_7$ antagonist, wherein A, B, C, Y, Y, Z, m, v, $R^1$, $R^2$, $R^3$, $R^4$, and $R^5$, are as defined in the description. Methods and compositions for treating disease or condition modulated by $P2X_7$ are also disclosed.

13 Claims, No Drawings

OTHER PUBLICATIONS

Michel, et al., N-S Arch Pharmacol, vol. 359, pp. 102-109, (1999).
Morita; et al., J. Heterocycl. Chem., vol. 23, pp. 1465-1469, (1986).
Narcisse, et al., Glia, vol. 49, pp. 245-258, (2005) (abstract only).
Parvathenani, et al., J. Biol. Chemistry, vol. 278, pp. 13300-13317, (2003).
Peel, Michael R.; Bioorg. Med. Chem. Lett, vol. 4 (23), pp. 2753-2758, (1994).
Perretti, M., et al., Agents Actions, vol. 35 (1-2), pp. 71-78, (1992).
Schlosser, et al., Eur. J. Org. Chem., vol. 3, pp. 452-462, (2003).
Schmelkes; J. Amer. Chem. Soc., vol. 61, p. 2562, (1939).
Torok, K., et al., Inflamm. Res., vol. 44 (6), pp. 248-252, (1995).
Turan-Zitouni, G.; et al., Farmaco Ed. Science, vol. 43, 7-8, pp. 643-656, (1988).
Verhoef, et al., The Journal of Immunlogy, vol. 170, pp. 5728-5738, (2003).
Wang, et al., Nature Medicine, vol. 10, pp. 821-827, (2004).
Database crossfire beilstein institut zur foederung der chemischen wissenschaften; database-accession No. 6427790 (brn) xp002350782 abstract & helv. Chim. Acta, vol. 71, 1988, pp. 33-46.
Debernardis, John F. "Conformationally defined adrenergic agents. 1. Design and synthesis of novel alfa2 selectivec adrenergic agents: Electrostatic repulsion based conformational prototypes," J.Med. Chem. 1985, 1398-1404, vol. 28—Issue 10.
International Search Report for application No. PCT/US2005/0014641, Mailed on Jul. 11, 2005, 4 pages.
Patini et al., Chem. Rev., vol. 96(8), pp. 3147-3176, especially p. 3158, 1996.
Vippagunta et al., "Crystalline solids," Advanced Drug Delivery Reviews, 2001, pp. 3-18, vol. 48.
Wolff, Mandred E. "Burger's Medicinal Chemistry and Drug Discovery," Principles and Practice, 1995, 975-977, 5th Ed,vol. 1, John Wiley & Sons.
Gunzenhauser, S. et al, Halochromic molecules. Part 7. Synthesis and acid-base properties of substituted heteroarenoquinazolines, Helvetica Chimica Acta, 1988, vol. 71, No. 1, pp. 33-46. (English Abstract Only).
Svetlik, J. et al, Preparation and spectral properties of tetrazoles, Chemicke Zvesti, 1979, vol. 33, No. 4, pp. 521-527.

* cited by examiner

AMINO-TETRAZOLES ANALOGUES AND METHODS OF USE

This application claims priority to U.S. Provisional Application Ser. No. 60/566,238 filed on Apr. 29, 2004.

TECHNICAL FIELD

This invention relates to substituted aminotetrazoles analogues that are antagonists of $P2X_7$ receptors, and to the use of such compounds for treating conditions related to $P2X_7$ receptor activation.

BACKGROUND OF THE INVENTION

P2X receptors are ionotropic receptors activated by ATP. The importance of P2X receptors in nociception is underscored by the variety of pain states in which this endogenous ligand can be released. Of the seven P2X receptors, the $P2X_7$ is distinguished by its ability to form a large pore upon prolonged or repeated agonist stimulation. It is partially activated by saturating concentrations of ATP, whereas it is fully activated by the synthetic ATP analog benzoylbenzoic ATP (BzATP) (Bianchi et al., *Eur. J. Pharmacol. Vol.* 376, pages 127-138, 1999). The $P2X_7$ receptor is expressed by presynaptic terminals in the central and peripheral nervous systems, antigen-presenting cells including macrophages, human epidermal Langerhans' cells, microglial cells and a number of tumor cell lines of varying origin (Jacobson K A, et al. "*Adenosine and Adenine Nucleotides: From Molecular Biology to Integrative Physiology*". L. Belardinelli and A. Pelleg (eds.), Kluwer, Boston, pages 149-166, 1995).

On glial cells, the $P2X_7$ receptor has been shown to mediate release of glutamate (Anderson C. et al. *Drug Dev. Res. Vol.* 50. page 92, 2000). Since glutamate is known to be involved in the neurotransmission of painful sensory signals, inhibition of $P2X_7$ may have therapeutic utility in the treatment of various pain states. Furthermore, oxidized ATP (oATP), a nonselective and irreversible $P2X_7$ antagonist, was recently reported to possess peripherally-mediated antinociceptive properties in inflamed rats (Dell'Antonio et al. *Neuroscience Lett., Vol.* 327 pages 87-90, 2002). Thus, $P2X_7$ antagonists may have utility in the treatment of a variety of pain states.

Recent data also suggested a possible role for $P2X_7$ receptor activation in neuroinflammation and neurodegeneration (Collo G. et al. *Neuropharmacology, Vol.* 36, pages 1277-1283, 1997). In the central nervous system, the $P2X_7$ receptor is predominately expressed by microglia, the resident macrophages of the brain. Recent studies indicate a role of the $P2X_7$ receptor in the generation of superoxide in microglia, and upregulation of $P2X_7$ receptors around β-amyloid plaques in a transgenic mouse model for Alzheimer's disease (Parvathenani et al., *J. Biol. Chemistry. Vol.* 278, pages 13300-13317, 2003) and in multiple sclerosis lesions from autopsy brain sections (Narcisse et al., Glia, Vol. 49, pages 245-258 (2005).

Thus, $P2X_7$ antagonists may have utility in the treatment of neurodegenerative conditions including stroke and Alzheimer's disease.

Activation of the $P2X_7$ receptor on cells of the immune system (macrophages, mast cells and lymphocytes) leads to release of interleukin-1β (IL-1β), giant cell formation, degranulation, and L-selectin shedding. Compounds acting at the $P2X_7$ receptor may therefore have utility in the treatment of various disease states and conditions such as rheumatoid arthritis, osteoarthritis, psoriasis, allergic dermatitis, asthma, chronic obstructive pulmonary disease, airways hyper-responsiveness, septic shock, glomerulonephritis, irritable bowel disease, Crohn's disease, ulcerative colitis, atherosclerosis, growth and metastases of malignant cells, myoblastic leukaemia, diabetes, Alzheimer's disease, meningitis, osteoporosis, burn injury, ischemic heart disease, stroke and varicose veins.

Neuropathic pain is another type of pain different from pain involved with inflammatory or neurodegenerative conditions. Neuropathic pain is associated with any disorder affecting any segment of the nervous system. Common causes of neuropathic pain are, among others, alcoholism, amputation, cancer chemotherapy, diabetes, trigeminal neuralgia, HIV infection, multiple sclerosis, shingles and spine surgery. One of the most dramatic examples of neuropathic pain is called "phantom limb syndrome" which occurs when an arm or a leg have been removed, but the brain still gets pain messages from the missing limb.

A recent study reported the localization of $P2X_7$ on presynaptic terminals in the central and peripheral nervous systems (Deuchars et al *J. Neuroscience, Vol.* 21, p 7143-7152, 2001) where its activation was linked to release of the excitatory amino acid neurotransmitter glutamate. This finding indicates a role for the $P2X_7$ receptor in the process of neuronal synaptic transmission and therefore a potential role for $P2X_7$ antagonists as novel therapeutic tool to treat neuropathic pain.

Oxidized ATP (oATP), a nonselective and irreversible $P2X_7$ antagonist, was recently reported to possess peripherally mediated antinociceptive properties in inflamed rats (Dell'Antonio et al. *Neuroscience Lett. Vol.* 327, pages 87-90, 2002).

Studies from mice lacking $P2X_7$ receptor resulted in absence of inflammatory and neuropathic hypersensitivity to mechanical and thermal stimuli, indicating a link between a $P2X_7$ purinoceptor gene and inflammatory and neuropathic pain (Chessell et al., *Pain, Vol* 114, pages 386-396 (2005)).

Antagonists to the $P2X_7$ receptor significantly improved functional recovery and decreased cell death in spinal cord injury (SCI) animal models. Rats with SCI were administered $P2X_7$ receptor irreversible antagonists oATP and PPADS with a resulting decrease of histological injury and improved recovery of motor function after the lesions (Wang et al., *Nature Medicine Vol.* 10, pages B21-B27, 2004).

In view of the above facts, there is a need for selective $P2X_7$ antagonist that can be efficiently used in preventing, treating, or ameliorating states as neuropathic pain, chronic inflammatory pain, inflammation and neurodegenerative conditions associated with several progressive CNS disorders, including, but not limited to, Alzheimer's disease, Parkinson's disease, depression, amyotrophic lateral sclerosis, Huntington's disease, dementia with Lewy bodies, multiple sclerosis as well as diminished CNS function resulting from traumatic brain injury.

SUMMARY OF THE INVENTION

In its principal embodiment, the present invention discloses a compound having Formula (I) or Formula (II),

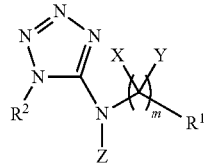

Formula (I)

-continued

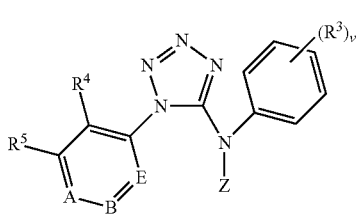

Formula (II)

or a therapeutically acceptable salt, solvate, prodrug, or salt of a prodrug thereof, in which $R^2$ is phenyl or pyridyl, in which each $R^2$ is substituted with one, two, three, four, or five substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;

$R^{2a}$ is —C$_1$-alkyl, —C$_2$-alkyl, —C$_3$-alkyl, —C$_4$-alkyl, —C$_5$-alkyl, —C$_6$-alkyl, or R$^{2b}$;

$R^{2b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{2c}$, —N(R$^{2c}$)$_2$, —CN, —SR$^{2c}$, and —SO$_2$R$^{2c}$;

$R^{2c}$ is —C$_1$-alkyl, —C$_2$-alkyl, —C$_3$-alkyl, —C$_4$-alkyl, —C$_5$-alkyl, or —C$_6$-alkyl;

m is 0, 1, 2, or 3;

X and Y are independently selected from the group consisting of —H, —C$_1$-alkyl, —C$_2$-alkyl, —C$_3$-alkyl, —C$_4$-alkyl, —C$_5$-alkyl, and C$_6$-alkyl; or X and Y together with the carbon atom to which they are attached form a ring selected from the group consisting of cyclopropane, cyclobutane, cyclopentane, cyclohexane, tetrahydrofuran, tetrahydrothiophene, pyrrolidine, dioxolane, tetrahydropyran, piperidine, morpholine, thiomorpholine, and piperazine, each or which is unsubstituted or substituted with one, two, three, or four substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;

Z is —H, —C$_1$-alkyl, —C$_2$-alkyl, —C$_3$-alkyl, —C$_4$-alkyl, —C$_5$-alkyl, or —C$_6$-alkyl; or Z and X together with the atoms to which they are attached form a ring selected from the group consisting of pyrrolidine, piperidine, morpholine, thiomorpholine, and piperazine;

$R^1$ is proximal phenyl which is unfused or fused with a distal cyclopentane, cyclohexane, cyclopentene, cyclohexene, dioxane, dioxolane, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, dioxolane, pyrazolidine, pyran, piperidine, morpholine, thiomorpholine, oxazolidinone, morpholinone, or piperazine ring, in which the proximal phenyl ring and the distal ring are, independently of each other, unsubstituted or substituted with one, two, three, or four substituents independently selected from the group consisting of —Cl, —F, —Br, —I, —OH, —NO$_2$, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$; proximal isoxazolyl, oxazolyl, pyrrolidinyl, pyridyl, thienyl, pyrrolyl, pyridazinyl, pyrazolyl, imidazolyl, thiazolyl, furyl, tetrahydrofuryl, tetrahydropyranyl, pyrimidinyl, pyrazinyl, or imidazopyridinyl, each of which is unfused or fused with a distal cyclopentane, cyclohexane, cyclopentene, cyclohexene, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, dioxolane, pyrazolidine, pyran, piperidine, morpholine, thiomorpholine, or piperazine ring, in which each of the proximal pyrrolidinyl, pyridyl, thienyl, pyrrolyl, pyridazinyl, pyrazolyl, imidazolyl, thiazolyl, furyl, tetrahydrofuryl, pyrimidinyl, pyrazinyl, or imidazopyridinyl ring and the distal ring are, independently of each other, unsubstituted or substituted with one, two, three, or four substitutents independently selected from the group consisting of —Cl, —F, —Br, —I, —NO$_2$, —OH, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O) OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N (H)(R$^{1e}$), —SO$_2$N(R$^{1d}$)(R$^{1e}$), —NH(R$^{1e}$), —N(R$^{1d}$) (R$^{1e}$), —NHC(O)R$^{1f}$, —N(R$^{1d}$)C(O)R$^{1f}$, and —R$^{1c}$; or proximal bicyclo[2,2,1]heptyl, cyclopentyl, cyclohexyl, cyclopentenyl, or cyclohexenyl, each of which is unfused or fused with a distal cyclopentane, cyclohexane, cyclopentene, cyclohexene, naphthalene, benzene, furan, imidazole, isothiazole, oxazole, isoxazole, pyrazine, pyrazole, pyridazine, pyridine, pyrimidine, pyrrole, imidazoline, tetrahydrofuran, tetrahydrothiophene, thiazole, thiophene, pyrrolidine, dioxolane, pyrazoline, pyrazolidine, pyran, piperidine, morpholine, thiomorpholine, or piperazine ring, in which the proximal cyclopentyl, cyclohexyl, cyclopentenyl, or cyclohexenyl ring and the distal ring are, independently of each other, unsubstituted or substituted with one, two, three, or four substituents independently selected from the group consisting of ═O, —Cl, —F, —Br, —I, —OH, —NO$_2$, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N (R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$;

adamantyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H) (R$^{1d}$), and —C(O)N(R$^{1d}$)$_2$; or 2,3-dihydrospiroindene-1,4'-piperidinyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H)(R$^{1d}$), and —C(O) N(R$^{1d}$)$_2$;

$R^{1a}$ is —C$_1$-alkyl, —C$_2$-alkyl, —C$_3$-alkyl, —C$_4$-alkyl, —C$_5$-alkyl, —C$_6$-alkyl, or —R$^{1b}$;

$R^{1b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NH_2$, —OH, —$OR^{1d}$, —$C_1$-alkyl, —$C_2$-alkyl, —$C_3$-alkyl, —$C_4$-alkyl, —$C_5$-alkyl, —$C_6$-alkyl, —$R^{1c}$, —$N(R^{1d})_2$, and —$NHR^{1d}$;

$R^{1c}$ is cycloalkyl, cycloalkenyl, aryl, heteroaryl or heterocycle, in which each $R^{1c}$ is unsubstituted or substituted with one, two, three, or four substituents independently selected from the group consisting of =O, —Cl, —F, —Br, —I, —$NO_2$, —CN, —OH, —$R^{1aa}$, —$NH_2$, —$OR^{1aa}$, —$SR^{1aa}$, —$NHR^{1aa}$, —$N(R^{1aa})_2$, —$C(O)R^{1aa}$, $S(O)_2R^{1aa}$, $S(O)_2NH_2$, $S(O)_2N(R^{1aa})_2$, —$C(O)NH_2$, —$C(O)N(H)(R^{1aa})$, —$C(O)N(R^{1aa})_2$, —$C(O)OH$, —$C(O)OR^{1aa}$, —$OR^{1h}$, —$N(H)R^{1h}$, —$N(R^{1d})(R^{1h})$ and —$R^{1h}$;

$R^{1aa}$ is —$C_1$-alkyl, —$C_2$-alkyl, —$C_3$-alkyl, —$C_4$-alkyl, —$C_5$-alkyl, —$C_6$-alkyl, or —$R^{1bb}$;

$R^{1bb}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NH_2$, —$NO_2$, —CN, haloalkyl, haloalkoxy, —OH, —$OR^{1d}$, —$SR^{1d}$, —$S(O)_2R^{1d}$, —$C_1$-alkyl, —$C_2$-alkyl, —$C_3$-alkyl, —$C_4$-alkyl, —$C_5$-alkyl, —$C_6$-alkyl, —$N(R^{1d})_2$, —$NHR^{1d}$, —$C(O)OH$, —$C(O)OR^{1d}$, —$C(O)NH_2$, —$C(O)N(H)(R^{1d})$, —$C(O)N(R^{1d})_2$, —$S(O)_2NH_2$, —$S(O)_2N(H)(R^{1d})$, —$S(O)_2N(R^{1d})_2$ and $R^{1h}$;

$R^{1d}$ is —$C_1$-alkyl, —$C_2$-alkyl, —$C_3$-alkyl, —$C_4$-alkyl, —$C_5$-alkyl, or —$C_6$-alkyl;

$R^{1e}$ is a monocyclic or bicyclic ring selected from the group consisting of cycloalkyl, heterocycle, aryl and heteroaryl, wherein each ring is unsubstituted or substituted with one, two, three or four substituents independently selected from the group consisting of =O, —Cl, —F, —Br, —I, —$NO_2$, —CN, —OH, —$R^{1aa}$, —$OR^{1aa}$, —$SR^{1aa}$, —$NH_2$, —$NHR^{1aa}$, and —$N(R^{1aa})_2$;

$R^{1f}$ is —$C_1$-alkyl, —$C_2$-alkyl, —$C_3$-alkyl, —$C_4$-alkyl, —$C_5$-alkyl, —$C_6$-alkyl, aryl, heteroaryl, —$R^{1h}$, or $R^{1g}$;

$R^{1g}$ is —$C_1$-alkyl, —$C_2$-alkyl, —$C_3$-alkyl, —$C_4$-alkyl, —$C_5$-alkyl, or —$C_6$-alkyl, each of which is substituted with one substituent selected from the group consisting of $R^{1h}$;

$R^{1h}$ is cycloalkyl, cycloalkenyl, aryl, heteroaryl or heterocycle, in which each $R^{1h}$ is unsubstituted or substituted with one or two or three or four or five substituents independently selected from the group consisting of —F, —Cl, —Br, —I, —$NO_2$, —CN, haloalkyl, haloalkoxy, —$NH_2$, —OH, —$OR^{1d}$, —$SR^{1d}$, —$S(O)_2R^{1d}$, —$C_1$-alkyl, —$C_2$-alkyl, —$C_3$-alkyl, —$C_4$-alkyl, —$C_5$-alkyl, —$C_6$-alkyl, —$N(R^{1d})_2$, —$NHR^{1d}$, —$C(O)OH$, —$C(O)OR^{1d}$, —$C(O)NH_2$, —$C(O)N(H)(R^{1d})$, —$C(O)N(R^{1d})_2$, —$S(O)_2NH_2$, —$S(O)_2N(H)(R^{1d})$, and —$S(O)_2N(R^{1d})_2$;

provided that when $R^1$ is proximal phenyl fused with a distal pyrrole, thiophene, furan, pyrazole, isoxazole, or isothiazole ring, the distal pyrrole, thiophene, furan, pyrazole, isoxazole, or isothiazole ring is not substituted with —$C_1$-alkyl, —$C_2$-alkyl, —$C_3$-alkyl, —$C_4$-alkyl, —$C_5$-alkyl, —$C_6$-alkyl, pyrrolidinyl, piperidyl, tetrahydropyridyl, pyrrolinyl, —$C_1$-alkyl substituted with pyrrolidinyl or piperidyl, —$C_2$-alkyl substituted with —$N(R^{1d})_2$, —$NH_2$, or —$NHR^{1d}$, —$C_3$-alkyl substituted with —$N(R^{1d})_2$, —$NH_2$, or —$NHR^{1d}$, —$C_4$-alkyl substituted with —$N(R^{1d})_2$, —$NH_2$, or —$NHR^{1d}$, —$C_5$-alkyl substituted with —$N(R^{1d})_2$, —$NH_2$, or —$NHR^{1d}$, or —$C_6$-alkyl substituted with —$N(R^{1d})_2$, —$NH_2$, or —$NHR^{1d}$;

and provided that when m is 0 and $R^2$ is phenyl, then $R^1$ is not proximal unfused phenyl;

A is N or $CR^6$;
B is N or $CR^7$;
E is N or $CR^8$;
provided that only one of A, B and E is N;

$R^3$ is —$NH_2$, —$R^{3a}$ is —$OR^{3a}$, —$NHR^{3a}$, —$N(R^{3a})_2$, —$NHC(O)R^{3f}$, —$N(R^{3d})C(O)R^{3c}$, —$R^{3c}$, —$OR^{3c}$, —$SR^{3e}$, —$NH(R^{3e})$ or —$N(R^{3d})(R^{3e})$;

$R^{3a}$ is —$C_1$-alkyl, —$C_2$-alkyl, —$C_3$-alkyl, —$C_4$-alkyl, —$C_5$-alkyl, —$C_6$-alkyl, or $R^{3b}$;

$R^{3b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —$NH_2$, —CN, —OH, —$OR^{3d}$, —$R^{3c}$, —$N(R^{3d})_2$, and —$NHR^{3d}$;

$R^{3c}$ is cycloalkyl, cycloalkenyl, aryl, heteroaryl or heterocycle, in which each $R^{3c}$ is unsubstituted or substituted with one, two, three, or four substituents independently selected from the group consisting of —Cl, —F, —Br, —I, —OH, —$R^{3aa}$, —$NH_2$, —$OR^{3aa}$, —$SR^{3aa}$, —$NHR^{3aa}$, and —$N(R^{3aa})_2$;

$R^{3d}$ is —$C_1$-alkyl, —$C_2$-alkyl, —$C_3$-alkyl, —$C_4$-alkyl, —$C_5$-alkyl, or —$C_6$-alkyl;

$R^{3aa}$ is —$C_1$-alkyl, —$C_2$-alkyl, —$C_3$-alkyl, —$C_4$-alkyl, —$C_5$-alkyl, —$C_6$-alkyl, or —$R^{3bb}$;

$R^{3bb}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NH_2$, —OH, —$OR^{3d}$, —$C_1$-alkyl, —$C_2$-alkyl, —$C_3$-alkyl, —$C_4$-alkyl, —$C_5$-alkyl, —$C_6$-alkyl, —$N(R^{3d})_2$, and —$NHR^{3d}$;

$R^{3e}$ is a monocyclic or bicyclic ring selected from the group consisting of cycloalkyl, heterocycle, aryl and heteroaryl, in which each ring is unsubstituted or substituted with one, two, three, or four substituents independently selected from the group consisting of =O, —Cl, —F, —Br, —I, —OH, —$R^{3aa}$, —$NH_2$, —$OR^{3aa}$, —$SR^{3aa}$, —$NHR^{3aa}$, and —$N(R^{3aa})_2$;

$R^{3f}$ is —$C_1$-alkyl, —$C_2$-alkyl, —$C_3$-alkyl, —$C_4$-alkyl, —$C_5$-alkyl, —$C_6$-alkyl, aryl, heteroaryl, or $R^{3g}$;

$R^{3g}$ is —$C_1$-alkyl, —$C_2$-alkyl, —$C_3$-alkyl, —$C_4$-alkyl, —$C_5$-alkyl, or —$C_6$-alkyl, each of which is substituted with one substituent selected from the group consisting of aryl and heteroaryl;

v is one, two, or three, and when v is two or three, $R^3$ may be the same or different;

$R^4$ is —Cl, —F, —Br, —I, —$NH_2$, —$R^{4a}$, —$OR^{4a}$, —$NHR^{4a}$, —$N(R^{4a})_2$, —CN, —$SR^{4a}$, or —$SO_2R^{4a}$;

$R^{4a}$ is —$C_1$-alkyl, —$C_2$-alkyl, —$C_3$-alkyl, —$C_4$-alkyl, —$C_5$-alkyl, —$C_6$-alkyl, or $R^{4b}$;

$R^{4b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{4c}$, —$N(R^4)_2$, —CN, —$SR^{4c}$, and —$SO_2R^{4c}$;

$R^{4c}$ is —$C_1$-alkyl, —$C_2$-alkyl, —$C_3$-alkyl, —$C_4$-alkyl, —$C_5$-alkyl, or —$C_6$-alkyl;

$R^5$ is —H, —Cl, —F, —Br, —I, —$NH_2$, —$R^{5a}$, —$OR^{5a}$, —$NHR^{5a}$, —$N(R^{5a})_2$, —CN, —$SR^{5a}$, or $SO_2R^{5a}$;

$R^{5a}$ is —$C_1$-alkyl, —$C_2$-alkyl, —$C_3$-alkyl, —$C_4$-alkyl, —$C_5$-alkyl, —$C_6$-alkyl, or $R^{5b}$;

$R^{5b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{5c}$, —$N(R^{5c})_2$, —CN, —$SR^{5c}$, and —$SO_2R^{5c}$;

$R^{5c}$ is —$C_1$-alkyl, —$C_2$-alkyl, —$C_3$-alkyl, —$C_4$-alkyl, —$C_5$-alkyl, or —$C_6$-alkyl;

$R^6$ is —H, —Cl, —F, —Br, —I, —$NH_2$, —$R^{6a}$, —$OR^{6a}$, —$NHR^{6a}$, —$N(R^{6a})_2$, —CN, —$SR^{6a}$, or —$SO_2R^{6a}$;

$R^{6a}$ is —$C_1$-alkyl, —$C_2$-alkyl, —$C_3$-alkyl, —$C_4$-alkyl, —$C_5$-alkyl, —$C_6$-alkyl, or $R^{6b}$;

$R^{6b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{6c}$, —$N(R^{6c})_2$, —CN, —$SR^{6c}$, and —$SO_2R^{6c}$;

$R^{6c}$ is —$C_1$-alkyl, —$C_2$-alkyl, —$C_3$-alkyl, —$C_4$-alkyl, —$C_5$-alkyl, or —$C_6$-alkyl;

$R^7$ is —H, —Cl, —F, —Br, —I, —$NH_2$, —$R^{7a}$, —$OR^{7a}$, —$NHR^{7a}$, —$N(R^{7a})_2$, —CN, —$SR^{7a}$, or —$SO_2^{7a}$;

$R^{7a}$ is —$C_1$-alkyl, —$C_2$-alkyl, —$C_3$-alkyl, —$C_4$-alkyl, —$C_5$-alkyl, —$C_6$-alkyl, or $R^{7b}$;

$R^{7b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{7c}$, —$N(R^{7c})_2$, —CN, —$SR^{7c}$, and —$SO_2R^{7c}$;

$R^{7c}$ is —$C_1$-alkyl, —$C_2$-alkyl, —$C_3$-alkyl, —$C_4$-alkyl, —$C_5$-alkyl, or —$C_6$-alkyl;

$R^8$ is —H, —Cl, —F, —Br, —I, —$NH_2$, —$R^{8a}$, —$OR^{8a}$, —$NHR^{8a}$, —$N(R^{8a})_2$, —CN, —$SR^{8a}$, or —$SO_2R^{8a}$;

$R^{8a}$ is —$C_1$-alkyl, —$C_2$-alkyl, —$C_3$-alkyl, —$C_4$-alkyl, —$C_5$-alkyl, —$C_6$-alkyl, or $R^{8b}$;

$R^{8b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{8c}$, —$N(R^{8c})_2$, —CN, —$SR^{8c}$, and —$SO_2R^{8c}$;

$R^{8c}$ is —$C_1$-alkyl, —$C_2$-alkyl, —$C_3$-alkyl, —$C_4$-alkyl, —$C_5$-alkyl, or —$C_6$-alkyl; and with the proviso that the following compounds are excluded: N-benzyl-1-(4-methoxyphenyl)-1H-tetraazol-5-amine; N,1-bis(4-methylphenyl)-1H-tetraazol-5-amine; N,1-bis(4-methoxyphenyl)-1H-tetraazol-5-amine; and N,1-bis(2,4-dimethylphenyl)-1H-tetraazol-5-amine.

Another embodiment of the present invention relates to a pharmaceutical composition comprising a compound of the present invention, or a therapeutically acceptable salt, prodrug, solvate, salt of a prodrug, or combination thereof, as defined hereinafter, in combination with a pharmaceutically acceptable carrier. Such compositions can be administered in accordance with a method of the invention, typically as part of a therapeutic regime for treatment or prevention of chronic inflammatory pain, neuropathic pain, spinal cord injury, neurodegeneration, or depression. The compositions may contain one or more compounds of the present invention.

A further embodiment of the present invention provides a method for treating or preventing rheumatoid arthritis, osteoarthritis, psoriasis, Crohn's disease, spinal cord injury, neurodegenerative disease, Alzheimer's disease, depression, chronic inflammatory pain and neuropathic pain. Accordingly, the present invention provides a compound of formula (I) or (II), or a therapeutically acceptable salt, solvate, prodrug, salt of a prodrug, or combination thereof, as defined hereinafter, for use in the treatment or prevention of the abovementioned diseases.

Yet another embodiment of the present invention provides the use of a compound of Formula (I) or (II), or a therapeutically acceptable salt, solvate, prodrug, salt of a prodrug, or combination thereof, as defined hereafter, in the preparation of a medicament for the treatment or prevention of the aforementioned diseases.

DETAILED DESCRIPTION OF THE INVENTION

In a first embodiment, the present invention provides a compound having Formula (I) or Formula (II),

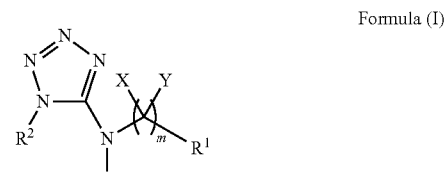

Formula (I)

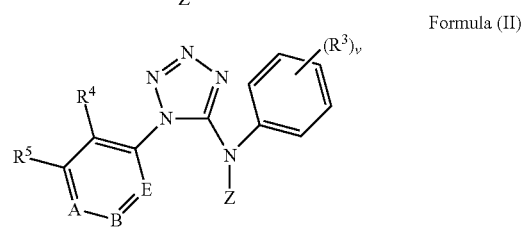

Formula (II)

or a therapeutically acceptable salt, solvate, prodrug, or salt of a prodrug thereof, in which $R^2$ is phenyl or pyridyl, in which each $R^2$ is substituted with one, two, three, four, or five substituents independently selected from the group consisting of —Cl, —F, —Br, —I, —$NH_2$, —$R^{2a}$, —$OR^{2a}$, —$NHR^{2a}$, —$N(R^{2a})_2$, —CN, —$SR^{2a}$, and —$SO_2R^{2a}$;

$R^{2a}$ is —$C_1$-alkyl, —$C_2$-alkyl, —$C_3$-alkyl, —$C_4$-alkyl, —$C_5$-alkyl, —$C_6$-alkyl, or $R^{2b}$;

$R^{2b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{2c}$, —$N(R^{2c})_2$, —CN, —$SR^{2c}$, and —$SO_2R^{2c}$;

$R^{2c}$ is —$C_1$-alkyl, —$C_2$-alkyl, —$C_3$-alkyl, —$C_4$-alkyl, —$C_5$-alkyl, or —$C_6$-alkyl;

m is 0, 1, 2, or 3;

X and Y are independently selected from the group consisting of —H, —$C_1$-alkyl, —$C_2$-alkyl, —$C_3$-alkyl, —$C_4$-alkyl, —$C_5$-alkyl, and $C_6$-alkyl; or X and Y together with the carbon atom to which they are attached form a ring selected from the group consisting of cyclopropane, cyclobutane, cyclopentane, cyclohexane, tetrahydrofuran, tetrahydrothiophene, pyrrolidine, dioxolane, tetrahydropyran, piperidine, morpholine, thiomorpholine, and piperazine, each or which is unsubstituted or substituted with one, two, three, or four substituents independently selected from the group consisting of —Cl, —F, —Br, —I, —$NH_2$, —$R^{2a}$, —$OR^{2a}$, —$NHR^{2a}$, —$N(R^{2a})_2$, —CN, —$SR^{2a}$, and —$SO_2R^{2a}$;

Z is —H, —$C_1$-alkyl, —$C_2$-alkyl, —$C_3$-alkyl, —$C_4$-alkyl, —$C_5$-alkyl, or —$C_6$-alkyl; or Z and X together with the atoms to which they are attached form a ring selected from the group consisting of pyrrolidine, piperidine, morpholine, thiomorpholine, and piperazine;

$R^1$ is proximal phenyl which is unfused or fused with a distal cyclopentane, cyclohexane, cyclopentene, cyclohexene, dioxane, dioxolane, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, dioxolane, pyrazolidine, pyran, piperidine, morpholine, thiomorpholine, oxazolidinone, morpholinone, or piperazine ring, in which the proximal phenyl ring and the distal ring are, independently of each other, unsubstituted or substituted with one, two, three, or four substituents independently selected from the group consisting of —Cl, —F, —Br, —I, —OH, —NH$_2$, —NO$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1d}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$;

proximal isoxazolyl, oxazolyl, pyrrolidinyl, pyridyl, thienyl, pyrrolyl, pyridazinyl, pyrazolyl, imidazolyl, thiazolyl, furyl, tetrahydrofuryl, tetrahydropyranyl, pyrimidinyl, pyrazinyl, or imidazopyridinyl, each of which is unfused or fused with a distal cyclopentane, cyclohexane, cyclopentene, cyclohexene, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, dioxolane, pyrazolidine, pyran, piperidine, morpholine, thiomorpholine, or piperazine ring, in which the proximal pyrrolidinyl, pyridyl, thienyl, pyrrolyl, pyridazinyl, pyrazolyl, imidazolyl, thiazolyl, furyl, tetrahydrofuryl, pyrimidinyl, pyrazinyl, or imidazopyridinyl ring and the distal ring are, independently of each other, unsubstituted or substituted with one, two, three, or four substituents independently selected from the group consisting of —Cl, —F, —Br, —I, —OH, —NO$_2$, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$—C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$; or proximal bicyclo[2,2,1]heptyl, cyclopentyl, cyclohexyl, cyclopentenyl, or cyclohexenyl, each of which is unfused or fused with a distal cyclopentane, cyclohexane, cyclopentene, cyclohexene, naphthalene, benzene, furan, imidazole, isothiazole, oxazole, isoxazole, pyrazine, pyrazole, pyridazine, pyridine, pyrimidine, pyrrole, imidazoline, tetrahydrofuran, tetrahydrothiophene, thiazole, thiophene, pyrrolidine, dioxolane, pyrazoline, pyrazolidine, pyran, piperidine, morpholine, thiomorpholine, or piperazine ring, in which the proximal cyclopentyl, cyclohexyl, cyclopentenyl, or cyclohexenyl ring and the distal ring are, independently of each other, unsubstituted or substituted with one, two, three, or four substituents independently selected from the group consisting of =O, —Cl, —F, —Br, —I, —OH, —NO$_2$, —NH$_2$, —R$^{1a}$, —OR$^{1aa}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$;

adamantyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H)(R$^{1d}$), and —C(O)N(R$^{1d}$)$_2$; or 2,3-dihydrospiroindene-1,4'-piperidinyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H)(R$^{1d}$), and —C(O)N(R$^{1d}$)$_2$;

R$^{1a}$ is —C$_1$-alkyl, —C$_2$-alkyl, —C$_3$-alkyl, —C$_4$-alkyl, —C$_5$-alkyl, —C$_6$-alkyl, or —R$^{1b}$;

R$^{1b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —OR$^{1d}$, —C$_1$-alkyl, —C$_2$-alkyl, —C$_3$-alkyl, —C$_4$-alkyl, —C$_5$-alkyl, —C$_6$-alkyl, —R$^{1c}$, —N(R$^{1d}$)$_2$, and —NHR$^{1d}$;

R$^{1c}$ is cycloalkyl, cycloalkenyl, aryl, heteroaryl or heterocycle, in which each R$^{1c}$ is unsubstituted or substituted with one, two, three, or four substituents independently selected from the group consisting of =O, —Cl, —F, —Br, —I, —NO$_2$, —CN, —OH, —R$^{1aa}$, —NH$_2$, —OR$^{1aa}$, —SR$^{1aa}$, —NHR$^{1aa}$, —N(R$^{1aa}$)$_2$, —C(O)R$^{1aa}$, S(O)$_2$R$^{1aa}$, S(O)$_2$NH$_2$, S(O)$_2$N(R$^{1aa}$)$_2$, —C(O)NH$_2$, —C(O)N(H)(R$^{1aa}$), —C(O)N(R$^{1aa}$)$_2$, —C(O)OH, —C(O)OR$^{1aa}$, —OR$^{1h}$, —N(H)R$^{1h}$), —N(R$^{1d}$)(R$^{1h}$) and —R$^{1h}$;

R$^{1aa}$ is —C$_1$-alkyl, —C$_2$-alkyl, —C$_3$-alkyl, —C$_4$-alkyl, —C$_5$-alkyl, —C$_6$-alkyl, or —R$^{1bb}$;

R$^{1bb}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$; —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), —S(O)$_2$N(R$^{1d}$)$_2$ and —R$^{1h}$;

R$^{1d}$ is —C$_1$-alkyl, —C$_2$-alkyl, —C$_3$-alkyl, —C$_4$-alkyl, —C$_5$-alkyl, or —C$_6$-alkyl;

R$^{1e}$ is a monocyclic or bicyclic ring selected from the group consisting of cycloalkyl, heterocycle, aryl and heteroaryl, wherein each ring is unsubstituted or substituted with one, two, three or four substituents independently selected from the group consisting of =O, —Cl, —F, —Br, —I, —NO$_2$, —CN, —OH, —R$^{1aa}$, —OR$^{1aa}$, —SR$^{1aa}$, —NH$_2$, —NHR$^{1aa}$, and —N(R$^{1aa}$)$_2$;

R$^{1f}$ is —C$_1$-alkyl, —C$_2$-alkyl, —C$_3$-alkyl, —C$_4$-alkyl, —C$_5$-alkyl, —C$_6$-alkyl, aryl, heteroaryl, R$^{1h}$; or R$^{1g}$;

R$^{1g}$ is —C$_1$-alkyl, —C$_2$-alkyl, —C$_3$-alkyl, —C$_4$-alkyl, —C$_5$-alkyl, or —C$_6$-alkyl, each of which is substituted with one substituent selected from the group consisting of R$^{1h}$;

R$^{1h}$ is cycloalkyl, cycloalkenyl, aryl, heteroaryl or heterocycle, in which each R$^{1h}$ is unsubstituted or substituted with one or two or three or four or five substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), and —S(O)$_2$N(R$^{1d}$)$_2$;

provided that when R$^1$ is proximal phenyl fused with a distal pyrrole, thiophene, furan, pyrazole, isoxazole, or isothiazole ring, the distal pyrrole, thiophene, furan, pyrazole, isoxazole, or isothiazole ring is not substituted with —C$_1$-alkyl, —C$_2$-alkyl, —C$_3$-alkyl, —C$_4$-alkyl, —C$_5$-alkyl, —C$_6$-alkyl, pyrrolidinyl, piperidyl, tetrahydropyridyl, pyrrolinyl, —C$_1$-alkyl substituted with pyrrolidinyl or piperidyl, —C$_2$-alkyl substituted with —N(R$^{1d}$)$_2$, —NH$_2$, or —NHR$^{1d}$, —C$_3$-alkyl substituted with —N(R$^{1d}$)$_2$, —NH$_2$, or —NHR$^{1d}$, —C$_4$-alkyl substituted with —N(R$^{1d}$)$_2$, —NH$_2$, or —NHR$^{1d}$, —C$_5$-alkyl substituted with —N(R$^{1d}$)$_2$, —NH$_2$, or —NHR$^{1d}$, or —C$_6$-alkyl substituted with —N(R$^{1d}$)$_2$, —NH$_2$, or —NHR$^{1d}$;

and provided that when m is 0 and R$^2$ is phenyl, then R$^1$ is not proximal unfused phenyl;

A is N or CR$^6$;
B is N or CR$^7$;
E is N or CR$^8$;
provided that only one of A, B and E is N;
R$^3$ is —NH$_2$, —R$^{3a}$, —OR$^{3a}$, —NHR$^{3a}$, —N(R$^{3a}$)$_2$, —NHC(O)R$^{3f}$, —N(R$^{3d}$)C(O)R$^{3f}$, —R$^{3c}$, —OR$^{3e}$, —SR$^{3e}$, —NH(R$^{3e}$), or —N(R$^{3d}$)(R$^{3e}$);
R$^{3a}$ is —C$_1$-alkyl, —C$_2$-alkyl, —C$_3$-alkyl, —C$_4$-alkyl, —C$_5$-alkyl, —C$_6$-alkyl, or R$^{3b}$;
R$^{3b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —NH$_2$, —CN, —OH, —OR$^{3d}$, —R$^{3c}$, —N(R$^{3d}$)$_2$, and —NHR$^{3d}$;
R$^{3c}$ is cycloalkyl, cycloalkenyl, aryl, heteroaryl or heterocycle, in which each R$^{3c}$ is unsubstituted or substituted with one, two, three, or four substituents independently selected from the group consisting of —Cl, —F, —Br, —I, —OH, —R$^{3aa}$, —NH$_2$, —OR$^{3aa}$, —SR$^{3aa}$, —NHR$^{3aa}$, and —N(R$^{3aa}$)$_2$;
R$^{3d}$ is —C$_1$-alkyl, —C$_2$-alkyl, —C$_3$-alkyl, —C$_4$-alkyl, —C$_5$-alkyl, or —C$_6$-alkyl;
R$^{3aa}$ is —C$_1$-alkyl, —C$_2$-alkyl, —C$_3$-alkyl, —C$_4$-alkyl, —C$_5$-alkyl, —C$_6$-alkyl, or —R$^{3bb}$;
R$^{3bb}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —OR$^{3d}$, —C$_1$-alkyl, —C$_2$-alkyl, —C$_3$-alkyl, —C$_4$-alkyl, —C$_5$-alkyl, —C$_6$-alkyl, —N(R$^{3d}$)$_2$, and —NHR$^{3d}$;
R$^{3e}$ is a monocyclic or bicyclic ring selected from the group consisting of cycloalkyl, heterocycle, aryl and heteroaryl, in which each ring is unsubstituted or substituted with one, two, three, or four substituents independently selected from the group consisting of =O, —Cl, —F, —Br, —I, —OH, —R$^{3aa}$, —NH$_2$, —OR$^{3aa}$, —SR$^{3aa}$, —NHR$^{3aa}$, and —N(R$^{3aa}$)$_2$;
R$^{3f}$ is —C$_1$-alkyl, —C$_2$-alkyl, —C$_3$-alkyl, —C$_4$-alkyl, —C$_5$-alkyl, —C$_6$-alkyl, aryl, heteroaryl, or R$^{3g}$;
R$^{3g}$ is —C$_1$-alkyl, —C$_2$-alkyl, —C$_3$-alkyl, —C$_4$-alkyl, —C$_5$-alkyl, or —C$_6$-alkyl, each of which is substituted with one substituent selected from the group consisting of aryl and heteroaryl;
v is one, two, or three, and when v is two or three, R$^3$ may be the same or different;
R$^4$ is —Cl, —F, —Br, —I, —NH$_2$, —R$^{4a}$, —OR$^{4a}$, —NHR$^{4a}$, —N(R$^{4a}$)$_2$, —CN, —SR$^{4a}$, or —SO$_2$R$^{4a}$;
R$^{4a}$ is —C$_1$-alkyl, —C$_2$-alkyl, —C$_3$-alkyl, —C$_4$-alkyl, —C$_5$-alkyl, —C$_6$-alkyl, or R$^{4b}$;
R$^{4b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{4c}$, —N(R$^{4c}$)$_2$, —CN, —SR$^{4c}$, and —SO$_2$R$^{4c}$;
R$^{4c}$ is —C$_1$-alkyl, —C$_2$-alkyl, —C$_3$-alkyl, —C$_4$-alkyl, —C$_5$-alkyl, or —C$_6$-alkyl;
R$^5$ is —H, —Cl, —F, —Br, —I, —NH$_2$, —R$^{5a}$, —OR$^{5a}$, —NHR$^{5a}$, —N(R$^{5a}$)$_2$, —CN, —SR$^{5a}$, or —SO$_2$R$^{5a}$;
R$^{5a}$ is —C$_1$-alkyl, —C$_2$-alkyl, —C$_3$-alkyl, —C$_4$-alkyl, —C$_5$-alkyl, —C$_6$-alkyl, or R$^{5b}$;
R$^{5b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{5c}$, —N(R$^{5c}$)$_2$, —CN, —SR$^{5c}$, and —SO$_2$R$^{5c}$;
R$^{5c}$ is —C$_1$-alkyl, —C$_2$-alkyl, —C$_3$-alkyl, —C$_4$-alkyl, —C$_5$-alkyl, or —C$_6$-alkyl;
R$^6$ is —H, —Cl, —F, —Br, —I, —NH$_2$, —R$^{6a}$, —OR$^{6a}$, —NHR$^{6a}$, —N(R$^{6a}$)$_2$, —CN, —SR$^{6a}$, or —SO$_2$R$^{6a}$;
R$^{6a}$ is —C$_1$-alkyl, —C$_2$-alkyl, —C$_3$-alkyl, —C$_4$-alkyl, —C$_5$-alkyl, —C$_6$-alkyl, or R$^{6b}$;
R$^{6b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{6c}$, —N(R$^{6c}$)$_2$, —CN, —SR$^{6c}$, and —SO$_2$R$^{6c}$;
R$^{6c}$ is —C$_1$-alkyl, —C$_2$-alkyl, —C$_3$-alkyl, —C$_4$-alkyl, —C$_5$-alkyl, or —C$_6$-alkyl;
R$^7$ is —H, —Cl, —F, —Br, —I, —NH$_2$, R$^{7a}$, —OR$^{7a}$, —NHR$^{7a}$, —N(R$^{7a}$)$_2$, —CN, —SR$^{7a}$, or —SO$_2$R$^{7a}$;
R$^{7a}$ is —C$_1$-alkyl, —C$_2$-alkyl, —C$_3$-alkyl, —C$_4$-alkyl, —C$_5$-alkyl, —C$_6$-alkyl, or R$^{7b}$;
R$^{7b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{7c}$, —N(R$^{7c}$)$_2$, —CN, —SR$^{7c}$, and —SO$_2$R$^{7c}$;
R$^{7c}$ is —C$_1$-alkyl, —C$_2$-alkyl, —C$_3$-alkyl, —C$_4$-alkyl, —C$_5$-alkyl, or —C$_6$-alkyl;
R$^8$ is —H, —Cl, —F, —Br, —I, —NH$_2$, —R$^{8a}$, —OR$^{8a}$, —NHR$^{8a}$, —N(R$^{8a}$)$_2$, —CN, —SR$^{8a}$, or —SO$_2$R$^{8a}$;
R$^{8a}$ is —C$_1$-alkyl, —C$_2$-alkyl, —C$_3$-alkyl, —C$_4$-alkyl, —C$_5$-alkyl, —C$_6$-alkyl, or R$^{8b}$;
R$^{8b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{8c}$, —N(R$^{8c}$)$_2$, —CN, —SR$^{8c}$, and —SO$_2$R$^{8c}$;
R$^{8c}$ is —C$_1$-alkyl, —C$_2$-alkyl, —C$_3$-alkyl, —C$_4$-alkyl, —C$_5$-alkyl, or —C$_6$-alkyl; and with the proviso that the following compounds are excluded: N-benzyl-1-(4-methoxyphenyl)-1H-tetraazol-5-amine; N,1-bis(4-methylphenyl)-1H-tetraazol-5-amine; N,1-bis(4-methoxyphenyl)-1H-tetraazol-5-amine; and N,1-bis(2,4-dimethylphenyl)-1H-tetraazol-5-amine.

In a second embodiment, the present invention provides a compound having Formula (I) or Formula (II)

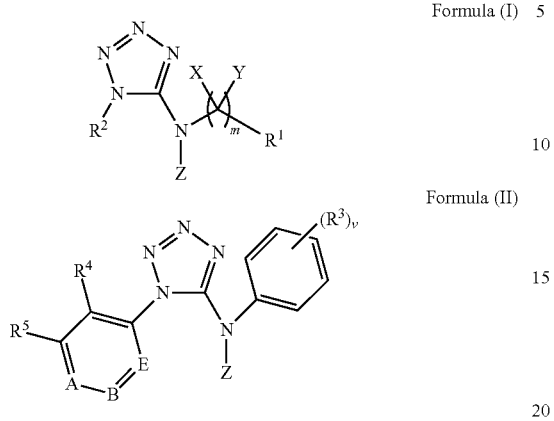

Formula (I)

Formula (II)

or a therapeutically acceptable salt, solvate, prodrug, or salt of a prodrug thereof, in which $R^2$ is phenyl or pyridyl, wherein each $R^2$ is substituted with one, two, three, four, or five substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;

$R^{2a}$ is —C$_1$-alkyl, —C$_2$-alkyl, —C$_3$-alkyl, —C$_4$-alkyl, —C$_5$-alkyl, —C$_6$-alkyl, or R$^{2b}$;

$R^{2b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{2c}$, —N(R$^2$)$_2$, —CN, —SR$^{2c}$, and —SO$_2$R$^{2c}$;

$R^{2c}$ is —C$_1$-alkyl, —C$_2$-alkyl, —C$_3$-alkyl, —C$_4$-alkyl, —C$_5$-alkyl, or —C$_6$-alkyl;

m is 0, 1, 2, or 3;

X and Y are independently selected from the group consisting of —H, —C$_1$-alkyl, —C$_2$-alkyl, —C$_3$-alkyl, —C$_4$-alkyl, —C$_5$-alkyl, and C$_6$-alkyl; or X and Y together with the carbon atom to which they are attached form a ring selected from the group consisting of cyclopropane, cyclobutane, cyclopentane, cyclohexane, tetrahydrofuran, tetrahydrothiophene, pyrrolidine, dioxolane, tetrahydropyran, piperidine, morpholine, thiomorpholine, and piperazine, each or which is unsubstituted or substituted with one, two, three, or four substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;

Z is —H, —C$_1$-alkyl, —C$_2$-alkyl, —C$_3$-alkyl, —C$_4$-alkyl, —C$_5$-alkyl, or —C$_6$-alkyl; or Z and X together with the atoms to which they are attached form a ring selected from the group consisting of pyrrolidine, piperidine, morpholine, thiomorpholine, and piperazine;

$R^1$ is proximal phenyl which is unfused or fused with a distal cyclopentane, cyclohexane, cyclopentene, cyclohexene, dioxane, dioxolane, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, dioxolane, pyrazolidine, pyran, piperidine, morpholine, thiomorpholine, oxazolidinone, morpholinone, or piperazine ring, in which the proximal phenyl ring and the distal ring are, independently of each other, unsubstituted or substituted with one, two, three, or four substituents independently selected from the group consisting of —Cl, —F, —Br, —I, —OH, —NO$_2$, —NH$_2$, R$^{1a}$, OR$^{1a}$, NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N (R$^{1a}$)$_2$, —C(O)R$^{1d}$, —C(O)OH, —C(O)OR$^{1a}$, —C(O) NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$) (R$^{1e}$), —NH(R$^{1e}$), —N(R$^{1d}$)(R$^{1e}$), —NHC(O)R$^{1f}$, —N(R$^{1d}$)C(O)R$^{1f}$ and —R$^{1c}$;

proximal isoxazolyl, oxazolyl, pyrrolidinyl, pyridyl, thienyl, pyrrolyl, pyridazinyl, pyrazolyl, imidazolyl, thiazolyl, furyl, tetrahydrofuryl, tetrahydropyranyl, pyrimidinyl, pyrazinyl, or imidazopyridinyl, each of which is unfused or fused with a distal cyclopentane, cyclohexane, cyclopentene, cyclohexene, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, dioxolane, pyrazolidine, pyran, piperidine, morpholine, thiomorpholine, or piperazine ring, in which the proximal pyrrolidinyl, pyridyl, thienyl, pyrrolyl, pyridazinyl, pyrazolyl, imidazolyl, thiazolyl, furyl, tetrahydrofuryl, pyrimidinyl, pyrazinyl, or imidazopyridinyl ring and the distal ring are, independently of each other, unsubstituted or substituted with one, two, three, or four substituents independently selected from the group consisting of —Cl, —F, —Br, —I, —OH, —NO$_2$, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O) OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N (H)(R$^{1e}$), —SO$_2$N(R$^{1d}$)(R$^{1e}$), —NH(R$^{1e}$), —N(R$^{1d}$) (R$^{1e}$), —NHC(O)R$^{1f}$, —N(R$^{1d}$)C(O)R$^{1f}$, and —R$^{1c}$; or proximal bicyclo[2,2,1]heptyl, cyclopentyl, cyclohexyl, cyclopentenyl, or cyclohexenyl, each of which is unfused or fused with a distal cyclopentane, cyclohexane, cyclopentene, cyclohexene, naphthalene, benzene, furan, imidazole, isothiazole, oxazole, isoxazole, pyrazine, pyrazole, pyridazine, pyridine, pyrimidine, pyrrole, imidazoline, tetrahydrofuran, tetrahydrothiophene, thiazole, thiophene, pyrrolidine, dioxolane, pyrazoline, pyrazolidine, pyran, piperidine, morpholine, thiomorpholine, or piperazine ring, in which the proximal cyclopentyl, cyclohexyl, cyclopentenyl, or cyclohexenyl ring and the distal ring are, independently of each other, unsubstituted or substituted with one, two, three, or four substituents independently selected from the group consisting of =O, —Cl, —F, —Br, —I, —OH, —NO$_2$, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N (R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$;

adamantyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H) (R$^{1d}$), and —C(O)N(R$^{1d}$)$_2$; or 2,3-dihydrospiroindene-1,4'-piperidinyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H)(R$^{1d}$), and —C(O)N(R$^{1d}$)$_2$;

R$^{1a}$ is —C$_1$-alkyl, —C$_2$-alkyl, —C$_3$-alkyl, —C$_4$-alkyl, —C$_5$-alkyl, —C$_6$-alkyl, or —R$^{1b}$;

R$^{1b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —OR$^{1d}$, —C$_1$-alkyl, —C$_2$-alkyl, —C$_3$-alkyl, —C$_4$-alkyl, —C$_5$-alkyl, —C$_6$-alkyl, —R$^{1c}$, —N(R$^{1d}$)$_2$, and —NHR$^{1d}$;

R$^{1c}$ is cyclopentyl, cyclohexyl, cyclopentenyl, cyclohexenyl, azetidinyl, naphthyl, quinolinyl, isoquinolinyl, phenyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl, thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, each of which is unsubstituted or substituted with one, two, three, or four substituents independently selected from the group consisting of —Cl, —F, —Br, —I, =O, —NO$_2$, —CN, —OH, —R$^{1aa}$, —NH$_2$, —OR$^{1aa}$, —SR$^{1aa}$, —NHR$^{1aa}$, —N(R$^{1aa}$)$_2$, —C(O)R$^{1aa}$, —S(O)$_2$R$^{1aa}$, S(O)$_2$NH$_2$, S(O)$_2$N(R$^{1aa}$)$_2$, —C(O)NH$_2$, —C(O)N(H)(R$^{1aa}$), —C(O)N(R$^{1aa}$)$_2$, —C(O)OH, —C(O)OR$^{1aa}$, —OR$^{1h}$, —N(H)R$^{1h}$, —N(R$^{1d}$)(R$^{1h}$) and —R$^{1h}$;

R$^{1aa}$ is —C$_1$-alkyl, —C$_2$-alkyl, —C$_3$-alkyl, —C$_4$-alkyl, —C$_5$-alkyl, —C$_6$-alkyl, or —R$^{1bb}$;

R$^{1bb}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), —S(O)$_2$N(R$^{1d}$)$_2$ and R$^{1h}$;

R$^{1d}$ is —C$_1$-alkyl, —C$_2$-alkyl, —C$_3$-alkyl, —C$_4$-alkyl, —C$_5$-alkyl, or —C$_6$-alkyl;

R$^{1e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each R$^{1e}$ is unsubstituted or substituted with one, two, three or four substituents independently selected from the group consisting of =O, —Cl, —F, —Br, —I, —NO$_2$, —CN, —OH, —R$^{1aa}$, —OR$^{1aa}$, —SR$^{1aa}$, —NH$_2$, —NHR$^{1aa}$, and —N(R$^{1aa}$)$_2$;

R$^{1f}$ is —C$_1$-alkyl, —C$_2$-alkyl, —C$_3$-alkyl, —C$_4$-alkyl, —C$_5$-alkyl, —C$_6$-alkyl, aryl, heteroaryl, R$^{1h}$; or R$^{1g}$;

R$^{1g}$ is —C$_1$-alkyl, —C$_2$-alkyl, —C$_3$-alkyl, —C$_4$-alkyl, —C$_5$-alkyl, or —C$_6$-alkyl, each of which is substituted with one substituent selected from the group consisting of R$^{1h}$;

R$^{1h}$ is cycloalkyl, cycloalkenyl, aryl, heteroaryl or heterocycle, in which each R$^{1h}$ is unsubstituted or substituted with one or two or three or four or five substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), and —S(O)$_2$N(R$^{1d}$)$_2$;

provided that when R$^1$ is proximal phenyl fused with a distal pyrrole, thiophene, furan, pyrazole, isoxazole, or isothiazole ring, the distal pyrrole, thiophene, furan, pyrazole, isoxazole, or isothiazole ring is not substituted with —C$_1$-alkyl, —C$_2$-alkyl, —C$_3$-alkyl, —C$_4$-alkyl, —C$_5$-alkyl, —C$_6$-alkyl, pyrrolidinyl, piperidyl, —C$_1$-alkyl substituted with pyrrolidinyl or piperidyl, —C$_2$-alkyl substituted with —N(R$^{1d}$)$_2$, —NH$_2$, or —NHR$^{1d}$, —C$_3$-alkyl substituted with —N(R$^{1d}$)$_2$, —NH$_2$, or —NHR$^{1d}$, —C$_4$-alkyl substituted with —N(R$^{1d}$)$_2$, —NH$_2$, or —NHR$^{1d}$, —C$_5$-alkyl substituted with —N(R$^{1d}$)$_2$, —NH$_2$, or —NHR$^{1d}$, or —C$_6$-alkyl substituted with —N(R$^{1d}$)$_2$, —NH$_2$, or —NHR$^{1d}$;

and provided that when m is 0 and R$^2$ is phenyl, then R$^1$ is not proximal unfused phenyl;

A is N or CR$^6$;

B is N or CR$^7$;

E is N or CR$^8$;

provided that only one of A, B and E is N;

R$^3$ is —NH$_2$, —R$^{3a}$, —OR$^{3a}$, —NHR$^{3a}$, N(R$^{3a}$)$_2$, —NHC(O)R$^{3f}$, N(R$^{3d}$)C(O)R$^{3f}$, R$^{3c}$, OR$^{3e}$, —SR$^{3e}$, —NH(R$^{3e}$), or N(R$^{3d}$)(R$^{3e}$);

R$^{3a}$ is —C$_1$-alkyl, —C$_2$-alkyl, —C$_3$-alkyl, —C$_4$-alkyl, —C$_5$-alkyl, —C$_6$-alkyl, or R$^{3b}$;

R$^{3b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —NH$_2$, —CN, —OH, —OR$^{3d}$, —R$^{3c}$, —N(R$^{3d}$)$_2$, and NHR$^{3d}$;

R$^{3c}$ is cyclopentyl, cyclohexyl, cyclopentenyl, cyclohexenyl, azetidinyl, naphthyl, quinolinyl, isoquinolinyl, phenyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, in which each ring is unsubstituted or substituted with one, two, three, or four substituents independently selected from the group consisting of —Cl, —F, —Br, —I, —OH, —R$^{3aa}$, —NH$_2$, —OR$^{3aa}$, —SR$^{3aa}$, —NHR$^{3aa}$, and —N(R$^{3aa}$)$_2$;

R$^{3d}$ is —C$_1$-alkyl, —C$_2$-alkyl, —C$_3$-alkyl, —C$_4$-alkyl, —C$_5$-alkyl, or —C$_6$-alkyl;

R$^{3aa}$ is —C$_1$-alkyl, —C$_2$-alkyl, —C$_3$-alkyl, —C$_4$-alkyl, —C$_5$-alkyl, —C$_6$-alkyl, or —R$^{3bb}$;

R$^{3bb}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —OR$^{3d}$, —C$_1$-alkyl, —C$_2$-alkyl, —C$_3$-alkyl, —C$_4$-alkyl, —C$_5$-alkyl, —C$_6$-alkyl, —N(R$^{3d}$)$_2$, and —NHR$^{3d}$;

R$^{3e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each R$^{3e}$ is unsubstituted or substituted with one, two, three or four substituents independently selected from the group consisting of =O, —Cl, —F, —Br, —I, —OH, —R$^{3aa}$, —OR$^{3aa}$, —SR$^{3aa}$, —NH$_2$, —NHR$^{3aa}$, and —N(R$^{3aa}$)$_2$;

R$^{3f}$ is —C$_1$-alkyl, —C$_2$-alkyl, —C$_3$-alkyl, —C$_4$-alkyl, —C$_5$-alkyl, —C$_6$-alkyl, aryl, heteroaryl, or R$^{3g}$;

R$^{3g}$ is —C$_1$-alkyl, —C$_2$-alkyl, —C$_3$-alkyl, —C$_4$-alkyl, —C$_5$-alkyl, or —C$_6$-alkyl, each of which is substituted with one substituent selected from the group consisting of aryl and heteroaryl;

v is one, two, or three, and when v is two or three, R$^3$ may be the same or different;

R$^4$ is —Cl, —F, —Br, —I, —NH$_2$, —R$^{4a}$, —OR$^{4a}$, —NHR$^{4a}$, —N(R$^{4a}$)$_2$, —CN, —SR$^{4a}$, or —SO$_2$R$^{4a}$;

R$^{4a}$ is —C$_1$-alkyl, —C$_2$-alkyl, —C$_3$-alkyl, —C$_4$-alkyl, —C$_5$-alkyl, —C$_6$-alkyl, or R$^{4b}$;

R$^{4b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{4c}$, —N(R$^{4c}$)$_2$, —CN, —SR$^{4c}$, and SO$_2$R$^{4c}$;

R$^{4c}$ is —C$_1$-alkyl, —C$_2$-alkyl, —C$_3$-alkyl, —C$_4$-alkyl, —C$_5$-alkyl, or —C$_6$-alkyl;

R$^5$ is —H, —Cl, —F, —Br, —I, —NH$_2$, —R$^{5a}$, —OR$^{5a}$, —NHR$^{5a}$, —N(R$^{5a}$)$_2$, —CN, —SR$^{5a}$, or —SO$_2$R$^{5a}$;

R$^{5a}$ is —C$_1$-alkyl, —C$_2$-alkyl, —C$_3$-alkyl, —C$_4$-alkyl, —C$_5$-alkyl, —C$_6$-alkyl, or R$^{5b}$;

R$^{5b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{5c}$, —N(R$^{5c}$)$_2$, —CN, —SR$^{5c}$, and —SO$_2$R$^{5c}$;

R$^{5c}$ is —C$_1$-alkyl, —C$_2$-alkyl, —C$_3$-alkyl, —C$_4$-alkyl, —C$_5$-alkyl, or —C$_6$-alkyl;

R$^6$ is —H, —Cl, —F, —Br, —I, —NH$_2$, —R$^{6a}$, —OR$^{6a}$, —NHR$^{6a}$, —N(R$^{6a}$)$_2$, —CN, —SR$^{6a}$ or —SO$_2$R$^{6a}$;

R$^{6a}$ is —C$_1$-alkyl, —C$_2$-alkyl, —C$_3$-alkyl, —C$_4$-alkyl, —C$_5$-alkyl, —C$_6$-alkyl, or R$^{6b}$;

R$^{6b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{6c}$, —N(R$^{6c}$)$_2$, —CN, —SR$^{6c}$, and —SO$_2$R$^{6c}$;

R$^{6c}$ is —C$_1$-alkyl, —C$_2$-alkyl, —C$_3$-alkyl, —C$_4$-alkyl, —C$_5$-alkyl, or —C$_6$-alkyl;

R$^7$ is —H, —Cl, —F, —Br, —I, —NH$_2$, R$^{7a}$, —OR$^{7a}$, NHR$^{7a}$, —N(R$^{7a}$)$_2$, —CN, —SR$^{7a}$, or —SO$_2$R$^{7a}$;

R$^{7a}$ is —C$_1$-alkyl, —C$_2$-alkyl, —C$_3$-alkyl, —C$_4$-alkyl, —C$_5$-alkyl, —C$_6$-alkyl, or R$^{7b}$;

R$^{7b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{7c}$, —N(R$^{7c}$)$_2$, —CN, —SR$^{7c}$, and —SO$_2$R$^{7c}$;

R$^{7c}$ is —C$_1$-alkyl, —C$_2$-alkyl, —C$_3$-alkyl, —C$_4$-alkyl, —C$_5$-alkyl, or —C$_6$-alkyl;

R$^8$ is —H, —Cl, —F, —Br, —I, —NH$_2$, —R$^{8a}$, —OR$^{8a}$, —NHR$^{8a}$, —N(R$^{8a}$)$_2$, —CN, —SR$^{8a}$ or —SO$_2$R$^{8a}$;

R$^{8a}$ is —C$_1$-alkyl, —C$_2$-alkyl, —C$_3$-alkyl, —C$_4$-alkyl, —C$_5$-alkyl, —C$_6$-alkyl, or R$^{8b}$;

R$^{8b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{8c}$, —N(R$^{8c}$)$_2$, —CN, —SR$^{8c}$, and —SO$_2$R$^{8c}$;

R$^{8c}$ is —C$_1$-alkyl, —C$_2$-alkyl, —C$_3$-alkyl, —C$_4$-alkyl, —C$_5$-alkyl, or —C$_6$-alkyl; and with the proviso that the following compounds are excluded: N-benzyl-1-(4-methoxyphenyl)-1H-tetraazol-5-amine; N,1-bis(4-methylphenyl)-1H-tetraazol-5-amine; N,1-bis(4-methoxyphenyl)-1H-tetraazol-5-amine; and N,1-bis(2,4-dimethylphenyl)-1H-tetraazol-5-amine.

In a third embodiment, the present invention relates to a compound having Formula (I)

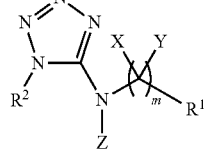

Formula (I)

or a therapeutically acceptable salt, solvate, prodrug, or salt of a prodrug thereof, in which R$^2$ is phenyl or pyridyl, in which each R$^2$ is substituted with one, two, three, four, or five substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;

R$^{2a}$ is —C$_1$-alkyl, —C$_2$-alkyl, —C$_3$-alkyl, —C$_4$-alkyl, —C$_5$-alkyl, —C$_6$-alkyl, or R$^{2b}$;

R$^{2b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{2c}$, —N(R$^{2c}$)$_2$, —CN, —SR$^{2c}$, and —SO$_2$R$^{2c}$;

R$^{2c}$ is —C$_1$-alkyl, —C$_2$-alkyl, —C$_3$-alkyl, —C$_4$-alkyl, —C$_5$-alkyl, or —C$_6$-alkyl;

m is 0, 1, 2, or 3;

X and Y are independently selected from the group consisting of —H, —C$_1$-alkyl, —C$_2$-alkyl, —C$_3$-alkyl, —C$_4$-alkyl, —C$_5$-alkyl, and C$_6$-alkyl; or X and Y together with the carbon atom to which they are attached form a ring selected from the group consisting of cyclopropane, cyclobutane, cyclopentane, cyclohexane, tetrahydrofuran, tetrahydrothiophene, pyrrolidine, dioxolane, tetrahydropyran, piperidine, morpholine, thiomorpholine, and piperazine, each of which is unsubstituted or substituted with one, two, three, or four substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;

Z is —H, —C$_1$-alkyl, —C$_2$-alkyl, —C$_3$-alkyl, —C$_4$-alkyl, —C$_5$-alkyl, or —C$_6$-alkyl; or Z and X together with the atoms to which they are attached form a ring selected from the group consisting of pyrrolidine, piperidine, morpholine, thiomorpholine, and piperazine;

R$^1$ is proximal phenyl which is unfused or fused with a distal cyclopentane, cyclohexane, cyclopentene, cyclohexene, dioxane, dioxolane, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, dioxolane, pyrazolidine, pyran, piperidine, morpholine, thiomorpholine, oxazolidinone, morpholidinone, or piperazine ring, in which the proximal phenyl ring and the distal ring are, independently of each other, unsubstituted or substituted with one, two, three, or four substituents independently selected from the group consisting of —Cl, —F, —Br, —I, —OH, —NO$_2$, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1d}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$ and —R$^{1c}$;

proximal isoxazolyl, oxazolyl, pyrrolidinyl, pyridyl, thienyl, pyrrolyl, pyridazinyl, pyrazolyl, imidazolyl, thiazolyl, furyl, tetrahydrofuryl, tetrahydropyranyl, pyrimidinyl, pyrazinyl, or imidazopyridinyl, each of which is unfused or fused with a distal cyclopentane, cyclohexane, cyclopentene, cyclohexene, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, dioxolane, pyrazolidine, pyran, piperidine, morpholine, thiomorpholine, or piperazine ring, in which the proximal pyrrolidinyl, pyridyl, thienyl, pyrrolyl, pyridazinyl, pyrazolyl, imidazolyl, thiazolyl, furyl, tetrahydrofuryl, pyrimidinyl, pyrazinyl, or imidazopyridinyl ring and the distal ring are, independently of each other, unsubstituted or substituted with one, two, three, or four substituents independently selected from the group consisting of —Cl, —F, —Br, —I, —OH, —NO$_2$, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$; or proximal bicyclo[2,2,1]heptyl, cyclopentyl, cyclohexyl, cyclopentenyl, or cyclohexenyl, each of which is unfused or fused with a distal cyclopentane, cyclohexane, cyclopentene, cyclohexene, naphthalene, benzene, furan, imidazole, isothiazole, oxazole, isoxazole, pyrazine, pyrazole, pyridazine, pyridine, pyrimidine, pyrrole, imidazoline, tetrahydrofuran, tetrahydrothiophene, thiazole, thiophene, pyrrolidine, dioxolane, pyrazoline, pyrazolidine, pyran, piperidine, morpholine, thiomorpholine, or piperazine ring, in which the proximal cyclopentyl, cyclohexyl, cyclopentenyl, or cyclohexenyl ring and the distal ring are, independently of each other, unsubstituted or substituted with one, two, three, or four substituents independently selected from the group consisting of =O, —Cl, —F, —Br, —I, —OH, —NO$_2$, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$ and —R$^{1c}$;

adamantyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H)(R$^{1d}$), and —C(O)N(R$^{1d}$)$_2$; or 2,3-dihydrospiroindene-1,4'-piperidinyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H)(R$^{1d}$), and —C(O)N(R$^{1d}$)$_2$;

R$^{1a}$ is —C$_1$-alkyl, —C$_2$-alkyl, —C$_3$-alkyl, —C$_4$-alkyl, —C$_5$-alkyl, —C$_6$-alkyl, or —R$^{1b}$;

R$^{1b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —OR$^{1d}$, —C$_1$-alkyl, —C$_2$-alkyl, —C$_3$-alkyl, —C$_4$-alkyl, —C$_5$-alkyl, —C$_6$-alkyl, —R$^{1c}$, —N(R$^{1d}$)$_2$, and —NHR$^{1d}$;

R$^{1c}$ is cyclopentyl, cyclohexyl, cyclopentenyl, cyclohexenyl, azetidinyl, naphthyl, quinolinyl, isoquinolinyl, phenyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl, thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, each of which is unsubstituted or substituted with one, two, three, or four substituents independently selected from the group consisting of =O, —Cl, —F, —Br, —I, —NO$_2$, —CN, —OH, —R$^{1aa}$, —NH$_2$, —OR$^{1aa}$, —SR$^{1aa}$, —NHR$^{1aa}$, —N(R$^{1aa}$)$_2$, —C(O)R$^{1aa}$, —S(O)$_2$R$^{1aa}$, S(O)$_2$NH$_2$, S(O)$_2$N(R$^{1aa}$)$_2$, —C(O)NH$_2$, —C(O)N(H)(R$^{1aa}$), —C(O)N(R$^{1aa}$)$_2$, —C(O)OH, —C(O)OR$^{1aa}$, —OR$^{1h}$, —N(H)R$^{1h}$), —N(R$^{1d}$)(R$^{1h}$) and —R$^{1h}$;

R$^{1aa}$ is —C$_1$-alkyl, —C$_2$-alkyl, —C$_3$-alkyl, —C$_4$-alkyl, —C$_5$-alkyl, —C$_6$-alkyl, or —R$^{1bb}$;

$R^{1bb}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NO_2$, —CN, haloalkyl, haloalkoxy, —$NH_2$, —OH, —$OR^{1d}$, —$SR^{1d}$, —$S(O)_2R^{1d}$, —$C_1$-alkyl, —$C_2$-alkyl, —$C_3$-alkyl, —$C_4$-alkyl, —$C_5$-alkyl, —$C_6$-alkyl, —$N(R^{1d})_2$, —$NHR^{1d}$, —C(O)OH, —$C(O)OR^{1d}$, —$C(O)NH_2$, —$C(O)N(H)(R^{1d})$, —$C(O)N(R^{1d})_2$, —$S(O)_2NH_2$, —$S(O)_2N(H)(R^{1d})$, —$S(O)_2N(R^{1d})_2$ and $R^{1h}$;

$R^{1d}$ is —$C_1$-alkyl, —$C_2$-alkyl, —$C_3$-alkyl, —$C_4$-alkyl, —$C_5$-alkyl, or —$C_6$-alkyl;

$R^{1e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each $R^{1e}$ is unsubstituted or substituted with one, two, three or four substituents independently selected from the group consisting of =O, —Cl, —F, —Br, —I, —$NO_2$, —CN, —OH, —$R^{1aa}$, —$OR^{1aa}$, —$SR^{1aa}$, —$NH_2$, —$NHR^{1aa}$, and —$N(R^{1aa})_2$;

$R^{1f}$ is —$C_1$-alkyl, —$C_2$-alkyl, —$C_3$-alkyl, —$C_4$-alkyl, —$C_5$-alkyl, —$C_6$-alkyl, aryl, heteroaryl, or $R^{1g}$;

$R^{1g}$ is —$C_1$-alkyl, —$C_2$-alkyl, —$C_3$-alkyl, —$C_4$-alkyl, —$C_5$-alkyl, or —$C_6$-alkyl, each of which is substituted with one substituent selected from the group consisting of aryl and heteroaryl;

provided that when $R^1$ is proximal phenyl fused with a distal pyrrole, thiophene, furan, pyrazole, isoxazole, or isothiazole ring, the distal pyrrole, thiophene, furan, pyrazole, isoxazole, or isothiazole ring is not substituted with —$C_1$-alkyl, —$C_2$-alkyl, —$C_3$-alkyl, —$C_4$-alkyl, —$C_5$-alkyl, —$C_6$-alkyl, pyrrolidinyl, piperidyl, —$C_1$-alkyl substituted with pyrrolidinyl or piperidyl, —$C_2$-alkyl substituted with —$N(R^{1d})_2$, —$NH_2$, or —$NHR^{1d}$, —$C_3$-alkyl substituted with —$N(R^{1d})_2$, —$NH_2$, or —$NHR^{1d}$, —$C_4$-alkyl substituted with —$N(R^{1d})_2$, —$NH_2$, or —$NHR^{1d}$, —$C_5$-alkyl substituted with —$N(R^{1d})_2$, —$NH_2$, or —$NHR^{1d}$, or —$C_6$-alkyl substituted with —$N(R^{1d})_2$, —$NH_2$, or —$NHR^{1d}$;

provided that when m is 0 and $R^2$ is phenyl, then $R^1$ is not proximal unfused phenyl; and with the proviso that N-benzyl-1-(4-methoxyphenyl)-1H-tetraazol-5-amine is excluded.

For example, the third embodiment of the present invention provides a compound having Formula (I), or a therapeutically acceptable salt, prodrug, solvate, salt of a prodrug, or combination thereof, wherein $R^2$ is phenyl substituted with one, two, three, four, or five substituents independently selected from the group consisting of —Cl, —F, —Br, —I, —$NH_2$, —$R^{2a}$, —$OR^{2a}$, —$NHR^{2a}$, —$N(R^{2a})_2$, —CN, —$SR^{2a}$, and —$SO_2R^{2a}$; $R^{2a}$ is —$C_1$-alkyl, —$C_2$-alkyl, —$C_3$-alkyl, —$C_4$-alkyl, —$C_5$-alkyl, —$C_6$-alkyl, or $R^{2b}$; $R^{2b}$ is —$C_1$-alkyl, —$C_2$-alkyl, —$C_3$-alkyl, —$C_4$-alkyl, —$C_5$-alkyl, or —$C_6$-alkyl, each of which is substituted with one, two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{2c}$, —$N(R^{2c})_2$, —CN, —$SR^{2c}$, and —$SO_2R^{2c}$; and $R^{2c}$ is —$C_1$-alkyl, —$C_2$-alkyl, —$C_3$-alkyl, —$C_4$-alkyl, —$C_5$-alkyl, or —$C_6$-alkyl.

For example, the third embodiment of the present invention provides a compound having Formula (I), or a therapeutically acceptable salt, prodrug, solvate, salt of a prodrug, or combination thereof, wherein $R^2$ is phenyl substituted with one or two substituents independently selected from the group consisting of —Cl, —F, —Br, —I, —$C_1$-alkyl, —$C_2$-alkyl, —$C_3$-alkyl, —$C_4$-alkyl, —$C_5$-alkyl, or —$C_6$-alkyl.

For example, the third embodiment of the present invention provides a compound having Formula (I), or a therapeutically acceptable salt, prodrug, solvate, salt of a prodrug, or combination thereof, wherein $R^2$ is pyridyl substituted with one, two, three, four, or five substituents independently selected from the group consisting of —Cl, —F, —Br, —I, —$NH_2$, —$R^{2a}$, —$OR^{2a}$, —$NHR^{2a}$, —$N(R^{2a})_2$, —CN, —$SR^{2a}$, and —$SO_2R^{2a}$; $R^{2a}$ is —$C_1$-alkyl, —$C_2$-alkyl, —$C_3$-alkyl, —$C_4$-alkyl, —$C_5$-alkyl, —$C_6$-alkyl, or $R^{2b}$; $R^{2b}$ is —$C_1$-alkyl, —$C_2$-alkyl, —$C_3$-alkyl, —$C_4$-alkyl, —$C_5$-alkyl, or —$C_6$-alkyl, each of which is substituted with one, two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{2c}$, —$N(R^{2c})_2$, —CN, —$SR^{2c}$, and —$SO_2R^{2c}$; and $R^{2c}$ is —$C_1$-alkyl, —$C_2$-alkyl, —$C_3$-alkyl, —$C_4$-alkyl, —$C_5$-alkyl, or —$C_6$-alkyl.

For example, the third embodiment of the present invention provides a compound having Formula (I), or a therapeutically acceptable salt, solvate, prodrug, or salt of a prodrug thereof, in which $R^2$ is phenyl substituted with one, two, three, four, or five substituents independently selected from the group consisting of —Cl, —F, —Br, —I, —$NH_2$, —$R^{2a}$, —$OR^{2a}$, —$NHR^{2a}$, —$N(R^{2a})_2$, —CN, —$SR^{2a}$, and —$SO_2R^{2a}$.

$R^{2a}$ is —$C_1$-alkyl, —$C_2$-alkyl, —$C_3$-alkyl, —$C_4$-alkyl, —$C_5$-alkyl, —$C_6$-alkyl, or $R^{2b}$;

$R^{2b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{2c}$, —$N(R^{2c})_2$, —CN, —$SR^{2c}$, and —$SO_2R^{2c}$;

$R^{2c}$ is —$C_1$-alkyl, —$C_2$-alkyl, —$C_3$-alkyl, —$C_4$-alkyl, —$C_5$-alkyl, or —$C_6$-alkyl, $R^1$ is proximal unfused phenyl, unsubstituted or substituted with one, two, three, or four substituents independently selected from the group consisting of —Cl, —F, —Br, —I, —OH, —$NO_2$, —$NH_2$, —$R^{1a}$, —$OR^{1a}$, —$NHR^{1a}$, —$N(R^{1a})_2$, —CN, —$SR^{1a}$, —$SO_2R^{1a}$, —$SO_2NH_2$, —$SO_2N(H)(R^{1a})$, —$SO_2N(R^{1a})_2$, —$C(O)R^{1a}$, —C(O)OH, —$C(O)OR^{1a}$, —$C(O)NH_2$, —$C(O)N(H)(R^{1a})$, —$C(O)N(R^{1a})_2$, —$OR^{1e}$, —$SR^{1e}$, —$SO_2R^{1e}$, —$SO_2N(H)(R^{1e})$, —$SO_2N(R^{1d})(R^{1e})$, —$NH(R^{1e})$, —$N(R^{1d})(R^{1e})$, —$NHC(O)R^{1f}$, —$N(R^{1d})C(O)R^{1f}$, and —$R^{1c}$;

proximal isoxazolyl, oxazolyl, pyrrolidinyl, pyridyl, thienyl, pyrrolyl, pyridazinyl, pyrazolyl, imidazolyl, thiazolyl, furyl, tetrahydrofuryl, tetrahydropyranyl, pyrimidinyl, pyrazinyl, or imidazopyridinyl, each of which is unfused or fused with a distal cyclopentane, cyclohexane, cyclopentene, cyclohexene or benzene ring, in which the proximal pyrrolidinyl, pyridyl, thienyl, pyrrolyl, pyridazinyl, pyrazolyl, imidazolyl, thiazolyl, furyl, tetrahydrofuryl, pyrimidinyl, pyrazinyl, or imidazopyridinyl rings and the distal ring are, independently of each other, unsubstituted or substituted with one, two, three, or four substitutents independently selected from the group consisting of —Cl, —F, —Br, —I, —OH, —$NO_2$, —$NH_2$, —$R^{1a}$, —$OR^{1a}$, —$NHR^{1a}$, —$N(R^{1a})_2$, —CN, —$SR^{1a}$, —$SO_2R^{1a}$, —$SO_2NH_2$, —$SO_2N(H)(R^{1a})$, —$SO_2N(R^{1a})_2$, —$C(O)R^{1a}$, —C(O)OH, —$C(O)OR^{1a}$, —$C(O)NH_2$, —$C(O)N(H)(R^{1a})$, —$C(O)N(R^{1a})_2$, —$OR^{1e}$, —$SR^{1e}$, —$SO_2R^{1e}$, —$SO_2N(H)(R^{1e})$, —$SO_2N(R^{1d})(R^{1e})$, —$NH(R^{1e})$, $N(R^{1d})(R^{1e})$, —$NHC(O)R^{1f}$, —$N(R^{1d})C(O)R^{1f}$, and —$R^{1c}$; or proximal bicyclo[2,2,1]heptyl, cyclopentyl, cyclohexyl, cyclopentenyl, or cyclohexenyl, each of which is fused with a distal benzene, furan, imidazole, isothiazole, oxazole, isoxazole, pyrazine, pyrazole, pyridazine, pyridine, pyrimidine, or pyrrole ring, in which the proximal cyclopentyl, cyclohexyl, cyclopentenyl, or cyclohexenyl ring and the distal ring are, independently of each other, unsubstituted or substituted with one, two, three, or four substituents independently selected from the group consisting of =O, —Cl, —F, —Br, —I, —OH, $NO_2$, —$NH_2$, —$R^{1a}$, —$OR^{1a}$, —$NHR^{1a}$, —$N(R^{1a})_2$, —CN, —$SR^{1a}$, —$SO_2R^{1a}$, —$SO_2NH_2$, —$SO_2N(H)(R^{1a})$, —$SO_2N(R^{1a})_2$, —$C(O)R^{1a}$, —C(O)OH, —C(O)$OR^{1a}$, —$C(O)NH_2$, —$C(O)N(H)(R^{1a})$, —$C(O)N(R^{1a})_2$, —$OR^{1e}$, —$SR^{1e}$, —$SO_2R^{1e}$, —$SO_2N(H)(R^{1e})$, —$SO_2N(R^{1d})(R^{1e})$, —$NH(R^{1e})$, —$N(R^{1d})(R^{1e})$, —$NHC(O)R^{1f}$, —$N(R^{1d})C(O)R^{1f}$, and —$R^{1c}$;

adamantyl unsubstituted or substituted with one, two, three, or four substituents independently selected from the group consisting of —Cl, —F, —Br, —I, —$NO_2$, —OH, —$NH_2$, —$R^{1d}$, —$OR^{1d}$, —$NHR^{1d}$, —$N(R^{1d})_2$, —CN, —$SR^{1d}$, —$SO_2R^{1d}$, —$SO_2NH_2$, —$SO_2N(H)(R^{1d})$, —$SO_2N(R^{1d})_2$, —$C(O)R^{1d}$, —COOH, —$C(O)OR^{1d}$, —$C(O)NH_2$, —$C(O)N(H)(R^{1d})$, and —$C(O)N(R^{1d})_2$; or 2,3-dihydrospiroindene-1,4'-piperidinyl unsubstituted or substituted with one, two, three, or four substituents independently selected from the group consisting of —Cl, —F, —Br, —I, —$NO_2$, —OH, —$NH_2$, —$R^{1d}$, —$OR^{1d}$, —$NHR^{1d}$, —$N(R^{1d})_2$, —CN, —$SR^{1d}$, —$SO_2R^{1d}$, —$SO_2NH_2$, —$SO_2N(H)(R^{1d})$, —$SO_2N(R^{1d})_2$, —$C(O)R^{1d}$, —COOH, —$C(O)OR^{1d}$, —$C(O)NH_2$, —$C(O)N(H)(R^{1d})$, and —$C(O)N(R^{1d})_2$, $R^{1a}$ is —$C_1$-alkyl, —$C_2$-alkyl, —$C_3$-alkyl, —$C_4$-alkyl, —$C_5$-alkyl, —$C_6$-alkyl, or —$R^{1b}$;

$R^{1b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NH_2$, —OH, —$OR^{1d}$, —$C_1$-alkyl, —$C_2$-alkyl, —$C_3$-alkyl, —$C_4$-alkyl, —$C_5$-alkyl, —$C_6$-alkyl, —$R^{1c}$, —$N(R^{1d})_2$, and $NHR^{1d}$;

$R^{1c}$ is cyclopentyl, cyclohexyl, cyclopentenyl, cyclohexenyl, azetidinyl, naphthyl, quinolinyl, isoquinolinyl, phenyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl, thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, each of which is unsubstituted or substituted with one, two, three, or four substituents independently selected from the group consisting of —Cl, —F, —Br, —I, =O, —OH, —$R^{1aa}$, —$SR^{1aa}$, —$NH_2$, —$NO_2$, —CN, —$OR^{1aa}$, —$NHR^{1aa}$, —$N(R^{1aa})_2$; —$C(O)R^{1aa}$, $S(O)_2R^{1aa}$, $S(O)_2NH_2$, $S(O)_2N(R^{1aa})_2$, —$C(O)NH_2$, —$C(O)N(H)(R^{1aa})$, —$C(O)N(R^{1aa})_2$, —C(O)OH, —$C(O)OR^{1aa}$, —$OR^{1h}$, —$N(H)R^{1h}$, —$N(R^{1d})(R^{1h})$ and —$R^{1h}$;

$R^{1aa}$ is —$C_1$-alkyl, —$C_2$-alkyl, —$C_3$-alkyl, —$C_4$-alkyl, —$C_5$-alkyl, —$C_6$-alkyl, or $R^{1bb}$;

$R^{1bb}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NO_2$, —CN, haloalkyl, haloalkoxy, —$NH_2$, —OH, —$OR^{1d}$, —$SR^{1d}$, —$S(O)_2R^{1d}$, —$C_1$-alkyl, —$C_2$-alkyl, —$C_3$-alkyl, —$C_4$-alkyl, —$C_5$-alkyl, —$C_6$-alkyl, —$N(R^{1d})_2$, —$NHR^{1d}$—C(O)OH, —$C(O)OR^{1d}$, —$C(O)NH_2$, —$C(O)N(H)(R^{1d})$, —$C(O)N(R^{1d})_2$, —$S(O)_2NH_2$, —$S(O)_2N(H)(R^{1d})$, —$S(O)_2N(R^{1d})_2$ and —$R^{1h}$;

$R^{1d}$ is —$C_1$-alkyl, —$C_2$-alkyl, —$C_3$-alkyl, —$C_4$-alkyl, —$C_5$-alkyl, or —$C_6$-alkyl;

$R^{1e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each $R^{1e}$ is unsubstituted or substituted with one, two, three or four substituents independently selected from the group consisting of =O, —Cl, —F, —Br, —I, —$NO_2$, —CN, —OH, —$R^{1aa}$, —$OR^{1aa}$, —$SR^{1aa}$, —$NH_2$, —$NHR^{1aa}$, and —$N(R^{1aa})_2$;

$R^{1f}$ is —$C_1$-alkyl, —$C_2$-alkyl, —$C_3$-alkyl, —$C_4$-alkyl, —$C_5$-alkyl, —$C_6$-alkyl, aryl, heteroaryl, $R^{1h}$; or $R^{1g}$; and $R^{1g}$ is —$C_1$-alkyl, —$C_2$-alkyl, —$C_3$-alkyl, —$C_4$-alkyl, —$C_5$-alkyl, or —$C_6$-alkyl, each of which is substituted with one substituent selected from the group consisting of $R^{1h}$;

For example, the third embodiment of the present invention provides a compound having Formula (I), or a therapeutically acceptable salt, solvate, prodrug, or salt of a prodrug thereof, in which $R^2$ is phenyl substituted with one, two, three, four, or five substituents independently selected from the group consisting of —Cl, —F, —Br, —I, —$NH_2$, —$R^{2a}$, —$OR^{2a}$, —$NHR^{2a}$, —$N(R^{2a})_2$, —CN, —$SR^{2a}$, and —$SO_2R^{2a}$;

$R^{2a}$ is —$C_1$-alkyl, —$C_2$-alkyl, —$C_3$-alkyl, —$C_4$-alkyl, —$C_5$-alkyl, —$C_6$-alkyl, or $R^{2b}$;

$R^{2b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, $NHR^{2c}$, —$N(R^{2c})_2$, —CN, —$SR^{2c}$, and —$SO_2R^{2c}$;

$R^{2c}$ is —$C_1$-alkyl, —$C_2$-alkyl, —$C_3$-alkyl, —$C_4$-alkyl, —$C_5$-alkyl, or —$C_6$-alkyl, $R^1$ is proximal unfused phenyl, unsubstituted or substituted with one, two, three, or four substituents independently selected from the group consisting of —Cl, —F, —Br, —I, —$NO_2$, —OH, —$NH_2$, $R^{1a}$, $OR^{1a}$, $NHR^{1a}$, —$N(R^{1a})_2$, —CN, —$SR^{1a}$, —$SO_2R^{1a}$, —$SO_2NH_2$, —$SO_2N(H)(R^{1a})$, —$SO_2N(R^{1a})_2$, —$C(O)R^{1d}$, —C(O)OH, —$C(O)OR^{1a}$, —$C(O)NH_2$, —$C(O)N(H)(R^{1a})$, —$C(O)N(R^{1a})_2$, —$OR^{1e}$, —$SR^{1e}$, —$SO_2R^{1e}$, —$SO_2N(H)(R^{1e})$, —$SO_2N(R^{1d})(R^{1e})$, —$NH(R^{1e}$, —$N(R^{1d})(R^{1e})$, —$NHC(O)R^{1f}$, —$N(R^{1d})C(O)R^{1f}$, and —$R^{1c}$;

proximal isoxazolyl, oxazolyl, pyrrolidinyl, pyridyl, thienyl, pyrrolyl, pyridazinyl, pyrazolyl, imidazolyl, thiazolyl, furyl, tetrahydrofuryl, tetrahydropyranyl, pyrimidinyl, pyrazinyl, or imidazopyridinyl ring, each of which is unfused and each of which is, independently of each other, unsubstituted or substituted with one, two, three, or four substituents independently selected from the group consisting of —Cl, —F, —Br, —I, —$NO_2$, —OH, —$NH_2$, —$R^{1a}$, —$OR^{1a}$, —$NHR^{1a}$, —$N(R^{1a})_2$, —CN, —$SR^{1a}$, —$SO_2R^{1a}$, —$SO_2NH_2$, —$SO_2N(H)$ ($R^{1a}$), —$SO_2N(R^{1a})_2$, —$C(O)R^{1a}$, —C(O)OH, —C(O)O$R^{1a}$, —$C(O)NH_2$, —C(O)N(H)($R^{1a}$), —C(O)N($R^{1a})_2$, —O$R^{1e}$, —S$R^{1e}$, —$SO_2R^{1e}$, —$SO_2$N(H)($R^{1e}$), —$SO_2$N($R^{1d}$)($R^{1e}$), —NH($R^{1e}$), —N($R^{1d}$)($R^{1e}$), —NH($R^{1e}$), —N($R^{1d}$)($R^{1e}$), —NHC(O)$R^{1f}$, —N($R^{1d}$)C(O)$R^{1f}$ and —$R^{1c}$; or proximal bicyclo[2,2,1]heptyl, cyclopentyl, cyclohexyl, cyclopentenyl, or cyclohexenyl ring, each of which is unfused and each of which is, independently of each other, unsubstituted or substituted with one, two, three, or four substituents independently selected from the group consisting of —Cl, —F, —Br, —I, =O, —$NO_2$, —OH, —$NH_2$, —$R^{1a}$, —O$R^{1a}$, —O$R^{1a}$, —NH$R^{1a}$, —N($R^{1a})_2$, —CN, —S$R^{1a}$, —$SO_2R^{1a}$, —$SO_2NH_2$, —$SO_2$N(H)($R^{1a}$), —$SO_2$N($R^{1a})_2$, —C(O)$R^{1a}$, —C(O)OH, —C(O)O$R^{1a}$, —$C(O)NH_2$, —C(O)N(H)($R^{1a}$), —C(O)N($R^{1a})_2$, —O$R^{1e}$, —S$R^{1e}$, $SO_2R^{1e}$, —$SO_2$N(H)($R^{1e}$), —$SO_2$N($R^{1d}$)($R^{1e}$), —NH($R^{1e}$), —N($R^{1d}$)($R^{1e}$), —NH($R^{1e}$), —N($R^{1d}$)($R^{1e}$), —NHC(O)$R^{1f}$, —N($R^{1d}$)C(O)$R^{1f}$, and —$R^{1c}$;

adamantyl unsubstituted or substituted with one, two, three, or four substituents independently selected from the group consisting of —Cl, —F, —Br, —I, —$NO_2$, —OH, —$NH_2$, —$R^{1d}$, —O$R^{1d}$, —NH$R^{1d}$, —N($R^{1d})_2$, —CN, —S$R^{1d}$, —$SO_2R^{1d}$, —$SO_2NH_2$, —$SO_2$N(H)($R^{1d}$), —$SO_2$N($R^{1d})_2$, —C(O)$R^{1d}$, —COOH, —C(O)O$R^{1d}$, —$C(O)NH_2$, —C(O)N(H)($R^{1d}$), and —C(O)N($R^{1d})_2$; or 2,3-dihydrospiroindene-1,4'-piperidinyl unsubstituted or substituted with one, two, three, or four substituents independently selected from the group consisting of —Cl, —F, —Br, —I, —$NO_2$, —OH, —$NH_2$, —$R^{1d}$, —O$R^{1d}$, —NH$R^{1d}$, —N($R^{1d})_2$, —CN, —S$R^{1d}$, —$SO_2R^{1d}$, —$SO_2NH_2$, —$SO_2$N(H)($R^{1d}$), —$SO_2$N($R^{1d})_2$, —C(O)$R^{1d}$, —COOH, —C(O)O$R^{1d}$, —$C(O)NH_2$, —C(O)N(H)($R^{1d}$), and —C(O)N($R^{1d})_2$;

$R^{1a}$ is —$C_1$-alkyl, —$C_2$-alkyl, —$C_3$-alkyl, —$C_4$-alkyl, —$C_5$-alkyl, —$C_6$-alkyl, or —$R^{1b}$;

$R^{1b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NH_2$, —OH, —O$R^{1d}$, —$C_1$-alkyl, —$C_2$-alkyl, —$C_3$-alkyl, —$C_4$-alkyl, —$C_5$-alkyl, —$C_6$-alkyl, —$R^{1c}$, —N($R^{1d})_2$, and —NH$R^{1d}$;

$R^{1c}$ is cyclopentyl, cyclohexyl, cyclopentenyl, cyclohexenyl, azetidinyl, naphthyl, quinolinyl, isoquinolinyl, phenyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl, thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, each of which is unsubstituted or substituted with one, two, three, or four substituents independently selected from the group consisting of =O, —Cl, —F, —Br, —I, —$NO_2$, —CN, —OH, —$R^{1aa}$, —S$R^{1aa}$, —$NH_2$, —O$R^{1aa}$, —NH$R^{1aa}$, —N($R^{1aa})_2$, —C(O)$R^{1aa}$, S(O)$_2R^{1aa}$, S(O)$_2NH_2$, S(O)$_2$N($R^{1aa})_2$, —$C(O)NH_2$, —C(O)N(H)($R^{1aa}$), —C(O)N($R^{1aa})_2$, —C(O)OH, —C(O)O$R^{1aa}$, —O$R^{1h}$, —N(H)$R^{1h}$, —N($R^{1d}$)($R^{1h}$) and —$R^{1h}$;

$R^{1aa}$ is —$C_1$-alkyl, —$C_2$-alkyl, —$C_3$-alkyl, —$C_4$-alkyl, —$C_5$-alkyl, —$C_6$-alkyl, or —$R^{1bb}$;

$R^{1bb}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NH_2$, —OH, —$NO_2$, —CN, haloalkyl, haloalkoxy, —O$R^{1d}$, —S$R^{1d}$, —S(O)$_2R^{1d}$, —$C_1$-alkyl, —$C_2$-alkyl, —$C_3$-alkyl, —$C_4$-alkyl, —$C_5$-alkyl, —$C_6$-alkyl, —N($R^{1d})_2$, —NH$R^{1d}$, —C(O)OH, —C(O)O$R^{1d}$, —$C(O)NH_2$, —C(O)N(H)($R^{1d}$), —C(O)N($R^{1d})_2$, —S(O)$_2NH_2$, —S(O)$_2$N(H)($R^{1d}$), —S(O)$_2$N($R^{1d})_2$ and —$R^{1h}$;

$R^{1d}$ is —$C_1$-alkyl, —$C_2$-alkyl, —$C_3$-alkyl, —$C_4$-alkyl, —$C_5$-alkyl, or —$C_6$-alkyl;

$R^{1e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each $R^{1e}$ is unsubstituted or substituted with one, two, three or four substituents independently selected from the group consisting of =O, —Cl, —F, —Br, —I, —OH, —$NO_2$, —CN, —$R^{1aa}$, —O$R^{1aa}$, —S$R^{1aa}$, —$NH_2$, —NH$R^{1aa}$, and —N($R^{1aa})_2$;

$R^{1f}$ is —$C_1$-alkyl, —$C_2$-alkyl, —$C_3$-alkyl, —$C_4$-alkyl, —$C_5$-alkyl, —$C_6$-alkyl, aryl, heteroaryl, $R^{1h}$ or $R^{1g}$; and $R^{1g}$ is —$C_1$-alkyl, —$C_2$-alkyl, —$C_3$-alkyl, —$C_4$-alkyl, —$C_5$-alkyl, or —$C_6$-alkyl, each of which is substituted with one substituent selected from the group consisting of $R^{1h}$ For example, the present invention provides a compound having Formula (I), or a therapeutically acceptable salt, solvate, prodrug, or salt of a prodrug thereof, in which $R^2$ is phenyl substituted with one, two, three, four, or five substituents independently selected from the group consisting of —Cl, —F, —Br, —I, —$NH_2$, —$R^{2a}$, —O$R^{2a}$, —NH$R^{2a}$, —N($R^{2a})_2$, —CN, —S$R^{2a}$, and —$SO_2R^{2a}$;

$R^{2a}$ is —$C_1$-alkyl, —$C_2$-alkyl, —$C_3$-alkyl, —$C_4$-alkyl, —$C_5$-alkyl, —$C_6$-alkyl, or $R^{2b}$;

$R^{2b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —NH$R^{2c}$, —N($R^{2c})_2$, —CN, —S$R^{2c}$ and —$SO_2R^{2c}$;

$R^{2c}$ is —$C_1$-alkyl, —$C_2$-alkyl, —$C_3$-alkyl, —$C_4$-alkyl, —$C_5$-alkyl, or —$C_6$-alkyl;

$R^1$ is proximal unfused phenyl, unsubstituted or substituted with one, substituent selected from the group consisting of —Cl, —F, —Br, —I, —$NO_2$, —OH, —$NH_2$, —$R^{1a}$, —O$R^{1a}$, —NH$R^{1a}$, —N($R^{1a})_2$, —CN, —S$R^{1a}$, —$SO_2R^{1a}$, —$SO_2NH_2$, —$SO_2$N(H)($R^{1a}$), —$SO_2$N($R^{1a})_2$, —C(O)$R^{1d}$, —C(O)OH, —C(O)O$R^{1a}$, —$C(O)NH_2$, —C(O)N(H)($R^{1a}$), —C(O)N($R^{1a})_2$, —O$R^{1e}$, —S$R^{1e}$, —$SO_2R^{1e}$, —$SO_2$N(H)($R^{1e}$), —$SO_2$N($R^{1d}$)($R^{1e}$), —NH($R^{1e}$), —N($R^{1d}$)($R^{1e}$), —NHC(O)$R^{1f}$, —N($R^{1d}$)C(O)$R^{1f}$, and —$R^{1c}$;

proximal isoxazolyl, oxazolyl, pyridyl, thienyl, pyrrolyl, tetrahydropyranyl, or pyrazolyl, each of which is unfused or fused with a distal cyclopentane, cyclohexane, or benzene ring, in which the proximal pyridyl, thienyl, pyrrolyl, or pyrazolyl rings and the distal ring are, independently of each other, unsubstituted or substituted with one, two, three or four substituents independently selected from the group consisting of —Cl, —F, —Br, —I, —NO$_2$, —OH, —NH$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$; or proximal cyclopentyl or cyclohexyl, each of which is fused with a distal benzene or pyridine ring, in which the proximal cyclopentyl or cyclohexyl ring and the distal ring are, independently of each other, unsubstituted or substituted with one, two, three or four substituents independently selected from the group consisting of =O, —Cl, —F, —Br, —I, —NO$_2$ —OH, —NH$_2$, —R$^{1a}$, —OR$^{1a}$, —NHR$^{1a}$, —N(R$^{1a}$)$_2$ —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), N(R$^{1d}$)(R$^{1e}$), —NHC(O)R$^{1f}$, —N(R$^{1d}$)C(O)R$^{1f}$, and —R$^{1c}$;

adamantyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H)(R$^{1d}$), and —C(O)N(R$^{1d}$)$_2$; or 2,3-dihydrospiroindene-1,4'-piperidinyl unsubstituted or substituted with one, two, three, or four substituents independently selected from the group consisting of —Cl, —F, —Br, —I, —NO$_2$, —OH, —NH$_2$, —R$^{1d}$, —OR$^{1d}$, —NHR$^{1d}$, —N(R$^{1d}$)$_2$, —CN, —SR$^{1d}$, —SO$_2$R$^{1d}$, —SO$_2$NH$_2$, —SO$_2$N(H)(R$^{1d}$), —SO$_2$N(R$^{1d}$)$_2$, —C(O)R$^{1d}$, —COOH, —C(O)OR$^{1d}$, —C(O)NH$_2$, —C(O)N(H)(R$^{1d}$), and —C(O)N(R$^{1d}$)$_2$;

R$^{1a}$ is —C$_1$-alkyl, —C$_2$-alkyl, —C$_3$-alkyl, —C$_4$-alkyl, —C$_5$-alkyl, —C$_6$-alkyl, or —R$^{1b}$;

R$^{1b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —OR$^{1d}$, —C$_1$-alkyl, —C$_2$-alkyl, —C$_3$-alkyl, —C$_4$-alkyl, —C$_5$-alkyl, —C$_6$-alkyl, —R$^{1c}$, —N(R$^{1d}$)$_2$, and NHR$^{1d}$;

R$^{1c}$ is cyclopentyl, cyclohexyl, cyclopentenyl, cyclohexenyl, azetidinyl, naphthyl, quinolinyl, isoquinolinyl, phenyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl, thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, each of which is unsubstituted or substituted with one, two, three, or four substituents independently selected from the group consisting of =O, —Cl, —F, —Br, —I, —NO$_2$, —CN, —OH, —R$^{1aa}$, —NH$_2$, —OR$^{1aa}$, —SR$^{1aa}$, —NHR$^{1aa}$, —N(R$^{1aa}$)$_2$, —C(O)R$^{1aa}$, S(O)$_2$R$^{1aa}$, S(O)$_2$NH$_2$, S(O)$_2$N(R$^{1aa}$)$_2$, —C(O)NH$_2$, —C(O)N(H)(R$^{1aa}$), —C(O)N(R$^{1aa}$)$_2$, —C(O)OH, —C(O)OR$^{1aa}$, —OR$^{1h}$, —N(H)R$^{1h}$), —N(R$^{1d}$)(R$^{1h}$) and —R$^{1h}$;

R$^{1aa}$ is —C$_1$-alkyl, —C$_2$-alkyl, —C$_3$-alkyl, —C$_4$-alkyl, —C$_5$-alkyl, —C$_6$-alkyl, or —R$^{1bb}$;

R$^{1bb}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), —S(O)$_2$N(R$^{1d}$)$_2$ and —R$^{1h}$;

R$^{1d}$ is —C$_1$-alkyl, —C$_2$-alkyl, —C$_3$-alkyl, —C$_4$-alkyl, —C$_5$-alkyl or —C$_6$-alkyl;

R$^{1e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each R$^{1e}$ is unsubstituted or substituted with one, two, three or four substituents independently selected from the group consisting of =O, —Cl, —F, —Br, —I, —NO$_2$, —CN, —OH, —R$^{1aa}$, —OR$^{1aa}$, —SR$^{1aa}$, —NH$_2$, —NHR$^{1aa}$, and —N(R$^{1aa}$)$_2$;

R$^{1f}$ is —C$_1$-alkyl, —C$_2$-alkyl, —C$_3$-alkyl, —C$_4$-alkyl, —C$_5$-alkyl, —C$_6$-alkyl, aryl, heteroaryl, or R$^{1h}$; R$^{1g}$; and R$^{1g}$ is —C$_1$-alkyl, —C$_2$-alkyl, —C$_3$-alkyl, —C$_4$-alkyl, —C$_5$-alkyl, or —C$_6$-alkyl, each of which is substituted with one substituent selected from the group consisting of R$^{1g}$;

R$^{1h}$ is cycloalkyl, cycloalkenyl, aryl, heteroaryl or heterocycle, in which each R$^{1h}$ is unsubstituted or substituted with one or two or three or four or five substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), and —S(O)$_2$N(R$^{1d}$)$_2$.

For example, the third embodiment of the present invention provides a compound having Formula (I), or a therapeutically acceptable salt, solvate, prodrug, salt of a prodrug thereof, in which R$^2$ is phenyl substituted with two substituents independently selected from the group consisting of —Cl, —F, —Br, —I and R$^{2a}$;

R$^{2a}$ is —C$_1$-alkyl, —C$_2$-alkyl, —C$_3$-alkyl, —C$_4$-alkyl, —C$_5$-alkyl, or —C$_6$-alkyl;

m is 0, 1 or 2;

X and Y are independently selected from the group consisting of —H, —C$_1$-alkyl, —C$_2$-alkyl, —C$_3$-alkyl, —C$_4$-alkyl, —C$_5$-alkyl, and C$_6$-alkyl;

Z is —H, —C$_1$-alkyl, —C$_2$-alkyl, —C$_3$-alkyl, —C$_4$-alkyl, —C$_5$-alkyl, or —C$_6$-alkyl;

R¹ is
  proximal unfused phenyl, unsubstituted or substituted with one, substituent selected from the group consisting of —R¹ᵃ, —N(R¹ᵃ)₂, —SR¹ᵃ, —O(pyridyl), —O(phenyl), —O(pyrazinyl), pyrrolyl or morpholinyl; in which the phenyl moiety of —O(phenyl) is unsubstituted or substituted with one substituent independently selected from the group consisting of —Cl, —F, —Br, and —I;
  proximal unfused pyridyl, unsubstituted or substituted with one —R¹ᵃ substituent;
  proximal pyridyl fused with a distal cyclopentane, cyclohexane, or benzene ring, in which the proximal pyridyl and the distal ring are, independently of each other, unsubstituted or substituted with one —R¹ᵃ substituent;
    proximal thienyl, pyrrolyl, or pyrazolyl, each of which is unfused and each of which is independently unsubstituted or substituted with one or two substitutents independently selected from the group consisting of —R¹ᵃ, unsubstituted phenyl and phenyl substituted with one —R¹ᵃ substituent; or
    proximal cyclopentyl or cyclohexyl, each of which is fused with a distal benzene or pyridine ring, in which the proximal cyclopentyl or cyclohexyl ring and the distal ring are, independently of each other, unsubstituted or substituted with one —R¹ᵃ substituent; and
  R¹ᵃ is —C₁-alkyl, —C₂-alkyl, —C₃-alkyl, —C₄-alkyl, —C₅-alkyl or —C₆-alkyl.

For example, the third embodiment of the present invention relates to a compound having Formula (I), or a therapeutically acceptable salt, solvate, prodrug or salt of a prodrug thereof, in which
  R² is phenyl substituted with two substituents independently selected from the group consisting of —Cl and —C₁-alkyl;
  m is 0, 1 or 2;
  X and Y are independently selected from the group consisting of —H and —C₁-alkyl;
  Z is H or —C₁-alkyl; and
  R¹ is
    proximal unfused phenyl, unsubstituted or substituted with one, substituent selected from the group consisting of —C₁-alkyl, —N(C₁-alkyl)₂, —S(C₁-alkyl), —O(pyridyl), —O(phenyl), —O(pyrazinyl), pyrrolyl or morpholinyl; in which the phenyl moiety of —O(phenyl) is unsubstituted or substituted with one —F substituent;
    proximal unfused pyridyl, unsubstituted or substituted with one —C₁-alkyl substituent;
    proximal pyridyl fused with a distal cyclopentane, cyclohexane, or benzene ring, in which the proximal pyridyl ring and the distal ring are, independently of each other, unsubstituted or substituted with one —C₁-alkyl substituent;
    proximal thienyl, pyrrolyl, or pyrazolyl, each of which is unfused and each of which is independently unsubstituted or substituted with one or two substitutents independently selected from the group consisting of —C₁-alkyl, unsubstituted phenyl and phenyl substituted with one —C₁-alkyl; or
    proximal cyclopentyl or cyclohexyl, each of which is fused with a distal benzene or pyridine ring, in which the proximal cyclopentyl or cyclohexyl ring and the distal ring are, independently of each other, unsubstituted or substituted with one —C₁-alkyl substituent.

For example, the third embodiment of the present invention relates to a compound having Formula (I), or a therapeutically acceptable salt, solvate, prodrug or salt of a prodrug thereof, in which,
  R² is phenyl substituted with two substituents independently selected from the group consisting of —Cl and —C₁-alkyl;
  m is 0;
  Z and X together with the atoms to which they are attached form a ring selected from the group consisting of pyrrolidine, piperidine, morpholine, thiomorpholine, and piperazine;
  Y is independently selected from the group consisting of —H, —C₁-alkyl, —C₂-alkyl, —C₃-alkyl, —C₄-alkyl, —C₅-alkyl, and C₆-alkyl;
  R¹ is
    proximal unfused phenyl, unsubstituted or substituted with one, substituent selected from the group consisting of —R¹ᵃ, —N(R¹ᵃ)₂, —SR¹ᵃ, —O(pyridyl), —O(phenyl), —O(pyrazinyl), pyrrolyl or morpholinyl; in which the phenyl moiety of —O(phenyl) is unsubstituted or substituted with one substituent independently selected from the group consisting of —Cl, —F, —Br, and —I;
    proximal unfused pyridyl, unsubstituted or substituted with one —R¹ᵃ substituent;
    proximal pyridyl fused with a distal cyclopentane, cyclohexane, or benzene ring, in which the proximal pyridyl and the distal ring are, independently of each other, unsubstituted or substituted with one —R¹ᵃ substituent;
    proximal thienyl, pyrrolyl, or pyrazolyl, each of which is unfused and each of which is independently unsubstituted or substituted with one or two substitutents independently selected from the group consisting of —R¹ᵃ, unsubstituted phenyl and phenyl substituted with one —R¹ᵃ substituent; or
    proximal cyclopentyl or cyclohexyl, each of which is fused with a distal benzene or pyridine ring, in which the proximal cyclopentyl or cyclohexyl ring and the distal ring are, independently of each other, unsubstituted or substituted with one —R¹ᵃ substituent; and
  R¹ᵃ is —C₁-alkyl, —C₂-alkyl, —C₃-alkyl, —C₄-alkyl, —C₅-alkyl or —C₆-alkyl.

For example, the third embodiment of the present invention provides a compound having Formula (I), or a therapeutically acceptable salt, solvate, prodrug or salt of a prodrug thereof, in which
  R² is 2,3-dichlorophenyl or 2-methylphenyl;
  m is 0, 1 or 2;
  X and Y are independently selected from the group consisting of —H and methyl;
  Z is —H or methyl; and
  R¹ is 2-methylphenyl, 2-(morpholin-4-yl)phenyl, 2-(dimethylamino)phenyl, 2-(pyridine-2-yloxy)phenyl, phenyl, 3-(dimethylamino)phenyl, 2-(methylthio)phenyl, 2-(4-fluorophenoxy)phenyl, 3-(pyrazin-2-yloxy)phenyl, 2-(1H-pyrrol-1-yl)phenyl, 4-(pyridine-2-yloxy)phenyl, 3-(pyridine-2-yloxy)phenyl, 4-(morpholin-4-yl)phenyl, pyridine-4-yl, pyridine-3-yl, pyridine-2-yl, quinolin-4-yl, 3-methylpyridin-4-yl, 6,7-dihydro-5H-cyclopenta[b]pyridine-3-yl, 5,6,7,8-tetrahydroquinolin-3-yl, 1-methyl-1H-pyrrol-2-yl, 2-methylthien-3-yl, 3-methyl-1-phenyl-1H-pyrazol-5-yl, 1,5-dimethyl-1H-pyrazol-4-yl, 2,3-dihydro-1H-inden-1-yl, or 5,6,7,8-tetrahydroquinolin-5-yl.

In a fourth embodiment, the present invention provides a compound having Formula (II),

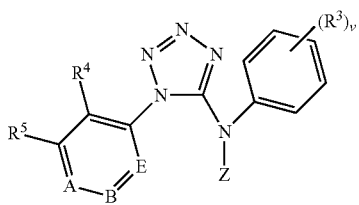

Formula (II)

or a therapeutically acceptable salt, solvate, prodrug, or salt of a prodrug thereof, in which Z is —H, —$C_1$-alkyl, —$C_2$-alkyl, —$C_3$-alkyl, —$C_4$-alkyl, —$C_5$-alkyl, or —$C_6$-alkyl;

A is N or $CR^6$;

B is N or $CR^7$;

E is N or $CR^8$;

provided that only one of A, B and E is N;

$R^3$ is —$NH_2$, —$R^{3a}$, —$OR^{3a}$, —$NHR^{3a}$, —$N(R^{3a})_2$, —NHC(O)$R^{3f}$, —N($R^{3d}$)C(O)$R^{3f}$, —$R^{3c}$, —$OR^{3e}$, —$SR^{3e}$, —NH($R^{3e}$), or —N($R^{3d}$)($R^{3e}$);

$R^{3a}$ is —$C_1$-alkyl, —$C_2$-alkyl, —$C_3$-alkyl, —$C_4$-alkyl, —$C_5$-alkyl, —$C_6$-alkyl, or $R^{3b}$;

$R^{3b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —$NH_2$, —CN, —OH, —$OR^{3d}$, —$R^{3c}$, —N($R^{3d}$)$_2$, and NH$R^{3d}$;

$R^{3c}$ is cyclopentyl, cyclohexyl, cyclopentenyl, cyclohexenyl, azetidinyl, naphthyl, quinolinyl, isoquinolinyl, phenyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, each of which is unsubstituted or substituted with one, two, three, or four substituents independently selected from the group consisting of —Cl, —F, —Br, —I, —OH, —$R^{3aa}$, —$NH_2$, —$OR^{3aa}$, —$SR^{3aa}$, —$NHR^{3aa}$, and —N($R^{3aa}$)$_2$;

$R^{3d}$ is —$C_1$-alkyl, —$C_2$-alkyl, —$C_3$-alkyl, —$C_4$-alkyl, —$C_5$-alkyl, or —$C_6$-alkyl;

$R^{3aa}$ is —$C_1$-alkyl, —$C_2$-alkyl, —$C_3$-alkyl, —$C_4$-alkyl, —$C_5$-alkyl, —$C_6$-alkyl, or —$R^{3bb}$;

$R^{3bb}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —F, —Cl, —Br, —I, —$NH_2$, —OH, —$OR^{3d}$, —$C_1$-alkyl, —$C_2$-alkyl, —$C_3$-alkyl, —$C_4$-alkyl, —$C_5$-alkyl, —$C_6$-alkyl, —N($R^{3d}$)$_2$, and —NH$R^{3d}$;

$R^{3e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each $R^{3e}$ is unsubstituted or substituted with one, two, three or four substituents independently selected from the group consisting of =O, —Cl, —F, —Br, —I, —OH, —$R^{3aa}$, —$OR^{3aa}$, —$SR^{3aa}$, —$NH_2$, $NR^{3aa}$, and —N($R^{3aa}$)$_2$;

$R^{3f}$ is —$C_1$-alkyl, —$C_2$-alkyl, —$C_3$-alkyl, —$C_4$-alkyl, —$C_5$-alkyl, —$C_6$-alkyl, aryl, heteroaryl, or $R^{3g}$;

$R^{3g}$ is —$C_1$-alkyl, —$C_2$-alkyl, —$C_3$-alkyl, —$C_4$-alkyl, —$C_5$-alkyl, or —$C_6$-alkyl, each of which is substituted with one substituent selected from the group consisting of aryl and heteroaryl;

v is one, two, or three, and when v is two or three, $R^3$ may be the same or different;

$R^4$ is —Cl, —F, —Br, —I, —$NH_2$, —$R^{4a}$, —$OR^{4a}$, —$NHR^{4a}$, —N($R^{4a}$)$_2$, —CN, $SR^{4a}$, or —$SO_2R^{4a}$;

$R^{4a}$ is —$C_1$-alkyl, —$C_2$-alkyl, —$C_3$-alkyl, —$C_4$-alkyl, —$C_5$-alkyl, —$C_6$-alkyl, or $R^{4b}$;

$R^{4b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{4c}$, —N($R^{4c}$)$_2$, —CN, —$SR^{4c}$, and —$SO_2R^{4c}$;

$R^{4c}$ is —$C_1$-alkyl, —$C_2$-alkyl, —$C_3$-alkyl, —$C_4$-alkyl, —$C_5$-alkyl, or —$C_6$-alkyl;

$R^5$ is —H, —Cl, —F, —Br, —I, —$NH_2$, $R^{5a}$, $OR^{5a}$, $NHR^{5a}$, N($R^{5a}$)$_2$, —CN, —$SR^{5a}$, or —$SO_2R^{5a}$;

$R^{5a}$ is —$C_1$-alkyl, —$C_2$-alkyl, —$C_3$-alkyl, —$C_4$-alkyl, —$C_5$-alkyl, —$C_6$-alkyl, or $R^{5b}$;

$R^{5b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{5c}$, —N($R^{5c}$)$_2$, —CN, —$SR^{5c}$, and —$SO_2R^{5c}$;

$R^{5c}$ is —$C_1$-alkyl, —$C_2$-alkyl, —$C_3$-alkyl, —$C_4$-alkyl, —$C_5$-alkyl, or —$C_6$-alkyl;

$R^6$ is —H, —Cl, —F, —Br, —I, —$NH_2$, —$R^{6a}$, —$OR^{6a}$, —$NHR^{6a}$, —N($R^{6a}$)$_2$, —CN, —$SR^{6a}$, or —$SO_2R^{6a}$;

$R^{6a}$ is —$C_1$-alkyl, —$C_2$-alkyl, —$C_3$-alkyl, —$C_4$-alkyl, —$C_5$-alkyl, —$C_6$-alkyl, or $R^{6b}$;

$R^{6b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{6c}$, —N($R^{6c}$)$_2$, —CN, —$SR^{6c}$, and —$SO_2R^{6c}$;

$R^{6c}$ is —$C_1$-alkyl, —$C_2$-alkyl, —$C_3$-alkyl, —$C_4$-alkyl, —$C_5$-alkyl, or —$C_6$-alkyl;

$R^7$ is —H, —Cl, —F, —Br, —I, —$NH_2$, —$R^{7a}$, —$OR^{7a}$, —$NHR^{7a}$, —N($R^{7a}$)$_2$, —CN, —$SR^{7a}$, or —$SO_2R^{7a}$;

$R^{7a}$ is —$C_1$-alkyl, —$C_2$-alkyl, —$C_3$-alkyl, —$C_4$-alkyl, —$C_5$-alkyl, —$C_6$-alkyl, or $R^{7b}$;

$R^{7b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{7c}$, —N($R^{7c}$)$_2$, —CN, —$SR^{7c}$, and —$SO_2R^{7c}$;

$R^{7c}$ is —$C_1$-alkyl, —$C_2$-alkyl, —$C_3$-alkyl, —$C_4$-alkyl, —$C_5$-alkyl, or —$C_6$-alkyl;

$R^8$ is —H, —Cl, —F, —Br, —I, —$NH_2$, —$R^{8a}$, —$OR^{8a}$, —$NHR^{8a}$, —N($R^{8a}$)$_2$, —CN, —$SR^{8a}$, or $SO_2R^{8a}$;

$R^{8a}$ is —$C_1$-alkyl, —$C_2$-alkyl, —$C_3$-alkyl, —$C_4$-alkyl, —$C_5$-alkyl, —$C_6$-alkyl, or $R^{8b}$;

$R^{8b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{8c}$, —$N(R^{8c})_2$, —CN, —$SR^{8c}$, and —$SO_2R^{8c}$;

$R^{8c}$ is —$C_1$-alkyl, —$C_2$-alkyl, —$C_3$-alkyl, —$C_4$-alkyl, —$C_5$-alkyl, or —$C_6$-alkyl; and with the proviso that the following compounds are excluded: N,1-bis(4-methylphenyl)-1H-tetraazol-5-amine; N,1-bis(4-methoxyphenyl)-1H-tetraazol-5-amine; and N,1-bis(2,4-dimethylphenyl)-1H-tetraazol-5-amine.

For example, the present invention provides a compound having Formula (II), or a therapeutically acceptable salt, solvate, prodrug, or salt of a prodrug thereof, in which A is $CR^6$;
B is $CR^7$;
E is $CR^8$;
$R^4$ is —Cl, —F, —Br, —I, —$NH_2$, —$R^{4a}$, —$OR^{4a}$, —$NHR^{4a}$, —$N(R^{4a})_2$, —CN, —$SR^{4a}$, or —$SO_2R^{4a}$, $R^{4a}$ is —$C_1$-alkyl, —$C_2$-alkyl, —$C_3$-alkyl, —$C_4$-alkyl, —$C_5$-alkyl, —$C_6$-alkyl, or $R^{4b}$;

$R^{4b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{4c}$, —$N(R^{4c})_2$, —CN, —$SR^{4c}$, and —$SO_2R^{4c}$;

$R^{4c}$ is —$C_1$-alkyl, —$C_2$-alkyl, —$C_3$-alkyl, —$C_4$-alkyl, —$C_5$-alkyl, or —$C_6$-alkyl;

$R^5$ is —H, —Cl, —F, —Br, —I, —$NH_2$, —$R^{5a}$, —$OR^{5a}$, —$NHR^{5a}$, —$N(R^{5a})_2$, —CN, —$SR^{5a}$, or $SO_2R^{5a}$;

$R^{5a}$ is —$C_1$-alkyl, —$C_2$-alkyl, —$C_3$-alkyl, —$C_4$-alkyl, —$C_5$-alkyl, —$C_6$-alkyl, or $R^{5b}$;

$R^{5b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{5c}$, —$N(R^{5c})_2$, —CN, —$SR^{5c}$, and —$SO_2R^{5c}$;

$R^{5c}$ is —$C_1$-alkyl, —$C_2$-alkyl, —$C_3$-alkyl, —$C_4$-alkyl, —$C_5$-alkyl, or —$C_6$-alkyl;

$R^6$ is —H, —Cl, —F, —Br, —I, —$NH_2$, —$R^{6a}$, —$OR^{6a}$, —$NHR^{6a}$, —$N(R^{6a})_2$, —CN, —$SR^{6a}$, or —$SO_2R^{6a}$;

$R^{6a}$ is —$C_1$-alkyl, —$C_2$-alkyl, —$C_3$-alkyl, —$C_4$-alkyl, —$C_5$-alkyl, —$C_6$-alkyl, or $R^{6b}$;

$R^{6b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{6c}$, —$N(R^{6c})_2$, —CN, —$SR^{6c}$, and —$SO_2R^{6c}$;

$R^{6c}$ is —$C_1$-alkyl, —$C_2$-alkyl, —$C_3$-alkyl, —$C_4$-alkyl, —$C_5$-alkyl, or —$C_6$-alkyl;

$R^7$ is —H, —Cl, —F, —Br, —I, —$NH_2$, —$R^{7a}$, —$OR^{7a}$, —$NHR^{7a}$, —$N(R^{7a})_2$, —CN, —$SR^{7a}$, or —$SO_2R^{7a}$;

$R^{7a}$ is —$C_1$-alkyl, —$C_2$-alkyl, —$C_3$-alkyl, —$C_4$-alkyl, —$C_5$-alkyl, —$C_6$-alkyl, or $R^{7b}$;

$R^{7b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{7c}$, —$N(R^{7c})_2$, —CN, —$SR^{7c}$, and —$SO_2R^{7c}$;

$R^{7c}$ is —$C_1$-alkyl, —$C_2$-alkyl, —$C_3$-alkyl, —$C_4$-alkyl, —$C_5$-alkyl, or —$C_6$-alkyl;

$R^8$ is —H, —Cl, —F, —Br, —I, —$NH_2$, —$R^{8a}$, —$OR^{8a}$, —$NHR^{8a}$, —$N(R^{8a})_2$, —CN, —$SR^{8a}$, or —$SO_2R^{8a}$;

$R^{8a}$ is —$C_1$-alkyl, —$C_2$-alkyl, —$C_3$-alkyl, —$C_4$-alkyl, —$C_5$-alkyl, —$C_6$-alkyl, or $R^{8b}$;

$R^{8b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{8c}$, —$N(R^{8c})_2$, —CN, —$SR^{8c}$, and —$SO_2R^{8c}$; and $R^{8c}$ is —$C_1$-alkyl, —$C_2$-alkyl, —$C_3$-alkyl, —$C_4$-alkyl, —$C_5$-alkyl, or —$C_6$-alkyl; with the proviso that the following compounds are excluded: N,1-bis(4-methylphenyl)-1H-tetraazol-5-amine; N,1-bis(4-methoxyphenyl)-1H-tetraazol-5-amine; and N,1-bis(2,4-dimethylphenyl)-1H-tetraazol-5-amine.

For example, the fourth embodiment of the present invention provides a compound having Formula (II), or a therapeutically acceptable salt, solvate, prodrug or salt of a prodrug thereof, in which A is $CR^6$;
B is $CR^7$;
E is $CR^8$;
$R^4$ is —Cl, —F, —Br, —I, —$NH_2$, —$R^{4a}$, —$OR^{4a}$, —$NHR^{4a}$, —$N(R^{4a})_2$, —CN, —$SR^{4a}$, or —$SO_2R^{4a}$;

$R^{4a}$ is —$C_1$-alkyl, —$C_2$-alkyl, —$C_3$-alkyl, —$C_4$-alkyl, —$C_5$-alkyl, —$C_6$-alkyl, or $R^{4b}$;

$R^{4b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{4c}$, —$N(R^{4c})_2$, —CN, —$SR^{4c}$, and —$SO_2R^{4c}$;

$R^{4c}$ is —$C_1$-alkyl, —$C_2$-alkyl, —$C_3$-alkyl, —$C_4$-alkyl, —$C_5$-alkyl, or —$C_6$-alkyl;

$R^5$ is —H, —Cl, —F, —Br, —I, —$NH_2$, —$R^{5a}$, —$OR^{5a}$, —$NHR^{5a}$, —$N(R^{5a})_2$, —CN, —$SR^{5a}$, or —$SO_2R^{5a}$;

$R^{5a}$ is —$C_1$-alkyl, —$C_2$-alkyl, —$C_3$-alkyl, —$C_4$-alkyl, —$C_5$-alkyl, —$C_6$-alkyl, or $R^{5b}$;

$R^{5b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{5c}$, —$N(R^{5c})_2$, —CN, —$SR^{5c}$, and —$SO_2R^{5c}$;

$R^{5c}$ is —$C_1$-alkyl, —$C_2$-alkyl, —$C_3$-alkyl, —$C_4$-alkyl, —$C_5$-alkyl, or —$C_6$-alkyl;

$R^6$ is —H, —Cl, —F, —Br, —I, —$NH_2$, —$R^{6a}$, —$OR^{6a}$, —$NHR^{6a}$, —$N(R^{6a})_2$, —CN, —$SR^{6a}$, or —$SO_2R^{6a}$;

$R^{6a}$ is —$C_1$-alkyl, —$C_2$-alkyl, —$C_3$-alkyl, —$C_4$-alkyl, —$C_5$-alkyl, —$C_6$-alkyl, or $R^{6b}$;

$R^{6b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{6c}$, —$N(R^{6c})_2$, —CN, —$SR^{6c}$, and —$SO_2R^{6c}$;

$R^{6c}$ is —$C_1$-alkyl, —$C_2$-alkyl, —$C_3$-alkyl, —$C_4$-alkyl, —$C_5$-alkyl, or —$C_6$-alkyl, $R^7$ is —H, —Cl, —F, —Br, —I, —$NH_2$, —$R^{7a}$, —$OR^{7a}$, —$NHR^{7a}$, —$N(R^{7a})_2$, —CN, —$SR^{7a}$, or —$SO_2R^{7a}$;

$R^{7a}$ is —$C_1$-alkyl, —$C_2$-alkyl, —$C_3$-alkyl, —$C_4$-alkyl, —$C_5$-alkyl, —$C_6$-alkyl, or $R^{7b}$;

$R^{7b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{7c}$, —$N(R^{7c})_2$, —CN, —$SR^{7c}$, and —$SO_2R^{7c}$;

$R^{7c}$ is —$C_1$-alkyl, —$C_2$-alkyl, —$C_3$-alkyl, —$C_4$-alkyl, —$C_5$-alkyl, or —$C_6$-alkyl;

$R^8$ is —H, —Cl, —F, —Br, —I, —$NH_2$, —$R^{8a}$, —$OR^{8a}$, —$NHR^{8a}$, —$N(R^{8a})_2$, —CN, —$SR^{8a}$, or —$SO_2R^{8a}$;

$R^{8a}$ is —$C_1$-alkyl, —$C_2$-alkyl, —$C_3$-alkyl, —$C_4$-alkyl, —$C_5$-alkyl, —$C_6$-alkyl, or $R^{8b}$;

$R^{8b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —$NH_2$, —$NHR^{8c}$, —$N(R^{8c})_2$, —CN, —$SR^{8c}$, and —$SO_2R^{8c}$;

$R^{8c}$ is —$C_1$-alkyl, —$C_2$-alkyl, —$C_3$-alkyl, —$C_4$-alkyl, —$C_5$-alkyl, or —$C_6$-alkyl;

$R^3$ is —$NH_2$, —$R^{3a}$, —$OR^{3a}$, —$NH(R^{3a})$, —$N(R^{3a})_2$, —$NHC(O)R^{3f}$, or —$N(R^{3d})C(O)R^{3f}$;

$R^{3a}$ is —$C_1$-alkyl, —$C_2$-alkyl, —$C_3$-alkyl, —$C_4$-alkyl, —$C_5$-alkyl, —$C_6$-alkyl or $R^{3b}$;

$R^{3b}$ is —$C_1$-alkyl, —$C_2$-alkyl, —$C_3$-alkyl, —$C_4$-alkyl, —$C_5$-alkyl, or —$C_6$-alkyl, each of which is substituted with one or two or three substituents independently selected from the group consisting —$NH_2$, —CN, —OH, —$OR^{3d}$, —$N(R^{3d})_2$, and —$NHR^{3d}$;

$R^{3d}$ is —$C_1$-alkyl, —$C_2$-alkyl, —$C_3$-alkyl, —$C_4$-alkyl, —$C_5$-alkyl, or —$C_6$-alkyl;

$R^{3f}$ is —$C_1$-alkyl, —$C_2$-alkyl, —$C_3$-alkyl, —$C_4$-alkyl, —$C_5$-alkyl, —$C_6$-alkyl, aryl, heteroaryl, or $R^{3g}$;

$R^{3g}$ is —$C_1$-alkyl, —$C_2$-alkyl, —$C_3$-alkyl, —$C_4$-alkyl, —$C_5$-alkyl, or —$C_6$-alkyl, each of which is substituted with one substituent selected from the group consisting of aryl and heteroaryl;

v is one, two, or three, and when v is two or three, $R^3$ may be the same or different; with the proviso that the following compounds are excluded: N,1-bis(4-methylphenyl)-1H-tetraazol-5-amine; N,1-bis(4-methoxyphenyl)-1H-tetraazol-5-amine; and N,1-bis(2,4-dimethylphenyl)-1H-tetraazol-5-amine.

For example, the fourth embodiment of the present invention provides a compound having Formula (II), or a therapeutically acceptable salt, solvate, prodrug, or salt of a prodrug thereof, in which A is $CR^6$;
B is $CR^7$;
E is $CR^8$;
$R^4$ is —Cl, —F, —Br, —I, —$C_1$-alkyl, —$C_2$-alkyl, —$C_3$-alkyl, —$C_4$-alkyl, —$C_5$-alkyl, or —$C_6$-alkyl;
$R^5$ is —H, —Cl, —F, —Br, —I, —$C_1$-alkyl, —$C_2$-alkyl, —$C_3$-alkyl, —$C_4$-alkyl, —$C_5$-alkyl or —$C_6$-alkyl;
$R^6$ is —H;
$R^7$ is —H;
$R^8$ is —H;
Z is —H, —$C_1$-alkyl, —$C_2$-alkyl, —$C_3$-alkyl, —$C_4$-alkyl, —$C_5$-alkyl, or —$C_6$-alkyl;
$R^3$ is —$C_1$-alkyl, —$C_2$-alkyl, —$C_3$-alkyl, —$C_4$-alkyl, —$C_5$-alkyl or —$C_6$-alkyl; and
v is one; with the proviso that the following compounds are excluded: N,1-bis(4-methylphenyl)-1H-tetraazol-5-amine; and N,1-bis(2,4-dimethylphenyl)-1H-tetraazol-5-amine.

For example, the fourth embodiment of the present invention provides a compound having Formula (II), or a therapeutically acceptable salt, ester, solvate, or prodrug thereof, in which A is $CR^6$; B is $CR^7$; E is $CR^8$; $R^4$ is —Cl, $R^5$ is —Cl, $R^6$ is —H; $R^7$ is —H; $R^8$ is —H; Z is —H; $R^3$ is —$C_1$-alkyl; and v is one.

A representative example of a compound having Formula (II) includes, but is not limited to, 1-(2,3-dichlorophenyl)-N-(2-methylphenyl)-1H-tetraazol-5-amine, or a therapeutically acceptable salt, solvate, prodrug, salt of a prodrug, or combination thereof.

In a fifth embodiment the present invention a relates to a method for treating a $P2X_7$ mediated disease in a patient in need of such treatment, which comprises administering to said patient a therapeutically effective amount of a compound of Formula (I) or Formula (II), or a therapeutically acceptable salt, solvate, prodrug, salt of a prodrug, or combination thereof.

For example, the present invention relates to a method for treating a condition selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, atherosclerosis, aortic aneurysm, congestive heart failure, neurodegeneration, inflammation, Alzheimer's disease, Parkinson's disease, peripheral neuropathy, depression, spinal cord injury, pain, burns, autoimmune disorders, and to promote neuroregeneration in a patient in need of such treatment, which comprises administering to said patient a therapeutically effective amount of a compound of Formula (I) or Formula (II), or a therapeutically acceptable salt, solvate, prodrug, salt of a prodrug, or combination thereof.

For example, the present invention provides a method for treating depression, spinal cord injury, neurodegeneration, chronic inflammatory pain or neuropathic pain in a patient, which comprises administering to a patient in need of such treatment a therapeutically effective amount of a compound having Formula (I) or Formula (II), or a therapeutically acceptable salt, solvate, prodrug, salt of a prodrug, or combination thereof.

For example, the present invention provides a method for treating inflammation in a patient, which comprises administering to a patient in need of such treatment a therapeutically effective amount of a compound having Formula (I) or Formula (II), or a therapeutically acceptable salt, solvate, prodrug, salt of a prodrug, or combination thereof.

For example, the present invention provides a method for treating neurodegeneration in a patient, which comprises administering to a patient in need of such treatment a therapeutically effective amount of a compound having Formula (I) or Formula (II), or a therapeutically acceptable salt, solvate, prodrug, salt of a prodrug, or combination thereof.

For example, the present invention provides a method for treating Crohn's disease in a patient, which comprises administering to a patient in need of such treatment a therapeutically effective amount of a compound having Formula (I) or Formula (II), or a therapeutically acceptable salt, solvate, prodrug, salt of a prodrug, or combination thereof.

In a sixth embodiment, the present invention provides a pharmaceutical composition comprising a therapeutically effective amount of a compound having Formula (I) or Formula (II), or a therapeutically acceptable salt, solvate, prodrug, salt of a prodrug, or combination thereof, and a pharmaceutically acceptable carrier.

The present invention relates to a pharmaceutical composition for the treatment of P2X$_7$ mediated disease in a patient, comprising administering to a patient in need of such treatment a therapeutically effective amount of a compound having Formula (I) or Formula (II), or a therapeutically acceptable salt, solvate, prodrug, salt of a prodrug, or combination thereof, and a pharmaceutically acceptable carrier.

For example, the present invention relates to a pharmaceutical composition for the treatment of a condition selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, atherosclerosis, aortic aneurysm, congestive heart failure, neurodegeneration, inflammation, Alzheimer's disease, Parkinson's disease, peripheral neuropathy, spinal cord injury, depression, pain, burns, autoimmune disorders, and to improve neuroregeneration in a patient, comprising administering to a patient in need of such treatment a therapeutically effective amount of a compound having Formula (I) or Formula (II), or a therapeutically acceptable salt, solvate, prodrug, salt of a prodrug, or combination thereof, and a pharmaceutically acceptable carrier.

For example, the present invention provides a method for treating chronic inflammatory pain or neuropathic pain in a patient, comprising administering to the patient in need of such treatment a therapeutically effective amount of a compound having Formula (I) or Formula (II), or a therapeutically acceptable salt, solvate, prodrug, salt of a prodrug, or combination thereof, and a pharmaceutically acceptable carrier.

For example, the present invention provides a method for treating Crohn's disease in a patient, comprising administering to a patient in need of such treatment a therapeutically effective amount of a compound having Formula (I) or Formula (II), or a therapeutically acceptable salt, solvate, prodrug, salt of a prodrug, or combination thereof, and a pharmaceutically acceptable carrier.

For example, the present invention provides a method for treating neurodegeneration in a patient, comprising administering to a patient in need of such treatment a therapeutically effective amount of a compound having Formula (I) or Formula (II), or a therapeutically acceptable salt, solvate, prodrug, salt of a prodrug, or combination thereof, and a pharmaceutically acceptable carrier.

For example, the present invention provides a method for treating depression in a patient, comprising administering to a patient in need of such treatment a therapeutically effective amount of a compound having Formula (I) or Formula (II), or a therapeutically acceptable salt, solvate, prodrug, salt of a prodrug, or combination thereof, and a pharmaceutically acceptable carrier.

For example, the present invention provides a method for treating spinal cord injury in a patient, comprising administering to a patient in need of such treatment a therapeutically effective amount of a compound having Formula (I) or Formula (II), or a therapeutically acceptable salt, solvate, prodrug, salt of a prodrug, or combination thereof, and a pharmaceutically acceptable carrier.

In a seventh embodiment, the present invention provides the use of a compound having Formula (I) or Formula (II), or a therapeutically acceptable salt, solvate, prodrug, salt of a prodrug, or combination thereof, to prepare a medicament for the treatment of a P2X$_7$ mediated disease in a patient.

For example, the present invention provides the use of a compound of having Formula (I) or Formula (II), or a therapeutically acceptable salt, solvate, prodrug, salt of a prodrug, or combination thereof, to prepare a medicament for the treatment of chronic inflammatory pain or neuropathic pain in a patient.

For example, the present invention provides the use of a compound having Formula (I) or Formula (II), or a therapeutically acceptable salt, solvate, prodrug, salt of a prodrug, or combination thereof, to prepare a medicament for the treatment of a condition selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, atherosclerosis, aortic aneurysm, congestive heart failure, neurodegeneration, inflammation, depression, neurodegeneration, spinal cord injury, Alzheimer's disease, Parkinson's disease, peripheral neuropathy, pain, burns, and autoimmune disorders in a patient.

In an eighth embodiment, the present invention provides a method for inhibiting P2X$_7$ activity in a patient, comprising administering to the patient a therapeutically effective amount of a compound of having Formula (I) or Formula (II), or a therapeutically acceptable salt, solvate, prodrug, salt of a prodrug, or combination thereof.

Compounds of the invention were named by ACD/ChemSketch version 5.06 (developed by Advanced Chemistry Development, Inc., Toronto, ON, Canada) or were given names consistent with ACD nomenclature.

When any variable (for example $R^{1a}$, $R^{1b}$, $R^{1c}$, $R^{1d}$, $R^{1e}$, $R^{1f}$, $R^{1g}$, $R^{1aa}$, $R^{1bb}$, $R^{2a}$, $R^{2b}$, $R^{2c}$, $R^{3a}$, $R^{3b}$, $R^{3c}$, $R^{3d}$, $R^{3e}$, $R^{3f}$, $R^{3g}$, $R^{3aa}$, $R^{3bb}$, $R^{4a}$, $R^{4b}$, $R^{4c}$, $R^{5a}$, $R^{5b}$, $R^{5c}$, $R^{6a}$, $R^{6b}$, $R^{6c}$, $R^{7a}$, $R^{7b}$, $R^{7c}$, $R^{8a}$, $R^{8b}$, $R^{8c}$, etc.) occurs more than one time in any substituent or in the compound of Formula (I) or (II) or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

As used throughout this specification and the appended claims, the following terms have the following meanings.

The term "$C_1$-alkyl" means methyl.

The term "$C_2$-alkyl" means ethyl.

The term "$C_3$-alkyl" means prop-1-yl and prop-2-yl (isopropyl).

The term "$C_4$-alkyl" means but-1-yl, but-2-yl, 2-methylprop-1-yl, and 2-methylprop-2-yl (tert-butyl).

The term "$C_5$-alkyl" means 2,2-dimethylprop-1-yl (neopentyl), 2-methylbut-1-yl, 2-methylbut-2-yl, 3-methylbut-1-yl, 3-methylbut-2-yl, pent-1-yl, pent-2-yl, and pent-3-yl.

The term "$C_6$-alkyl" means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl, and 4-methylpent-2-yl.

The term "aryl" as used herein, refers to a phenyl group, or a bicyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Representative examples of aryl groups include, but not limited to, indanyl, indenyl, naphthyl, phenyl and tetrahydronaphthyl. The aryl groups of the present invention can be substituted or unsubstituted, and are connected to the parent molecular moiety through any substitutable carbon atom of the group.

The term "cycloalkenyl," as used herein, refers to a non-aromatic, partially unsaturated, monocyclic hydrocarbon ring system, having three to ten carbon atoms and zero heteroatom. Representative examples of cycloalkenyl groups include, but not limited to, adamantyl, cyclobutenyl, cyclopentenyl, cyclohexenyl, and octahydronaphthalenyl. The cycloalkenyl groups of the present invention can be unsubstituted or substituted, and are attached to the parent molecular moiety through any substitutable carbon atom of the group.

The term "cycloalkyl," as used herein, refers to a saturated monocyclic or bicyclic hydrocarbon ring system having three to eight carbon atoms and zero heteroatom. Examples of monocyclic ring systems include cyclopropyl, cyclobutyl, cyclopentyl, cyclohexyl, cycloheptyl, and cyclooctyl. The cycloalkyl groups of the present invention can be unsubstituted or substituted, and are connected to the parent molecular moiety through any substitutable carbon atom of the group.

The term "heterocycle" as used herein, refers to a monocyclic or bicyclic, non-aromatic, saturated or partially unsaturated ring system. Monocyclic ring systems are exemplified by any 4-membered ring containing a heteroatom independently selected from oxygen, nitrogen and sulfur; or a 5-, 6-, 7-, or 8-membered ring containing one, two or three heteroatoms wherein the heteroatoms are independently selected from nitrogen, oxygen and sulfur. The 5-membered ring has 0 or 1 double bond. The 6-membered ring has 0, 1 or 2 double bonds. The 7- or 8-membered ring has 0, 1, 2 or 3 double bonds. Representative examples of monocyclic ring systems include, but are not limited to, azetidinyl, azepanyl, azepinyl, diazepinyl, diazepanyl, dioxolanyl, dioxanyl, dithianyl, imidazolinyl, imidazolidinyl, isothiazolinyl, isothiazolidinyl, isoxazolinyl, isoxazolidinyl, morpholinyl, 3-oxo-morpholinyl, oxadiazolinyl, oxadiazolidinyl, oxazolinyl, 2-oxo-oxazolinyl, oxazolidinyl, piperazinyl, piperidyl, pyranyl, pyrazolinyl, pyrazolidinyl, pyrrolinyl, pyrrolidinyl, tetrahydrofuryl, tetrahydropyranyl, tetrahydropyridyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, 1,4-diazepanyl and trithianyl. Bicyclic ring systems are exemplified by any of the above monocyclic ring systems fused to a phenyl group, a monocyclic cycloalkenyl group, as defined herein, a monocyclic cycloalkyl group, as defined herein, or an additional monocyclic heterocycle group, as defined herein. Representative examples of bicyclic ring systems include but are not limited to, benzodioxinyl, benzopyranyl, benzothiopyranyl, 2,3-dihydroindolyl, indolizinyl, pyranopyridinyl, tetrahydroisoquinolinyl, tetrahydroquinolinyl, thiopyranopyridinyl, 2-oxo-1,3-benzoxazolyl, 3-oxo-benzoxazinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, and octahydropyrrolo[3,4-c]pyrrolyl. The monocyclic or bicyclic ring systems as defined herein may have two of the non-adjacent carbon atoms connected by a heteroatom selected from nitrogen, oxygen or sulfur, or an alkylene bridge of between one and three additional carbon atoms. Representative examples of monocyclic or bicyclic ring systems that contain such connection between two non-adjacent carbon atoms include, but not limited to, 2-azabicyclo[2.2.2]octyl, 3-azabicyclo[3.2.2]nonyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 3,4-diazabicyclo[3.2.0]heptyl, 2-azabicyclo[2.1.1]hexyl, 5-azabicyclo[2.1.1]hexyl, 3-azabicyclo[3.1.1]heptyl, 6-oxa-3-azabicyclo[3.1.1]heptyl, 8-azabicyclo[3.2.1]octyl, 3-oxa-8-azabicyclo[3.2.1]octyl, 1,4-oxazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, octahydro-1H-4,7-methanoisoindolyl, (3aR,7a5)octahydro-2H-4,7-epoxyisoindolyl and octahydro-1H-4,7-epoxyisoindolyl. The heterocycle groups of the invention are substituted or unsubstituted, and are connected to the parent molecular moiety through any substitutable carbon or nitrogen atom in the groups. The nitrogen heteroatom may or may not be quaternized, and may or may not be oxidized to the N-oxide. In addition, the nitrogen containing heterocyclic rings may or may not be N-protected.

The term "heteroaryl" as used herein, refers to an aromatic five- or six-membered ring where at least one atom is selected from the group consisting of N, O, and S, and the remaining atoms are carbon. The five membered rings have two double bonds, and the six membered rings have three double bonds. The term "heteroaryl" also includes bicyclic systems where a heteroaryl ring is fused to a phenyl group, a monocyclic cycloalkyl group, as defined herein, a heterocycle group, as defined herein, or an additional heteroaryl group. Representative examples of heteroaryl groups include, but not limited to, benzothienyl, benzoxazolyl, benzimidazolyl, benzoxadiazolyl, 4,5-dibenzofuranyl, 6,7-dibenzofuranyl, 6,7-dihydro-1,3-benzothiazolyl, furyl, imidazolyl, imidazo[1,2-a]pyridinyl, indazolyl, indolyl, isoindolyl, isoxazolyl, isoquinolinyl, isothiazolyl, naphthyridinyl, oxadiazolyl, oxazolyl, pyridoimidazolyl, pyridyl, pyridazinyl, pyrimidinyl, pyrazinyl, pyrazolyl, pyrrolyl, quinolinyl, thiazolyl, thienopyridinyl, thienyl, triazolyl, thiadiazolyl, tetrazolyl, 1,2,3,4-tetrahydro-1,8-naphthyridine, 5,6,7,8-tetrahydroquinoline 2,3-dihydrospiro[indene-1,4-piperidine]amine, and triazinyl. The heteroaryl groups of the present invention can be substituted or unsubstituted, and are connected to the parent molecular moiety through any substitutable carbon or nitrogen atom in the groups. In addition, the nitrogen heteroatom may or may not be quaternized, and may or may not be oxidized to the N-oxide. Also, the nitrogen containing rings may or may not be N-protected.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis,* 2nd edition, John Wiley & Sons, New York (1991). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—), t-butylsulfinyl (t-Bu-S(O)—) and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The term "treating" as used herein, refers to reversing, alleviating, inhibiting the progress of, or preventing the disorder or condition, or one or more symptoms of such disorder or condition to which such term applies. The term "treatment", as used herein, refers to the act of treating, as "treating" is defined immediately above.

A "patient" is any individual treated with a compound of the present invention, or a therapeutically acceptable salt, solvate, prodrug, or salt of a prodrug, as defined herein. Patients include humans, as well as other animals such as companion animals (e.g. dogs and cats) and livestock. Patients may be experiencing one or more symptoms of a condition responsive to $P2X_7$ modulation (e.g. pain, inflammation, arthritis), or may be free of such symptom(s) (i.e. treatment may be prophylactic).

This invention is intended to encompass compounds having Formula (I) or (II), when prepared by synthetic processes or by metabolic processes. Preparation of the compounds of the invention by metabolic processes includes those occurring in the human or animal body (in vivo) or processes occurring in vitro.

The compounds of the invention can comprise asymmetrically substituted carbon atoms known as chiral centers. These chiral centers are designated as "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The compounds of this invention may exist as single stereoisomers (e.g., single enantiomers or single diastereomer), mixtures of stereoisomers (e.g. any mixture of enantiomers or diastereomers) or racemic mixtures. All such single stereoisomers, mixtures and racemates are intended to be encompassed within the scope of the invention. Compounds identified herein as single stereoisomers are meant to describe compounds that are present in a form that are substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral carbons present in the chemical structures illustrated herein is not specified, the chemical structure is intended to encompass compounds containing either stereoisomer of each chiral center present in the compound.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate optically pure (enantiomerically pure) or substantial optically pure materials and synthetic reactions which do not cause racemization or inversion of stereochemistry at the chiral centers. Mixtures of stereoisomers of compounds, including racemic mixtures, resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography or crystallization/re-crystallization. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

Alternatively, salts of the enantiomers in the mixture can be prepared by any suitable method known in the art, including treatment of the carboxylic acid with a suitable optically pure base such as, but are not limited to, alkaloids and phenethylamine, followed by precipitation or crystallization/re-crystallization of the enantiomerically pure salts. Methods mentioned herein above and other useful methods for the resolution/separation of a mixture of stereoisomers, including racemic mixtures, may be found in "*Enantiomers, Racemates, and Resolutions*," J. Jacques et al., 1981, John Wiley and Sons, New York, N.Y., the disclosure of which is incorporated herein by reference.

The compounds of this invention may possess one or more unsaturated carbon-carbon double bonds. All double bond isomers, both the cis (Z) and trans (E) isomers, and mixtures thereof are intended to be encompassed within the scoped of the present invention. Where a compound exists in various tautomeric forms, a recited compound is not limited to any one specific tautomer, but rather is intended to encompass all tautomeric forms.

The term "therapeutically acceptable salt" or "pharmaceutically acceptable salt" is intended to describe a salt or zwitterions of a compound of the invention and retains the biological effectiveness of the free acid or base of the specified compound without undue toxicity, irritation, and allergic response, commensurate with a reasonable benefit/risk ratio, effective for their intended use and is not biologically or otherwise undesirable; and as used herein, the term "therapeutically acceptable salt" or "pharmaceutically acceptable salt" refers to salts that are well known in the art. For example, S. M Berge et al. describe pharmaceutically acceptable salts in detail in *J. Pharmaceutical Sciences,* 66:p 1-19, 1977).

The invention also relates to acid addition salts of Formula (I) or Formula (II). If an inventive compound contains a basic moiety a desired salt may be prepared by any suitable method known in the art, including treatment of the free base with an inorganic acid such as, but are not limited to, hydrochloric acid, hydrobromic acid, sulfuric acid, nitric acid, and phosphoric acid, or with an organic acid such as, but are not limited to, acetic acid, trichloroacetic acid, trifluoroacetic acid, maleic acid, succinic acid, mandelic acid, fumaric acid, malonic acid, pyruvic acid, oxalic acid, glycolic acid, salicylic acid, pyranosidyl acid such as glucuronic acid or galacturonic acid, alpha-hydroxy acid such as citric acid or tartaric acid, amino acid such as aspartic acid or glutamic acid, aromatic acid such as benzoic acid or cinnamic acid, sulfonic acid such as p-toluenesulfonic acid, methanesulfonic acid, ethanesulfonic acid or the like. Examples of therapeutically acceptable salts include acetates, acrylates, adipates, alginates, aspartates, benzenesulfonates, benzoates, bisulfates, bisulfites, bromides, butyne-1,4-dioates, butyrates, camphorates, camphorsulfonates, caproates, caprylates, chlorides, chlorobenzoates, citrate, decanoates, digluconate, dinitrobenzoates, formates, fumarates, glutamates, glycerophosphate, glycollates, hemisulfate, heptanoates, hexanoates, hexyne-1,6-dioates, hydroxybenzoates, γ-hydroxybutyrates, iodides, isethionate, isobutyrates, lactates, mandelates, malonates, maleates, methanesulfonates, methoxybenzoates, methylbenzoates, naphthylenesulfonate, nicotinates, oxalates, pamoates, pectinates, persulfates, phenylacetates, phenylbutrates, phenylpropionates, phthalates, phosphates, picrates, pivalates, propanesulfonates, propionates, propiolates, p-toluenesulfonates, pyrosulfates, sebacates, suberates, succinates, sulfates, sulfites, tartrates, trichloroacetates, trifluoroacetates, undecanoates, and the like. Also, the basic nitrogen-containing groups can be quaternized with such agents as acids such as hydrochloric acid, hydrobromic acid, trifluoroacetic acid or acetic acid, lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Compounds of the present invention may contain an acid moiety such as a carboxyl group, it is understood that the invention also encompasses the base addition salts. Such a desired salt may be prepared by any suitable method known to the art, including treatment of the free acid with an inorganic or organic base, such as amine (primary, secondary, or tertiary), an alkali metal or alkaline earth metal hydroxide, carbonates, bicarbonates or the like. Illustrative examples of suitable salts include organic salts derived from amino acids such as glycine and arginice, ammonia, primary, secondary, and tertiary amines, and cyclic amines, such as ethylene diamine, dicyclohexylamine, ethanolamine, piperidine, morpholine, and peperazine, as well as inorganic salts derived from sodium, calcium, potassium, magnesium, manganese, iron, copper, zinc, aluminum, and lithium.

In addition, solvates of the compounds of Formula (I) or Formula (II) are meant to be included in this invention. The term "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, or solvates may exist is different crystal forms, all of which are intended to be within the scope of the present invention.

This invention also encompasses pharmaceutical compositions containing and methods of treating or preventing comprising administering prodrugs or salt of a prodrug of compounds having Formula (I) or Formula (II). The term "prodrug" are considered to be any covalently bonded carriers which release the active parent drug of formula (I) or (II) in vivo metabolically or by solvolysis when such prodrugs is administered to a mammalian subject. Prodrugs of the compounds of formula (I) or (II) can be prepared by modifying functional groups present in the compounds in such a way that the modifications are cleaved, either in routine manipulation or in vivo, to the parent compounds respectively. Examples of such modification include, but not limited to, treatment of a compound of formula (I) or (II), containing an amino, amido, or hydroxyl moiety with a suitable derivatising agent, for example, a carboxylic acid halide or acid anhydride, or treatment of a compound of formula (I) or (II) containing a carboxyl moiety, to an ester, amide, carbonates or carbamates, or conversion of a compound of formula (I) or (H), containing a carboxylic acid ester moiety to an enol-ester. Compounds of Formula (I) or (II) having free amino, hydroxyl or carboxylic groups can also be converted to prodrugs by peptide bond formation with an amino acid residue, or a polypeptide chain of two or more (e.g. two, three or four) amino acid residues. The amino acid residues include the 20 naturally occurring amino acids commonly designated by three letters symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs include, but are not limited to, compounds of Formula (I) or (II) wherein hydroxy, amine, carboxy, or sulfhydryl groups are covalently bonded to any group that, when administered to a mammalian subject, cleaves under physiological conditions to form a free hydroxyl, amino, carboxy, or sulfhydryl group, respectively. Examples of prodrugs include, but are not limited to, acetate, formate, and benzoate derivatives of the hydroxy, carboxy and amine functional groups in the compounds of formula (I) or (II). A thorough discussion is provided in T. Higuchi and V. Stella, *Pro-drugs as Novel Delivery Systems,* V. 14 of the A.C.S. Symposium Series, and in Edward B. Roche, ed., Bioreversible Carriers in Drug Design, American Pharmaceutical Association and Pergamon Press, 1987, hereby incorporated by reference.

In accordance with methods of treatment and pharmaceutical compositions of the invention, the compounds of formula (I) or (II), or therapeutically acceptable salt, solvate, prodrug or salt of a prodrug thereof, can be administered alone or be administered in the form of a pharmaceutical composition in which the compound of Formula (I) or Formula (II), or a therapeutically acceptable salt, solvate, prodrug, salt of a prodrug, or combination thereof, in combination with a pharmaceutically acceptable carriers, adjuvants, diluents, vehicles, or combinations thereof.

The term "pharmaceutically acceptable carrier, adjuvants, diluents or vehicles" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be formulated in a conventional manner using one or more of the aforementioned pharmaceutically acceptable carriers. Thus the compounds of the present invention, its therapeutically acceptable salt, solvate, prodrug, salt of its prodrug, may be administered to humans and other mammals in solid or liquid form, orally, rectally, parenterally, intracisternally, intravaginally, topically (as by powders, ointments, drops, inhalants, spray, transdermal patch, and the like), or bucally. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions that can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin); f) absorption accelerators such as quaternary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions that can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

When used in the above or other treatments, a therapeutically effective amount of one of the compounds of the present invention can be employed in pure form or, where such forms exist, in therapeutically acceptable salt, solvate, ester, amide, prodrug, salt of a prodrug, or combination thereof. Alternatively, the compound can be administered as a pharmaceutical composition containing a therapeutical effective amount of the compound of present invention, or a therapeutically acceptable salt, solvate, ester, amide, prodrug, salt of a prodrug, or combination thereof, in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated; the treatment desired; the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds having Formula (I) or Formula (II), or a therapeutically acceptable salt, solvate, prodrug, or salt of a prodrug, administered to a human or other mammal may range from about 0.003 to about 50 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade, CDP-870 and Humira) and TNF receptor immunoglobulin molecules (such as Enbrel®), or COX-2 inhibitors (such as meloxicam, celecoxib, rofecoxib, valdecoxib and eoricoxib).

The compounds of the present invention may also be used in combination with existing therapeutic agents for the treatment of osteoarthritis. Suitable agents to be used in combination include standard non-steroidal anti-inflammatory agents such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as asprin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comp inhibitors such as Tasmar, A-2 inhibitors, dopamine reuptake inhibitors, NMDA antagonists, Nicotine agonists, dopamine agonists and inhibitors or neuronal nitric oxide synthase), and anti-Alzheimer's drugs such as donepezil, tacrine, COX-2 inhibitors, propentofyline or metryfonate.

The compounds of the present invention may also be used in combination with osteoporosis agents such as roloxifene, droloxifene, lasofoxifene or fosomax.

The compounds of the present invention may also be used in combination with immunosuppressant agents such as FK-506, rapamycin, cyclosporine, azathioprine, and methotrexate.

Synthetic Methods

Abbreviations which have been used in the descriptions of the schemes and the examples that follow are: DMSO is dimethylsulfoxide and THF is tetrahydrofuran.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, B, E, Z, $R^1$, $R^2$, $R^3$, $R^4$, $R^5$, $R^6$, $R^7$, $R^8$, m and v are as defined above unless otherwise noted below.

Compounds of the invention may be prepared by a variety of synthetic routes. Representative procedures are described in Scheme 1 as shown below:

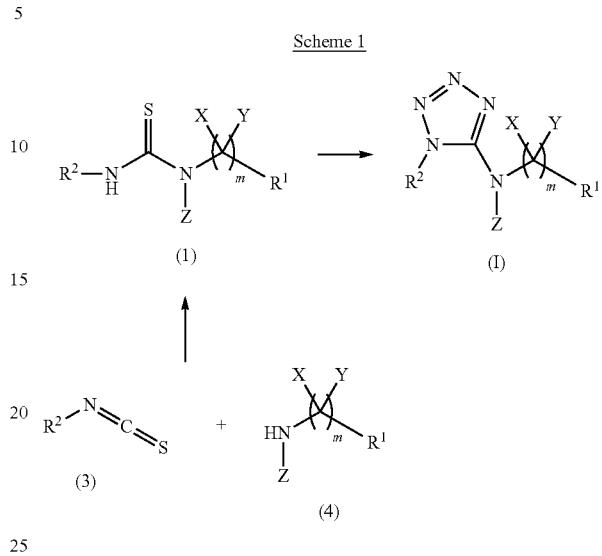

Aminotetrazoles can be prepared by a variety of procedures. Examples of such construction can be found in Atherton, F. R.; Lambert, R. W., *Tetrahedron* 1983, 39, 2599-2608, Imhof, R.; Ladner, D. W.; Muchowski, J. M. *J. Org. Chem.* 1977, 42, 3709-3713, or Robert A. Batey and David A. Powell, *Org. Lett.* 2000, 2, 3237-3240. In particular, aminotetrazoles of formula (I) can be prepared from thioureas of formula (1), an azide reagent and mercury (II) salts, in the presence or absence of a base, and in a solvent such as, but not limited to, tetrahydrofuran, N,N-dimethylformamide, acetonitrile, 1,4-dioxane and methanol. Examples of the azide reagents include, but are not limited to, sodium azide and trimethylsilyl azide. Examples of the mercury (II) salts include, but are not limited to, mercury (II) chloride, mercury (II) bromide, mercury (II) iodide and mercury (II) acetate. Examples bases include, but are not limited to, triethylamine, diisopropylethyl amine, pyridine, 4-dimethylaminopyridine, 1,8-diazabicyclo[5.4.0]undec-7-ene, potassium carbonate and N-methylmorpholine. The thioureas of formula (1) can be purchased commercially or prepared from amines of formula (4) and isothiocyanates of formula (3) in a solvent such as, but are not limited to, dichloromethane, tetrahydrofuran, chloroform, diethylether, acetonitrile, 1,4-dioxane, N,N-dimethylformamide and toluene. The resulting thioureas can be used in situ or purified and isolated. Compounds of Formula (II) may be prepared similarly.

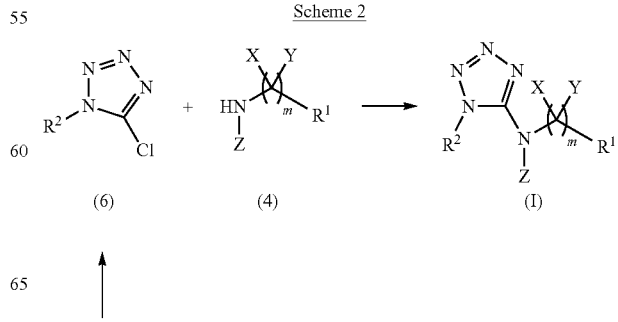

-continued

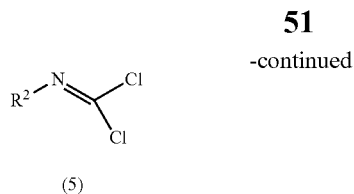

(5)

Alternatively, compounds of formula (I) wherein $R^2$, X, Y, Z, m, and $R^1$ are as defined in formula (I) can also be prepared from compounds of formula (5) as shown in Scheme 2.

Compounds of formula (5) wherein $R^2$ is as defined in formula (I) can be prepared as described in Kuehle, Engelbert; Anders, Bertram, Zumach and Gerhard; *Angewandte Chemie* (1967), 79(15), 663-80. Chloro-tetrazoles of formula (6) can be obtained from the reaction of compounds of formula (5) with an azide reagent such as, but not limited to, sodium azide, and tetrabutyl ammonium bromide. The reaction is generally conducted in a mixture of solvents such as, but not limited to, toluene/water, benzene/water, dichloromethane/water or xilene/water.

Displacement of the chloro-tetrazoles of formula (6) with amines of formula (4) can be achieved in the presence of a base such as, but not limited to, triethylamine. The reaction is generally conducted in a solvent such as, but not limited to, tetrahydrofuran, dioxane or 1,2-dimethoxyethane at a temperature from about room temperature to about 150° C.

Compounds of formula (II) can also be prepared similarly.

Scheme 3

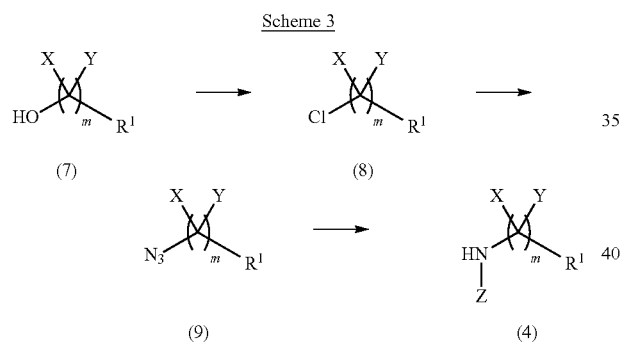

Amines of formula (4) wherein Z is hydrogen, and X, Y, m and $R^1$ are as defined in formula (I), can be prepared from alcohols of formula (7) as shown in Scheme 3. Alcohols of formula (7) can be reacted with neat thionyl chloride or using a solvent such as, but not limited to, dichloromethane or chloroform to provide chlorides of formula (8). Displacement of chlorides of formula (8) with sodium azide in a solvent such as, but not limited to, N,N-dimethylformamide or acetone, provides azides of formula (9), which can be reduced to amines of formula (4) in the presence of a reducing agent such as, but not limited to, palladium/carbon or $PtO_2$/carbon. The reaction can be performed in a solvent such as, but not limited to, ethanol, methanol or ethyl acetate.

Scheme 4

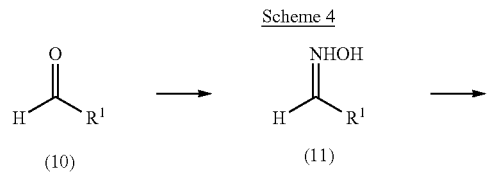

-continued

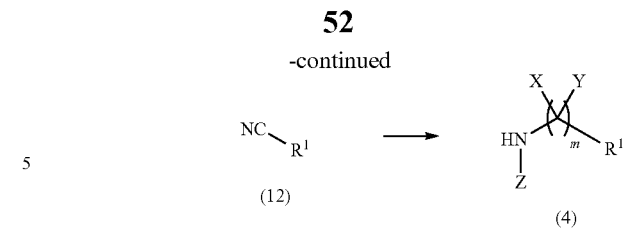

Amines of formula (4) wherein X, Y and Z are hydrogen and m is 1, can be prepared from the corresponding aldehydes of formula (10) as depicted in Scheme 4. Reaction of the aldehydes of formula (10) with hydroxylamine hydrochloride in an alcoholic solvent such as, but not limited to, ethanol, provides oximes of formula (11). Oximes of formula (11) can be converted to nitriles of formula (12) in the presence of acetic anhydride and a base such as, but not limited to, potassium hydroxide or sodium hydroxide. Reduction of the nitriles of formula (12) with Raney/nickel and ammonia can be performed in an alcoholic solvent such as, but not limited to, methanol.

Scheme 5

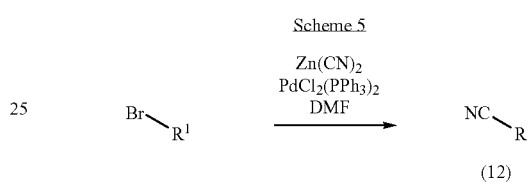

Nitriles of formula (12) wherein $R^1$ is aryl or heteroaryl can be prepared by displacement of an the corresponding 1 bromides with zinc cyanide in the presence of a palladium catalyst, such as but not limited to, bis(triphenylphospine)palladium (II) chloride and in a solvent such as N,N-dimethylformamide.

Scheme 6

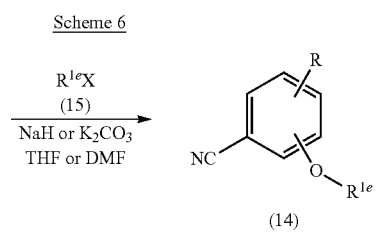

Certain ether-containing arylnitriles of formula (14) wherein R hydrogen or the substituents of $R^1$ of formula (I) and $R^{1e}$ is as defined in formula (I), can be prepared by reaction of a hydroxybenzonitriles of formula (13) with halides of formula (15) wherein X is fluoro or chloro, in the presence of a base such as, but not limited to, sodium hydride or potassium carbonate. The reaction can be conducted in a solvent such as tetrahydrofuran, dimethylformamide or dioxane at a temperature from about room temperature to about 150° C.

Scheme 7

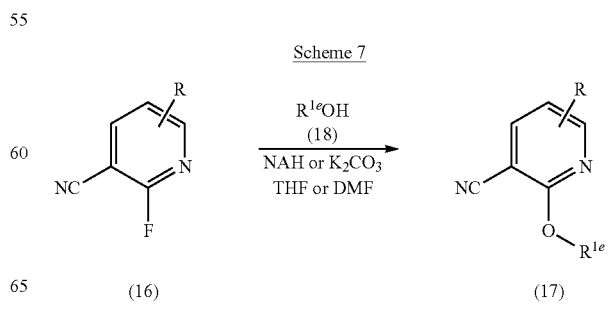

Nicotinonitriles of formula (17) with an ether linkage in the 2-position wherein $R^{1e}$ is as defined in formula (I), and R is hydrogen or the substitutent of $R^1$ in formula (I), can be prepared by reaction of optionally substituted 2-fluoronicotinonitriles of formula (16), with alcohols of formula (18) in the presence of a base such as sodium hydride or potassium carbonate. The reaction can be conducted in a solvent such as tetrahydrofuran, dimethylformamide or dioxane at a temperature from about room temperature to about 150° C.

Scheme 8

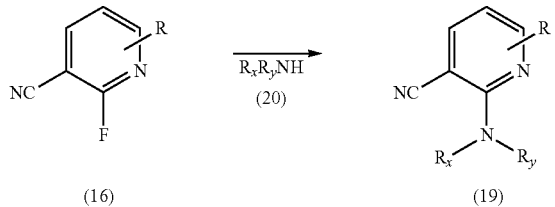

Nicotinonitriles of formula (19) with an amino linkage in the 2-position, wherein $R_x$ and $R_y$ are independently selected from the group consisting of hydrogen, aryl, heteroaryl, alkyl, cycloalkyl and heterocycle and R is hydrogen or the same as the substituent of $R^1$ of formula (I), can be prepared by reaction of optionally substituted 2-fluoronicotinonitriles of formula (16) with an appropriate primary or secondary amine of formula (20), in the presence of a base such as sodium hydride or potassium carbonate. The reaction can be conducted in a solvent such as tetrahydrofuran, dimethylformamide or dioxane at a temperature from about room temperature to about 150° C.

Scheme 9

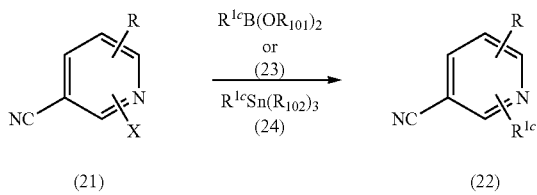

Nicotinonitriles of formula (22) wherein R is hydrogen or the same as the substituents of $R^1$ in formula (I) and $R^{1c}$ is as defined in formula (I), can be prepared by reaction of nitriles of formula (21) wherein X is Cl, Br, I or triflate with an appropriate boronic acid or ester of formula (23) wherein $R_{101}$ is hydrogen or alkyl, in the presence of a palladium catalyst, such as but not limited to, bis(triphenylphospine) palladium (II) chloride and a base such as triethylamine or sodium carbonate. The reaction can be effected by heating from 50-90° C. in solvents such as isopropanol, ethanol, dimethoxyethane, water or dioxane. Alternatively, this transformation can be accomplished using an tin reagent of formula (24) wherein $R_{102}$ is alkyl, with a palladium catalyst such as, but not limited to, tetrakis(triphenylphosphine)palladium(0), and cesium fluoride and heating in a solvent such as dioxane. These transformations can also be effected by heating in a microwave reactor.

Scheme 10

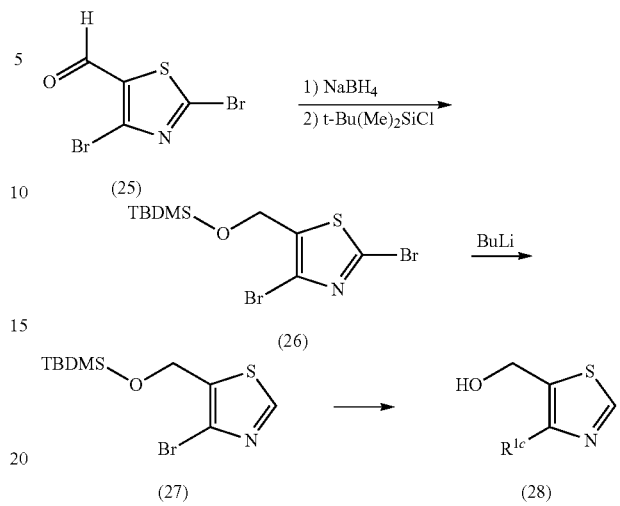

Alcohols of formula (7) where $R^1$ is a substituted thiazole can be prepared as shown in Scheme 10. The aldehyde of formula (25) can be reduced with sodium borohydride then protected as the t-butyldimethylsilyl ether, followed by mono-debromination with n-butyl lithium. The mono-bromothiazole of formula (27) can then be reacted with boronic acid of formula (23) using a palladium catalyst such as but not limited to, bis(triphenylphospine)palladium (II) chloride, and a base such as triethylamine or sodium carbonate with heating from 50-90° C. in a solvent such as isopropanol or dioxane. Solvent mixtures of dimethoxyethane, water and ethanol can also be used. Alternatively, this transformation can be accomplished using tin reagent of formula (24), a palladium catalyst such as, but not limited to, tetrakis(triphenylphosphine)palladium(0), and cesium fluoride and heating in a solvent such as dioxane. These transformations can also be effected by heating in a microwave reactor.

Scheme 11

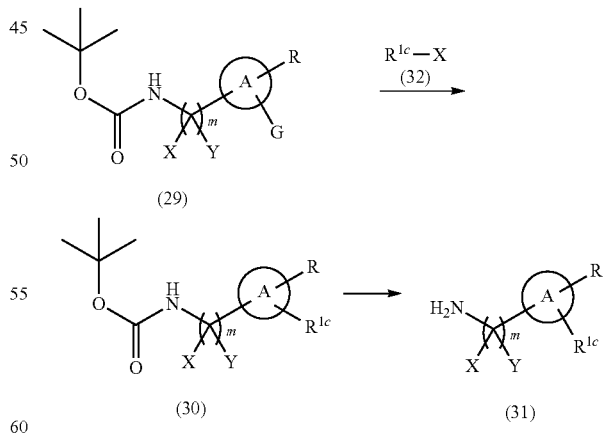

Amines of formula (31) wherein A is the ring as represented as $R^1$ of formula (I), R is hydrogen or the same as the substituents of $R^1$ in formula (I), and X, Y, m and $R^{1c}$ are as defined in formula (I), can be prepared as shown in Scheme 11. The N-boc protected boronic acid of formula (29) wherein G is $B(OH)_2$ can be reacted with compounds of formula (32)

wherein X is Cl, I, Br, or triflate, in the presence of a palladium catalyst, such as but not limited to, bis(triphenylphosphine)palladium (II) chloride, and a base such as triethylamine or sodium carbonate. The reaction can be effected by heating from 50-90° C. and is generally conducted in a solvent such as, but not limited to, isopropanol or dioxane. Solvent mixtures of dimethoxyethane, water and ethanol can also be used. Alternatively, this transformation can be accomplished using tin reagent of formula (29) wherein G is $Sn(alkyl)_3$ in the presence of a palladium catalyst such as, but not limited to, tetrakis(triphenylphosphine)palladium(0), and cesium fluoride. The reaction is generally effected by heating and performed in a solvent such as dioxane. These transformations can also be effected by heating in a microwave reactor. The N-boc protecting group can be removed by reaction with an acid such as, but not limited to, trifluoroacetic acid or hydrochloric acid in a solvent such as dichloromethane or ether.

Determination of Biological Activity

Tissue Culture: Cells of the THP-1 monocytic cell line (American Type Culture Collection, Rockville, Md.) were maintained in the log phase of growth in RPMI medium containing high glucose and 10% fetal calf serum (Invitrogen, Carlsbad, Calif.) according to established procedures (Humphrey B D and Dubyak G R (1996), Induction of the P2z/P2X7 Nucleotide Receptor and Associated Phospholipase D Activity by Lipopolysaccharide and IFN-γ in the Human THP-1 Monocytic Cell Line. *J. Immunology* 157:5627-37). Fresh vials of frozen THP-1 cells were initiated for growth every eight weeks. To differentiate THP-1 cells into a macrophage phenotype, a final concentration of 25 ng/ml of lipopolysaccharide (LPS) and 10 ng/ml of IFNγ were added to the cells either for 3 hours for IL-1β release assays or overnight (16 hours) for pore formation studies.

$P2X_7$ Mediated Pore Formation. Activation of the $P2X_7$ receptor induces nonspecific pore formation and eventually cell lysis (Verhoef et al., *The Journal of Immunology*, Vol. 170, pages 5728-5738, 2003). Accordingly, the inhibitory activity of the antagonists of the present invention was determined by their capacity to inhibit the agonist-induced pore formation using the fluorescent dye YO-PRO (MW=629) and Fluorometric Imaging Plate Reader (FLIPR, Molecular Devices, Sunnydale, Calif.). Prior to YO-PRO dye addition, the cells were rinsed once in PBS without $Mg^{2+}$ or $Ca^{2+}$ ions, which have been shown to inhibit pore formation (Michel et al., *N-S Arch Pharmacol* 359:102-109, 1999). The YO-PRO iodide dye (1 mM in DMSO) was diluted to a final concentration of 2 μM in phosphate buffered saline (PBS without $Mg^{2+}$ or $Ca^{2+}$) and then placed on the cells prior to the addition of the agonist BzATP. Since the THP-1 cells are a non-adherent cell line, the cells were washed in PBS and loaded with the dye in a conical tube prior to spinning the cells onto poly-lysine-coated black-walled 96-well plates, which were utilized to reduce light scattering. After the addition of the agonist BzATP (50 μM, the $EC_{70}$ value for agonist activation), the YO-PRO dye uptake was observed in the FLIPR apparatus equipped with an Argon laser (wavelength=488 nm) and a CCD camera. The intensity of the fluorescence was captured by the CCD camera every 15 seconds for the first 10 minutes of agonist exposure followed by every 20 seconds for an additional 50 minutes with the data being digitally transferred to an interfaced PC. The exposure setting of the camera was 0.25 sec with an f-stop setting of 2. Solutions of antagonist compounds were prepared by serial dilutions of a 10 mM DMSO solution of the antagonist into the buffer solution with the YO-PRO dye. Antagonist compounds were tested for activity over a concentration range from 0.003 to 100 μM. The test compounds were incubated for 10 minutes with the THP-1 cells at room temperature, after which the cells were stimulated with BzATP and fluorescence measured as described above in the absence of the antagonist. For antagonist activity measurements, the percent maximal intensity was normalized to that induced by 50 μM BzATP and plotted against each concentration of compound to calculate $IC_{50}$ values and account for plate-to-plate variability.

The potency of the compounds was inversely proportional to their $IC_{50}$ value. Representative compounds of the present invention when tested with the above assay demonstrated antagonist activity at the $P2X_7$ receptor.

$P2X_7$ Mediated IL-1β Release: Activation of P2X7 receptors also induces secretion of IL-1β (Verhoef et al., above; Brough et al., *Molecular and Cellular Neuroscience*, Vol. 19, pages 272-280, 2002). THP-1 cells were plated in 24-well plates at a density of $1 \times 10^6$ cells/well/ml. On the day of the experiment, cells were differentiated with 25 ng/ml LPS and 10 ng/ml final concentration of γIFN for 3 hours at 37° C. Solutions of antagonist compounds were prepared by serial dilutions of a 10 mM DMSO solution of the antagonist into the PBS solution. In the presence of the differentiation media, the cells were incubated with the antagonists of the present invention for 30 minutes at 37° C. followed by a challenge with 1 mM BzATP for an additional 30 minutes at 37° C. Supernatants of the samples were collected after a 5 minute centrifugation in microfuge tubes to pellet the cells and debris and to test for mature IL-1β released into the supernatant using either R & D Systems Human IL-1β ELISA assay or Endogen Human IL-1β ELISA, following the manufacturer's instructions. The maximum IL-1β, release at each concentration of test compound was normalized to that induced by BzATP alone to determine the activity of the test compound. Antagonist compounds were tested for activity over a concentration range from 0.001 to 100 μM. Antagonist potency was expressed as the concentration producing a 50% reduction in release of IL-1β or $IC_{50}$. For each experiment, differentiated control cells were also measured over the 60 min time course of the assay to assess background IL-1β accumulation. This non-specific background IL-1β release, typically averaged 3-8% of the maximum BzATP response, was subtracted from the maximum BzATP-induced release and all release values normalized to the BzATP-induced response. Representative compounds of the present invention when tested with the above assay demonstrated antagonist activity at the $P2X_7$ receptor.

For all in vitro experiments, compounds of the present invention had $IC_{50}$ lower than 10 μM, preferably lower than 0.5 μM, and most preferably lower than 0.05 μM.

Determination of Analgesic Activity

Adult male Sprague-Dawley rats (250-300 g), Charles River Laboratories, Portage, Mich. were used in this study. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Spinal Nerve ligation: A model of spinal nerve ligation-induced neuropathic pain was produced using the procedure originally described by Kim and Chung (Kim and Chung, *Pain*, Vol. 50 pages 355-363, 1992). The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least 1 week and not more than 3 weeks prior to assessment of mechanical allodynia. Mechanical allodynia in the left hind paw was confirmed by comparing the paw withdrawal threshold in grams for the injured left paw and the uninjured right paw. Mechanical allodynia was measured using calibrated von Frey filaments (Stoelting, Wood Dale, Ill.). Rats were placed into inverted individual plastic containers (20×12.5×20 cm) on top of a suspended wire mesh grid, and acclimated to the test chambers for 20 min. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, *Ann. Rev. Pharmacol. Toxicol. Vol.* 20, pages 441-462, 1980). Prior to compound administration, animals demonstrating motor deficit or failure to exhibit subsequent mechanical allodynia were excluded from further studies. The antinociceptive activity of a test compound was determined by comparing its ability to increase the paw withdrawal threshold of the injured left paw relative to vehicle (0%) and the uninjured right paw (100%). Activity of test compounds was determined 60 minutes after an oral dose or 30 minutes after an intraperitoneal dose. Dose-response curves as well as single dose responses were performed. Representative compounds of the present invention exhibited antinociceptive activity in this assay.

C Freund's adjuvant-induced thermal hyperalgesia: Unilateral inflammation was induced by injecting 150 μl of a 50% solution of complete Freund's adjuvant (CFA) (Sigma Chemical Co., St. Louis, Mo.) in physiological saline into the plantar surface of the right hindpaw of the rat. The hyperalgesia to thermal stimulation was determined 48 hr after CFA injections using a commercially available paw thermal stimulator (UARDG, Department of Anesthesiology, University of California, San Diego, La Jolla, Calif.). Rats were placed individually in Plexiglass cubicles mounted on a glass surface maintained at 30° C., and allowed a 30 min habituation period. A thermal stimulus, in the form of radiant heat emitted from a focused projection bulb, was then applied to the plantar surface of each hind paw. The stimulus current was maintained at 4.5 Amp and the maximum time of exposure was set at 20 sec to limit possible tissue damage. In each test session, each rat was tested in 3 sequential trials at approximately 5 min intervals. Paw withdrawal latencies were calculated as the mean of the two shortest latencies. The antinociceptive activity of a test compound was determined by comparing its ability to increase the paw withdrawal threshold of the injured right paw relative to vehicle (0%) and the uninjured left paw (100%). Activity of test compounds was determined 60 minutes after an oral dose or 30 minutes after an intraperitoneal dose. Dose-response curves as well as single dose responses were performed. Representative compounds of the present invention exhibited antinociceptive activity in this assay.

Zymosan Method: Mice were dosed with experimental compounds orally or subcutaneously 30 minutes prior to injection of zymosan. Mice were then injected intraperitonealy with 2 mgs/animal of zymosan suspended in saline. Four hours later the animals were euthanized by $CO_2$ inhalation and the peritoneal cavities were lavaged with 2×1.5 mL of ice cold phosphate buffered saline containing 10 units of heparin/mL. For IL-1β determination the samples were spun at 10,000×g in a refrigerated microfuge (4° C.), supernatants removed and frozen until ELISAs (Enzyme Linked Immuno-Assay) were performed. ELISAs were performed according to manufacture's instructions. IL-1β was determined relative to vehicle control. Representative compounds of the invention demonstrated inhibition of IL-1β release in a dose-dependent fashion. (Perretti M, Solito E, Parente L, *Agents Actions Vol.* 35(1-2) pages 71-78, 1992; Torok K, Nemeth K, Erdo F, Aranyi P, Szekely, J I, *Inflamm Res. Vol.* 44(6) pages 248-252, 1995.). Representative compounds of this invention exhibited inhibition of IL-1β release in this assay.

For all in vivo experiments, the compounds of the present invention had ED50 lower than 500 μmol/kg, preferably 50 μmol/kg.

The present invention will now be described in connection with certain preferred embodiments, which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Example 1

1-(2,3-dichlorophenyl)-N-[(2-methylphenyl)methyl]-1H-tetraazol-5-amine

2-Methylbenzylamine (89.1 mg, 0.735 mmol) in 8 ml of dry THF was treated with 2,3-dichlorophenylisothiocyanate (150 mg, 0.735 mmol). After stirring at room temperature for 1 hour, the mixture was treated with mercuric acetate (234.2 mg, 0.735 mmol) and sodium azide (143.3 mg, 2.21 mmol) and stirred at room temperature for 16 hours. The mixture was filtered through a pad of Celite and washed with ethyl acetate. The filtrate was concentrated under reduced pressure and purified by preparative HPLC on a Waters Symmetry C8 column (40 mm×100 mm, 7 μm particle size) using a gradient of 10% to 100% acetonitrile to ammonium acetate (10 mM) over 15 minutes at a flow rate of 70 mL/min to provide the title compound. MS (ESI$^+$) m/z 334 (M+H)$^+$; $^1$H NMR (300 MHz, DMSO-d$_6$) δ 2.29 (s, 3H), 4.46 (d, J=5.42 Hz, 2H), 7.16 (m, 3H), 7.26 (m, 1H), 7.57 (t, J=5.42 Hz, 1H), 7.60 (t, J=8.14 Hz, 1H), 7.71 (dd, J=7.97, 1.53 Hz, 1H), 7.93 (dd, J=8.14, 1.70 Hz, 1H).

Example 2

1-(2,3-dichlorophenyl)-N-[(1R)-2,3-dihydro-1H-inden-1-yl]-1H-tetraazol-5-amine

The title compound was prepared using the procedure described in Example 1 except using (1R)-2,3-dihydro-1H-inden-1-ylamine instead of 2-methylbenzylamine. MS (ESI$^+$) m/z 346 (M+H)$^+$; $^1$H NMR (300 MHz, DMSO-d$_6$) δ 1.90 (m, 1H), 2.53 (m, 1H), 2.84 (m, 2H), 5.35 (m, 1H), 7.22 (m, 4H), 7.53 (d, J=9.15 Hz, 1H), 7.57 (t, J=8.14 Hz, 1H), 7.70 (dd, J=9.00, 1.70 Hz, 1H), 7.90 (dd, J=9.00, 1.36 Hz, 1H).

Example 3

1-(2,3-dichlorophenyl)-N-[(2-morpholin-4-ylphenyl)methyl]-1H-tetraazol-5-amine

The title compound was prepared using the procedure described in Example 1 except using (2-morpholin-4-ylphenyl)methylamine instead of 2-methylbenzylamine. MS (ESI$^+$) m/z 405 (M+H)$^+$; $^1$H NMR (300 MHz, DMSO-d$_6$) δ 2.83 (m, 4H), 3.71 (m, 4H), 4.59 (d, J=5.76 Hz, 2H), 7.07 (m, 1H), 7.14 (dd, J=7.97, 1.19 Hz, 1H), 7.24 (dd, J=7.12, 1.70 Hz, 1H), 7.28 (m, 1H), 7.56 (t, J=5.76 Hz, 1H), 7.60 (t, J=7.97 Hz, 1H), 7.72 (dd, J=8.50, 1.70 Hz, 1H), 7.94 (dd, J=8.14, 1.70 Hz, 1H).

Example 4

1-(2,3-dichlorophenyl)-N-(pyridin-4-ylmethyl)-1H-tetraazol-5-amine

The title compound was prepared using the procedure described in Example 1 except using pyridin-4-ylmethylamine instead of 2-methylbenzylamine. MS (ESI$^+$) m/z 321 (M+H)$^+$; $^1$H NMR (300 MHz, DMSO-d$_6$) δ 4.51 (d, J=5.76 Hz, 2H), 7.31 (dd, J=6.00, 1.70 Hz, 2H), 7.64 (t, J=8.14 Hz, 1H), 7.77 (dd, J=8.45, 1.36 Hz, 1H), 7.82 (d, J=6.10 Hz, 1H), 7.97 (dd, J=8.45, 1.36 Hz, 1H), 8.51 (dd, J=6.00, 1.70 Hz, 2H).

Example 5

1-(2,3-dichlorophenyl)-N-{[2-(dimethylamino)phenyl]methyl}-1H-tetraazol-5-amine

The title compound was prepared using the procedure described in Example 1 except using 2-(aminomethyl)-N,N-dimethylaniline instead of 2-methylbenzylamine. MS (ESI$^+$) m/z 363 (M+H)$^+$; $^1$H NMR (300 MHz, DMSO-d$_6$) δ 2.62 (m, 6H), 4.57 (d, J=5.76 Hz, 2H), 7.01 (m, 1H), 7.12 (dd, J=7.97, 1.19 Hz, 1H), 7.20 (dd, J=7.29, 1.53 Hz, 1H), 7.26 (m, 1H), 7.59 (t, J=5.76 Hz, 1H), 7.61 (t, J=7.97 Hz, 1H), 7.72 (dd, J=8.45, 1.70 Hz, 1H), 7.94 (dd, J=8.14, 1.70 Hz, 1H).

Example 6

1-(2,3-dichlorophenyl)-N-(pyridin-3-ylmethyl)-1H-tetraazol-5-amine

The title compound was prepared using the procedure described in Example 1 except using pyridin-3-ylmethylamine instead of 2-methylbenzylamine. MS (ESI$^+$) m/z 321 (M+H)$^+$; $^1$H NMR (500 MHz, DMSO-d$_6$) δ 4.51 (d, J=5.62 Hz, 2H), 7.36 (dd, J=7.80, 4.68 Hz, 1H), 7.62 (t, J=8.11 Hz, 1H), 7.72 (m, 3H), 7.95 (dd, J=8.27, 1.40 Hz, 1H), 8.46 (dd, J=4.68, 1.56 Hz, 1H), 8.55 (d, J=1.87 Hz, 1H).

Example 7

1-(2,3-dichlorophenyl)-N-{[2-(pyridin-2-yloxy)phenyl]methyl}-1H-tetraazol-5-amine The title compound was prepared using the procedure described in Example 1 except using [2-(pyridin-2-yloxy)phenyl]methylamine hydrochloride and 1 equivalent of triethylamine instead of 2-methylbenzylamine. MS (ESI$^+$) m/z 413 (M+H)$^+$; $^1$H NMR (500 MHz, DMSO-d$_6$) δ 4.41 (d, J=5.93 Hz, 2H), 7.01 (d, J=8.11 Hz, 1H), 7.07 (dd, J=7.80, 0.94 Hz, 1H), 7.12 (dd, J=7.18, 4.99 Hz, 1H), 7.21 (m, 1H), 7.31 (m, 1H), 7.40 (d, J=7.49 Hz, 1H), 7.55 (t, J=5.77 Hz, 1H), 7.59 (t, J=7.80 Hz, 1H), 7.62 (dd, J=4.10, 1.87 Hz, 1H), 7.85 (m, 1H), 7.93 (dd, J=7.64, 2.03 Hz, 1H), 8.10 (dd, J=4.84, 2.03 Hz, 1H).

Example 8

1-(2,3-dichlorophenyl)-N-(2-pyridin-2-ylethyl)-1H-tetraazol-5-amine

The title compound was prepared using the procedure described in Example 1 except using 2-pyridin-2-ylethylamine instead of 2-methylbenzylamine. MS (ESI$^+$) m/z 335 (M+H)$^+$; $^1$H NMR (300 MHz, DMSO-d$_6$) δ 3.02 (t, J=7.29 Hz, 2H), 3.64 (m, 2H), 7.22 (m, 3H), 7.59 (t, J=7.63 Hz, 1H), 7.64 (dd, J=8.50, 2.03 Hz, 1H), 7.69 (m, 1H), 7.93 (dd, J=6.00, 2.37 Hz, 1H), 8.47 (m, 1H).

Example 9

1-(2,3-dichlorophenyl)-N-(1-methyl-1-phenylethyl)-1H-tetraazol-5-amine

The title compound was prepared using the procedure described in Example 1 except using 1-methyl-1-phenylethylamine instead of 2-methylbenzylamine. MS (ESI$^+$) m/z 348 (M+H)$^+$; $^1$H NMR (300 MHz, DMSO-d$_6$) δ 1.67 (s, 6H), 7.19 (t, J=7.17 Hz, 1H), 7.29 (m, 3H), 7.38 (m, 2H), 7.63 (t, J=7.91 Hz, 1H), 7.70 (dd, J=8.00, 1.84 Hz, 1H), 7.96 (dd, J=7.91, 1.65 Hz, 1H).

Example 10

1-(2,3-dichlorophenyl)-N-(2-pyridin-3-ylpropyl)-1H-tetraazol-5-amine

The title compound was prepared using the procedure described in Example 1 except using 2-pyridin-3-ylpropan-1-amine instead of 2-methylbenzylamine. MS (ESI$^+$) m/z 349 (M+H)$^+$; $^1$H NMR (300 MHz, DMSO-d$_6$) δ 1.18 (d, 3H), 2.83 (m, 2H), 4.00 (m, 1H), 7.02 (d, 1H), 7.28 (dd, 1H), 7.60 (m, 3H), 7.94 (m, 1H), 8.39 (m, 2H).

Example 11

1-(2,3-dichlorophenyl)-N-(quinolin-4-ylmethyl)-1H-tetraazol-5-amine

The title compound was prepared using the procedure described in Example 1 except using 1-quinolin-4-ylmethanamine instead of 2-methylbenzylamine. MS (ESI$^+$) m/z 371 (M+H)$^+$; $^1$H NMR (300 MHz, DMSO-d$_6$) δ 5.02 (d, 2H), 7.45 (d, 1H), 7.65 (m, 2H), 7.79 (m, 2H), 7.91 (t, 1H), 7.97 (dd, 1H), 8.05 (d, 1H), 8.19 (d, 1H), 8.85 (d, 1H).

Example 12

1-(2,3-dichlorophenyl)-N-(2-pyridin-3-ylethyl)-1H-tetraazol-5-amine

The title compound was prepared using the procedure described in Example 1 except using 2-pyridin-3-ylethanamine instead of 2-methylbenzylamine. MS (ESI$^+$) m/z 335 (M+H)$^+$; $^1$H NMR (300 MHz, DMSO-d$_6$) δ 2.89 (t, 2H), 3.52 (q, 2H), 7.22 (t, 1H), 7.30 (dd, 1H), 7.62 (m, 3H), 7.93 (dd, 1H), 8.41 (m, 2H).

Example 13

1-(2,3-dichlorophenyl)-N-[2-(2-methylphenyl)ethyl]-1H-tetraazol-5-amine

The title compound was prepared using the procedure described in Example 1 except using 2-(2-methylphenyl)ethanamine instead of 2-methylbenzylamine. MS (ESI$^+$) m/z 348 (M+H)$^+$; $^1$H NMR (300 MHz, DMSO-d$_6$) δ 2.30 (s, 3H), 2.86 (t, 2H), 3.42 (q, 2H), 7.11 (m, 4H), 7.23 (t, 1H), 7.58-7.67 (m, 2H), 7.94 (dd, 1H).

Example 14

1-(2,3-dichlorophenyl)-N-[(3-methylpyridin-4-yl)methyl]-1H-tetraazol-5-amine

The title compound was prepared using the procedure described in Example 1 except using (3-methylpyridin-4-yl)methylamine instead of 2-methylbenzylamine. MS (ESI$^+$) m/z 335 (M+H)$^+$; $^1$H NMR (300 MHz, DMSO-d$_6$) δ 2.28 (s, 3H), 4.48 (d, 2H), 7.21 (d, 1H), 7.63 (t, 1H), 7.74 (t, 1H), 7.78 (dd, 1H), 7.97 (dd, 1H), 8.36 (m, 2H).

Example 15

1-(2,3-dichlorophenyl)-N-[(1-methyl-1H-pyrrol-2-yl)methyl]-1H-tetraazol-5-amine

The title compound was prepared using the procedure described in Example 1 except using (1-methyl-1H-pyrrol-2-yl)methylamine instead of 2-methylbenzylamine. MS (ESI$^+$) m/z 323 (M+H)$^+$; $^1$H NMR (300 MHz, DMSO-d$_6$) δ 3.54 (s, 3H), 4.44 (d, 2H), 5.87 (t, 1H), 5.97 (dd, 1H), 6.66 (t, 1H), 7.45 (t, 1H), 7.57 (t, 1H), 7.66 (dd, 1H), 7.91 (dd, 1H).

Example 16

N-[1-(2,3-dichlorophenyl)-1H-tetraazol-5-yl]-5,6,7,8-tetrahydroquinolin-5-amine

The title compound was prepared using the procedure described in Example 1 except using 5,6,7,8-tetrahydroquinolin-5-amine instead of 2-methylbenzylamine. MS (ESI$^+$) m/z 361 (M+H)$^+$; $^1$H NMR (300 MHz, DMSO-d$_6$) δ 1.75-2.07 (m, 4H), 2.81 (t, 2H), 5.01 (m, 1H), 7.19 (dd, 1H), 7.55-7.60 (m, 2H), 7.64 (br d, 1H), 7.71 (dd, 1H), 7.90 (dd, 1H), 8.37 (dd, 1H).

Example 17

1-(2,3-dichlorophenyl)-N-[(2-methylthien-3-yl)methyl]-1H-tetraazol-5-amine

The title compound was prepared using the procedure described in Example 1 except using (2-methylthien-3-yl)methylamine instead of 2-methylbenzylamine. MS (ESI$^+$) m/z 340 (M+H)$^+$; $^1$H NMR (300 MHz, DMSO-d$_6$) δ 2.19 (s, 3H), 4.56 (d, 2H), 6.82 (d, 1H), 7.28 (d, 1H), 7.57-7.72 (m, 3H), 7.94 (dd, 1H).

Example 18

1-(2,3-dichlorophenyl)-N-[3-(dimethylamino)benzyl]-1H-tetraazol-5-amine

The title compound was prepared using the procedure described in Example 1 except using N-[3-(aminomethyl)phenyl]-N,N-dimethylamine instead of 2-methylbenzylamine. MS (ESI$^+$) m/z 363 (M+H)$^+$; $^1$H NMR (300 MHz, DMSO-d$_6$) δ 2.86 (s, 6H), 4.42 (d, 2H), 6.60 (m, 2H), 6.67 (t, 1H), 7.11 (t, 1H), 7.58-7.66 (m, 2H), 7.69 (dd, 1H), 7.94 (dd, 1H).

Example 19

1-(2,3-dichlorophenyl)-N-[2-(4-fluorophenoxy)benzyl]-1H-tetraazol-5-amine

The title compound was prepared using the procedure described in Example 1 except using 1-[2-(4-fluorophenoxy)phenyl]methanamine instead of 2-methylbenzylamine. MS (ESI$^+$) m/z 430 (M+H)$^+$; $^1$H NMR (300 MHz, DMSO-d$_6$) δ 4.52 (d, 2H), 6.82 (d, 1H), 7.02 (m, 2H), 7.13 (td, 1H), 7.19-7.31 (m, 3H), 7.41 (dd, 1H), 7.58-7.69 (m, 3H), 7.95 (dd, 1H).

Example 20

1-(2,3-dichlorophenyl)-N-[2-(methylthio)benzyl]-1H-tetraazol-5-amine

The title compound was prepared using the procedure described in Example 1 except using 1-[2-(methylthio)phenyl]methanamine instead of 2-methylbenzylamine. MS (ESI$^+$) m/z 366 (M+H)$^+$; $^1$H NMR (300 MHz, DMSO-d$_6$) δ 2.48 (s, 3H), 4.49 (d, 2H), 7.15 (m, 1H), 7.26-7.33 (m, 3H), 7.61 (t, 1H), 7.65 (t, 1H), 7.73 (dd, 1H), 7.95 (dd, 1H).

Example 21

N-benzyl-1-(2,3-dichlorophenyl)-1H-tetraazol-5-amine

The title compound was prepared using the procedure described in Example 1 except using 1-phenylmethanamine instead of 2-methylbenzylamine. MS (ESI$^+$) m/z 320 (M+H)$^+$; $^1$H NMR (300 MHz, DMSO-d$_6$) δ 4.48 (d, 2H), 7.26 (m, 1H), 7.32 (m, 4H), 7.61 (t, 1H), 7.68-7.73 (m, 2H), 7.95 (dd, 1H).

Example 22

1-(2,3-dichlorophenyl)-N-[3-(pyrazin-2-yloxy)benzyl]-1H-tetraazol-5-amine

The title compound was prepared using the procedure described in Example 1 except using 1-[3-(pyrazin-2-yloxy)phenyl]methanamine instead of 2-methylbenzylamine. MS (ESI$^+$) m/z 414 (M+H)$^+$; $^1$H NMR (300 MHz, DMSO-d$_6$) δ 4.51 (d, 2H), 7.08-7.15 (m, 2H), 7.22 (d, 1H), 7.40 (t, 1H), 7.60 (t, 1H), 7.70-7.77 (m, 2H), 7.95 (dd, 1H), 8.19 (m, 1H), 8.38 (d, 1H), 8.53 (d, 1H).

Example 23

1-(2,3-dichlorophenyl)-N-[2-(1H-pyrrol-1-yl)benzyl]-1H-tetraazol-5-amine

The title compound was prepared using the procedure described in Example 1 except using 1-[2-(1H-pyrrol-1-yl)phenyl]methanamine instead of 2-methylbenzylamine. MS (ESI$^+$) m/z 385 (M+H)$^+$; $^1$H NMR (300 MHz, DMSO-d$_6$) δ

4.35 (d, 2H), 6.24 (t, 2H), 6.99 (t, 2H), 7.25-7.34 (m, 1H), 7.37-7.45 (m, 2H), 7.46-7.51 (m, 1H), 7.59-7.64 (m, 2H), 7.71 (dd, 1H), 7.95 (dd, 1H).

Example 24

1-(2,3-dichlorophenyl)-N-[4-(pyridin-2-yloxy)benzyl]-1H-tetraazol-5-amine

The title compound was prepared using the procedure described in Example 1 except using 1-[4-(pyridin-2-yloxy) phenyl]methanamine instead of 2-methylbenzylamine. MS (ESI$^+$) m/z 413 (M+H)$^+$; $^1$H NMR (300 MHz, DMSO-d$_6$) δ 4.49 (d, 2H), 7.01 (d, 1H), 7.05-7.15 (m, 3H), 7.36 (d, 2H), 7.62 (t, 1H), 7.70-7.75 (m, 2H), 7.81-7.87 (m, 1H), 7.95 (dd, 1H), 8.13 (dd, 1H).

Example 25

1-(2,3-dichlorophenyl)-N-[3-(pyridin-2-yloxy)benzyl]-1H-tetraazol-5-amine

The title compound was prepared using the procedure described in Example 1 except using 1-[3-(pyridin-2-yloxy) phenyl]methanamine instead of 2-methylbenzylamine. MS (ESI$^+$) m/z 413 (M+H)$^+$; $^1$H NMR (300 MHz, DMSO-d$_6$) δ 4.49 (d, 2H), 7.01 (m, 2H), 7.06 (m, 1H), 7.1-7.2 (m, 2H), 7.36 (t, 1H), 7.60 (t, 1H), 7.69 (dd, 1H), 7.72 (t, 1H), 7.82-7.88 (m, 1H), 7.94 (dd, 1H), 8.13 (ddd, 1H).

Example 26

1-(2,3-dichlorophenyl)-N-[(3-methyl-1-phenyl-1H-pyrazol-5-yl)methyl]-1H-tetraazol-5-amine The title compound was prepared using the procedure described in Example 1 except using (3-methyl-1-phenyl-1H-pyrazol-5-yl)methylamine instead of 2-methylbenzylamine. MS (ESI$^+$) m/z 400 (M+H)$^+$; $^1$H NMR (300 MHz, DMSO-d$_6$) δ 2.19 (s, 3H), 4.53 (d, 2H), 6.21 (s, 1H), 7.42 (m, 1H), 7.46-7.52 (m, 4H), 7.59-7.62 (m, 2H), 7.71 (t, 1H), 7.94 (dd, 1H).

Example 27

1-(2,3-dichlorophenyl)-N-(2-methylphenyl)-1H-tetraazol-5-amine

The title compound was prepared using the procedure described in Example 1 except using 2-methylphenylamine instead of 2-methylbenzylamine. MS (ESI$^+$) m/z 320 (M+H)$^+$; $^1$H NMR (300 MHz, DMSO-d$_6$) δ 2.18 (s, 3H), 7.07-7.25 (m, 3H), 7.30 (dd, 1H), 7.61 (t, 1H), 7.80 (dd, 1H), 7.93 (dd, 1H), 8.86 (s, 1H).

Example 28

1-(2,3-dichlorophenyl)-N-[(1,5-dimethyl-1H-pyrazol-4-yl)methyl]-1H-tetraazol-5-amine The title compound was prepared using the procedure described in Example 1 except using (1,5-dimethyl-1H-pyrazol-4-yl)methylamine instead of 2-methylbenzylamine. MS (ESI$^+$) m/z 338 (M+H)$^+$; $^1$H NMR (300 MHz, DMSO-d$_6$) δ 2.21 (s, 3H), 3.67 (s, 3H), 4.24 (d, 2H), 7.26 (s, 1H), 7.33 (t, 1H), 7.58 (t, 1H), 7.64 (dd, 1H), 7.92 (dd, 1H).

Example 29

1-(2,3-dichlorophenyl)-N-[(1R)-1-phenylethyl]-1H-tetraazol-5-amine

The title compound was prepared using the procedure described in Example 1 except using (1R)-1-phenylethanamine instead of 2-methylbenzylamine. MS (ESI$^+$) m/z 334 (M+H)$^+$; $^1$H NMR (300 MHz, DMSO-d$_6$) δ 1.44 (d, 3H), 4.91 (m, 1H), 7.22 (m, 1H), 7.28-7.37 (m, 4H), 7.57-7.64 (m, 2H), 7.96 (dd, 1H).

Example 30

1-(2,3-dichlorophenyl)-N-methyl-N-[(1R)-1-phenylethyl]-1H-tetraazol-5-amine

The title compound was prepared using the procedure described in Example 1 except using N-methyl-N-[(1R)-1-phenylethyl]amine instead of 2-methylbenzylamine. MS (ESI$^+$) m/z 348 (M+H)$^+$; $^1$H NMR (300 MHz, DMSO-d$_6$) δ 1.50 (d, 3H), 2.43 (s, 3H), 5.17 (m, 1H), 7.25-7.40 (m, 5H), 7.62 (t, 1H), 7.93 (d, 2H).

Example 31

1-(2,3-dichlorophenyl)-N-[(1S)-2,3-dihydro-1H-inden-1-yl]-1H-tetraazol-5-amine

The title compound was prepared using the procedure described in Example 1 except using (1S)-2,3-dihydro-1H-inden-1-ylamine instead of 2-methylbenzylamine. MS (ESI$^+$) m/z 346 (M+H)$^+$; $^1$H NMR (300 MHz, DMSO-d$_6$) δ 1.92 (m, 1H), 2.5 (m, 1H), 2.7-3.0 (m, 2H), 5.34 (m, 1H), 7.15-7.30 (m, 4H), 7.55 (t, 1H), 7.58 (t, 1H), 7.70 (dd, 1H), 7.91 (dd, 1H).

Example 32

1-(2,3-dichlorophenyl)-N-[(1S)-1-phenylethyl]-1H-tetraazol-5-amine

The title compound was prepared using the procedure described in Example 1 except using (1S)-1-phenylethanamine instead of 2-methylbenzylamine. MS (ESI+) m/z 334 (M+H)$^+$; $^1$H NMR (300 MHz, DMSO-d$_6$) δ 1.45 (d, 3H), 4.91 (m, 1H), 7.23 (m, 1H), 7.29-7.38 (m, 4H), 7.56-7.64 (m, 2H), 7.68 (dd, 1H), 7.96 (dd, 1H).

Example 33

1-(2,3-dichlorophenyl)-N-(6,7-dihydro-5H-cyclopenta[b]pyridin-3-ylmethyl)-1H-tetraazol-5-amine The title compound was prepared using the procedure described in Example 1 except using 1-(6,7-dihydro-5H-cyclopenta[b]pyridin-3-yl)methanamine instead of 2-methylbenzylamine. MS (ESI$^+$) m/z 361 (M+H)$^+$; $^1$H NMR (300 MHz, DMSO-d$_6$) δ 2.04 (m, 2H), 2.85 (m, 4H), 4.44 (d, 2H), 7.53 (br s, 1H), 7.61 (t, 1H), 7.68 (br t, 1H), 7.71 (dd, 1H), 7.96 (dd, 1H), 8.25 (br s, 1H).

Example 34

1-(2,3-dichlorophenyl)-N-(5,6,7,8-tetrahydroquinolin-3-ylmethyl)-1H-tetraazol-5-amine The title compound was prepared using the procedure described in Example 1 except using 1-(5,6,7,8-tetrahydroquinolin-3-yl)methanamine instead of 2-methylbenzylamine. MS (ESI⁺) m/z 375 (M+H)⁺; ¹H NMR (300 MHz, DMSO-d₆) δ 1.77 (m, 4H), 2.73 (m, 4H), 4.42 (d, 2H), 7.37 (br s, 1H), 7.61 (t, 1H), 7.67 (br t, 1H), 7.71 (dd, 1H), 7.95 (dd, 1H), 8.25 (br d, 1H).

Example 35

1-(2,3-dichlorophenyl)-N-(4-morpholin-4-ylbenzyl)-1H-tetraazol-5-amine

The title compound was prepared using the procedure described in Example 1 except using 1-(4-morpholin-4-ylphenyl)methanamine instead of 2-methylbenzylamine. MS (ESI⁺) m/z 405 (M+H)⁺; ¹H NMR (300 MHz, DMSO-d₆) δ 3.06 (m, 4H), 3.72 (m, 4H), 4.37 (d, 2H), 6.89 (d, 2H), 7.18 (d, 2H), 7.55-7.62 (m, 2H), 7.68 (dd, 1H), 7.93 (dd, 1H).

Example 36

1-(2-methylphenyl)-N-[(1R)-1-phenylethyl]-1H-tetraazol-5-amine

The title compound was prepared using the procedure described in Example 1 except using (1R)-1-phenylethanamine instead of 2-methylbenzylamine. MS (ESI⁺) m/z 280 (M+H)⁺; ¹H NMR (300 MHz, DMSO-d₆) δ 1.44 (d, 3H), 1.98 (s, 3H), 4.88 (m, 1H), 7.22 (m, 1H), 7.26-7.58 (m, 9H).

Example 37

1-(2,3-dichlorophenyl)-N-[(2-methylpyridin-3-ylmethyl]-1H-tetraazol-5-amine

C-(2-methyl-pyridin-3-yl)-methylamine was reacted with 2,3-dichlorophenylisothiocyanate according to the method of Example 78C to provide the title compound. MS (ESI⁺) m/z 336 (M+H)⁺; ¹H NMR (300 MHz, DMSO-d₆) δ ppm 2.49 (s, 3H) 4.48 (d, J=5.42 Hz, 2H) 7.19 (dd, J=7.80, 4.75 Hz, 1H) 7.57-7.70 (m, 4H) 7.74 (dd, J=7.36, 1.36 Hz, 1H) 7.95 (dd, J=8.14, 1.36 Hz, 1H) 8.33 (dd, J=4.75, 1.70 Hz, 1H).

Example 38

1-(2,3-dichlorophenyl)-N-2,3-dihydro-1-benzofuran-3-yl-1H-tetraazol-5-amine 2,3-dihydro-benzofuran-3-ylamine (Turan-Zitouni, G.; Berge, G.; Noel-Artis, A. M.; Chevallet, P.; Fulcrand, P.; Castel, J.; *Farmaco Ed. Sci.* 43; 7-8; 1988; 643-656) was reacted with 2,3-dichlorophenylisothiocyanate according to the method of Example 78C to provide the title compound. MS (ESI⁺) m/z 349 (M+H)⁺; ¹H NMR (300 MHz, DMSO-d₆) δ ppm 4.33 (dd, J=9.83, 4.75 Hz, 1H) 4.76 (dd, J=9.83, 8.48 Hz, 1H) 5.55-5.65 (m, 1H) 6.84 (d, J=8.14 Hz, 1H) 6.86-6.92 (m, 1H) 7.18-7.26 (m, 1H) 7.37 (d, J=7.46 Hz, 1H) 7.56 (t, J=8.14 Hz, 1H) 7.68 (dd, J=7.30, 1.70 Hz, 1H) 7.84 (d, J=7.80 Hz, 1H) 7.90 (dd, J=8.14, 1.70 Hz, 1H).

Example 39

N-(1,1'-biphenyl-2-ylmethyl)-1-(2,3-dichlorophenyl)-1H-tetraazol-5-amine 2-phenylbenzylamine was reacted with 2,3-dichlorophenylisothiocyanate according to the method of Example 78C to provide the title compound. MS (ESI⁺) m/z 397 (M+H)⁺; ¹H NMR (300 MHz, DMSO-d₆) δ ppm 4.42 (d, J=5.49 Hz, 2H) 7.22-7.25 (m, 1H) 7.43-7.48 (m, 5H) 7.42-7.48 (m, 3H) 7.58-7.63 (m, 2H) 7.65 (dd, J=3.00, 1.53 Hz, 1H) 7.93 (dd, J=7.93, 1.53 Hz, 1H).

Example 40

1-(2,3-dichlorophenyl)-N-(2-ethoxybenzyl)-1H-tetraazol-5-amine 2-ethoxybenzylamine was reacted with 2,3-dichlorophenylisothiocyanate according to the method of Example 78C to provide the title compound. MS (ESI) m/z 365 (M+H)⁺; ¹H NMR (300 MHz, DMSO-d₆) δ ppm 1.31 (t, J=7.02 Hz, 3H) 4.04 (q, J=6.86 Hz, 2H) 4.47 (d, J=5.62 Hz, 2H) 6.88 (t, J=7.49 Hz, 1H) 6.96 (d, J=7.80 Hz, 1H) 7.19-7.24 (m, 2H) 7.45 (t, J=5.77 Hz, 1H) 7.61 (t, J=8.11 Hz, 1H) 7.70 (dd, J=8.11, 1.56 Hz, 1H) 7.94 (dd, J=8.11, 1.56 Hz, 1H).

Example 41

1-(2,3-dichlorophenyl)-N-(2-isopropoxybenzyl)-1H-tetraazol-5-amine 1-(2-isopropoxyphenyl)methanamine was reacted with 2,3-dichlorophenylisothiocyanate according to the method of Example 78C to provide the title compound. MS (ESI⁺) m/z 379 (M+H)⁺; ¹H NMR (300 MHz, DMSO-d₆) δ ppm 1.26 (d, J=5.93 Hz, 6H) 4.45 (d, J=5.93 Hz, 2H) 4.57-4.65 (m, 1H) 6.86 (t, J=7.49 Hz, 1H) 6.99 (d, J=8.42 Hz, 1H) 7.18-7.23 (m, 2H) 7.40 (t, J=5.77 Hz, 1H) 7.61 (t, J=8.11 Hz, 1H) 7.70 (dd, J=8.11, 1.56 Hz, 1H) 7.93 (dd, J=8.11, 1.56 Hz, 1H).

Example 42

N-(2-adamantylmethyl)-1-(2,3-dichlorophenyl)-1H-tetraazol-5-amine 1-adamantanemethylamine was reacted with 2,3-dichlorophenylisothiocyanate according to the method of Example 78C to provide the title compound. MS (ESI⁺) m/z 379 (M+H)⁺; ¹H NMR (300 MHz, DMSO-d₆) δ ppm 1.43-1.49 (m, 6H) 1.54-1.69 (m, 6H) 1.89-1.96 (m, 3H) 3.02 (d, J=4.68 Hz, 2H) 6.98 (t, J=6.40 Hz, 1H) 7.61 (t, J=8.11 Hz, 1H) 7.65 (dd, J=3.00, 1.56 Hz, 1H) 7.93 (dd, J=7.80, 1.56 Hz, 1H).

Example 43

1-(2-fluorophenyl)-N-[2-(pyridin-2-yloxy)benzyl]-1H-tetraazol-5-amine 2-(pyridin-2-yloxy)benzylamine hydrochloride was reacted with 2-fluorophenylisothiocyanate according to the method of Example 78C to provide the title compound. MS (ESI⁺) m/z 363 (M+H)⁺; ¹H NMR (300 MHz, DMSO-d₆) δ ppm 4.42 (d, J=6.10 Hz, 2H) 7.02 (d, J=8.24 Hz, 1H) 7.08 (d, J=8.24 Hz, 1H) 7.12 (dd, J=7.02, 4.88 Hz, 1H) 7.19-7.23 (m, 1H) 7.29-7.34 (m, 1H) 7.38 (dd, J=7.63, 0.92 Hz, 1H) 7.43 (t, J=7.63 Hz, 1H) 7.53-7.62 (m, 3H) 7.65-7.71 (m, 1H) 7.82-7.87 (m, 1H) 8.09 (dd, J=4.88, 1.83 Hz, 1H).

Example 44

1-(2-chlorophenyl)-N-[2-(pyridin-2-yloxy)benzyl]-1H-tetraazol-5-amine 2-(pyridin-2-yloxy)benzylamine hydrochloride was reacted with 2-chlorophenylisothiocyanate according to the method of Example 78C to provide the title compound. MS (ESI+) m/z 379 (M+H)+; 1H NMR (300 MHz, DMSO-d6) δ ppm 4.40 (d, J=5.80 Hz, 2H) 7.02 (d, J=8.24 Hz, 1H) 7.07 (d, J=7.93 Hz, 1H) 7.12 (dd, J=6.87, 5.34 Hz, 1H) 7.18-7.23 (m, 1H) 7.31 (s, 1H) 7.40 (dd, J=7.63, 1.22 Hz, 1H) 7.48 (t, J=5.80 Hz, 1H) 7.55-7.60 (m, 1H) 7.60-7.63 (m, 1H) 7.64-7.69 (m, 1H) 7.78 (dd, J=7.93, 1.22 Hz, 1H) 7.83-7.88 (m, 1H) 8.09 (dd, J=5.03, 1.68 Hz, 1H).

Example 45

1-(2,3-dichlorophenyl)-N-[(2-phenoxypyridin-3-yl)methyl]-1H-tetraazol-5-amine

Example 45A (2-phenoxypyridin-3-yl)methylamine 2-phenoxynicotinonitrile and Raney/nickel were processed according to the Example 78B to afford the title compound. MS (ESI+) m/z 201 (M+H)+

Example 45B 1-(2,3-dichlorophenyl)-N-[(2-phenoxypyridin-3-yl)methyl]-1H-tetraazol-5-amine The product from Example 45A was reacted with 2,3-dichlorophenylisothiocyanate according to the method of Example 78C to provide the title compound. MS (ESI+) m/z 414 (M+H)+; 1H NMR (300 MHz, DMSO-d6) δ ppm 4.60 (d, J=5.49 Hz, 2H) 7.10-7.14 (m, 3H) 7.18-7.23 (m, 1H) 7.38-7.44 (m, 2H) 7.62 (t, J=8.09 Hz, 1H) 7.72-7.79 (m, 3H) 7.95 (dd, J=6.00, 1.53 Hz, 1H) 7.99-8.02 (m, 1H).

Example 46

1-(2,3-dichlorophenyl)-N-[2-(2-methoxyphenoxy)benzyl]-1H-tetraazol-5-amine 2-(2-methoxyphenoxy)benzylamine hydrochloride was reacted with 2,3-dichlorophenylisothiocyanate according to the method of Example 78C to provide the title compound. MS (ESI+) m/z 443 (M+H)+; 1H NMR (300 MHz, DMSO-d6) δ ppm 3.74 (s, 3H) 4.60 (d, J=5.93 Hz, 2H) 6.55 (dd, J=8.11, 0.94 Hz, 1H) 6.93-6.99 (m, 2H) 7.00-7.04 (m, 1H) 7.14-7.21 (m, 3H) 7.34 (dd, J=7.49, 1.56 Hz, 1H) 7.57-7.61 (m, 1H) 7.62 (t, J=8.11 Hz, 1H) 7.71 (dd, J=6.00, 1.25 Hz, 1H) 7.95 (dd, J=8.27, 1.40 Hz, 1H).

Example 47

1-(2,3-dichlorophenyl)-N-3,4-dihydro-2H-chromen-4-yl-1H-tetraazol-5-amine 3,4-dihydro-2H-chromen-4-ylamine (Sebok, P.; Levai, A.; Timar, T. Heterocyclic Communications (1998), 4(6), 547-557) was reacted with 2,3-dichlorophenylisothiocyanate according to the method of Example 78C to provide the title compound. MS (ESI+) m/z 363 (M+H)+; 1H NMR (300 MHz, DMSO-d6) δ ppm 2.00-2.20 (m, 2H) 4.12-4.27 (m, 2H) 4.95-5.04 (m, 1H) 6.77 (dd, J=8.14, 1.02 Hz, 1H) 6.83-6.90 (m, 1H) 7.12-7.19 (m, 1H) 7.25 (dd, J=7.63, 1.19 Hz, 1H) 7.57 (t, J=7.97 Hz, 1H) 7.69 (d, J=9.00 Hz, 1H) 7.70 (dd, J=7.97, 1.53 Hz, 1H) 7.90 (dd, J=8.14, 1.70 Hz, 1H).

Example 48

1-(2,3-dichlorophenyl)-N-((2,3-dihydrobenzofuran-7-yl)methyl)-1H-tetrazol-5-amine

Example 48A 2,3-dihydro-1-benzofuran-7-ylmethanol 2,3-Dihydrobenzofuran carboxylic acid (5.047 g) in tetrahydrofuran at −10° C. was treated dropwise with a solution of 1.0 M borane-tetrahydrofuran (20 mL). The temperature was allowed to warm to room temperature overnight, treated with additional 1.0 M borane-tetrahydrofuran (10 mL), and stirred at room temperature for 2 hours. The mixture was cooled to 5° C., slowly treated with methanol (20 mL), and concentrated under reduced pressure. The residue was dissolved in ethyl acetate, washed with saturated sodium bicarbonate (2×), saturated sodium chloride, dried (sodium sulfate), filtered, and the filtrate was concentrated under reduced pressure. The residue was purified by flash chromatography (hexanes:ethyl acetate, 3:2) to provide the title compound. MS (DCI/NH3) m/z 168 (M+NH4)+; 1H NMR (CDCl3) δ 3.21 (t, 2H), 4.60 (t, 2H), 4.68 (s, 2H), 6.83 (t, 1H), 7.08 (dd, 1H), 7.14 (dd, 1H).

Example 48B 7-(bromomethyl)-2,3-dihydro-1-benzofuran

The product of Example 48A (4.06 g) and carbon tetrabromide (10.9 g) were combined in methylene chloride (100 mL) at 0° C. and treated with triphenylphosphine (8.53 g) portionwise. The mixture was allowed to warm to room temperature, stirred overnight, concentrated under reduced pressure, and the residue was purified by flash chromatography (2% ethyl acetate/hexanes) to provide the title compound. 1H NMR (CDCl3) δ 3.22 (t, 2H), 4.50 (s, 2H), 4.65 (t, 2H), 6.81 (t, 1H), 7.12 (m, 2H).

Example 48C 7-(azidomethyl)-2,3-dihydro-1-benzofuran

The product of Example 48B (4.40 g) in N,N-dimethylformamide (60 mL) at room temperature was treated in one portion with sodium azide (5.37 g), stirred for 3 hours, poured into water and extracted with diethylether (2×100 mL). The organics were dried (sodium sulfate), filtered, and the filtrate concentrated under reduced pressure. The residue was purified by flash chromatography (5% ethyl acetate/hexane) to provide the title compound. 1H NMR (CDCl3) δ 3.23 (t, 2H), 4.31 (s, 2H), 4.60 (t, 2H), 6.85 (t, 1H), 7.06 (d, 1H), 7.19 (dd, 1H).

Example 48D 1-(2,3-dihydro-1-benzofuran-7-yl)methanamine

The product of Example 48C (2.2 g) in tetrahydrofuran (10 mL) was treated with lithium aluminumhydride (0.71 g) in tetrahydrofuran (20 mL) at 0° C. dropwise. The mixture was stirred at 0° C. for 90 minutes then carefully treated in succession with water (0.7 mL), 15% sodium hydroxide (0.7 mL) and water (2.1 mL). After stirring overnight, the mixture was filtered through celite, the filter cake was washed with tetrahydrofuran (70 mL), and the filtrate concentrated under reduced pressure. The crude was dissolved in diethylether, washed with water, and extracted with 1N hydrochloric acid (2×20 mL). The acidic extracts were combined, basified with potassium carbonate, and extracted with methylene chloride (4×). The organic extracts were combined, dried (potassium carbonate), filtered, and the filtrate was concentrated under reduced pressure to provide the title compound. MS (DCI/NH$_3$) m/z 150 (M+H)$^+$;
$^1$H NMR (CDCl$_3$) δ 3.21 (t, 2H), 3.82 (s, 2H), 4.59 (t, 2H), 6.81 (t, 1H), 7.03 (d, 1H), 7.10 (dd, 1H).

Example 48E 1-(2,3-dichlorophenyl)-N-((2,3-dihydrobenzofuran-7-yl)methyl)-1H-tetrazol-5-amine The product of Example 48D was reacted with 2,3-dichlorophenylisothiocyanate according to the method of Example 78C to provide the title compound. MS (ESI$^+$) m/z 363 (M+H)$^+$; $^1$HNMR (300 MHz, DMSO-d$_6$) δ ppm 3.17 (t, J=8.81 Hz, 2H) 4.40 (d, J=5.76 Hz, 2H) 4.53 (t, J=8.65 Hz, 2H) 6.77 (t, J=7.46 Hz, 1H), 7.01-7.06 (m, 1H) 7.12 (dd, J=7.46 1.02 Hz, 1H) 7.56-7.64 (m, 2H) 7.69 (dd, J=9.00 Hz, 1.70 Hz, 1H) 7.94 (dd, J=7.97, 1.53 Hz, 1H).

Example 49

1-(2,3-dichlorophenyl)-N-[(5-methyl-3-phenylisoxazol-4-yl)methyl]-1H-tetraazol-5-amine (5-methyl-3-phenyl-4-isoxazolyl)methylamine was reacted with 2,3-dichlorophenylisothiocyanate according to the method of Example 78C to provide the title compound. MS (ESI$^+$) m/z 402 (M+H)$^+$; $^1$H NMR (300 MHz, DMSO-d$_6$) δ ppm 2.46 (s, 3H) 4.39 (d, J=4.75 Hz, 2H) 7.39-7.52 (m, 5H) 7.55 (t, J=7.97 Hz, 1H) 7.63-7.68 (m, 2H) 7.91 (dd, J=7.80, 1.70 Hz, 1H).

Example 50

1-(2,3-dichlorophenyl)-N-[2-(2-methylphenoxy)benzyl]-1H-tetraazol-5-amine 2-(2-methylphenoxy)benzylamine hydrochloride was reacted with 2,3-dichlorophenylisothiocyanate according to the method of Example 78C to provide the title compound. MS (ESI$^+$) m/z 427 (M+H)$^+$; $^1$H NMR (300 MHz, DMSO-d$_6$) δ ppm 2.18 (s, 3H) 4.57 (d, J=5.76 Hz, 2H) 6.62 (dd, J=8.14, 1.02 Hz, 1H) 6.81 (dd, J=7.80, 1.02 Hz, 1H) 7.04-7.12 (m, 2H) 7.16-7.26 (m, 2H) 7.29-7.34 (m, 1H) 7.39 (dd, J=7.63, 1.53 Hz, 1H) 7.57-7.69 (m, 3H) 7.95 (dd, J=7.80, 1.70 Hz, 1H).

Example 51

1-(2,3-dichlorophenyl)-N-[2-(pyrazin-2-yloxy)benzyl]-1H-tetraazol-5-amine 2-(pyrazin-2-yloxy)benzylamine was reacted with 2,3-dichlorophenylisothiocyanate according to the method of Example 78C to provide the title compound. MS (ESI$^+$) m/z 415 (M+H)$^+$; $^1$H NMR (300 MHz, DMSO-d$_6$) δ ppm 4.43 (d, J=5.76 Hz, 2H) 7.17 (dd, J=7.97, 1.19 Hz, 1H) 7.22-7.29 (m, 1H) 7.31-7.39 (m, 1H) 7.44 (dd, J=7.46, 1.70 Hz, 1H) 7.55-7.63 (m, 3H) 7.93 (dd, J=6.44, 3.39 Hz, 1H) 8.16 (dd, J=2.71, 1.36 Hz, 1H) 8.36 (dd, J=2.71, 0.68 Hz, 1H) 8.51 (d, J=1.02, 0.68 Hz, 1H).

Example 52

1-(2,3-dichlorophenyl)-N-(3-nitrobenzyl)-1H-tetraazol-5-amine 3-nitrobenzylamine hydrochloride was reacted with 2,3-dichlorophenylisothiocyanate according to the method of Example 78C to provide the title compound. MS (ESI$^+$) m/z 366 (M+H)$^+$; $^1$H NMR (300 MHz, DMSO-d$_6$) δ ppm 4.61 (d, J=6.10 Hz, 2H) 7.60-7.68 (m, 2H) 7.74 (dd, J=9.00, 1.36 Hz, 1H) 7.80 (d, J=7.80 Hz, 1H) 7.88 (t, J=5.93 Hz, 1H) 7.97 (dd, J=8.14, 1.36 Hz, 1H) 8.10-8.16 (m, 1H) 8.20 (t, J=1.70 Hz, 1H).

Example 53

1-(2,3-dichlorophenyl)-N-[(2-methoxypyridin-3-yl)methyl]-1H-tetraazol-5-amine (2-methoxypyridin-3-yl)methylamine (WO2001060803) was reacted with 2,3-dichlorophenylisothiocyanate according to the method of Example 78C to provide the title compound. MS (ESI$^+$) m/z 352 (M+H)$^+$; $^1$H NMR (300 MHz, DMSO-d$_6$) δ ppm 3.89 (s, 3H) 4.42 (d, J=5.76 Hz, 2H) 6.97 (dd, J=7.12, 5.09 Hz, 1H) 7.54-7.61 (m, 1H) 7.61-7.67 (m, 2H) 7.75 (dd, J=9.00, 1.70 Hz, 1H) 7.96 (dd, J=8.14, 1.36 Hz, 1H) 8.07 (dd, J=5.09, 1.70 Hz, 1H).

Example 54

1-(2,3-dichlorophenyl)-N-{[2-(2,2,2-trifluoroethoxy)pyridin-3-yl]methyl}-1H-tetraazol-5-amine Example 54A 1-[2-(2,2,2-trifluoroethoxy)pyridin-3-yl]methanamine 2-(2,2,2-trifluoroethoxy)nicotinonitrile was processed according to the method of Example 78B to provide the intermediate I. MS (ESI$^+$) m/z 207 (M+H)$^+$.

Example 54B 1-(2,3-dichlorophenyl)-N-{[2-(2,2,2-trifluoroethoxy)pyridin-3-yl]methyl}-1H-tetraazol-5-amine The product of Example 54A was reacted with 2,3-dichlorophenylisothiocyanate according to the method of Example 78C to provide the title compound. MS (ESI$^+$) m/z 420 (M+H)$^+$; $^1$H NMR (300 MHz, DMSO-d$_6$) δ ppm 4.46 (d, J=5.76 Hz, 2H) 5.03 (q, J=8.93 Hz, 2H) 7.11 (dd, J=7.46, 5.09 Hz, 1H) 7.59-7.70 (m, 3H) 7.75 (dd, J=8.14, 1.70 Hz, 1H) 7.96 (dd, J=8.14, 1.70 Hz, 1H) 8.11 (dd, J=5.09, 2.03 Hz, 1H).

Example 55

1-(2,3-dichlorophenyl)-N-[2-(4-methylpiperazin-1-yl)benzyl]-1H-tetraazol-5-amine 1-[2-(4-methylpiperazin-1-yl)phenyl]methanamine was reacted with 2,3-dichlorophenylisothiocyanate according to the method of Example 78C to provide the title compound. MS (ESI$^+$) m/z 385 (M+H)$^+$; $^1$H NMR (300 MHz, DMSO-d$_6$) δ ppm 2.22 (s, 3H) 2.37-2.48 (m, 4H) 2.83 (t, J=4.58 Hz, 4H) 4.56 (d, J=5.76 Hz, 2H) 7.01-7.08 (m, 1H) 7.11 (dd, J=7.63, 1.02 Hz, 1H) 7.19-7.24 (m, 1H) 7.24-7.30 (m, 1H) 7.55 (t, J=5.76 Hz, 1H) 7.60 (t, J=7.97 Hz, 1H) 7.68-7.73 (m, J=8.80, 1.36 Hz, 1H) 7.94 (dd, J=7.97, 1.53 Hz, 1H).

Example 56

N-(5-chloro-2-methoxybenzyl)-1-(2,3-dichlorophenyl)-1H-tetraazol-5-amine 5-chloro-2-methoxybenzylamine was reacted with 2,3-dichlorophenylisothiocyanate according to the method of Example 78C to provide the title compound. MS (ESI$^+$) m/z 385 (M+H)$^+$; $^1$H NMR (300 MHz, DMSO-d$_6$) δ ppm 3.81 (s, 3H) 4.43 (d, J=5.76 Hz, 2H) 7.02 (d, J=8.82 Hz, 1H) 7.22 (d, J=2.71 Hz, 1H) 7.29 (dd, J=8.48, 2.71 Hz, 1H) 7.58-7.67 (m, 2H) 7.76 (dd, J=6.96, 1.70 Hz, 1H) 7.96 (dd, J=8.14, 1.36 Hz, 1H).

Example 57

1-(2,3-dichlorophenyl)-N-[(6-fluoro-4H-1,3-benzodioxin-8-yl)methyl]-1H-tetraazol-5-amine (6-fluoro-4H-1,3-benzodioxin-8-yl)methylamine was reacted with 2,3-dichlorophenylisothiocyanate according to the method of Example 78C to provide the title compound. MS (ESI$^+$) m/z 397 (M+H)$^+$; $^1$H NMR (300 MHz, DMSO-d$_6$) δ ppm 4.43 (d, J=5.76 Hz, 2H) 4.88 (s, 2H) 5.28 (s, 2H) 6.84-6.96 (m, 2H) 7.61 (t, J=8.14 Hz, 1H) 7.63 (d, J=5.77 Hz, 1H) 7.77 (dd, J=8.14, 1.36 Hz, 1H) 7.96 (dd, J=8.14, 1.70 Hz, 1H).

Example 58

1-(2,3-dichlorophenyl)-N-(1-pyridin-3-ylethyl)-1H-tetraazol-5-amine 1-pyridin-3-yl-ethylamine was reacted with 2,3-dichlorophenylisothiocyanate according to the method of Example 78C to provide the title compound. MS (ESI$^+$) m/z 336 (M+H)$^+$; $^1$H NMR (300 MHz, DMSO-d$_6$) δ ppm 1.48 (d, J=7.12 Hz, 3H) 4.90-5.01 (m, 1H) 7.31-7.39 (m, 1H) 7.61 (t, J=10.50 Hz, 1H) 7.65 (d, J=7.80 Hz, 1H) 7.72 (dd, J=9.00, 1.70 Hz, 1H) 7.74-7.78 (m, 1H) 7.97 (dd, J=8.14, 1.70 Hz, 1H) 8.45 (dd, J=4.75, 1.70 Hz, 1H) 8.59 (d, J=2.03 Hz, 1H).

Example 59

4-({[1-(2,3-dichlorophenyl)-1H-tetraazol-5-yl]amino}methyl)-3-methoxybenzonitrile 4-(aminomethyl)-3-methoxybenzonitrile (WO9625426) was reacted with 2,3-dichlorophenylisothiocyanate according to the method of Example 78C to provide the title compound. MS (ESI$^+$) m/z 376 (M+H)$^+$; $^1$H NMR (300 MHz, DMSO-d$_6$) δ ppm 3.88 (s, 3H) 4.49 (d, J=5.76 Hz, 2H) 7.34-7.43 (m, 2H) 7.47 (d, J=1.36 Hz, 1H) 7.63 (t, J=8.14 Hz, 1H) 7.69 (t, J=5.93 Hz, 1H) 7.76 (dd, J=9.00, 1.36 Hz, 1H) 7.96 (dd, J=8.14, 1.36 Hz, 1H).

Example 60

1-(2,3-dichlorophenyl)-N-(quinolin-3-ylmethyl)-1H-tetraazol-5-amine

C-quinolin-3-yl-methylamine (Peel, Michael R.; Sternbach, Daniel D. *Bioorg. Med. Chem. Lett.* (1994), 4(23), 2753-8) was reacted with 2,3-dichlorophenylisothiocyanate according to the method of Example 78C to provide the title compound. MS (ESI$^+$) m/z 372 (M+H)$^+$; $^1$H NMR (300 MHz, DMSO-d$_6$) δ ppm 4.68 (d, J=5.76 Hz, 2H) 7.52 (dd, J=8.31, 4.24 Hz, 1H) 7.63 (t, J=8.14 Hz, 1H) 7.72 (dd, J=9.00, 1.70 Hz, 1H) 7.77 (dd, J=9.00, 1.70 Hz, 1H) 7.82-7.88 (m, 2H) 7.93-8.01 (m, 2H) 8.33 (dd, J=8.31, 1.19 Hz, 1H) 8.87 (dd, J=4.41, 1.70 Hz, 1H).

Example 61

1-(2,3-dichlorophenyl)-N-(2-piperidin-1-ylbenzyl)-1H-tetraazol-5-amine 2-piperidinobenzylamine was reacted with 2,3-dichlorophenylisothiocyanate according to the method of Example 78C to provide the title compound. MS (ESI$^+$) m/z 404 (M+H)$^+$; $^1$H NMR (300 MHz, DMSO-d$_6$) δ ppm 1.47-1.66 (m, 6H) 2.74-2.81 (m, 4H) 4.56 (d, J=5.76 Hz, 2H) 6.99-7.06 (m, 1H) 7.10 (dd, J=9.00, 1.02 Hz, 1H) 7.18-7.29 (m, 2H) 7.55 (t, J=5.76 Hz, 1H) 7.61 (t, J=7.97 Hz, 1H) 7.71 (dd, J=6.50, 1.70 Hz, 1H) 7.94 (dd, J=8.14, 1.36 Hz, 1H).

Example 62

1-(2,3-dichlorophenyl)-N-({2-[(6-methylpyridin-3-yl)oxy]pyridin-3-yl}methyl)-1H-tetraazol-5-amine Example 62A 2-[(6-methylpyridin-3-yl)oxy]nicotinonitrile 5-hydroxy-2-methylpyridine and 2-fluoronicotinonitrile were processed according to the method of Example 128B to provide the product. MS (ESI$^+$) m/z 212 (M+H)$^+$;

Example 62B

{2-[(6-methylpyridin-3-yl)oxy]pyridin-3-yl}methylamine

The product of Example 62A and Raney/nickel were processed according to the method of Example 131C to provide the product. MS (ESI$^+$) m/z 216 (M+H)$^+$.

Example 62C 1-(2,3-dichlorophenyl)-N-({2-[(6-methylpyridin-3-yl)oxy]pyridin-3-yl}methyl)-1H-tetraazol-5-amine The product of Example 62B was reacted with 2,3-dichlorophenylisothiocyanate according to the method of Example 78C to provide the title compound. MS (ESI$^+$) m/z 429 (M+H)$^+$; $^1$H NMR (300 MHz, DMSO-d$_6$) δ ppm 2.48 (s, 3H) 4.61 (d, J=5.43 Hz, 2H) 7.13 (dd, J=7.29, 4.92 Hz, 1H) 7.31 (d, J=8.48 Hz, 1H) 7.50 (dd, J=8.31, 2.88 Hz, 1H) 7.62 (t, J=8.14 Hz, 1H) 7.72-7.82 (m, 3H) 7.96 (dd, J=8.14, 1.70 Hz, 1H) 7.99 (dd, J=4.92, 1.86 Hz, 1H) 8.28 (d, J=2.71 Hz, 1H).

Example 63

N-[1-(2,3-dichlorophenyl)-1H-tetraazol-5-yl]-2,3-dihydrofuro[2,3-b]pyridin-3-amine Example 63A Furo[2,3-b]pyridin-3(2H)-one O-methyloxime Furo[2,3-b]pyridin-3(2H)-one (Morita, Hiroyuki; Shiotani, Shunsaku; *J. Heterocycl. Chem.;* 23; 1986; 1465-1469).

and the hydrochloride salt of methoxylamine were processed according to the method of Example 135A to provide the product. MS (ESI$^+$) m/z 165 (M+H)$^+$.

Example 63B 2,3-dihydrofuro[2,3-b]pyridin-3-amine

The product of Example 63A and Raney/nickel were processed according to the method of Example 131C to provide the product. MS (ESI$^+$) m/z 136 (M+H)$^+$.

Example 63C

N-[1-(2,3-dichlorophenyl)-1H-tetraazol-5-yl]-2,3-dihydrofuro[2,3-b]pyridin-3-amine The product of Example 63B was reacted with 2,3-dichlorophenylisothiocyanate according to the method of Example 78C to provide the title compound.
MS (ESI$^+$) m/z 350 (M+H)$^+$. $^1$H NMR (300 MHz, DMSO-d$_6$) δ ppm 4.37 (dd, J=9.83, 4.41 Hz, 1H) 4.81 (dd, J=9.83, 8.82 Hz, 1H) 5.58-5.67 (m, 1H) 6.94 (dd, J=7.12, 5.09 Hz, 1H) 7.58 (t, J=7.97 Hz, 1H) 7.70 (dd, J=8.50, 1.70 Hz, 1H) 7.75-7.80 (m, 1H) 7.86 (d, J=7.80 Hz, 1H) 7.92 (dd, J=8.14, 1.70 Hz, 1H) 8.06 (dd, J=4.92, 1.53 Hz, 1H).

Example 64

1-(2,3-dichlorophenyl)-N-(2,4-difluorobenzyl)-1H-tetraazol-5-amine 2,4-difluorobenzylamine was reacted with 2,3-dichlorophenylisothiocyanate according to the method of Example 78C to provide the title compound. MS (ESI$^+$) m/z 356 (M+H)$^+$; $^1$H NMR (300 MHz, DMSO-d$_6$) δ ppm 4.49 (d, J=5.76 Hz, 2H) 7.02-7.11 (m, 1H) 7.18-7.27 (m, 1H) 7.39-7.50 (m, 1H) 7.61 (t, J=8.14 Hz, 1H) 7.69-7.75 (m, 2H) 7.95 (dd, J=8.14, 1.36 Hz, 1H).

Example 65

N-(2-chloro-4-fluorobenzyl)-1-(2,3-dichlorophenyl)-1H-tetraazol-5-amine 2-chloro-4-fluorobenzylamine was reacted with 2,3-dichlorophenylisothiocyanate according to the method of Example 78C to provide the title compound. MS (ESI$^+$) m/z 373 (M+H)$^+$; $^1$H NMR (300 MHz, DMSO-d$_6$) δ ppm 4.53 (d, J=5.76 Hz, 2H) 7.18-7.26 (m, 1H) 7.41-7.48 (m, 2H) 7.62 (t, J=8.14 Hz, 1H) 7.71-7.78 (m, 2H) 7.96 (dd, J=8.14, 1.36 Hz, 1H)

Example 66

N-[3-({[1-(2,3-dichlorophenyl)-1H-tetraazol-5-yl]amino}methyl)phenyl]-N-methylacetamide N-[3-(aminomethylphenyl]-N-methylacetamide hydrochloride was reacted with 2,3-dichlorophenylisothiocyanate according to the method of Example 78C to provide the title compound. MS (ESI$^+$) m/z 392 (M+H)$^+$; $^1$H NMR (300 MHz, DMSO-d$_6$) δ ppm 1.74 (s, 3H) 3.13 (s, 3H) 4.51 (d, J=5.76 Hz, 2H) 7.18-7.32 (m, 3H) 7.40 (t, J=7.80 Hz, 1H) 7.62 (t, J=7.97 Hz, 1H) 7.69-7.76 (m, 2H) 7.95 (dd, J=8.14, 1.70 Hz, 1H).

Example 67

1-(2,3-dichlorophenyl)-N-[4-fluoro-2-(trifluoromethyl)benzyl]-1H-tetraazol-5-amine 4-fluoro-2-trifluoromethylbenzylamine was reacted with 2,3-dichlorophenylisothiocyanate according to the method of Example 78C to provide the title compound. MS (ESI$^+$) m/z 407 (M+H)$^+$; $^1$H NMR (300 MHz, DMSO-d$_6$) δ ppm 4.64 (d, J=5.42 Hz, 2H) 7.50-7.59 (m, 1H) 7.59-7.67 (m, 3H) 7.76 (dd, J=7.97, 1.53 Hz, 1H) 7.82 (t, J=5.76 Hz, 1H) 7.97 (dd, J=8.14, 1.36 Hz, 1H).

Example 68

1-(2,3-dichlorophenyl)-N-(5-fluoro-2-methylbenzyl)-1H-tetraazol-5-amine 5-fluoro-2-methylbenzylamine was reacted with 2,3-dichlorophenylisothiocyanate according to the method of Example 78C to provide the title compound. MS (ESI$^+$) m/z 352 (M+H)$^+$; $^1$H NMR (300 MHz, DMSO-d$_6$) δ ppm 4.45 (d, J=5.76 Hz, 2H) 6.94-7.02 (m, 1H) 7.05 (dd, J=10.17, 2.71 Hz, 1H) 7.20 (dd, J=8.14, 6.10 Hz, 1H) 7.59-7.67 (m, 2H) 7.75 (dd, J=8.50, 1.70 Hz, 1H) 7.95 (dd, J=8.14, 1.36 Hz, 1H).

Example 69

1-(2,3-dichlorophenyl)-N-(2,4,5-trifluorobenzyl)-1H-tetraazol-5-amine 2,4,5-trifluorobenzylamine was reacted with 2,3-dichlorophenylisothiocyanate according to the method of Example 78C to provide the title compound. MS (ESI$^+$) m/z 375 (M+H)$^+$; $^1$H NMR (300 MHz, DMSO-d$_6$) δ ppm 4.48 (d, J=5.76 Hz, 2H) 7.39-7.48 (m, 1H) 7.49-7.58 (m, 1H) 7.63 (t, J=8.14 Hz, 1H) 7.71-7.78 (m, 2H) 7.96 (dd, J=8.14, 1.70 Hz, 1H).

Example 70

1-(2,3-dichlorophenyl)-N-(5-fluoro-2,3-dihydro-1H-inden-1-yl)-1H-tetraazol-5-amine 5-fluoro-2,3-dihydro-1H-Inden-1-amine (EP538134) was reacted with 2,3-dichlorophenylisothiocyanate according to the method of Example 78C to provide the title compound. MS (ESI$^+$) m/z 365 (M+H)$^+$; $^1$H NMR (300 MHz, DMSO-d$_6$) δ ppm 1.86-2.02 (m, 1H) 2.52-2.59 (m, 1H) 2.75-3.01 (m, 2H) 5.24-5.36 (m, 1H) 6.95-7.04 (m, 1H) 7.08 (dd, J=9.15, 2.37 Hz, 1H) 7.27 (dd, J=8.31, 5.26 Hz, 1H) 7.52 (d, J=8.48 Hz, 1H) 7.58 (t, J=7.97 Hz, 1H) 7.70 (dd, J=8.50, 1.36 Hz, 1H) 7.91 (dd, J=8.14, 1.36 Hz, 1H).

Example 71

1-(2,3-difluorophenyl)-N-[2-(pyridin-2-yloxy)benzyl]-1H-tetraazol-5-amine 2-(pyridin-2-yloxy)benzylamine hydrochloride was reacted with 2,3-dichlorophenylisothiocyanate according to the method of Example 78C to provide the title compound. MS (ESI$^+$) m/z 381 (M+H)$^+$; $^1$H NMR (300 MHz, DMSO-d$_6$) δ ppm 4.43 (d, J=6.10 Hz, 2H) 6.98-7.03 (m, 1H) 7.06-7.11 (m, 1H) 7.11-7.14 (m, 1H) 7.22 (dt, J=7.54, 1.19 Hz, 1H)

7.29-7.36 (m, 1H) 7.39 (dd, J=7.46, 1.70 Hz, 1H) 7.42-7.48 (m, 2H) 7.65-7.79 (m, 2H) 7.81-7.88 (m, 1H) 8.08-8.12 (m, 1H).

Example 72

N-({6-chloro-5-fluoro-2-[(1-methylpyrrolidin-3-yl)oxy]pyridin-3-yl}methyl)-1-(2,3-dichlorophenyl)-1H-tetraazol-5-amine

Example 72A 6-chloro-5-fluoro-2-[(1-methylpyrrolidin-3-yl)oxy]nicotinonitrile 3-cyano-2,6-dichloro-5-fluoropyridine was reacted with 1-methyl-pyrrolidin-3-ol according to the method of Example 85A to provide the title compound. MS (ESI$^+$) m/z 256 (M+H)$^+$.

Example 72B

{6-chloro-5-fluoro-2-[(1-methylpyrrolidin-3-yl)oxy]pyridin-3-yl}methylamine

The product from Example 72A according to the method of Example 78B provided the title compound. MS (ESI$^+$) m/z 260 (M+H)$^+$.

Example 72C

N-({6-chloro-5-fluoro-2-[(1-methylpyrrolidin-3-yl)oxy]pyridin-3-yl}methyl)-1-(2,3-dichlorophenyl)-1H-tetraazol-5-amine The product of Example 72B was reacted with 2,3-dichlorophenylisothiocyanate according to the method of Example 78C to provide the title compound. MS (ESI$^+$) m/z 473 (M+H)$^+$. $^1$HNMR (300 MHz, DMSO-d$_6$) δ ppm 1.76-1.88 (m, 1H) 2.25 (s, 3H) 2.26-2.36 (m, 2H) 2.63-2.78 (m, 3H) 4.45 (d, J=5.42 Hz, 2H) 5.29-5.38 (m, 1H) 7.63 (t, J=7.97 Hz, 1H) 7.68-7.75 (m, 2H) 7.78 (dd, J=6.50, 1.36 Hz, 1H) 7.96 (dd, J=8.14, 1.36 Hz, 1H).

Example 73

1-(2,3-dichlorophenyl)-N-{[4-(4-fluorophenyl)-1,3-thiazol-5-yl]methyl}-1H-tetraazol-5-amine

Example 73A 5-({[tert-butyl(dimethyl)silyl]oxy}methyl)-4-(4-fluorophenyl)-1,3-thiazole 4-fluoro-phenyl-boronic acid and the product from Example 113C were treated according to the method of Example 113D to provide the title compound. MS (DCI/NH$_3$) m/z 324 (M+H)$^+$.

Example 73B

[4-(4-fluorophenyl)-1,3-thiazol-5-yl]methanol

The product from Example 73A following the same procedure as Example 76D gave the title compound. MS (DCI/NH$_3$) m/z 210 (M+H)$^+$.

Example 73C 5-(azidomethyl)-4-(4-fluorophenyl)-1,3-thiazole

The product from Example 73B following the same procedure as Example 77A gave the title compound. MS (DCI/NH$_3$) m/z 235 (M+H)$^+$.

Example 73D

[4-(4-fluorophenyl)-1,3-thiazol-5-yl]methylamine

The product from Example 73C following the same procedure as Example 77B gave the title compound. MS (DCI/NH$_3$) m/z 209 (M+H)$^+$

Example 73E 1-(2,3-dichlorophenyl)-N-{[4-(4-fluorophenyl)-1,3-thiazol-5-yl]methyl}-1H-tetraazol-5-amine The product from Example 73D was reacted with 2,3-dichlorophenylisothiocyanate according to the method of Example 78C to provide the title compound. MS (ESI$^+$) m/z 422 (M+H)$^+$. $^1$HNMR (300 MHz, DMSO-d$_6$) δ ppm 4.79 (d, J=5.43 Hz, 2H) 7.27-7.36 (m, 2H) 7.61 (t, J=7.97 Hz, 1H) 7.68 (dd, J=6.00, 1.70 Hz, 1H) 7.71-7.79 (m, 2H) 7.95 (dd, J=6.10, 3.00 Hz, 1H) 7.96-8.02 (m, 1H) 9.04 (s, 1H).

Example 74

1-(2,3-dichlorophenyl)-N-[(4-thien-3-yl-1,3-thiazol-5-yl)methyl]-1H-tetraazol-5-amine

Example 74A 5-({[tert-butyl(dimethyl)silyl]oxy}methyl)-4-thien-3-yl-1,3-thiazole 3-thiopheneboranic acid and the product from Example 113C were treated according to the method of Example 113D to provide the title compound. MS (DCI/NH$_3$) m/z 312 (M+H)$^+$.

Example 74B (4-thien-3-yl-1,3-thiazol-5-yl)methanol

The product from Example 74A following the same procedure as Example 76D gave the title compound. MS (DCI/NH$_3$) m/z 198 (M+H)$^+$.

Example 74C 5-(azidomethyl)-4-thien-3-yl-1,3-thiazole

The product from Example 74B following the same procedure as Example 77A gave the title compound. MS (DCI/NH$_3$) m/z 223 (M+H)$^+$.

Example 74D (4-thien-3-yl-1,3-thiazol-5-yl)methylamine

The product from Example 74C following the same procedure as Example 77B gave the title compound. MS (DCI/NH$_3$) m/z 197 (M+H)$^+$

Example 74E 1-(2,3-dichlorophenyl)-N-[(4-thien-3-yl-1,3-thiazol-5-yl)methyl]-1H-tetraazol-5-amine The product from Example 74D was reacted with 2,3-dichlorophenylisothiocyanate according to the method of Example 78C to provide the title compound. MS (ESI$^+$) m/z 410 (M+H)$^+$. $^1$HNMR (300 MHz, DMSO-d$_6$) δ ppm 4.84 (d, J=5.76 Hz, 2H) 7.53 (dd, J=5.09, 1.36 Hz, 1H) 7.61 (t, J=8.14 Hz, 1H) 7.67 (dd, J=6.00, 1.36 Hz, 1H) 7.69 (dd, J=9.00, 1.70 Hz, 1H) 7.85 (dd, J=3.05, 1.36 Hz, 1H) 7.95 (dd, J=8.14, 1.70 Hz, 1H) 8.00 (t, J=5.59 Hz, 1H) 8.99 (s, 1H).

Example 75

1-(2,3-dichlorophenyl)-N-(pyridin-2-ylmethyl)-1H-tetraazol-5-amine

Example 75A 2,3-dichlorophenylisocyanide dichloride

The title compound was prepared according to the procedure as described in Kuehle, Engelbert; Anders, Bertram; Zumach, Gerhard, *Angewandte Chemie* (1967), 79(15), 663-80.

Example 75B 5-chloro-1-(2,3-dichlorophenyl)-1H-tetraazole

A solution of sodium azide (2.47 g, 17.24 mmol) and tetra-n-butylammonium bromide (548 mg, 1.7 mmol) in 8 ml of water was added to a solution of the product of Example 75A (5.95 g, 25.5 mmol) in 40 ml of toluene. The reaction was stirred at room temperature for 3 h. The organic layer was separated off and the aqueous layer was extracted with toluene. The combined organic extracts were dried, filtered and concentrated. The product was purified by flash chromatography on SiO$_2$ with Hex:EtOAc (1:1) to provide the title compound. MS (ESI$^+$) m/z 250 (M+H)$^+$.

Example 75C 1-(2,3-dichlorophenyl)-N-(pyridin-2-ylmethyl)-1H-tetraazol-5-amine A mixture of the product from Example 75B (150 mg, 0.604 mmol), 2-(aminomethyl)pyridine (98 mg, 0.903 mmol) and triethylamine (252 μL, 1.807 mmol) in 5 ml of THF was heated at reflux for 8 h. The solvent was evaporated under reduced pressure at the product purified by preparative HPLC on a waters Symmetry C8 column (40 mm×100 mm, 7 μm particle size) using a gradient of 10% to 100% acetonitrile:ammonium acetate (10 mM) over 15 min at a flow rate of 70 mL/min to provide the title compound. MS (ESI$^+$) m/z 322 (M+H)$^+$. $^1$HNMR (300 MHz, DMSO-d$_6$) δ ppm 4.56 (d, J=5.76 Hz, 2H) 7.24-7.30 (m, 1H) 7.31-7.36 (m, 1H) 7.63 (t, J=7.97 Hz, 1H) 7.75 (dd, J=7.80, 1.70 Hz, 2H) 7.77-7.83 (m, 1H) 7.96 (dd, J=8.14, 1.70 Hz, 1H) 8.48-8.52 (m, 1H).

Example 76

3-{[1-(2,3-Dichloro-phenyl)-1H-tetrazol-5-ylamino]-methyl}-phenol

Example 76A 3-(tert-butyl dimethyl-silanyloxy)-benzonitrile

A mixture of 3-hydroxy-benzonitrile (5.0 g, 42.0 mmol) and imidazole (7.15 g, 105 mmol) in N,N-dimethylformamide (100 mL) was treated with tert-butyl-chloro-dimethyl-silane (7.6 g, 50.4 mmol) in N,N-dimethylformamide (50 mL) over 10 min. The reaction was stirred at rt overnight. The reaction mixture was poured into water, and extracted with ethyl acetate (2×). The solvent was removed, and the resulting residue was chromatographed using hexane/ethyl acetate (10:1) to give the title compound (9.27 g, 95%). MS (DCI/NH$_3$) m/z 234 (M+1)$^+$. $^1$HNMR (500 MHz, DMSO-d$_6$) δ ppm 0.26 (s, 6H) 1.00 (s, 9H) 7.26 (dq, J=7.93, 1.22 Hz, 1H) 7.35 (t, J=2.44 Hz, 1H) 7.50 (m, 2H).

Example 76B

1-[3-(tert-Butyl-dimethyl-silanyloxy)-benzyl]-3-(2,3-dichloro-phenyl)-thiourea

Part A

To a solution of the product from Example 76A (200 mg, 0.86 mmol) in diethyl ether (20 mL) was added lithium aluminium hydride (1 M in tetrahydrofuran) (1.72 mL, 1.72 mmol) dropwise at rt. The reaction mixture was refluxed for 2 hr. Quenched with water, the mixture was extracted with ethyl acetate (2×). The organic layers were combined, washed with water, and concentrated to afford a residue (181 mg, 0.76 mmol).

Part B

A solution of the product from part A of Example 76B in tetrahydrofuran (10 mL) was treated with 2,3-dichlorophenyl isothiocyanate (155 mg, 0.76 mmol). The reaction was stirred for 1 hr at rt. The solution was concentrated to dryness and the residue was chromatographed using dichloromethane/hexane (1:1) then dichloromethane to give the title compound (173 mg, 52%). MS (DCI/NH$_3$) m/z 441 (M)$^+$, 442 (M+2)$^+$. $^1$HNMR (400 MHz, DMSO-d$_6$) δ ppm 0.18 (s, 6H) 0.95 (s, 9H) 4.69 (s, 2H) 6.73 (dd, J=7.36, 1.84 Hz, 1H) 6.84 (brs, 1H) 6.91 (d, J=7.36 Hz, 1H) 7.21 (t, J=7.67 Hz, 1H) 7.35 (t, J=7.98 Hz, 1H) 7.51 (dd, J=8.29, 1.53 Hz, 1H) 7.59 (d, J=7.36 Hz, 1H) 8.41 (s, 1H) 9.41 (s, 1H).

Example 76C

[3-(tert-Butyl-dimethyl-silanyloxy)-benzyl]-[1-(2,3-dichloro-phenyl)-1H-tetrazol-5-yl]-amine A mixture of the product from Part B of Example 76B (170 mg, 0.4 mmol), mercury acetate (127 mg, 0.4 mmol) and sodium azide (85 mg, 1.32 mmol) in tetrahydrofuran (8 mL) was stirred overnight at rt. The solution was concentrated to dryness and the residue was chromatographed using dichloromethane to give the title compound (137 mg, 76%). MS (DCI/NH$_3$) m/z 450 (M)$^+$, 452 (M+2)$^+$. $^1$HNMR (500 MHz, DMSO-d$_6$) δ ppm 0.15 (s, 6H) 0.93 (s, 9H) 4.43 (d, J=5.93 Hz, 2H) 6.71 (dd, J=8.11, 2.50 Hz, 1H) 6.82 (t, J=1.87 Hz, 1H) 6.91 (d, J=8.11 Hz, 1H) 7.19 (t, J=7.80 Hz, 1H) 7.61 (t, J=8.11 Hz, 1H) 7.66 (t, J=6.24 Hz, 1H) 7.67 (dd, J=7.80, 1.56 Hz, 1H) 7.94 (dd, J=8.11, 1.56 Hz, 1H).

Example 76D

3-{[1-(2,3-Dichloro-phenyl)-1H-tetrazol-5-ylamino]-methyl}-phenol

The product from Example 76C (240 mg, 0.53 mmol) in tetrahydrofuran (10 mL) was treated with tetrabutylammonium fluoride (1 M in tetrahydrofuran) (800 µL, 0.8 mmol). The reaction mixture was stirred for 1 hr at rt. The solution was concentrated to dryness and the residue was partitioned between ethyl acetate and water. The organic layer was dried and the resulting residue was chromatographed using hexane/ethyl acetate (1:1) to give the title compound (140 mg, 79%). MS (DCI/NH$_3$) m/z 336 (M)$^+$, 338 (M+2)$^+$. $^1$HNMR (500 MHz, DMSO-d$_6$) δ ppm 4.39 (d, J=5.93 Hz, 2H) 6.63 (dd, J=8.11, 1.56 Hz, 1H) 6.73 (m, 2H) 7.10 (t, J=7.80 Hz, 1H) 7.61 (m, 3H) 7.68 (dd, J=8.11, 1.56 Hz, 1H) 7.94 (dd, J=8.11, 1.25 Hz, 1H) 9.27 (brs, 1H). Anal. Calcd for C$_{14}$H$_{11}$N$_5$Cl$_2$O: C, 50.02; H, 3.30; N, 20.83. Found: C, 50.37; H, 3.44; N, 19.56.

Example 77

[1-(2,3-Dichloro-phenyl)-1H-tetrazol-5-yl]-[3-(pyrimidin-2-yloxy)-benzyl]-amine

Example 77A 2-(3-Azidomethyl-phenoxy)-pyrimidine

To a mixture of 3-(pyrimidin-2-yloxy)-phenyl-methanol (500 mg, 2.47 mmol) and triethylamine (625 µL, 4.5 mmol) in dichloromethane (40 mL) was added MsCl (2.33 uL, 3.0 mmol) at 0° C. The reaction was kept at 0° C. for 15 min. Removal of the solvent, the residue was dissolved in N,N-dimethylformamide (30 mL) and then treated with sodium azide (803 mg, 12.4 mmol). The reaction mixture was heated at 80° C. for 4 hr. The reaction mixture was poured into water, and extracted with ethyl acetate (2×). The solvent was removed, and the resulting residue was chromatographed using hexane/ethyl acetate (2:1) to give the title compound (483 mg, 86%). MS (DCI/NH$_3$) m/z 228 (M+1)$^+$. $^1$H NMR (500 MHz, DMSO-d$_6$) δ ppm 4.49 (s, 2H) 7.19 (dd, J=8.11, 2.18 Hz, 1H) 7.21 (t, J=1.87 Hz, 1H) 7.26 (d, J=7.18 Hz, 1H) 7.27 (t, J=4.68 Hz, 1H) 7.47 (t, J=7.80 Hz, 1H) 8.64 (s, 1H) 8.65 (s, 1H).

Example 77B 3-(Pyrimidin-2-yloxy)-benzylamine

The product from Example 77A (480 mg, 2.13 mmol) in ethanol (40 mL) was treated with Pd/C (75 mg) at rt. The reaction mixture was stirred for 3 hr at rt under the hydrogen balloon. Removal of the solvent gave the title compound (428 mg, 100%). MS (DCI/NH$_3$) m/z 202 (M+1)$^+$. $^1$HNMR (500 MHz, DMSO-d$_6$) δ ppm 3.74 (s, 2H) 7.01 (dd, J=7.93, 1.83 Hz, 1H) 7.16 (s, 1H) 7.21 (d, J=7.93 Hz, 1H) 7.25 (t, J=4.88 Hz, 1H) 7.35 (t, J=7.63 Hz, 1H) 8.63 (s, 1H) 8.65 (s, 1H).

Example 77C 1-(2,3-Dichloro-phenyl)-3-[3-(pyrimidin-2-yloxy)-benzyl]-thiourea The title compound was prepared using the procedure as described in Part B of Example 76B, substituting the product of Example 77B for the product from Part A of Example 76B. MS (DCI/NH$_3$) m/z 403 (M)$^+$, 405 (M+2)$^+$. $^1$HNMR (500 MHz, DMSO-d$_6$) δ ppm 4.77 (s, 2H) 7.09 (dd, J=8.24, 1.83 Hz, 1H) 7.15 (s, 1H) 7.22 (d, J=7.63 Hz, 1H) 7.27 (t, J=4.58 Hz, 1H) 7.34 (t, J=8.24 Hz, 1H) 7.41 (t, J=7.93 Hz, 1H) 7.51 (dd, J=7.93, 1.22 Hz, 1H) 7.60 (d, J=7.02 Hz, 1H) 8.46 (brs, 1H) 8.64 (s, 1H) 8.65 (s, 1H) 9.45 (s, 1H).

Example 77D

[1-(2,3-Dichloro-phenyl)-1H-tetrazol-5-yl]-[3-(pyrimidin-2-yloxy)-benzyl]-amine

The title compound was prepared using the procedure as described in Example 76C, substituting the product of Example 77C for the product from part B of Example 76B. MS (DCI/NH$_3$) m/z 414 (M), 416 (M+2). $^1$H (400 MHz, DMSO-d$_6$) δ ppm 4.51 (d, J=5.83 Hz, 2H) 7.07 (dd, J=7.36, 1.84 Hz, 1H) 7.12 (t, J=2.15 Hz, 1H) 7.20 (d, J=7.67 Hz, 1H) 7.25 (t, J=4.91 Hz, 1H) 7.38 (t, J=7.67 Hz, 1H) 7.59 (t, J=7.98 Hz, 1H) 7.70 (dd, J=7.98, 1.53 Hz, 1H) 7.71 (t, J=6.44 Hz, 1H) 7.93 (dd, J=8.29, 1.53 Hz, 1H) 8.61 (s, 1H) 8.62 (s, 1H).

Example 78

[1-(2,3-Dichloro-phenyl)-1H-tetrazol-5-yl]-[3-(5-methyl-pyridin-2-yloxy)-benzyl]-amine

Example 78A 3-(5-Methyl-pyridin-2-yloxy)-benzonitrile

A mixture of 3-hydroxy-benzonitrile (500 mg, 4.17 mmol), 2-fluoro-5-methylpyridine (467 mg, 4.17 mmol) and K$_2$CO$_3$ (150 mg) in N,N-dimethylformamide (5 mL) was heated at 150° C. overnight. The reaction mixture was poured into water, and extracted with ethyl acetate (2×). The solvent was removed, and the resulting residue was chromatographed using hexane/ethyl acetate (2:1) to give the title compound (315 mg, 36%). MS (DCI/NH$_3$) m/z 211 (M+1)$^+$. $^1$HNMR (400 MHz, DMSO-d$_6$) δ ppm 2.25 (s, 3H) 7.02 (d, J=8.59 Hz, 1H) 7.45 (ddd, J=8.29, 1.53, 0.92 Hz, 1H) 7.61 (m, 3H) 7.71 (ddd, J=8.29, 2.46, 0.61 Hz, 1H) 7.99 (dt, J=2.45, 0.61 Hz, 1H).

Example 78B 3-(5-Methyl-pyridin-2-yloxy)-benzylamine

The product of Example 78A (315 mg, 1.49 mmol) in 20% NH$_3$-methanol (30 mL) was treated with Raney Nickel (3.15 g). The mixture was hydrogenated under the pressure of 60 psi in a shaker for 19 hr. The solution was filtered through a nylon membrane and the filtrate was concentrated to afford the title compound (315 mg, 98%). MS (DCI/NH$_3$) m/z 215 (M+1)$^+$.

Example 78C

[1-(2,3-Dichloro-phenyl)-1H-tetrazol-5-yl]-[3-(5-methyl-pyridin-2-yloxy)-benzyl]-amine The product from Example 78B (315 mg, 1.49 mmol) in tetrahydrofuran (40 mL) was treated with 2,3-dichlorophenyl isothiocyanate (213 µL, 1.49 mmol). The reaction mixture was stirred for 1 hr at rt. To the solution was added mercury acetate (473 mg, 1.49 mmol) and sodium azide (316 mg, 4.93 mmol), and the mixture was stirred overnight at rt. Filtered the precipitate, ant the filtrate was concentrated to dryness and the residue was purified by C18 HPLC (20%-95%-ammonium acetate) to give the title compound (80.9 mg, 13%). MS (DCI/NH$_3$) m/z 427 (M)$^+$, 429 (M+2)$^+$. $^1$HNMR (400 MHz, DMSO-d$_6$) δ ppm 2.24 (s, 3H) 4.47 (d, J=6.14 Hz, 2H) 6.90 (d, J=8.29 Hz, 1H) 6.95 (dd, J=7.98, 1.23 Hz, 1H) 7.00 (t, J=1.53 Hz, 1H) 7.12 (d, J=7.36 Hz, 1H) 7.33 (t, J=7.67 Hz, 1H) 7.59 (t, J=7.98 Hz, 1H) 7.67 (m, 3H) 7.92 (dd, J=7.98, 1.53 Hz, 1H) 7.96 (d, J=2.45 Hz, 1H).

Example 79

[1-(2,3-Dichloro-phenyl)-1H-tetrazol-5-yl]-[3-(1-methyl-piperidin-4-yloxy)-benzyl]amine Example 79A 3-(1-Methyl-piperidin-4-yloxy)-benzonitrile To a solution of 3-hydroxy-benzonitrile (500 mg, 4.17 mmol), 1-methyl-piperidin-4-ol (467 mg, 4.17 mmol) and triphenyl phosphine (1.64 g, 6.26 mmol) in tetrahydrofuran (40 mL) was added diisopropyl azodicarboxylate (1.23 µL, 6.26 mmol) dropwise. The reaction mixture was stirred for 4 hr at rt. The solution was concentrated to dryness and the residue was chromatographed using ethyl acetate then ethyl acetate/methanol (8:1) to give the title compound (380 mg, 42%). MS (DCI/NH$_3$) m/z 217 (M+1)$^+$. $^1$H NMR (400 MHz, DMSO-d$_6$) δ ppm 1.60 (m, 2H) 1.91 (m, 2H) 2.15 (m, 2H) 2.16 (s, 3H) 2.60 (m, 2H) 4.46 (m, 1H) 7.28 (dd, J=7.67, 1.84 Hz, 1H) 7.35 (d, J=7.36 Hz, 1H) 7.45 (m, 2H).

Example 79B 3-(1-Methyl-piperidin-4-yloxy)-benzylamine

The title compound was prepared using the procedure as described in Example 78B, substituting the product of Example 79A for the product of Example 78A. MS (DCI/NH$_3$) m/z 221 (M+1)$^+$.

Example 79C

[1-(2,3-Dichloro-phenyl)-1H-tetrazol-5-yl]-[3-(1-methyl-piperidin-4-yloxy)-benzyl]-amine The product of Example 79B was reacted with 2,3-dichlorophenylisothiocyanate according to the method of Example 78C to provide the title compound MS (DCI/NH$_3$) m/z 433 (M)$^+$, 435 (M+2)$^+$. $^1$HNMR (500 MHz, DMSO-d$_6$) δ ppm 1.60 (m, 2H) 1.88 (m, 2H) 2.14 (m, 2H) 2.16 (s, 3H) 2.59 (m, 2H) 4.29 (m, 1H) 4.44 (d, J=5.93 Hz, 2H) 6.81 (dd, J=8.11, 2.50 Hz, 1H) 6.86 (d, J=8.11 Hz, 1H) 6.89 (d, J=1.87 Hz, 1H) 7.20 (t, J=8.11 Hz, 1H) 7.61 (t, J=8.11 Hz, 1H) 7.65 (t, J=5.93 Hz, 1H) 7.94 (dd, J=8.11, 1.56 Hz, 1H).

Example 80

[1-(2,3-Dichloro-phenyl)-1H-tetrazol-5-yl]-[3-(5-nitro-pyridin-2-yloxy)-benzyl]-amine Example 80A

[3-(5-Nitro-pyridin-2-yloxy)-benzyl]-carbamic acid tert-butyl ester

A mixture of (3-hydroxy-benzyl)-carbamic acid tert-butyl ester (250 mg, 1.12 mmol), 2-fluoro-5-nitro-pyridine (150 mg, 1.12 mmol) and K$_2$CO$_3$ (120 mg) in N,N-dimethylformamide (3 mL) was heated under microwave condition at 100° C. for 10 min. The reaction mixture was poured into water, and extracted with ethyl acetate (2×). The solvent was removed, and the resulting residue was chromatographed using hexane/ethyl acetate (7:1) to give the title compound (165 mg, 43%). MS (DCI/NH$_3$) m/z 346 (M+1)$^+$.

Example 80B

[1-(2,3-Dichloro-phenyl)-1H-tetrazol-5-yl]-[3-(5-nitro-pyridin-2-yloxy)-benzyl]-amine The product of Example 80A (165 mg, 0.478 mmol) was treated with trifluoroacetic acid (2 mL) for 5 min at rt. Removal of trifluoroacetic acid, the residue was dissolved in tetrahydrofuran (15 mL) and basified with triethylamine (167 µL, 1.2 mmol). To the mixture was added 2,3-dichlorophenyl isothiocyanate (68 µL, 0.478 mmol). The reaction mixture was stirred for 1 hr at it. To the solution was added mercury chloride (130 mg, 0.478 mmol), sodium azide (101 mg, 1.58 mmol) and triethylamine (134 µL, 0.96 mmol), and the mixture was stirred overnight at rt. Filtered the precipitate, and the filtrate was concentrated to dryness and the residue was purified by C18 HPLC (20%-95%-ammonium acetate) purification to give the title compound (87.8 mg, 40%). MS (DCI/NH$_3$) m/z 458 (M)$^+$, 460 (M+2)$^+$. $^1$HNMR (500 MHz, DMSO-d$_6$) δ ppm 4.53 (d, J=5.93 Hz, 2H) 7.12 (ddd, J=8.11, 2.50, 0.94 Hz, 1H) 7.16 (t, J=1.87 Hz, 1H) 7.25 (d, J=9.67 Hz, 1H) 7.26 (d, J=7.80 Hz, 1H) 7.43 (t, J=7.80 Hz, 1H) 7.60 (t, J=8.11 Hz, 1H) 7.71 (dd, J=7.80, 1.56 Hz, 1H) 7.73 (t, J=5.93 Hz, 1H) 7.94 (dd, J=8.11, 1.56 Hz, 1H) 8.62 (dd, J=9.05, 2.81 Hz, 1H) 9.01 (dd, J=2.81, 0.62 Hz, 1H)

Example 81

[3-(5-Chloro-pyridin-2-yloxy)-benzyl]-[1-(2,3-dichloro-phenyl)-1H-tetrazol-5-yl]-amine Example 81A 3-(5-Chloro-pyridin-2-yloxy)-benzonitrile 3-Hydroxy-benzonitrile was reacted with 2,5-dichloro-pyridine according to the method of Example 78A to provide the title compound. MS (DCI/NH$_3$) m/z 231 (M)$^+$, 233 (M+2)$^+$.

Example 81B 3-(5-Chloro-pyridin-2-yloxy)-benzylamine

The title compound was prepared according to the method of Example 78B, substituting the product of Example 81A for the product of Example 78A. MS (DCI/NH$_3$) m/z 235 (M)$^+$, 237 (M+2)$^+$.

Example 81C

[3-(5-Chloro-pyridin-2-yloxy)-benzyl]-[1-(2,3-dichloro-phenyl)-1H-tetrazol-5-yl]-amine The product from Example 81B was reacted with 2,3-dichlorophenylisothiocyanate according to the method of Example 78C to provide the title compound. MS (DCI/NH$_3$) m/z 447 (M)$^+$, 449 (M+2)$^+$. $^1$HNMR 1H NMR (500 MHz, DMSO-d$_6$) δ ppm 4.50 (d, J=6.24 Hz, 2H) 7.03 (dd, J=8.73, 2.50 Hz, 1H) 7.07 (t, J=1.56 Hz, 1H) 7.08 (dd, J=8.73, 0.62

Hz, 1H) 7.18 (d, J=7.49 Hz, 1H) 7.37 (t, J=8.11 Hz, 1H) 7.60 (t, J=7.80 Hz, 1H) 7.70 (m, 2H) 7.94 (dd, J=8.11, 1.25 Hz, 1H) 7.95 (dd, J=8.73, 2.81 Hz, 1H) 8.18 (d, J=3.12 Hz, 1H).

Example 82

[1-(2,3-Dichloro-phenyl)-1H-tetrazol-5-yl]-[3-(3-methyl-pyridin-2-yloxy)-benzyl]-amine Example 82A 3-(3-Methyl-pyridin-2-yloxy)-benzonitrile 3-Hydroxy-benzonitrile was reacted with 2-fluoro-3-methylpyridine according to the method of Example 78A to provide the title compound. MS (DCI/NH$_3$) m/z 211 (M+1)$^+$.

Example 82B

1-{3-[(3-methylpyridin-2-yl)oxy]phenyl}methanamine

The title compound was prepared using the method of Example 78B, substituting the product of Example 82A for the product of Example 78A. MS (DCI/NH$_3$) m/z 215 (M+1)$^+$.

Example 82C

[1-(2,3-Dichloro-phenyl)-1H-tetrazol-5-yl]-[3-(3-methyl-pyridin-2-yloxy)-benzyl]-amine The product from Example 82B was reacted with 2,3-dichlorophenylisothiocyanate according to the method of Example 78C to provide the title compound. MS (DCI/NH$_3$) m/Z 427 (M)$^+$, 429 (M+2)$^+$. $^1$HNMR (500 MHz, DMSO-d$_6$) δ ppm 2.28 (s, 3H) 4.49 (d, J=6.24 Hz, 2H) 6.97 (dd, J=7.80, 2.18 Hz, 1H) 7.02 (t, J=1.87 Hz, 1H) 7.05 (dd, J=7.18, 4.68 Hz, 1H) 7.13 (d, J=7.49 Hz, 1H) 7.34 (t, J=7.80 Hz, 1H) 7.60 (t, J=7.80 Hz, 1H) 7.67 (d, J=1.56 Hz, 1H) 7.69 (d, J=1.56 Hz, 1H) 7.71 (dq, J=7.18, 0.94 Hz, 1H) 7.92 (m, 1H) 7.93 (dd, J=8.11, 1.56 Hz, 1H).

Example 83

[1-(2,3-Dichloro-phenyl)-1H-tetrazol-5-yl]-[3-(4-methyl-pyridin-2-yloxy)-benzyl]-amine Example 83A 3-(4-Methyl-pyridin-2-yloxy)-benzonitrile 3-Hydroxy-benzonitrile was reacted with 2-fluoro-4-methylpyridine according to the method of Example 78A to provide the title compound. MS (DCI/NH$_3$) m/z 211 (M+1)$^+$.

Example 83B 3-(4-Methyl-pyridin-2-yloxy)-benzylamine

The title compound was prepared using the method of Example 78B, substituting the product of Example 83A for the product of Example 78A. MS (DCI/NH$_3$) m/z 215 (M+1)$^+$.

Example 83C

[1-(2,3-Dichloro-phenyl)-1H-tetrazol-5-yl]-[3-(4-methyl-pyridin-2-yloxy)-benzyl]-amine The product from Example 83B was reacted with 2,3-dichlorophenylisothiocyanate according to the method of Example 78C to provide the title compound. MS (DCI/NH$_3$) m/z 427 (M)$^+$, 429 (M+2)$^+$. $^1$HNMR (500 MHz, DMSO-d$_6$) δ ppm 2.32 (s, 3H) 4.49 (d, J=5.93 Hz, 2H) 6.82 (m, 1H) 6.97 (m, 2H) 7.03 (t, J=1.87 Hz, 1H) 7.15 (d, J=7.49 Hz, 1H) 7.35 (t, J=8.11 Hz, 1H) 7.60 (t, J=8.11 Hz, 1H) 7.68 (dd, J=7.80, 1.25 Hz, 1H) 7.70 (t, J=6.24 Hz, 1H) 7.93 (dd, J=8.11, 1.56 Hz, 1H) 7.99 (d, J=4.99 Hz, 1H).

Example 84

[1-(2,3-Dichloro-phenyl)-1H-tetrazol-5-yl]-[2-(1-methyl-piperidin-4-yloxy)-benzyl]-amine Example 84A 2-(1-Methyl-piperidin-4-yloxy)-benzonitrile To a mixture of 2-fluoro-benzonitrile (1.6 g, 13.2 mmol) and 1-methyl-piperidin-4-ol (1.52 g, 13.2 mmol) in dioxane (50 mL) was added NaH (60%)(634 mg, 15.8 mmol) in portion. The reaction was heated at 50° C. overnight. The mixture was poured into water, and extracted with ethyl acetate (2×). The solvent was removed, and the resulting residue was chromatographed using ethyl acetate/methanol (20:1-10:1) to give the title compound (870 mg, 31%). MS (DCI/NH$_3$) m/z 217 (M+1)$^+$. $^1$HNMR (400 MHz, DMSO-d$_6$) δ ppm 1.63 (m, 2H) 1.86 (m, 2H) 2.11 (s, 3H) 2.18 (m, 2H) 2.48 (m, 2H) 4.55 (m, 1H) 7.00 (td, J=7.67, 0.61 Hz, 1H) 7.23 (d, J=8.59 Hz, 1H) 7.56 (td, J=10.13, 7.36, 1.84 Hz, 1H) 7.63 (dd, J=7.67, 1.84 Hz, 1H).

Example 84B 2-(1-Methyl-piperidin-4-yloxy)-benzylamine

The title compound was prepared using the method of Example 78B, substituting the product of Example 84A for the product of Example 78A. MS (DCI/NH$_3$) m/z 221 (M+1)$^+$.

Example 84C

[1-(2,3-Dichloro-phenyl)-1H-tetrazol-5-yl]-[2-(1-methyl-piperidin-4-yloxy)-benzyl]-amine The product of Example 84B was reacted with 2,3-dichlorophenylisothiocyanate according to the method of Example 78C to provide the title compound. MS (DCI/NH$_3$) m/z 433 (M)$^+$, 435 (M+2)$^+$. $^1$HNMR (400 MHz, DMSO-d$_6$) δ ppm 1.65 (m, 2H) 1.88 (m, 2H) 2.05 (s, 1H) 2.15 (s, 3H) 2.20 (m, 2H) 2.54 (m, 1H) 4.41 (m, 1H) 4.48 (d, J=5.83 Hz, 2H) 6.86 (td, J=7.36, 0.61 Hz, 1H) 7.00 (d, J=7.98 Hz, 1H) 7.19 (m, 2H) 7.41 (t, J=5.83 Hz, 1H) 7.60 (t, J=7.98 Hz, 1H) 7.69 (dd, J=7.98, 1.53 Hz, 1H) 7.93 (dd, J=7.98, 1.53 Hz, 1H).

Example 85

[1-(2,3-Dichloro-phenyl)-1H-tetrazol-5-yl]-[2-(1-methyl-piperidin-4-yloxy)-pyridin-3-ylmethyl]-amine

Example 85A 2-(1-Methyl-piperidin-4-yloxy)-nicotinonitrile

To a mixture of 2-fluoro-nicotinonitrile (400 mg, 3.3 mmol) and 1-methyl-piperidin-4-ol (380 mg, 3.3 mmol) in N,N-dimethylformamide (30 mL) was added NaH (60%) (160 mg, 4.0 mmol) in portions. The reaction was stirred overnight at rt. The mixture was poured into water, and extracted with ethyl acetate (2×). The solvent was removed, and the resulting residue was chromatographed using ethyl acetate/methanol (8:1) to give the title compound (210 mg, 29%). MS (DCI/NH$_3$) m/z 218 (M+1)$^+$
$^1$HNMR (400 MHz, DMSO-d$_6$) δ ppm 1.73 (m, 2H) 1.96 (m, 2H) 2.18 (s, 3H) 2.22 (m, 2H) 2.59 (m, 2H) 5.15 (m, 1H) 7.15 (dd, J=7.67, 5.22 Hz, 1H) 8.24 (dd, J=7.67, 2.15 Hz, 1H) 8.44 (dd, J=4.91, 1.84 Hz, 1H).

Example 85B

C-[2-(1-Methyl-piperidin-4-yloxy)-pyridin-3-yl]-methylamine

The title compound was prepared using the method of Example 78B, substituting the product of Example 85A for the product of Example 78A. MS (DCI/NH$_3$) m/z 222 (M+1)$^+$.

Example 85C

[1-(2,3-Dichloro-phenyl)-1H-tetrazol-5-yl]-[2-(1-methyl-piperidin-4-yloxy)-pyridin-3-ylmethyl]-amine The product from Example 85B was reacted with 2,3-dichlorophenylisothiocyanate according to the method of Example 78C to provide the title compound. MS (DCI/NH$_3$) m/z 434 (M)$^+$, 436 (M+2)$^+$. $^1$HNMR (400 MHz, DMSO-d$_6$) δ ppm 1.69 (m, 2H) 1.92 (m, 2H) 2.07 (s, 1H) 2.19 (s, 3H) 2.25 (m, 2H) 2.58 (m, 1H) 4.43 (d, J=5.83 Hz, 2H) 5.08 (m, 1H) 6.93 (dd, J=7.36, 4.91 Hz, 1H) 7.51 (t, J=5.52 Hz, 1H) 7.56 (dd, J=7.06, 1.84 Hz, 1H) 7.62 (t, J=7.98 Hz, 1H) 7.73 (dd, J=7.98, 1.53 Hz, 1H) 7.95 (dd, J=8.29, 1.53 Hz, 1H) 8.04 (dd, J=4.91, 1.84 Hz, 1H).

Example 86

[1-(2,3-Dichloro-phenyl)-1H-tetrazol-5-yl]-[2-(1-methyl-piperidin-3-yloxy)-pyridin-3-ylmethyl]-amine

Example 86A 2-(1-Methyl-piperidin-3-yloxy)-nicotinonitrile

2-Fluoro-nicotinonitrile was reacted with 1-methyl-piperidin-3-ol according to the method of Example 85A to provide the title compound. MS (DCI/NH$_3$) m/z 218 (M+1)$^+$.

Example 86B

C-[2-(1-Methyl-piperidin-3-yloxy)-pyridin-3-yl]-methylamine

The product from Example 86A according to the method of Example 78B provided the title compound. MS (DCI/NH$_3$) m/z 222 (M+1)$^+$.

Example 86C

[1-(2,3-Dichloro-phenyl)-1H-tetrazol-5-yl]-[2-(1-methyl-piperidin-3-yloxy)-pyridin-3-ylmethyl]-amine The product from Example 86B was reacted with 2,3-dichlorophenylisothiocyanate according to the method of Example 78C to provide the title compound. MS (DCI/NH$_3$) m/z 434 (M)$^+$, 436 (M+2)$^+$. $^1$HNMR (400 MHz, DMSO-d$_6$) δ ppm 1.38 (m, 1H) 1.52 (m, 1H) 1.71 (m, 1H) 1.93 (m, 2H) 2.06 (m, 2H) 2.18 (s, 3H) 2.85 (d, J=10.74 Hz, 1H) 4.40 (d, J=5.52 Hz, 2H) 5.07 (m, 1H) 6.93 (dd, J=7.36, 5.22 Hz, 1H) 7.49 (t, J=5.52 Hz, 1H) 7.56 (dd, J=7.06, 1.84 Hz, 1H) 7.62 (t, J=7.98 Hz, 1H) 7.73 (dd, J=7.98, 1.53 Hz, 1H) 7.95 (dd, J=7.98, 1.53 Hz, 1H) 8.04 (dd, J=4.91, 1.84 Hz, 1H).

Example 87

[1-(2,3-Dichloro-phenyl)-1H-tetrazol-5-yl]-[2-(1-methyl-pyrrolidin-3-yloxy)-pyridin-3-ylmethyl]-amine

Example 87A 2-(1-Methyl-pyrrolidin-3-yloxy)-nicotinonitrile

2-Fluoro-nicotinonitrile was reacted with 1-methyl-pyrrolidin-3-ol according to the method of Example 85A to provide the title compound. MS (DCI/NH$_3$) m/z 204 (M+1)$^+$.

Example 87B

C-[2-(1-Methyl-pyrrolidin-3-yloxy)-pyridin-3-yl]-methylamine

The product from Example 87A according to the method of Example 78B provided the title compound. MS (DCI/NH$_3$) m/z 208 (M+1)$^+$.

Example 87C

[1-(2,3-Dichloro-phenyl)-1H-tetrazol-5-yl]-[2-(1-methyl-pyrrolidin-3-yloxy)-pyridin-3-ylmethyl]-amine The product from Example 87B was reacted with 2,3-dichlorophenylisothiocyanate according to the method of Example 78C to provide the title compound. MS (DCI/NH$_3$) m/z 420 (M)$^+$, 422 (M+2)$^+$. $^1$HNMR (400 MHz, DMSO-d$_6$) δ ppm 1.82 (m, 1H) 2.26 (m, 1H) 2.31 (s, 3H) 2.45 (dd, J=14.12, 7.36 Hz, 1H) 2.66 (dd, J=10.74, 2.76 Hz, 1H) 2.72 (dd, J=15.04, 7.98 Hz, 1H) 2.88 (dd, J=10.74, 6.14 Hz, 1H) 4.07 (brs, 1H) 4.42 (d, J=5.83 Hz, 2H) 5.39 (m, 1H) 6.94 (dd, J=7.06, 4.91 Hz, 1H) 7.54 (t, J=5.52 Hz, 1H) 7.57 (dd, J=7.06, 1.84 Hz, 1H) 7.62 (t, J=7.98 Hz, 1H) 7.74 (dd, J=7.98, 1.53 Hz, 1H) 7.94 (dd, J=8.29, 1.53 Hz, 1H) 8.04 (dd, J=4.91, 1.84 Hz, 1H).

Example 88

[1-(2,3-Dichloro-phenyl)-1H-tetrazol-5-yl]-[2-(2-oxa-5-aza-bicyclo[2.2.1]hept-5-yl)-pyridin-3-ylm-ethyl]-amine

Example 88A

4-Hydroxy-2-hydroxymethyl-pyrrolidine-1-carboxylic acid tert-butyl ester

To the solution of 4-hydroxy-pyrrolidine-1,2-dicarboxylic acid 1-tert-butyl ester (3.5 g, 16.5 mmol) was added $BH_3$-tetrahydrofuran (1M in tetrahydrofuran) (32.9 mL, 32.9 mmol). The reaction was stirred at rt overnight. Quenched with water, the mixture was extracted with ethyl acetate (2×), The organic layers were combined and washed with saturated sodium bicarbonate, brine, dried. The resulting residue was chromatographed using ethyl acetate to give the title compound (2.66 g, 74%). MS ($DCI/NH_3$) m/z 218 $(M+1)^+$.

Example 88B

2-Oxa-5-aza-bicyclo[2.2.1]heptane-5-carboxylic acid tert-butyl ester

A mixture of the product from Example 88A (2.66 g, 12.3 mmol) and triphenyl phosphine (3.9 g, 13.5 mmol) in dichloromethane (125 mL) was added diisopropyl azodicarboxylate (2.66 mL, 13.5 mmol) dropwise at 0° C. The reaction mixture was allowed to warm up to rt for 12 hr. The solution was concentrated to dryness and the residue was chromatographed using hexane/ethyl acetate (20:1-5:1) to give the title compound (1.57 g, 64%). MS ($DCI/NH_3$) m/z 200 $(M+1)^+$.

Example 88C 2-(2-Oxa-5-aza-bicyclo[2.2.1]hept-5-yl)-nicotinonitrile

The product from Example 88B (1.57 g, 7.9 mmol) in dichloromethane (25 mL) was treated with trifluoroacetic acid (5 mL) for 30 min at rt. The reaction mixture was concentrated to dryness. To the residue was added 2-fluoronicotinonitrile (1.0 g, 8.19 mmol) and diisopropyl ethylamine (3.2 mL) in tetrahydrofuran (8 mL). The reaction mixture was heated at 115° C. for 10 min under microwave condition. The mixture was concentrated to dryness, and the residue was chromatographed using hexane/ethyl acetate (9:1-6:1) to give the title compound (806 mg, 51%). MS ($DCI/NH_3$) m/z 202 $(M+1)^+$. $^1HNMR$ (400 MHz, $CDCl_3$) δ ppm 1.98 (s, 2H) 3.67 (d, J=10.13 Hz, 1H) 3.91 (dd, J=7.98, 1.53 Hz, 1H) 3.96 (m, 2H) 4.69 (s, 1H) 5.16 (s, 1H) 6.64 (dd, J=7.67, 4.91 Hz, 1H) 7.71 (dd, J=7.36, 1.84 Hz, 1H) 8.26 (dd, J=4.60, 1.84 Hz, 1H).

Example 88D

C-[2-(2-Oxa-5-aza-bicyclo[2.2.1]hept-5-yl)-pyridin-3-yl]methylamine

The product from Example 88C according to the method of Example 78B provided the title compound. MS ($DCI/NH_3$) m/z 206 $(M+1)^+$.

Example 88E

[1-(2,3-Dichloro-phenyl)-1H-tetrazol-5-yl]-[2-(2-oxa-5-aza-bicyclo[2.2.1]hept-5-yl)-pyridin-3-ylm-ethyl]-amine The product from Example 88D was reacted 2,3-dichlorophenylisothiocyanate according to the method of Example 78C to provide the title compound. MS ($DCI/NH_3$) m/z 418 $(M)^+$, 420 $(M+2)^+$. $^1HNMR$ (500 MHz, DMSO-$d_6$) δ ppm 1.77 (dt, J=9.67, 0.94 Hz, 1H) 1.82 (dd, J=9.67, 2.18 Hz, 1H) 3.25 (d, J=9.05 Hz, 1H) 3.61 (dd, J=9.05, 1.56 Hz, 1H) 3.77 (dd, J=7.18, 1.56 Hz, 1H) 3.93 (d, J=7.18 Hz, 1H) 4.34 (dd, J=15.60, 5.30 Hz, 1H) 4.43 (dd, J=15.60, 5.62 Hz, 1H) 4.56 (s, 1H) 4.66 (s, 1H) 6.76 (dd, J=7.18, 4.68 Hz, 1H) 7.50 (dd, J=7.49, 1.56 Hz, 1H) 7.59 (t, J=4.68 Hz, 1H) 7.61 (t, J=7.80 Hz, 2H) 7.71 (dd, J=7.80, 1.56 Hz, 1H) 7.94 (dd, J=8.11, 1.56 Hz, 1H) 8.02 (dd, J=4.99, 1.87 Hz, 1H). Anal. Calcd for $C_{18}H_{17}N_7Cl_2O$: C, 51.69; H, 4.10; N, 23.44. Found: C, 51.55; H, 4.21; N, 21.62.

Example 89

[1-(2,3-Dichloro-phenyl)-1H-tetrazol-5-yl]-[2-methyl-3-(pyridin-2-yloxy)-benzyl]-amine

Example 89A

3-Hydroxymethyl-2-methyl-phenol

3-Hydroxy-2-methyl-benzoic acid (1.0 g, 7.2 mmol) in tetrahydrofuran (80 mL) was treated with dropwise added $BH_3$-tetrahydrofuran (1M in tetrahydrofuran) (10 mL). The reaction mixture was stirred at rt overnight. Quenched with 10% NaOH, the mixture was adjusted pH to 7 with 10% HCl and extracted with isopropanol/dichloromethane (1:3) (2×), The organic layers were combined and washed with water, brine, dried to afford the title compound (795 mg, 80%). MS ($DCI/NH_3$) m/z 139 $(M+1)^+$.

Example 89B

[2-Methyl-3-(pyridin-2-yloxy)-phenyl]-methanol

A mixture of the product from Example 89A (740 mg, 5.36 mmol), 2-fluoropyridine (565 mg, 5.92 mmol) and $K_2CO_3$ (600 mg) in N,N-dimethylformamide (30 mL) was heated at 150° C. for 3 hr. The reaction mixture was poured into water, and extracted with ethyl acetate (2×). The solvent was removed, and the resulting residue was chromatographed using Hexane/ethyl acetate (6:1-4:1) to give the title compound (190 mg, 16%). MS ($DCI/NH_3$) m/z 216 $(M+1)^+$.

Example 89C 2-(3-Azidomethyl-2-methyl-phenoxy)-pyridine

The title compound was prepared using the procedure as described in Example 77A, substituting the product from Example 89B for 3-(pyrimidin-2-yloxy)-phenyl-methanol. MS ($DCI/NH_3$) m/z 241 $(M+1)^+$.

Example 89D

2-Methyl-3-(pyridin-2-yloxy)-benzylamine

The product from Example 89C followed the same procedure as described for Example 77B to give the title compound. MS (DCI/NH$_3$) m/z 215 (M+1)$^+$.

Example 89E

[1-(2,3-Dichloro-phenyl)-1H-tetrazol-5-yl]-[2-methyl-3-(pyridin-2-yloxy)-benzyl]-amine The product from Example 89D was reacted with 2,3-dichlorophenylisothiocyanate according to the method of Example 78C to provide the title compound. MS (DCI/NH$_3$) m/z 427 (M)$^+$, 429 (M+2)$^+$. $^1$HNMR (500 MHz, DMSO-d$_6$) δ ppm 2.06 (s, 3H) 4.51 (d, J=5.62 Hz, 2H) 6.96 (dd, J=7.18, 2.81 Hz, 1H) 6.99 (dt, J=8.42, 0.94 Hz, 1H) 7.08 (ddd, J=7.18, 4.99, 0.94 Hz, 1H) 7.19 (dd, J=12.48, 7.80 Hz, 1H) 7.18 (s, 1H) 7.62 (m, 2H) 7.72 (dd, J=8.11, 1.56 Hz, 1H) 7.83 (ddd, J=9.05, 7.18, 2.18 Hz, 1H) 7.94 (dd, J=8.11, 1.25 Hz, 1H) 8.09 (ddd, J=4.68, 1.87, 0.62 Hz, 1H).

Example 90

2-{[1-(2,3-Dichloro-phenyl)-1H-tetrazol-5-ylamino]-methyl}-benzonitrile

Example 90A

2-Azidomethyl-benzonitrile

A mixture of 2-bromomethyl-benzonitrile (300 mg, 1.53 mmol) and sodium azide (129 mg, 1.99 mmol) in acetone was stirred overnight at rt. The solvent was removed, and the resulting residue was chromatographed using hexane/ethyl acetate (6:1) to give the title compound (212 mg, 88%). MS (DCI/NH$_3$) m/z 176 (M+18)$^+$. $^1$HNMR (400 MHz, DMSO-d$_6$) δ ppm 4.69 (s, 2H) 7.58 (td, J=7.67, 1.23 Hz, 1H) 7.66 (d, J=7.67 Hz, 1H) 7.76 (td, J=7.67, 1.23 Hz, 1H) 7.91 (dd, J=7.67, 1.53 Hz, 1H).

Example 90B

2-Aminomethyl-benzonitrile

The product from Example 90A followed the same procedure as described for Example 77B to give the title compound. MS (DCI/NH$_3$) m/z 133 (M+1)$^+$.

Example 90C

2-{[1-(2,3-Dichloro-phenyl)-1H-tetrazol-5-ylamino]-methyl}-benzonitrile

The product from Example 90B was reacted with 2,3-dichlorophenylisothiocyanate according to the method of Example 78C to provide the title compound. MS (DCI/NH$_3$) m/z 345 (M)$^+$, 347 (M+2)$^+$. $^1$HNMR (500 MHz, DMSO-d$_6$) δ ppm 4.67 (d, J=5.62 Hz, 2H) 7.48 (t, J=7.80 Hz, 1H) 7.56 (d, J=8.11 Hz, 1H) 7.63 (t, J=8.11 Hz, 1H) 7.69 (td, J=7.80, 1.25 Hz, 1H) 7.73 (dd, J=8.11, 1.56 Hz, 1H) 7.83 (dd, J=7.49, 0.94 Hz, 1H) 7.89 (t, J=5.62 Hz, 1H) 7.96 (dd, J=8.42, 1.56 Hz, 1H).

Example 91

[1-(2,3-Dichloro-phenyl)-1H-tetrazol-5-yl]-[2-(2-methyl-pyridin-3-yloxy)-pyridin-3-ylmethyl]-amine

Example 91A

2-(2-Methyl-pyridin-3-yloxy)-nicotinonitrile

2-Fluoro-nicotinonitrile was reacted with 2-methyl-pyridin-3-ol according to the method of Example 85A to provide the title compound. MS (DCI/NH$_3$) m/z 212 (M+1)$^+$.

Example 91B

C-[2-(2-Methyl-pyridin-3-yloxy)-pyridin-3-yl]-methylamine

The title compound was prepared using the procedure as described in Example 78B, substituting the product from Example 91A for the product from Example 78A. MS (DCI/NH$_3$) m/z 216 (M+1)$^+$.

Example 91C

[1-(2,3-Dichloro-phenyl)-1H-tetrazol-5-yl]-[2-(2-methyl-pyridin-3-yloxy)-pyridin-3-ylmethyl]-amine The product from Example 91B was reacted with 2,3-dichlorophenylisothiocyanate according to the method of Example 78C to provide the title compound. MS (DCI/NH$_3$) m/z 428 (M)$^+$, 430 (M+2)$^+$. $^1$HNMR (500 MHz, DMSO-d$_6$) δ ppm 2.26 (s, 3H) 4.64 (d, J=5.62 Hz, 2H) 7.12 (dd, J=7.18, 4.68 Hz, 1H) 7.30 (dd, J=8.11, 4.68 Hz, 1H) 7.51 (dd, J=8.11, 1.25 Hz, 1H) 7.63 (t, J=8.11 Hz, 1H) 7.73 (dd, J=8.11, 1.56 Hz, 1H) 7.76 (t, J=5.62 Hz, 1H) 7.80 (dd, J=7.18, 1.87 Hz, 1H) 7.95 (dd, J=8.11, 1.56 Hz, 1H) 7.97 (dd, J=4.68, 1.87 Hz, 1H) 8.32 (dd, J=4.68, 1.25 Hz, 1H).

Example 92

[2-(5-Chloro-pyridin-3-yloxy)-pyridin-3-ylmethyl]-[1-(2,3-dichloro-phenyl)-1H-tetrazol-5-yl]-amine

Example 92A

2-(5-Chloro-pyridin-3-yloxy)-nicotinonitrile

2-Fluoro-nicotinonitrile was reacted with 5-chloro-pyridin-3-ol according to the method of Example 85A to provide the title compound. MS (DCI/NH$_3$) m/z 232 (M)$^+$, 234 (M+2)$^+$.

Example 92B

C-[2-(5-Chloro-pyridin-3-yloxy)-pyridin-3-yl]-methylamine

The title compound was prepared using the procedure as described in Example 78B, substituting the product from Example 92A for the product from Example 78A. MS (DCI/NH$_3$) m/z 236 (M)$^+$, 238 (M+2)$^+$.

Example 92C

[2-(5-Chloro-pyridin-3-yloxy)-pyridin-3-ylmethyl]-[1-(2,3-dichloro-phenyl)-1H-tetrazol-5-yl]-amine The product from Example 92B was reacted with 2,3-dichlorophenylisothiocyanate according to the method of Example 78C to provide the title compound. MS (DCI/NH$_3$) m/z 448 (M)$^+$, 450 (M+2)$^+$. $^1$HNMR (400 MHz, DMSO-d$_6$) δ ppm 4.62 (d, J=5.52 Hz, 2H) 7.20 (dd, J=7.36, 4.91 Hz, 1H) 7.62 (t, J=8.29 Hz, 1H) 7.74 (m, 2H) 7.84 (dd, J=7.36, 1.53 Hz, 1H) 7.89 (t, J=2.15 Hz, 1H) 7.96 (dd, J=8.29, 1.53 Hz, 1H) 8.06 (dd, J=4.91, 1.53 Hz, 1H) 8.46 (d, J=2.15 Hz, 1H) 8.51 (d, J=2.15 Hz, 1H).

Example 93

[1-(2,3-Dichloro-phenyl)-1H-tetrazol-5-yl]-[6-methyl-2-(pyridin-3-yloxy)-pyridin-3-ylmethyl]-amine Example 93A 6-Methyl-2-(pyridin-3-yloxy)-nicotinonitrile 2-chloro-6-methyl-nicotinonitrile was reacted with pyridin-3-ol according to the method of Example 85A to provide the title compound. MS (DCI/NH$_3$) m/z 212 (M+1)$^+$.

Example 93B

C-[6-Methyl-2-(pyridin-3-yloxy)-pyridin-3-yl]-methylamine

The title compound was prepared using the procedure as described in Example 78B, substituting the product from Example 93A for the product from Example 78A. MS (DCI/NH$_3$) m/z 216 (M+1)$^+$.

Example 93C

[1-(2,3-Dichloro-phenyl)-1H-tetrazol-5-yl]-[6-methyl-2-(pyridin-3-yloxy)-pyridin-3-ylmethyl]-amine The product from Example 93B was reacted with 2,3-dichlorophenylisothiocyanate according to the method of Example 78C to provide the title compound. MS (DCI/NH$_3$) m/z 428 (M)$^+$, 430 (M+2)$^+$. $^1$HNMR (400 MHz, DMSO-d$_6$) δ ppm 2.25 (s, 3H) 4.57 (d, J=5.52 Hz, 2H) 7.01 (d, J=7.36 Hz, 1H) 7.46 (dd, J=8.29, 4.60 Hz, 1H) 7.59 (m, 1H) 7.62 (d, J=7.98 Hz, 1H) 7.70 (m, 3H) 7.94 (dd, J=8.29, 1.53 Hz, 1H) 8.41 (dd, J=4.91, 1.23 Hz, 1H) 8.43 (d, J=2.76 Hz, 1H).

Example 94

[1-(2,3-Dichloro-phenyl)-1H-tetrazol-5-yl]-[2-(pyridin-3-yloxy)-pyridin-3-ylmethyl]-amine Example 94A 2-(2-Chloro-pyridin-3-yloxy)-nicotinonitrile 2-Fluoro-nicotinonitrile was reacted with 2-chloro-pyridin-3-ol according to the method of Example 85A to provide the title compound. MS (DCI/NH$_3$) m/z 232 (M)$^+$, 234 (M+2)$^+$.

Example 94B

C-[2-(Pyridin-3-yloxy)-pyridin-3-yl]-methylamine

The title compound was prepared using the procedure as described in Example 78B, substituting the product from Example 94A for the product from Example 78A. MS (DCI/NH$_3$) m/z 202 (M+1)$^+$.

Example 94C

[1-(2,3-Dichloro-phenyl)-1H-tetrazol-5-yl]-[2-(pyridin-3-yloxy)-pyridin-3-ylmethyl]-amine The product from Example 94B was reacted with 2,3-dichlorophenylisothiocyanate according to the method of Example 78C to provide the title compound. MS (DCI/NH$_3$) m/z 414 (M)$^+$, 416 (M+2)$^+$. $^1$HNMR (400 MHz, DMSO-d$_6$) δ ppm 4.63 (d, J=5.52 Hz, 2H) 7.16 (dd, J=7.36, 4.91 Hz, 1H) 7.47 (dd, J=8.29, 4.60 Hz, 1H) 7.62 (m, 2H) 7.75 (m, 2H) 7.81 (dd, J=7.06, 1.23 Hz, 1H) 7.96 (dd, J=7.98, 1.23 Hz, 1H) 8.02 (dd, J=4.91, 1.53 Hz, 1H) 8.43 (dd, J=4.91, 1.23 Hz, 1H) 8.44 (d, J=3.07 Hz, 1H).

Example 95

[1-(2,3-Dichloro-phenyl)-1H-tetrazol-5-yl]-[2-(5-fluoro-pyridin-3-yloxy)-pyridin-3-ylmethyl]-amine Example 95A 2-(6-Chloro-5-fluoro-pyridin-3-yloxy)-nicotinonitrile 2-Fluoro-nicotinonitrile was reacted with 6-chloro-5-fluoro-pyridin-3-ol according to the method of Example 85A to provide the title compound. MS (DCI/NH$_3$) m/z 250 (M)$^+$, 252 (M+2)$^+$.

Example 95B

C-[2-(5-Fluoro-pyridin-3-yloxy)-pyridin-3-yl]-methyl amine

The title compound was prepared using the procedure as described in Example 78B, substituting the product from Example 95A for the product from Example 78A. MS (DCI/NH$_3$) m/z 220 (M+1)$^+$.

Example 95C

[1-(2,3-Dichloro-phenyl)-1H-tetrazol-5-yl]-[2-(5-fluoro-pyridin-3-yloxy)-pyridin-3-ylmethyl]-amine The product from Example 95B was reacted with 2,3-dichlorophenylisothiocyanate according to the method of Example 78C to provide the title compound. MS (DCI/NH$_3$) m/z 432 (M)$^+$, 434 (M+2)$^+$. $^1$HNMR (400 MHz, DMSO-d$_6$) δ ppm 4.62 (d, J=4.30 Hz, 2H) 7.20 (dd, J=7.36, 4.91 Hz, 1H) 7.62 (t, J=7.98 Hz, 1H) 7.74 (m, 3H) 7.84 (dd, J=7.36, 1.53 Hz, 1H) 7.95 (dd, J=8.29, 1.53 Hz, 1H) 8.06 (dd, J=4.91, 1.53 Hz, 1H) 8.38 (brs, 1H) 8.48 (d, J=2.45 Hz, 1H).

Example 96

[2-(2-Chloro-pyridin-3-yloxy)-pyridin-3-ylmethyl]-[1-(2,3-dichloro-phenyl-1H-tetrazol-5-yl]-amine Example 96A 2-(2-Chloro-pyridin-3-yloxy)-nicotinonitrile 2-fluoro-nicotinonitrile was reacted with 2-chloro-pyridine following the same procedure as described for Example 85A to provide the title compound. MS (DCI/NH$_3$) m/z 232 (M)$^+$, 234 (M+2)$^+$. $^1$HNMR (400 MHz, DMSO-d$_6$) δ ppm 7.40 (dd, J=7.67, 5.22 Hz, 1H) 7.60 (dd, J=7.98, 4.91 Hz, 1H)

8.02 (dd, J=7.98, 1.84 Hz, 1H) 8.39 (d, J=1.84 Hz, 1H) 8.41 (d, J=1.53 Hz, 1H) 8.51 (dd, J=7.67, 1.84 Hz, 1H).

Example 96B

C-[2-(2-Chloro-pyridin-3-yloxy)-pyridin-3-yl]-methylamine

The product from Example 96A (330 mg, 1.43 mmol) in 20% $NH_3$-methanol (30 mL) was treated with Raney Nickel (165 mg). The mixture was hydrogenated under the pressure of 60 psi in a shaker for 4 hr. The solution was filtered through a nylon membrane and the filtrate was concentrated to afford the title compound. MS (DCI/$NH_3$) m/z 236 (M)$^+$, 238 (M+2)$^+$.

Example 96C

[2-(2-Chloro-pyridin-3-yloxy)-pyridin-3-ylmethyl]-[1-(2,3-dichloro-phenyl)-1H-tetrazol-5-yl]-amine The product from Example 96B was reacted with 2,3-dichlorophenylisothiocyanate according to the method of Example 78C to provide the title compound. MS (DCI/$NH_3$) m/z 448 (M)$^+$, 450 (M+2)$^+$. $^1$HNMR (400 MHz, DMSO-$d_6$) δ ppm 4.66 (d, J=5.83 Hz, 2H) 7.17 (dd, J=7.36, 4.91 Hz, 1H) 7.54 (dd, J=7.98, 4.91 Hz, 1H) 7.63 (t, J=8.29 Hz, 1H) 7.76 (m, 2H) 7.83 (td, J=7.98, 1.53 Hz, 2H) 7.96 (dd, J=8.29, 1.53 Hz, 1H) 8.00 (dd, J=4.91, 1.84 Hz, 1H) 8.32 (dd, J=4.60, 1.53 Hz, 1H).

Example 97

[2-(6-Chloro-5-fluoro-pyridin-3-yloxy)-pyridin-3-ylmethyl]-[1-(2,3-dichloro-phenyl)-1H-tetrazol-5-yl]-amine

Example 97A

1-{2-[(6-chloro-5-fluoropyridin-3-yl)oxy]pyridin-3-yl}methanamine

The title compound was prepared according to the method of Example 96B, substituting the product from Example 95A for the product of Example 96A. MS (DCI/$NH_3$) m/z 254 (M)$^+$, 256 (M+2)$^+$.

Example 97B

[2-(6-Chloro-5-fluoro-pyridin-3-yloxy)-pyridin-3-ylmethyl]-[1-(2,3-dichloro-phenyl)-1H-tetrazol-5-yl]-amine The product from Example 97A was reacted with 2,3-dichlorophenylisothiocyanate according to the method of Example 78C to provide the title compound. MS (DCI/$NH_3$) m/z 466 (M)$^+$, 468 (M+2)$^+$. $^1$HNMR (400 MHz, DMSO-$d_6$) δ ppm 4.62 (d, J=5.52 Hz, 2H) 7.22 (dd, J=7.36, 4.91 Hz, 1H) 7.62 (t, J=7.98 Hz, 1H) 7.75 (m, 2H) 7.85 (dd, J=7.36, 1.53 Hz, 1H) 7.96 (dd, J=7.98, 1.23 Hz, 1H) 8.02 (dd, J=9.51, 2.46 Hz, 1H) 8.06 (dd, J=4.91, 1.53 Hz, 1H) 8.27 (d, J=2.45 Hz, 1H).

Example 98

[1-(2,3-Dichloro-phenyl)-1H-tetrazol-5-yl]-[5-fluoro-2-(pyridin-2-yloxy)-benzyl]-amine

Example 98A

5-Fluoro-2-hydroxy-benzaldehyde oxime

A solution of sodium acetate trihydrate (1.94 g, 14.28 mmol) in $H_2O$ (8 mL) was added to a warm solution of 5-fluoro-2-hydroxy-benzaldehyde (1.0 g, 7.14 mmol) and $NH_2OH$ HCl (992 mg, 14.28 mmol) in 80% ethanol (30 mL). The reaction mixture was refluxed for 3 hr. Removal of ethanol, the mixture was cooled to rt, collected the precipitate and washed with water, dried to afford the title compound (920 mg, 83%). MS (DCI/$NH_3$) m/z 217 (M+62)$^+$. $^1$HNMR (500 MHz, DMSO-$d_6$) δ ppm 6.89 (dd, J=9.15, 4.88 Hz, 1H) 7.07 (td, J=8.54, 3.05 Hz, 1H) 7.29 (dd, J=9.46, 3.05 Hz, 1H) 8.30 (s, 1H) 10.02 (brs, 1H) 11.46 (brs, 1H).

Example 98B

5-Fluoro-2-hydroxy-benzonitrile

The product from Example 98A (920 mg, 5.93 mmol) in acetic anhydride (15 mL) µanhydride. A solution of KOH (2 g) in $H_2O$ (10 mL) and ethanol (10 mL) was added to the above residue. The mixture was heated at 80° C. for 2 hr then cooled to rt. The pH of the solution was adjusted to 7 with 6N HCl, and extracted with isopropanol/dichloromethane (1:3) (2×). The organic layers were combined, dried. The resulting residue was chromatographed using hexane/ethyl acetate (5:1) to give the title compound (800 mg, 100%). MS (DCI/$NH_3$) m/z 136 (M+1)$^+$. $^1$HNMR (500 MHz, DMSO-$d_6$) δ ppm 6.99 (dd, J=9.05, 4.37 Hz, 1H) 7.36 (td, J=9.05, 3.12 Hz, 1H) 7.53 (dd, J=8.42, 3.43 Hz, 1H) 11.04 (m, 1H).

Example 98C

5-Fluoro-2-(pyridin-2-yloxy)-benzonitrile

The product from Example 98B was reacted with 2-fluoropyridine following the procedure as described for Example 78A to give the title compound. MS (DCI/$NH_3$) m/z 215 (M+1)$^+$.

Example 98D

5-Fluoro-2-(pyridin-2-yloxy)-benzylamine

The product from Example 98C followed the same procedure as described for Example 78B to afford the title compound. MS (DCI/$NH_3$) m/z 219 (M+1)$^+$.

Example 98E

[1-(2,3-Dichloro-phenyl)-1H-tetrazol-5-yl]-[5-fluoro-2-(pyridin-2-yloxy)-benzyl]-amine The product from Example 98D was reacted with 2,3-dichlorophenylisothiocyanate according to the method of Example 78C to provide the title compound. MS (DCI/$NH_3$) m/z 431 (M)$^+$, 433 (M+2)$^+$. $^1$HNMR (500 MHz, DMSO-$d_6$) δ ppm 4.38 (d, J=5.93 Hz, 2H) 7.04 (d, J=8.11 Hz, 1H) 7.12 (dd, J=7.18, 4.99 Hz, 1H) 7.14 (m, 1H) 7.15 (d, J=1.56 Hz, 1H) 7.18 (d, J=9.05 Hz, 1H) 7.59 (dd, J=5.93, 4.37 Hz, 1H) 7.62

(d, J=7.80 Hz, 1H) 7.66 (dd, J=7.80, 1.56 Hz, 1H) 7.86 (td, J=8.11, 1.87 Hz, 1H) 7.94 (dd, J=8.11, 1.87 Hz, 1H) 8.10 (dd, J=4.99, 1.87 Hz, 1H).

Example 99

[1-(2,3-Dichloro-phenyl)-1H-tetrazol-5-yl]-[5-fluoro-2-(pyridin-3-yloxy)-benzyl]-amine Example 99A 2-(2-Chloro-pyridin-3-yloxy)-5-fluoro-benzonitrile 2,5-Difluoro-benzonitrile was reacted with 2-chloropyridin-3-ol according to the method of Example 78A to provide the title compound. MS (DCI/NH$_3$) m/z 249 (M)$^+$, 251 (M+2)$^+$.

Example 99B

5-Fluoro-2-(pyridin-3-yloxy)-benzylamine

The product from Example 99A followed the same procedure as described for Example 78B to afford the title compound. MS (DCI/NH$_3$) m/z 219 (M+1)$^+$.

Example 99C

[1-(2,3-Dichloro-phenyl)-1H-tetrazol-5-yl]-[5-fluoro-2-(pyridin-3-yloxy)-benzyl]-amine The product from Example 99B was reacted with 2,3-dichlorophenylisothiocyanate according to the method of Example 78C to provide the title compound. MS (DCI/NH$_3$) m/z 431 (M)$^+$, 433 (M+2)$^+$. $^1$HNMR (500 MHz, DMSO-d$_6$) δ ppm 4.50 (d, J=5.62 Hz, 2H) 7.04 (dd, J=9.05, 4.68 Hz, 1H) 7.16 (td, J=8.73, 3.12 Hz, 1H) 7.25 (dd, J=9.36, 3.12 Hz, 1H) 7.34 (ddd, J=8.42, 3.12, 1.56 Hz, 1H) 7.41 (ddd, J=8.42, 4.37, 0.62 Hz, 1H) 7.61 (t, J=8.11 Hz, 1H) 7.66 (m, 2H) 7.95 (dd, J=8.11, 1.56 Hz, 1H) 8.33 (d, J=2.81 Hz, 1H) 8.34 (dd, J=4.68, 1.25 Hz, 1H).

Example 100

[1-(2,3-Dichloro-phenyl)-1H-tetrazol-5-yl]-[5-fluoro-2-(2,2,2-trifluoro-ethoxy)-benzyl]-amine Example 100A 5-Fluoro-2-(2,2,2-trifluoro-ethoxy)-benzonitrile 2,5-difluoro-benzonitrile was reacted with 2,2,2-trifluoroethanol according to the method of Example 84A to provide the title compound. MS (DCI/NH$_3$) m/z 220 (M+1)$^+$.

Example 100B

5-Fluoro-2-(2,2,2-trifluoro-ethoxy)-benzylamine

The product from Example 100A followed the same procedure as described for Example 78B to afford the title compound. MS (DCI/NH$_3$) m/z 224 (M+1)$^+$.

Example 100C

[1-(2,3-Dichloro-phenyl)-1H-tetrazol-5-yl]-[5-fluoro-2-(2,2,2-trifluoro-ethoxy)-benzyl]-amine The product from Example 100B was reacted with 2,3-dichlorophenylisothiocyanate according to the method of Example 78C to provide the title compound. MS (DCI/NH$_3$) m/z 436 (M)$^+$, 438 (M+2)$^+$. $^1$HNMR (500 MHz, DMSO-d$_6$) δ ppm 4.47 (d, J=5.93 Hz, 2H) 4.77 (q, J=8.74 Hz, 2H) 7.04 (dd, J=9.36, 3.12 Hz, 1H) 7.12 (m, 2H) 7.58 (t, J=5.62 Hz, 1H) 7.62 (t, J=8.11 Hz, 1H) 7.75 (dd, J=7.80, 1.56 Hz, 1H) 7.95 (dd, J=8.42, 1.56 Hz, 1H).

Example 101

[1-(2,3-Dichloro-phenyl)-1H-tetrazol-5-yl]-[4,5-difluoro-2-(pyridin-2-yloxy)-benzyl]-amine Example 101A 2-(2-Bromo-4,5-difluoro-phenoxy)-pyridine A mixture of 2-(2-bromo-4,5-difluoro-phenoxy)-pyridine (800 mg, 3.83 mmol), 2-fluoro-pyridine (371 mg, 3.83 mmol) and K$_2$CO$_3$ (435 mg, 4.6 mmol) in N,N-dimethylformamide (5 mL) was heated at 120° C. overnight. The reaction mixture was poured into water, and extracted with ethyl acetate (2×). The solvent was removed, and the resulting residue was chromatographed using hexane/ethyl acetate (7:1) to give the title compound (448 mg, 41%). MS (DCI/NH$_3$) m/z 286 (M)$^+$, 288 (M+2)$^+$. $^1$HNMR (400 MHz, CDCl$_3$) δ ppm 7.01 (d, J=8.29 Hz, 1H) 7.03 (dd, J=6.44, 4.91 Hz, 1H) 7.10 (dd, J=10.43, 7.36 Hz, 1H) 7.47 (dd, J=9.21, 8.29 Hz, 1H) 7.74 (td, J=9.21, 1.84 Hz, 1H) 8.13 (dd, J=4.91, 1.23 Hz, 1H).

Example 101B 4,5-Difluoro-2-(pyridin-2-yloxy)-benzonitrile

A flask was charged with the product from Example 101A (440 mg, 1.54 mmol), Zn(CN)$_2$ (99 mg, 0.85 mmol) and Pd(PPh$_3$)$_4$ (178 mg, 0.154 mmol) in N,N-dimethylformamide (2 mL), and was purged with nitrogen. The reaction mixture was heated at 120° C. overnight. After cooling to room temperature, the mixture was diluted with ethyl acetate and washed with water, dried (MgSO$_4$), filtered and concentrated. The resulting residue was chromatographed using hexane/ethyl acetate (7:1) to give the title compound (151 mg, 42%). MS (DCI/NH$_3$) m/z 233 (M+1)$^+$, $^1$H NMR (400 MHz, CDCl$_3$) δ ppm 7.11 (m, 2H) 7.23 (dd, J=10.74, 6.75 Hz, 1H) 7.50 (t, J=8.29 Hz, 1H) 7.79 (td, J=8.29, 2.15 Hz, 1H) 8.15 (dd, J=4.91, 0.92 Hz, 1H).

Example 101C 4,5-Difluoro-2-(pyridin-2-yloxy)-benzylamine

The product from Example 101B followed the same procedure as described for Example 78B to afford the title compound. MS (DCI/NH$_3$) m/z 237 (M+1)$^+$.

Example 101D

[1-(2,3-Dichloro-phenyl)-1H-tetrazol-5-yl]-[4,5-difluoro-2-(pyridin-2-yloxy)-benzyl]-amine The product from Example 101C was reacted with 2,3-dichlorophenylisothiocyanate according to the method of Example 78C to provide the title compound. MS (DCI/NH$_3$) m/z 449 (M)$^+$, 451 (M+2)$^+$. $^1$HNMR (500 MHz, DMSO-d$_6$) δ ppm 4.35 (d, J=5.93 Hz, 2H) 7.06 (d, J=8.11 Hz, 1H) 7.15 (ddd, J=7.18, 4.99, 0.94 Hz, 1H) 7.35 (dd, J=11.23, 7.18 Hz, 1H) 7.40 (dd, J=11.54, 9.36 Hz, 1H) 7.56 (m, 1H) 7.60 (d, J=8.11 Hz, 1H) 7.64 (dd, J=7.80, 1.56 Hz, 1H) 7.86 (td, J=8.42, 1.87 Hz, 1H) 7.93 (dd, J=8.11, 1.56 Hz, 1H) 8.11 (dd, J=4.99, 1.25 Hz, 1H).

Example 102

[1-(2,3-Dichloro-phenyl)-1H-tetrazol-5-yl]-[4-fluoro-2-(pyridin-2-yloxy)-benzyl]-amine

Example 102A 2-(2-Bromo-5-fluoro-phenoxy)-pyridine

2-Bromo-5-fluoro-phenol was reacted with 2-fluoro-pyridine according to the method of Example 101A to provide the title compound. MS (DCI/NH$_3$) m/z 268 (M)$^+$, 270 (M+2)$^+$.

Example 102B

4-Fluoro-2-(pyridin-2-yloxy)-benzonitrile

The product from Example 102A followed the same procedure as described for Example 101B to afford the title compound. MS (DCI/NH$_3$) m/z 215 (M+1)$^+$.

Example 102C

4-Fluoro-2-(pyridin-2-yloxy)-benzylamine

The product from Example 102B followed the same procedure as described for Example 78B to afford the title compound. MS (DCI/NH$_3$) m/z 219 (M+1)$^+$.

Example 102D

[1-(2,3-Dichloro-phenyl)-1H-tetrazol-5-yl]-[4-fluoro-2-(pyridin-2-yloxy)-benzyl]-amine The product from Example 102C was reacted with 2,3-dichlorophenylisothiocyanate according to the method of Example 78C to provide the title compound. MS (DCI/NH$_3$) m/z 431 (M)$^+$, 433 (M+2)$^+$. $^1$HNMR (500 MHz, DMSO-d$_6$) δ ppm 4.37 (d, J=5.80 Hz, 2H) 7.06 (m, 3H) 7.16 (dd, J=6.41, 4.88 Hz, 1H) 7.43 (dd, J=8.24, 6.71 Hz, 1H) 7.56 (m, 3H) 7.88 (td, J=8.54, 2.14 Hz, 1H) 7.93 (dd, J=7.02, 2.44 Hz, 1H) 8.13 (dd, J=5.19, 2.14 Hz, 1H).

Example 103

[1-(2,3-Dichloro-phenyl)-1H-tetrazol-5-yl]-(4-fluoro-2-pyridin-2-yl-benzyl)-amine

Example 103A (4-Fluoro-2-pyridin-2-yl-benzyl)-carbamic acid tert-butyl ester A round bottle flask was charged with (2-boronic acid-4-fluoro-benzyl)-carbamic acid tert-butyl ester (100 mg, 0.37 mmol), 2-chloro-pyridine (42 mg, 0.37 mmol), CsF (202 mg, 1.11 mmol) and Pd(PPh$_3$)$_4$ (43 mg, 0.037 mmol) in 1,2-dimethoxyethane (DME)/methanol (2:1) (10 mL), and was purged with nitrogen. The reaction mixture was heated at 85° C. overnight. After cooling to room temperature, the mixture was diluted with ethyl acetate and washed with water, dried (MgSO$_4$), filtered and concentrated. The resulting residue was chromatographed using hexane/ethyl acetate (6:1) to give the title compound (83 mg, 74%). MS (DCI/NH$_3$) m/z 303 (M+1)$^+$, $^1$H NMR (500 MHz, CDCl$_3$) δ ppm 1.44 (s, 9H) 4.21 (d, J=4.68 Hz, 2H) 5.90 (brs, 2H) 7.08 (td, J=8.42, 2.81 Hz, 1H) 7.14 (dd, J=9.36, 2.50 Hz, 1H) 7.30 (ddd, J=7.80, 4.99, 1.25 Hz, 1H) 7.48 (d, J=7.80 Hz, 1H) 7.55 (t, J=6.55 Hz, 1H) 7.80 (td, J=7.80, 1.87 Hz, 1H) 8.70 (d, J=4.37 Hz, 1H).

Example 103B

[1-(2,3-Dichloro-phenyl)-1H-tetrazol-5-yl]-(4-fluoro-2-pyridin-2-yl-benzyl)-amine The product from Example 103A was reacted with 2,3-dichlorophenylisothiocyanate according to the method of Example 80B provided the title compound. MS (DCI/NH$_3$) m/z 415 (M)$^+$, 417 (M+2)$^+$. $^1$HNMR (500 MHz, DMSO-d$_6$) δ ppm 4.57 (d, J=5.49 Hz, 2H) 7.27 (td, J=8.54, 2.75 Hz, 1H) 7.31 (dd, J=9.76, 2.75 Hz, 1H) 7.42 (ddd, J=7.32, 4.58, 0.61 Hz, 1H) 7.51 (dd, J=8.85, 6.10 Hz, 1H) 7.55 (t, J=5.80 Hz, 1H) 7.63 (m, 2H) 7.74 (dd, J=7.93, 1.53 Hz, 1H) 7.93 (m, 1H) 7.96 (dd, J=8.24, 1.53 Hz, 1H) 8.60 (d, J=4.88 Hz, 1H).

Example 104

[6-Chloro-5-fluoro-2-(2,2,2-trifluoro-ethoxy)-pyridin-3-ylmethyl]-[1-(2,3-dichloro-phenyl)-1H-tetrazol-5-yl]-amine

Example 104A

6-Chloro-5-fluoro-2-(2,2,2-trifluoro-ethoxy)-nicotinonitrile

A mixture of 2,6-dichloro-5-fluoro-nicotinonitrile (900 mg, 5.7 mmol), 2,2,2-trifluoro-ethanol (570 mg, 5.7 mmol), and NaH (60%) (273 mg, 6.8 mmol) in N,N-dimethylformamide (15 mL) was heated at 120° C. overnight. The reaction mixture was poured into water, and extracted with ethyl acetate (2×). The solvent was removed to give the title compound (1100 mg, 76%). MS (DCI/NH$_3$) m/z 255 (M)$^+$, 257 (M+2)$^+$.

Example 104B

C-[6-Chloro-5-fluoro-2-(2,2,2-trifluoro-ethoxy)-pyridin-3-yl]-methylamine

The product from Example 104A according to the method of Example 96B provided the title compound. MS (DCI/NH$_3$) m/z 259 (M)$^+$.

Example 104C

[6-Chloro-5-fluoro-2-(2,2,2-trifluoro-ethoxy)-pyridin-3-ylmethyl]-[1-(2,3-dichloro-phenyl)-1H-tetrazol-5-yl]-amine The product from Example 104B was reacted with 2,3-dichlorophenylisothiocyanate according to the method of Example 78C to provide the title compound. MS (DCI/NH$_3$) m/z 472 (M)$^+$, 474 (M+2)$^+$. $^1$HNMR (500 MHz, DMSO-d$_6$) δ ppm 4.49 (d, J=5.62 Hz, 2H) 5.06 (q, J=8.73 Hz, 2H) 7.63 (t, J=8.11 Hz, 1H) 7.74 (t, J=5.62 Hz, 1H) 7.78 (dd, J=8.11, 1.56 Hz, 1H) 7.86 (d, J=10.29 Hz, 1H) 7.96 (dd, J=8.11, 1.25 Hz, 1H).

Example 105

[1-(2,3-Dichloro-phenyl)-1H-tetrazol-5-yl]-[4-fluoro-2-(3-fluoro-pyridin-2-yl)-benzyl]-amine

Example 105A

[4-Fluoro-2-(3-fluoro-pyridin-2-yl)-benzyl]-carbamic acid tert-butyl ester (2-boronic acid-4-fluoro-benzyl)-carbamic acid tert-butyl ester was reacted with 2-chloro-3-fluoro-pyridine according to the method of Example 103A to provide the title compound. MS (DCI/NH$_3$) m/z 321 (M+1)$^+$.

Example 105B

[1-(2,3-Dichloro-phenyl)-1H-tetrazol-5-yl]-[4-fluoro-2-(3-fluoro-pyridin-2-yl)-benzyl]-amine The product from Example 105A was reacted with 2,3-dichlorophenylisothiocyanate according to the method of Example 80B to provide the title compound. MS (DCI/NH$_3$) m/z 433 (M)$^+$, 435 (M+2)$^+$. $^1$HNMR (500 MHz, DMSO-d$_6$) δ ppm 4.84 (d, J=5.80 Hz, 2H) 7.68 (dd, J=9.46, 1.83 Hz, 1H) 7.73 (td, J=8.54, 2.75 Hz, 1H) 7.92 (m, 3H) 8.00 (m, 1H) 8.01 (d, J=1.83 Hz, 1H) 8.28 (td, J=8.54, 1.22 Hz, 1H) 8.34 (dd, J=5.49, 3.97 Hz, 1H) 8.91 (d, J=4.58 Hz, 1H).

Example 106

[1-(2,3-Dichloro-phenyl)-1H-tetrazol-5-yl]-[4-fluoro-2-(6-fluoro-pyridin-3-yl)-benzyl]-amine

Example 106A

[4-Fluoro-2-(6-fluoro-pyridin-3-yl)-benzyl]-carbamic acid tert-butyl ester (2-boronic acid-4-fluoro-benzyl)-carbamic acid tert-butyl ester was reacted with 5-bromo-2-fluoro-pyridine according to the method of Example 103A to provide the title compound. MS (DCI/NH$_3$) m/z 321 (M+1)$^+$.

Example 106B

[1-(2,3-Dichloro-phenyl)-1H-tetrazol-5-yl]-[4-fluoro-2-(6-fluoro-pyridin-3-yl)-benzyl]-amine The product from Example 106A was reacted with 2,3-dichlorophenylisothiocyanate according to the method of Example 80B to provide the title compound. MS (DCI/NH$_3$) m/z 433 (M)$^+$, 435 (M+2)$^+$. $^1$HNMR (500 MHz, DMSO-d$_6$) δ ppm 4.36 (d, J=5.49 Hz, 2H) 7.19 (dd, J=9.46, 2.75 Hz, 1H) 7.28 (m, 2H) 7.53 (dd, J=8.54, 5.80 Hz, 1H) 7.62 (m, 3H) 7.94 (dd, J=7.93, 1.83 Hz, 1H) 8.08 (td, J=8.24, 2.44 Hz, 1H) 8.29 (d, J=2.14 Hz, 1H).

Example 107

[1-(2,3-Dichloro-phenyl)-1H-tetrazol-5-yl]-[2-(5,6-difluoro-pyridin-3-yl)-4-fluoro-benzyl]-amine

Example 107A

[2-(5,6-Difluoro-pyridin-3-yl)-4-fluoro-benzyl]-carbamic acid tert-butyl ester (2-Boronic acid-4-fluoro-benzyl)-carbamic acid tert-butyl ester was reacted with 5-chloro-2,3-difluoro-pyridine according to the method of Example 103A to provide the title compound. MS (DCI/NH$_3$) m/z 339 (M+1)$^+$.

Example 107B

[1-(2,3-Dichloro-phenyl)-1H-tetrazol-5-yl]-[2-(5,6-difluoro-pyridin-3-yl)-4-fluoro-benzyl]-amine The product from Example 107A was reacted with 2,3-dichlorophenylisothiocyanate according to the method of Example 80B to provide the title compound. MS (DCI/NH$_3$) m/z 451 (M)$^+$, 453 (M+2)$^+$. $^1$HNMR (500 MHz, DMSO-d$_6$) δ ppm 4.40 (d, J=5.30 Hz, 2H) 7.21 (dd, J=9.67, 2.81 Hz, 1H) 7.30 (td, J=8.73, 2.81 Hz, 1H) 7.55 (m, 2H) 7.62 (m, 2H) 7.93 (dd, J=7.80, 1.87 Hz, 1H) 8.10 (m, 1H) 8.20 (td, J=10.61, 2.18 Hz, 1H).

Example 108

[1-(2,3-Dichloro-phenyl)-1H-tetrazol-5-yl]-[4,5-difluoro-2-(2,2,2-trifluoro-ethoxy)-benzyl]-amine

Example 108A

1-Bromo-4,5-difluoro-2-trifluoromethoxy-benzene

A mixture of 2-bromo-4,5-difluoro-phenol (1.0 g, 4.8 mmol), 1,1,1-trifluoro-2-iodo-ethane (706 mg, 7.2 mmol) and CsF (882 mg, 5.8 mmol) in DMSO (20 mL) was heated at 120° C. overnight. The reaction mixture was poured into water, and extracted with ethyl acetate (2×). The solvent was removed, and the resulting residue was chromatographed using hexane/ethyl acetate (10:1) to give the title compound (697 mg, 50%). $^1$HNMR (500 MHz, CDCl$_3$) δ ppm 4.36 (q, J=7.93 Hz, 2H) 6.85 (dd, J=10.98, 7.02 Hz, 1H) 7.43 (t, J=8.85 Hz, 1H).

Example 108B 4,5-Difluoro-2-(2,2,2-trifluoro-ethoxy)-benzonitrile

The product from Example 108A followed the same procedure as described for Example 101B to give the title compound. MS (DCI/NH$_3$) m/z 238 (M+1)$^+$.

Example 108C 4,5-Difluoro-2-(2,2,2-trifluoro-ethoxy)-benzylamine

The product from Example 108B followed the same procedure as described for Example 78B to afford the title compound. MS (DCI/NH$_3$) m/z 242 (M+1)$^+$.

Example 108D

[1-(2,3-Dichloro-phenyl)-1H-tetrazol-5-yl]-[4,5-difluoro-2-(2,2,2-trifluoro-ethoxy)-benzyl]-amine The product from Example 108C was reacted with 2,3-dichlorophenylisothiocyanate according to the method of Example 78C to provide the title compound. MS (DCI/NH$_3$) m/z 454 (M)$^+$, 456 (M+2)$^+$. $^1$HNMR (500 MHz, DMSO-d$_6$) δ ppm 4.44 (d, J=5.80 Hz, 2H) 4.83 (q, J=8.85 Hz, 2H) 7.28 (dd, J=10.98, 9.46 Hz, 1H) 7.37 (dd, J=12.21, 6.71 Hz, 1H) 7.60 (t, J=5.80 Hz, 1H) 7.63 (t, J=8.24 Hz, 1H) 7.77 (dd, J=7.93, 1.53 Hz, 1H) 7.96 (dd, J=7.93, 1.22 Hz, 1H).

Example 109

4-[1-(2,3-Dichloro-phenyl)-1H-tetrazol-5-ylamino]-4,5-dihydro-cyclopenta[b]thiophen-6-one 4-Amino-4,5-dihydro-cyclopenta[b]thiophen-6-one was reacted with 2,3-dichlorophenylisothiocyanate according to the method of Example 78C to provide the title compound. MS (DCI/NH$_3$) m/z 366 (M)$^+$, 368 (M+2)$^+$. $^1$HNMR (400 MHz, DMSO-d$_6$) δ ppm 3.41 (d, J=6.75 Hz, 1H) 3.46 (d, J=6.75 Hz, 1H) 5.45 (m, 1H) 7.21 (d, J=4.91 Hz, 1H) 7.59 (t, J=8.29 Hz, 1H) 7.65 (d, J=8.29 Hz, 1H) 7.70 (dd, J=7.98, 1.53 Hz, 1H) 7.92 (dd, J=7.98, 1.23 Hz, 1H) 8.25 (d, J=4.60 Hz, 1H).

Example 110

[1-(2,3-Dichloro-phenyl)-1H-tetrazol-5-yl]-(4-methyl-oxazol-5-ylmethyl)-amine

Example 110A

4-Methyl-oxazole-5-carbonitrile

4-Methyl-oxazole-5-carboxylic acid amide (200 mg, 1.59 mmol) in POCl$_3$ (2 mL) was refluxed for 7 h. The reaction mixture was poured into water, and extracted with ethyl acetate (2×). The solvent was removed, and the resulting residue was chromatographed using hexane/ethyl acetate (3:1) to give the title compound (240 mg). $^1$HNMR (500 MHz, CDCl$_3$) δ ppm 2.41 (s, 3H) 7.93 (s, 1H)

Example 110B

C-(4-Methyl-oxazol-5-yl)-methylamine

The product from Example 110A followed the same procedure as described for Example 78B to afford the title compound. MS (DCI/NH$_3$) m/z 113 (M+1)$^+$.

Example 110C

[1-(2,3-Dichloro-phenyl)-1H-tetrazol-5-yl]-(4-methyl-oxazol-5-ylmethyl)-amine

The product from Example 110B was reacted with 2,3-dichlorophenylisothiocyanate according to the method of Example 78C to provide the title compound. MS (DCI/NH$_3$) m/z 325 (M)$^+$, 327 (M+2)$^+$. $^1$HNMR (500 MHz, DMSO-d$_6$) δ ppm 2.14 (s, 3H) 4.49 (d, J=5.62 Hz, 2H) 7.59 (t, J=8.11 Hz, 1H) 7.63 (t, J=5.62 Hz, 1H) 7.66 (dd, J=7.80, 1.25 Hz, 1H) 7.93 (dd, J=8.11, 1.56 Hz, 1H) 8.16 (s, 1H).

Example 111

[1-(2,3-Dichloro-phenyl)-1H-tetrazol-5-yl]-(6-fluoro-2-methyl-pyridin-3-ylmethyl)-amine

Example 111A

C-(6-Fluoro-2-methyl-pyridin-3-yl)-methylamine

The title compound was prepared using the procedure as described in Example 78B, substituting 6-fluoro-2-methyl-nicotinonitrile for the product of Example 78A. MS (DCI/NH$_3$) m/z 141 (M+1)$^+$.

Example 111B

[1-(2,3-Dichloro-phenyl)-1H-tetrazol-5-yl]-(6-fluoro-2-methyl-pyridin-3-ylmethyl)-amine The product from Example 111A was reacted with 2,3-dichlorophenylisothiocyanate according to the method of Example 78C to provide the title compound. MS (DCI/NH$_3$) m/z 353 (M)$^+$, 355 (M+2)$^+$. $^1$HNMR (400 MHz, DMSO-d$_6$) δ ppm 2.45 (s, 3H) 4.48 (d, J=5.52 Hz, 2H) 6.95 (dd, J=8.29, 2.76 Hz, 1H) 7.61 (t, J=8.29 Hz, 1H) 7.65 (t, J=5.52 Hz, 1H) 7.73 (dd, J=7.98, 1.53 Hz, 1H) 7.82 (t, J=8.29 Hz, 1H) 7.95 (dd, J=7.98, 1.23 Hz, 1H).

Example 112

[1-(2,3-Dichloro-phenyl)-1H-tetrazol-5-yl]-[4-fluoro-2-(2,2,2-trifluoro-ethoxy)-benzyl]-amine

Example 112A

1-Bromo-4-fluoro-2-(2,2,2-trifluoro-ethoxy)-benzene

2-Bromo-5-fluoro-phenol was reacted with 1,1,1-trifluoro-2-iodo-ethane according to the method of Example 108A to provide the title compound. MS (DCI/NH$_3$) m/z 273 (M)$^+$, 275 (M+2)$^+$.

Example 112B

4-Fluoro-2-(2,2,2-trifluoro-ethoxy)-benzylamine

The product from Example 112A followed the same procedures as described for Example 101B and Example 101C to give the title compound. MS (DCI/NH$_3$) m/z 223 (M+1)$^+$.

Example 112C

[1-(2,3-Dichloro-phenyl)-1H-tetrazol-5-yl]-[4-fluoro-2-(2,2,2-trifluoro-ethoxy)-benzyl]-amine The product from Example 112B was reacted with 2,3-dichlorophenylisothiocyanate according to the method of Example 78C to provide the title compound. MS (DCI/NH$_3$) m/z 436 (M)$^+$, 438 (M+2)$^+$. $^1$HNMR (400 MHz, DMSO-d$_6$) δ ppm 4.44 (d, J=5.52 Hz, 2H) 4.82 (q, J=8.59 Hz, 2H) 6.85 (td, J=8.59, 2.45 Hz, 1H) 7.09 (dd, J=11.05, 2.45 Hz, 1H) 7.28 (t, J=8.29, 7.06 Hz, 1H) 7.52 (t, J=5.83 Hz, 1H) 7.61 (t, J=8.29 Hz, 1H) 7.70 (dd, J=7.98, 1.53 Hz, 1H) 7.94 (dd, J=8.29, 1.53 Hz, 1H).

Example 113

[4-(4-Chloro-phenyl)-thiazol-5-ylmethyl]-[1-(2,3-dichloro-phenyl)-1H-tetrazol-5-yl]-amine

Example 113A (2,4-Dibromo-thiazol-5-yl)-methanol 2,4-Dibromo-thiazole-5-carbaldehyde (2.0 g, 7.4 mmol) in methanol (80 mL) was treated with NaBH$_4$ (419 mg, 11.0 mmol). The reaction mixture was stirred at rt overnight, quenched with 10% NaOH, diluted with water and extracted with ethyl acetate (2×). The solvent was removed, and the resulting residue was chromatographed using hexane/ethyl acetate (3:1) to give the title compound (1.84 g, 91%). MS (DCI/NH$_3$) m/z 274 (M)$^+$. $^1$HNMR (500 MHz, CDCl$_3$) δ ppm 2.11 (s, 1H) 4.78 (s, 2H).

Example 113B 2,4-Dibromo-5-(tert-butyl-dimethyl-silanyloxymethyl)-thiazole

The product from Example 113A following the same procedure as Example 76A gave the title compound. MS (DCI/NH$_3$) m/z 386 (M)$^+$, 388 (M+2)$^+$. $^1$HNMR (400 MHz, CDCl$_3$) δ ppm 0.11 (s, 6H) 0.92 (s, 9H) 4.74 (s, 2H).

Example 113C

4-Bromo-5-(tert-butyl-dimethyl-silanyloxymethyl)-thiazole

The product from Example 113B (1.85 g, 4.78 mmol) in diethyl ether (100 mL) was treated with drop wise n-BuLi (2.5 M in tetrahydrofuran) (1.9 mL, 4.78 mmol) at −78° C. for 1 hr. The reaction was quenched with H$_2$O (10 mL), stirred 45 min until reaching rt, diluted with water and extracted with ethyl acetate (2×). The solvent was removed, and the resulting residue was chromatographed using hexane/ethyl acetate (3:1) to give the title compound (970 mg, 66%). MS (DCI/NH$_3$) m/z 308 (M)$^+$, 310 (M+2)$^+$. $^1$HNMR (400 MHz, CDCl$_3$) δ ppm 0.12 (s, 6H) 0.93 (s, 9H) 4.83 (s, 2H) 8.68 (s, 1H).

Example 113D 5-(tert-Butyl-dimethyl-silanyloxymethyl)-4-(4-chloro-phenyl)-thiazole A flask was charged with the product from Example 113C (300 mg, 0.97 mmol), 4-chloro-phenyl-boronic acid (183 mg, 1.17 mmol), Na$_2$CO$_3$ (2M) (1.46 mL, 2.91 mmol) and PdCl$_2$(PPh$_3$)$_2$ (34 mg, 0.05 mmol) in DME/H$_2$O/ethanol (7:3:2) (20 mL). The reaction mixture was heated at 85° C. overnight. After cooling to room temperature, the mixture was diluted with ethyl acetate and washed with water, dried (MgSO$_4$), filtered and concentrated. The resulting residue was chromatographed using hexane/ethyl acetate (9:1) to give the title compound (185 mg, 56%). MS (DCI/NH$_3$) m/z 340 (M)$^+$,
$^1$H NMR (500 MHz, CDCl$_3$) δ ppm 0.10 (s, 6H) 0.94 (s, 9H) 4.94 (s, 2H) 7.43 (d, J=8.24 Hz, 2H) 7.61 (d, J=8.24 Hz, 2H) 8.75 (s, 1H).

Example 113E

[4-(4-Chloro-phenyl)-thiazol-5-yl]-methanol

The product from Example 113D following the same procedure as Example 76D gave the title compound. MS (DCI/NH$_3$) m/z 226 (M)$^+$. $^1$HNMR (400 MHz, CDCl$_3$) δ ppm 4.95 (d, J=4.60 Hz, 2H) 7.43 (d, J=8.59 Hz, 2H) 7.64 (d, J=8.59 Hz, 2H) 8.79 (s, 1H).

Example 113F

5-Azidomethyl-4-(4-chloro-phenyl)-thiazole

The product from Example 113E following the same procedure as Example 77A gave the title compound. MS (DCI/NH$_3$) m/z 251 (M)$^+$.

Example 113G

C-[4-(4-Chloro-phenyl)-thiazol-5-yl]-methylamine

The product from Example 113F following the same procedure as Example 77B gave the title compound. MS (DCI/NH$_3$) m/z 225 (M)$^+$.

Example 113H

[4-(4-Chloro-phenyl)-thiazol-5-ylmethyl]-[1-(2,3-dichloro-phenyl)-1H-tetrazol-5-yl]-amine The product from Example 113G was reacted with 2,3-dichlorophenylisothiocyanate according to the method of Example 78C to provide the title compound. MS (DCI/NH$_3$) m/z 437 (M)$^+$, 439 (M+2)$^+$. $^1$HNMR (400 MHz, DMSO-d$_6$) δ ppm 4.79 (d, J=5.22 Hz, 2H) 7.52 (s, 1H) 7.54 (s, 1H) 7.61 (d, J=7.98 Hz, 1H) 7.66 (dd, J=7.98, 1.84 Hz, 1H) 7.71 (s, 1H) 7.73 (s, 1H) 7.94 (dd, J=7.98, 1.53 Hz, 1H) 7.97 (t, J=5.22 Hz, 1H) 9.04 (s, 1H).

Example 114

1-(2,3-dichlorophenyl)-N-(quinolin-5-ylmethyl)-1H-tetraazol-5-amine 1-quinolin-5-ylmethanamine (Adachi; Oota; Kanazawa *Daigaku Yakugakubu Kenkyo Nempo;* 7; 1957; 10) was treated with 2,3-dichlorophenylisothiocyanate according to the method of Example 78C to provide the title compound. MS (ESI$^+$) m/z 371 (M+H)$^+$; $^1$H NMR (300 MHz, DMSO-d$_6$) δ ppm 4.97 (d, J=5.42 Hz, 2H) 7.52-7.64 (m, 3H) 7.67-7.76 (m, 2H) 7.79 (t, J=5.59 Hz, 1H) 7.92 (dd, J=8.14, 1.70 Hz, 1H) 7.96 (d, J=8.48 Hz, 1H) 8.56 (dq, J=8.65, 0.85 Hz, 1H) 8.92 (dd, J=4.07, 1.70 Hz, 1H). Anal. calcd for C$_{17}$H$_{12}$Cl$_2$N$_6$: C, 55.00; H, 3.26; N, 22.64. Found: C, 54.86; H, 2.98; N, 22.63.

Example 115

1-(2,3-dichlorophenyl)-N-[(2-morpholin-4-ylpyridin-3-yl)methyl]-1H-tetraazol-5-amine Example 115A 4-[3-(azidomethyl)pyridin-2-yl]morpholine To a solution of (2-morpholino-3-pyridinyl)methanol (1 g, 5.01 mmol) in dichloromethane (20 ml) was added thionyl chloride (3 ml) dropwise at 0° C. and allowed to warm to room temperature. After stirring at room temperature for 6 h, solvents were removed under reduced pressure and the residue was dissolved and concentrated repeatedly in dichloromethane to remove excess of thionyl chloride. The obtained crude chloride intermediate, (2-morpholino-3-pyridinyl)methylchloride, was immediately dissolved in acetone (25 ml) and added sodium azide (1.63 g, 25.05 mmol) at room temperature. The reaction was refluxed for overnight, solvents were removed under reduced pressure, dissolved in dichloromethane (25 ml) and washed with 1M NaHCO$_3$ (25 ml). The aqueous layer was extracted with dichloromethane (2×20 ml). The combined organic extracts were dried (Na$_2$SO$_4$), filtered and concentrated to yield 0.62 g (57%) of product as a thick yellowish liquid. MS (ESI$^+$) m/z 220 (M+H)$^+$;

Example 115B (2-morpholin-4-ylpyridin-3-yl)methylamine

To a solution of the product from Example 115A (0.62 g) in methanol (10 ml) was added Pd/C (0.06 g) under $N_2$ atmosphere. The reaction mixture was stirred at room temperature under $H_2$ atmosphere. After 6 h, the reaction mixture was filtered through celite and concentrated to yield 0.42 g (78%) of product. MS (ESI$^+$) m/z 194 (M+H)$^+$;

Example 115C 1-(2,3-dichlorophenyl)-N-[(2-morpholin-4-ylpyridin-3-yl)methyl]-1H-tetraazol-5-amine The product of Example 115B was treated with 2,3-dichlorophenylisothiocyanate according to the method of Example 78C to provide the title compound. MS (ESI$^+$) m/z 406 (M+H)$^+$; $^1$H NMR (300 MHz, DMSO-d$_6$) δ ppm 2.88-3.17 (m, 4H) 3.62-3.80 (m, 4H) 4.51 (d, J=5.76 Hz, 2H) 7.04 (dd, J=7.46, 4.75 Hz, 1H) 7.60-7.66 (m, 2H) 7.69-7.76 (m, 2H) 7.95 (dd, J=8.14, 1.70 Hz, 1H) 8.20 (dd, J=4.92, 1.86 Hz, 1H). Anal. calcd for $C_{17}H_{17}Cl_2N_7O$: C, 50.26; H, 4.22; N, 24.13. Found: C, 50.50; H, 3.92; N, 24.33.

Example 116

1-[2-fluoro-3-(trifluoromethyl)phenyl]-N-[2-(pyridin-2-yloxy)benzyl]-1H-tetraazol-5-amine

Example 116A 2-fluoro-1-isothiocyanato-3-trifluoromethyl-benzene

To a two phase solution of 2-fluoro-3-trifluoromethyl-phenylamine (2 g, 11.17 mmole) in dichloromethane (40 ml) and sodium bicarbonate (6.57 g, 78.19 mmole) in water (30 ml) at 0° C. was added dropwise a solution of thiophosgene (1.28 g, 11.17 mmole) in dichloromethane (10 ml). After 2 hrs, the organic layer was separated, washed sequentially with 1M NaHCO$_3$, brine and water. The organic layer was dried over Na$_2$SO$_4$, filtered and concentrated to yield 2.2 g (91%) of product as a viscous liquid. MS (ESI$^+$) m/z 221 (M+H)$^+$.

Example 116B

1-[2-fluoro-3-(trifluoromethyl)phenyl]-N-[2-(pyridin-2-yloxy)benzyl]-1H-tetraazol-5-amine The product from Example 116A was treated with 2-(pyridin-2-yloxy)benzylamine hydrochloride according to the method of Example 78C to provide the title compound. MS (ESI$^+$) m/z 431 (M+H)$^+$; $^1$H NMR (300 MHz, DMSO-d$_6$) δ ppm 4.44 (d, J=5.76 Hz, 2H) 7.01 (d, J=8.48 Hz, 1H) 7.05-7.16 (m, 2H) 7.22 (td, J=7.46, 1.36 Hz, 1H) 7.33 (td, J=7.63, 1.70 Hz, 1H) 7.40 (dd, J=7.63, 1.53 Hz, 1H) 7.64 (t, J=7.97 Hz, 1H) 7.76 (t, J=5.60 Hz, 1H) 7.81-7.89 (m, 1H) 7.96 (t, J=7.63 Hz, 1H) 8.03-8.13 (m, 2H). Anal. calcd for $C_{20}H_{14}F_4N_6O$: C, 55.82; H, 3.28; N, 19.53. Found: C, 55.60; H, 3.05; N, 19.56.

Example 117

1-[2-chloro-3-(trifluoromethyl)phenyl]-N-[2-(pyridin-2-yloxy)benzyl]-1H-tetraazol-5-amine 2-chloro-1-isothiocyanato-3-trifluoromethyl-benzene
Thiophosgene and 2-chloro-3-trifluoromethyl-phenylamine were processed according to the method of Example 116A to provide the product. MS (ESI$^+$) m/z 237 (M+H)$^+$.

Example 117B

1-[2-chloro-3-(trifluoromethyl)phenyl]-N-[2-(pyridin-2-yloxy)benzyl]-1H-tetraazol-5-amine The product of Example 117A was treated with 2-(pyridin-2-yloxy)benzylamine hydrochloride according to the method of Example 78C to provide the title compound. MS (ESI$^+$) m/z 447 (M+H)$^+$; $^1$H NMR (300 MHz, DMSO-d$_6$) δ ppm 4.42 (d, J=5.76 Hz, 2H) 7.02 (d, J=8.14 Hz, 1H) 7.06-7.15 (m, 2H) 7.21 (td, J=7.38, 1.19 Hz, 1H) 7.32 (td, J=7.71, 1.87 Hz, 1H) 7.40 (dd, J=7.46, 1.70 Hz, 1H) 7.63 (t, J=5.76 Hz, 1H) 7.75-7.89 (m, 2H) 7.92-7.98 (m, 1H) 8.07-8.18 (m, 2H). Anal. calcd for $C_{20}H_{14}ClF_4N_6O$: C, 53.76; H, 3.16; N, 18.81. Found: C, 53.74; H, 2.93; N, 18.86.

Example 118

1-(2,3-dichlorophenyl)-N-[2-(pyridin-3-yloxy)benzyl]-1H-tetraazol-5-amine

The compound, 2,3-dichlorophenylisothiocyanate was treated with 2-(pyridin-3-yloxy)benzylamine hydrochloride according to the method of Example 78C to provide the title compound. MS (ESI$^+$) m/z 413 (M+H)$^+$; $^1$H NMR (300 MHz, DMSO-d$_6$) δ ppm 4.52 (d, J=5.76 Hz, 2H) 6.90-6.96 (m, 1H) 7.20 (td, J=7.54, 0.85 Hz, 1H) 7.28-7.48 (m, 4H) 7.55-7.69 (m, 3H) 7.94 (dd, J=7.29, 2.54 Hz, 1H) 8.31-8.38 (m, 2H).

Example 119

1-(2,3-dichlorophenyl)-N-(2-pyridin-3-ylbenzyl)-1H-tetraazol-5-amine

Example 119A (2-pyridin-3-yl-phenyl)-methanol

To a solution of 2-pyridin-3-yl-benzaldehyde (1 g, 5.46 mmole) in methanol (10 ml) was added a solution of NaBH$_4$ (0.26 g, 6.82 mmole) in methanol (10 ml) at 0° C. and stirred for 30 min at same temperature and then refluxed for 1 h. The unreacted NaBH$_4$ was decomposed by solution of 6N HCl. The solvent was removed under reduced pressure and the residue was dissolved in 5N NaOH (20 ml) and extracted with ethyl acetate (3×20 ml). Combined organic extracts were dried (Na$_2$SO$_4$), filtered and concentrated to yield 0.95 g (94%) of product. MS (ESI$^+$) m/z 186 (M+H)$^+$.

Example 119B

3-[2-(azidomethyl)phenyl]pyridine

The product of Example 119A, thionyl chloride and sodium azide were processed according to the method of Example 115A to provide the product. MS (ESI$^+$) m/z 211 (M+H)$^+$.

Example 119C 1-(2-pyridin-3-ylphenyl)methanamine

The product of Example 119B and Pd/C were processed according to the method of Example 115B to provide the product. MS (ESI$^+$) m/z 185 (M+H)$^+$.

Example 119D 1-(2,3-dichlorophenyl)-N-(2-pyridin-3-ylbenzyl)-1H-tetraazol-5-amine The product of Example 119C was treated with 2,3-dichlorophenylisothiocyanate according to the method of Example 78C to provide the title compound. MS (ESI$^+$) m/z 397 (M+H)$^+$; $^1$H NMR (300 MHz, DMSO-d$_6$) δ ppm 4.41 (d, J=5.43 Hz, 2H) 7.25-7.31 (m, 1H) 7.35-7.52 (m, 4H) 7.59-7.67 (m, 3H) 7.83-7.88 (m, J=8.14, 2.03, 1.70 Hz, 1H) 7.93 (dd, J=7.46, 2.37 Hz, 1H) 8.57-8.63 (m, 2H).

Example 120

1-(2,3-dichlorophenyl)-N-(2-pyridin-4-ylbenzyl)-1H-tetraazol-5-amine

Example 120A (2-pyridin-4-ylphenyl)methanol 2-pyridin-4-yl-benzaldehyde was treated with NaBH$_4$ according to the method of Example 119A to provide the title compound. MS (ESI$^+$) m/z 185 (M+H)$^+$;

Example 120B

4-[2-(azidomethyl)phenyl]pyridine

The product of Example 120A, thionyl chloride and sodium azide were processed according to the method of Example 115A to provide the product. MS (ESI$^+$) m/z 211 (M+H)$^+$.

Example 120C 1-(2-pyridin-4-ylphenyl)methanamine

The product of Example 120B and Pd/C were processed according to the method of Example 115B to provide the product. MS (ESI$^+$) m/z 186 (M+H)$^+$;

Example 120D 1-(2-pyridin-4-ylphenyl)methanamine

The product of Example 120C was treated with 2,3-dichlorophenylisothiocyanate according to the method of Example 78C to provide the title compound. MS (ESI$^+$) m/z 397 (M+H)$^+$; $^1$H NMR (300 MHz, DMSO-d$_6$) δ ppm 4.43 (d, J=5.42 Hz, 2H) 7.25-7.30 (m, 1H) 7.36-7.52 (m, 5H) 7.58-7.67 (m, 3H) 7.94 (dd, J=7.29, 2.54 Hz, 1H) 8.61-8.66 (m, 2H).

Example 121

1-(2,3-dichlorophenyl)-N-[(4-methyl-1,3-thiazol-5-yl)methyl]-1H-tetraazol-5-amine C-(4-methyl-thiazol-5-yl)-methylamine (Buchman; Sargent; J. Amer. Chem. Soc Vol. 67, page 400, 1945) was treated with 2,3-dichlorophenylisothiocyanate according to the method of Example 78C to provide the title compound. MS (ESI$^+$) m/z 341 (M+H)$^+$; $^1$H NMR (300 MHz, DMSO-d$_6$) δ ppm 2.39 (s, 3H) 4.62 (d, J=5.76 Hz, 2H) 7.56-7.70 (m, 2H) 7.76 (t, J=5.76 Hz, 1H) 7.95 (d, J=8.14 Hz, 1H) 8.85 (s, 1H).

Example 122

1-(2,3-dichlorophenyl)-N-{[6-(trifluoromethyl)pyridin-3-yl]methyl}-1H-tetraazol-5-amine 2,3-dichlorophenylisothiocyanate was treated with 3-aminomethyl-6-(trifluoromethyl)pyridine according to the method of Example 78C to provide the title compound. MS (ESI$^+$) m/z 389 (M+H)$^+$; $^1$H NMR (400 MHz, DMSO-d$_6$) δ ppm 4.62 (d, J=5.76 Hz, 2H) 7.63 (t, J=7.97 Hz, 1H) 7.77 (d, J=9.49 Hz, 1H) 7.82-8.05 (m, 4H) 8.74 (s, 1H).

Example 123

{1-[2-({[1-(2,3-dichlorophenyl)-1H-tetraazol-5-yl]amino}methyl)phenyl]piperidin-4-yl}methanol 2,3-dichlorophenylisothiocyanate was treated with [1-[2-(aminomethyl)phenyl]-4-piperdinyl]methanol according to the method of Example 78C to provide the title compound. MS (ESI$^+$) m/z 433 (M+H)$^+$; $^1$H NMR (400 MHz, DMSO-d$_6$) δ ppm 1.15-1.33 (m, 2H) 1.47 (br. s., 1H) 1.74 (d, J=11.19 Hz, 2H) 2.61 (t, J=10.85 Hz, 2H) 3.00 (d, J=11.87 Hz, 2H) 4.47 (t, J=5.26 Hz, 1H) 4.55 (d, J=5.76 Hz, 2H) 7.02 (t, J=7.46 Hz, 1H) 7.11 (d, J=7.12 Hz, 1H) 7.18-7.30 (m, 2H) 7.54 (t, J=5.76 Hz, 1H) 7.60 (t, J=7.97 Hz, 1H) 7.68-7.73 (m, 1H) 7.93 (dd, J=8.31, 1.19 Hz, 1H).

Example 124

1-(2,3-dichlorophenyl)-N-[(2-ethylpyridin-3-yl)methyl]-1H-tetraazol-5-amine

Example 124A (2-ethylpyridin-3-yl)methanol

To a suspension of LiAlH$_4$ (0.83 g, 21.76 mmol) in tetrahydrofuran (50 ml) was added drop wise a solution of 2-ethylnicotinic acid ethyl ester (Breitmaier et al, Tetrahedron, 26, 1970, 5907-5910) (3 g, 16.74 mmol) in tetrahydrofuran (25 ml) at −50° C. After addition, the temperature was slowly allowed to increase to 0° C. After 3 h, the reaction was quenched with saturated NH$_4$Cl, filtered and washed with 1M NaHCO$_3$ (50 ml). The aqueous layer was extracted with ethyl acetate (3×50 ml). Combined organic extract were dried (Na$_2$SO$_4$), filtered and concentrated to yield 1.6 g (54%) of product as a yellowish liquid. MS (ESI$^+$) m/z 138 (M+H)$^+$;

Example 124B 3-(azidomethyl)-2-ethylpyridine

The product of Example 124A, thionyl chloride and sodium azide were processed according to the method of Example 115A to provide the product. MS (ESI$^+$) m/z 163 (M+H)$^+$.

Example 124C (2-ethylpyridin-3-yl)methylamine

The product of Example 124B and Pd/C were processed according to the method of Example 115B to provide the product. MS (ESI$^+$) m/z 137 (M+H)$^+$.

Example 124D 1-(2,3-dichlorophenyl)-N-[(2-ethylpyridin-3-yl)methyl]-1H-tetraazol-5-amine The product of Example 124C was treated with 2,3-dichlorophenylisothiocyanate according to the method of product of Example 78C to provide the title compound. MS (ESI$^+$) m/z 349 (M+H)$^+$; $^1$H NMR (300 MHz, DMSO-d$_6$) δ ppm 1.21 (t, J=7.46 Hz, 3H) 2.80 (q, J=7.46 Hz, 2H) 4.51 (d, J=5.76 Hz, 2H) 7.19 (dd, J=7.80, 4.75 Hz, 1H) 7.57-7.70 (m, 3H) 7.71-7.76 (m, 1H) 7.95 (dd, J=8.14, 1.36 Hz, 1H) 8.39 (dd, J=4.75, 1.70 Hz, 1H).

Example 125

1-(2,3-dichlorophenyl)-N-[(2-fluoropyridin-3-yl)methyl]-1H-tetraazol-5-amine 2,3-dichlorophenylisothiocyanate was treated with product from Example 193C according to the method of product of Example 78C to provide the title compound. MS (ESI$^+$) m/z 339 (M+H)$^+$; $^1$H NMR (400 MHz, DMSO-d$_6$) δ ppm 4.51 (d, J=5.76 Hz, 2H) 7.30-7.39 (m, 1H) 7.62 (t, J=7.97 Hz, 1H) 7.71-7.83 (m, 2H) 7.86-7.99 (m, 2H) 8.15 (td, J=3.22, 1.70 Hz, 1H)

Example 126

1-(2,3-dichlorophenyl)-N-{2-[2-(diethylamino)ethoxy]benzyl}-1H-tetraazol-5-amine

Example 126A

N-{2-[2-(azidomethyl)phenoxy]ethyl}-N,N-diethylamine

[2-(2-diethylamino-ethoxy)-phenyl]methanol (Cossey, H. D. et al.; *J. Chem. Soc.* 1965; 954-973), thionyl chloride and sodium azide were processed according to the method of Example 115A to provide the product. MS (ESI$^+$) m/z 249 (M+H)$^+$.

Example 126B

N-{2-[2-(aminomethyl)phenoxy]ethyl}-N,N-diethylamine

The product of Example 126A and Pd/C were processed according to the method of Example 115B to provide the product. MS (ESI$^+$) m/z 223 (M+H)$^+$.

Example 126C 1-(2,3-dichlorophenyl)-N-{2-[2-(diethylamino)ethoxy]benzyl}-1H-tetraazol-5-amine The product of Example 126B was treated with 2,3-dichlorophenylisothiocyanate according to the method of Example 78C to provide the title compound. MS (ESI$^+$) m/z 435 (M+H)$^+$; $^1$H NMR (400 MHz, DMSO-d$_6$) δ ppm 0.98 (t, J=7.12 Hz, 6H) 2.50-2.53 (m, 2H) 2.53-2.63 (m, 2H) 2.69-2.87 (m, 2H) 3.97-4.10 (m, 2H) 4.46 (d, J=5.76 Hz, 2H) 6.89 (t, J=7.80 Hz, 1H) 6.98 (d, J=7.80 Hz, 1H) 7.13-7.30 (m, 2H) 7.46 (t, J=5.59 Hz, 1H) 7.61 (t, J=7.97 Hz, 1H) 7.68-7.78 (m, 1H) 7.94 (dd, J=8.14, 1.70 Hz, 1H).

Example 127

N-[(2-chloro-5-fluoropyridin-3-yl)methyl]-1-(2,3-dichlorophenyl)-1H-tetraazol-5-amine

Example 127A 3-(azidomethyl)-2-chloro-5-fluoropyridine (2-chloro-5-fluoro-pyridin-3-yl)-methanol, thionyl chloride and sodium azide were processed according to the method of Example 115A to provide the product. MS (ESI$^+$) m/z 187 (M+H)$^+$.

Example 127B (2-chloro-5-fluoropyridin-3-yl)methylamine

The product of Example 127A was processed according to the method of Example 115B except that Pt/C was used instead of Pd/C as catalyst. MS (ESI$^+$) m/z 161 (M+H)$^+$.

Example 127C

N-[(2-chloro-5-fluoropyridin-3-yl)methyl]-1-(2,3-dichlorophenyl)-1H-tetraazol-5-amine The product of Example 127B was treated with 2,3-dichlorophenylisothiocyanate according to the method of Example 78C to provide the title compound. MS (ESI$^+$) m/z 373 (M+H)$^+$; $^1$H NMR (400 MHz, DMSO-d$_6$) δ ppm 4.54 (d, J=5.76 Hz, 2H) 7.65 (t, J=8.14 Hz, 1H) 7.75 (dd, J=8.81, 2.71 Hz, 1H) 7.83 (dd, J=7.97, 1.53 Hz, 2H) 7.97 (dd, J=8.14, 1.36 Hz, 1H) 8.41 (d, J=3.05 Hz, 1H).

Example 128

1-(2,3-dichlorophenyl)-N-[4-fluoro-3-(pyrazin-2-yloxy)benzyl]-1H-tetraazol-5-amine

Example 128A ethyl 4-fluoro-3-hydroxybenzoate

To a solution of 4-fluoro-3-hydroxy-benzoic acid (2 g, 12.81 mmol) in absolute ethanol (30 ml) was added thionyl chloride (1 ml) drop wise at 0° C. After refluxing for overnight, the solvents were driven off, the residue was dissolved in dichloromethane (50 ml), cooled on ice bath, neutralized slowly with 1M NaHCO$_3$, and the layers were separated. The aqueous layer was extracted with dichloromethane (50 ml) for one more time. Combined organic extracts were dried (Na$_2$SO$_4$), filtered, concentrated, and purified by flash column chromatography using dichloromethane to yield 2.2 g (93%) of product. MS (ESI$^+$) m/z 185 (M+H)$^+$.

Example 128B ethyl 4-fluoro-3-(pyrazin-2-yloxy)benzoate

To a solution of 4-fluoro-3-hydroxy-benzoic acid ethyl ester (2.2 g, 11.95 mmol) in N,N-dimethylformamide (50 ml) was added 60% NaH in mineral oil (0.72 g, 17.93 mmol) and chloropyrazine (1.64 g, 14.34 mmol) and heated at 80° C. for overnight. One more equivalent of chloropyrazine was added and heated at the same temperature for 10 h. The reaction mixture was poured into a flask containing 150 ml of aqueous saturated NaCl solution and 0.6 ml of acetic acid. The mixture was extracted with ethyl acetate (3×100 ml), the combined organic extracts were washed with sat NaCl (150 ml), dried (Na$_2$SO$_4$), filtered and concentrated. The crude product was purified by flash column chromatography using dichloromethane to yield 1.55 g (50%) of product. MS (ESI$^+$) m/z 263 (M+H)$^+$;

Example 128C

[4-fluoro-3-(pyrazin-2-yloxy)phenyl]methanol

The product of Example 128B and LiAlH$_4$ were processed according to the method of Example 124B to provide the product. MS (ESI$^+$) m/z 221 (M+H)$^+$.

Example 128D

2-[5-(azidomethyl)-2-fluorophenoxy]pyrazine

The product of Example 128C, thionyl chloride and sodium azide were processed according to the method of Example 115A to provide the product. MS (ESI$^+$) m/z 237 (M+H)$^+$.

Example 128E

1-[4-fluoro-3-(pyrazin-2-yloxy)phenyl]methanamine

The product of Example 128B was processed according to the method of Example 115B except that Pt/C was used instead of Pd/C as catalyst. MS (ESI$^+$) m/z 220 (M+H)$^+$.

Example 128F 1-(2,3-dichlorophenyl)-N-[4-fluoro-3-(pyrazin-2-yloxy)benzyl]-1H-tetraazol-5-amine The product of Example 128E was treated with 2,3-dichlorophenylisothiocyanate according to the method of Example 78C to provide the title compound. MS (ESI$^+$) m/z 432 (M+H)$^+$; $^1$H NMR (400 MHz, DMSO-d$_6$) δ ppm 4.49 (d, J=5.76 Hz, 2H) 7.23-7.41 (m, 3H) 7.61 (t, J=7.97 Hz, 1H) 7.69-7.78 (m, 2H) 7.95 (dd, J=8.14, 1.36 Hz, 1H) 8.18 (dd, J=2.54, 1.53 Hz, 1H) 8.42 (d, J=2.71 Hz, 1H) 8.66 (d, J=1.36 Hz, 1H).

Example 129

1-(2,3-dichlorophenyl)-N-[(3-fluoropyridin-4-yl)methyl]-1H-tetraazol-5-amine

Example 129A ethyl 3-fluoroisonicotinate 3-fluoro-isonicotinic acid and ethyl alcohol were processed according to the method of Example 128A to provide the product. MS (ESI$^+$) m/z 170 (M+H)$^+$;

Example 129B (3-fluoropyridin-4-yl)methanol

The product of Example 129A and LiAlH$_4$ were processed according to the method of Example 124B to provide the product. MS (ESI$^+$) m/z 128 (M+H)$^+$;

Example 129C 4-(azidomethyl)-3-fluoropyridine

The product of Example 129B, thionyl chloride and sodium azide were processed according to the method of Example 115A to provide the product. MS (ESI$^+$) m/z 153 (M+H)$^+$.

Example 129D (3-fluoropyridin-4-yl)methylamine

The product of Example 129C was processed according to the method of Example 115B except that Pt/C was used instead of Pd/C as catalyst. MS (ESI$^+$) m/z 127 (M+H)$^+$;

Example 129E 1-(2,3-dichlorophenyl)-N-[(3-fluoropyridin-4-yl)methyl]-1H-tetraazol-5-amine The product of Example 129D was treated with 2,3-dichlorophenylisothiocyanate according to the method of Example 78C to provide the title compound. MS (ESI$^+$) m/z 339 (M+H)$^+$; $^1$H NMR (400 MHz, DMSO-d$_6$) δ ppm 4.58 (d, J=5.76 Hz, 2H) 7.39 (dd, J=6.27, 5.26 Hz, 1H) 7.64 (t, J=8.14 Hz, 1H) 7.73-7.81 (m, 1H) 7.86 (t, J=5.76 Hz, 1H) 7.94-8.00 (m, 1H) 8.40 (dd, J=4.75, 1.02 Hz, 1H) 8.53 (d, J=1.70 Hz, 1H).

Example 130

N-[(3-chloropyridin-4-yl)methyl]-1-(2,3-dichlorophenyl)-1H-tetraazol-5-amine

Example 130A (3-chloropyridin-4-yl)methanol

The title compound was prepared using the procedure as described in Marsais, Francis; Breant, Patrice; Ginguene, Alain; Queguiner, Guy; Organomet. Chem. Vol. 216 page 139-147 1981. MS (ESI$^+$) m/z 144 (M+H)$^+$.

Example 130A 4-(azidomethyl)-3-chloropyridine 3-chloro-pyridin-4-yl)-methanol (Marsais, Francis; Breant, Patrice; Ginguene, Alain; Queguiner, Guy; *Organomet. Chem. Vol.* 216 page 139-147, 1981), thionyl chloride and sodium azide were processed according to the method of Example 115A to provide the product. MS (ESI$^+$) m/z 170 (M+H)$^+$.

Example 130C (3-chloropyridin-4-yl)methylamine

The product of Example 130B was processed according to the method of Example 115B except that Pt/C was used instead of Pd/C as catalyst. MS (ESI$^+$) m/z 143 (M+H)$^+$;

Example 130D

N-[(3-chloropyridin-4-yl)methyl]-1-(2,3-dichlorophenyl)-1H-tetraazol-5-amine The product of Example 130C was treated with 2,3-dichlorophenylisothiocyanate according to the method of Example 78C to provide the title compound. MS (ESI$^+$) m/z 355 (M+H)$^+$; $^1$H NMR (400 MHz, DMSO-d$_6$) δ ppm 4.58 (d, J=5.76 Hz, 2H) 7.37 (d, J=5.09 Hz, 1H) 7.65 (t, J=8.14 Hz, 1H) 7.78-7.83 (m, 1H) 7.90 (t, J=5.76 Hz, 1H) 7.98 (dd, J=8.14, 1.70 Hz, 1H) 8.50 (d, J=5.09 Hz, 1H) 8.61 (s, 1H).

Example 131

1-(2,3-dichlorophenyl)-N-[1-(2-methylpyridin-3-yl)ethyl]-1H-tetraazol-5-amine

Example 131A

1-(2-methylpyridin-3-yl)ethanone

To a solution of 1-(2-methyl-pyridin-3-yl)-ethanone (Schmelkes; Joiner; *J. Amer. Chem. Soc.;* 61; 1939; 2562) (0.8 g, 6 mmol) in absolute ethanol (10 ml) was added HCl salt of methoxylamine (0.5 g, 6 mmol) and stirred 60° C. for overnight. To drive the reaction to the completion, 0.5 equivalent more of methoxylamine chloride was added and heated at the same temperature for 6 h. Solvents were driven off and the residue was dissolved in ethyl acetate and washed with 1M NaHCO$_3$. The solution was dried (Na$_2$SO$_4$) and concentrated to yield 0.66 (67%) g of product. MS (ESI$^+$) m/z 165 (M+H)$^+$.

Example 131C

1-(2-methylpyridin-3-yl)ethanamine

To a solution of the product of Example 131B (0.61 g, 3.72 mmol) in 7N N$_3$ in methanol (50 ml) was added Raney nickel (6.1 g) under argon atmosphere. The reaction mixture was kept on shaker under 60 psi H$_2$ atmosphere. After 6 h at room temperature, the reaction mixture was filtered through micro pore filter and concentrated to yield 0.45 g (88%) of product. MS (ESI$^+$) m/z 137 (M+H)$^+$.

Example 131D

1-(2,3-dichlorophenyl)-N-[1-(2-methylpyridin-3-yl)ethyl]-1H-tetraazol-5-amine The product of Example 131C was treated with 2,3-dichlorophenylisothiocyanate according to the method of Example 78C to provide the title compound. MS (ESI$^+$) m/z 349 (M+H)$^+$; $^1$H NMR (400 MHz, DMSO-d$_6$) δ ppm 1.43 (d, J=6.78 Hz, 3H) 2.58 (s, 3H) 4.93-5.13 (m, 1H) 7.19 (dd, J=7.63, 4.92 Hz, 1H) 7.52-7.77 (m, 4H) 7.97 (dd, J=7.97, 1.86 Hz, 1H) 8.30 (dd, J=4.75, 1.70 Hz, 1H).

Example 132

1-(2,3-dichlorophenyl)-N-[(2,2-difluoro-1,3-benzodioxol-4-yl)methyl]-1H-tetraazol-5-amine C-(2,2-difluoro-benzo[1,3]dioxol-4-yl)-methylamine (Schlosser et al. *Eur. J. Org. Chem.* Vol. 3, page 452-462, 2003) was treated with 2,3-dichlorophenylisothiocyanate according to the method of Example 78C to provide the title compound. MS (ESI$^+$) m/z 400 (M+H)$^+$; $^1$H NMR (400 MHz, DMSO-d$_6$) δ ppm 4.56 (d, J=5.76 Hz, 2H) 7.16-7.19 (m, 2H) 7.29-7.34 (m, 1H) 7.58-7.65 (m, 1H) 7.68-7.74 (m, 1H) 7.84 (t, J=5.76 Hz, 1H) 7.96 (dd, J=8.14, 1.70 Hz, 1H).

Example 133

1-[2-fluoro-3-(trifluoromethyl)phenyl]-N-{[2-(2,2,2-trifluoroethoxy)pyridin-3-yl]methyl}-1H-tetraazol-5-amine The C-[2-(2,2,2-trifluoro-ethoxy)-pyridin-3-yl]-methylamine was treated with 2,3-dichlorophenylisothiocyanate according to the method of Example 78C to provide the title compound. MS (ESI$^+$) m/z 437 (M+H)$^+$; $^1$H NMR (300 MHz, DMSO-d$_6$) δ ppm 4.49 (d, J=5.42 Hz, 2H) 5.03 (q, J=9.04 Hz, 2H) 7.11 (dd, J=7.29, 4.92 Hz, 1H) 7.61-7.73 (m, 2H) 7.83 (t, J=5.76 Hz, 1H) 8.03-8.14 (m, 3H).

Example 134

1-(2,3-dichlorophenyl)-N-{[2-(2,6-dimethylmorpholin-4-yl)pyridin-3-yl]methyl}-1H-tetraazol-5-amine

Example 134A

2-(2,6-dimethylmorpholin-4-yl)nicotinonitrile

A solution of 2-fluoro-nicotinonitrile (1.06 g, 8.69 mmol) and 2,6-dimethyl-morpholine (1.0 g, 8.69 mmol) in tetrahydrofuran (10 ml) was heated at 110° C. for 10 min in a microwave reactor. The reaction mixture was concentrated and purified by flash column chromatography using hexanes: ethylacetate (2:1) to yield 0.37 g (40%) of product. MS (ESI$^+$) m/z 218 (M+H)$^+$;

Example 134B

[2-(2,6-dimethylmorpholin-4-yl)pyridin-3-yl]methylamine

The product of Example 134A and Raney/nickel were processed according to the method of Example 131C to provide the product. MS (ESI$^+$) m/z 222 (M+H)$^+$;

Example 134C

1-(2,3-dichlorophenyl)-N-{[2-(2,6-dimethylmorpholin-4-yl)pyridin-3-yl]methyl}-1H-tetraazol-5-amine The product of Example 134B was treated with 2,3-dichlorophenylisothiocyanate according to the method of Example 78C to provide the title compound. MS (ESI$^+$) m/z 434 (M+H)$^+$; $^1$HNMR (300 MHz, DMSO-d$_6$) δ ppm 1.10 (d, J=6.44 Hz, 6H) 2.44 (d, J=10.17 Hz, 2H) 3.20 (d, J=11.87 Hz, 2H) 3.65-3.82 (m, 2H) 4.50 (d, J=5.42 Hz, 2H) 7.02 (dd, J=7.63, 4.92 Hz, 1H) 7.56-7.75 (m, 4H) 7.94 (dd, J=7.97, 1.53 Hz, 1H) 8.18 (dd, J=4.75, 2.03 Hz, 1H).

Example 135

1-(2,3-dichlorophenyl)-N-(6-fluoro-2,3-dihydro-1H-inden-1-yl)-1H-tetraazol-5-amine

Example 135A

6-fluoroindan-1-one O-methyloxime

To a solution of 6-fluoro-indan-1-one (0.5 g, 3.33 mmol) in pyridine (10 ml) was added the HCl salt of methoxylamine (0.31 g, 3.66 mmol) and stirred at room temperature for overnight. The reaction mixture was diluted with ethylacetate (50 ml), acidified with 3N HCl, and washed with 1N HCl, water and brine sequentially. The solution was dried ($Na_2SO_4$) and concentrated to yield 0.48 g (81%) of product. MS ($ESI^+$) m/z 180 $(M+H)^+$;

Example 135B 6-fluoro-2,3-dihydro-1H-inden-1-ylamine

The product of Example 135A and Raney/nickel were processed according to the method of Example 131C to provide the product. MS ($ESI^+$) m/z 152 $(M+H)^+$;

Example 135C 1-(2,3-dichlorophenyl)-N-(6-fluoro-2,3-dihydro-1H-inden-1-yl)-1H-tetraazol-5-amine The product of Example 135B was treated with 2,3-dichlorophenylisothiocyanate according to the method of Example 78C to provide the title compound. MS ($ESI^+$) m/z 364 $(M+H)^+$; $^1H$ NMR (300 MHz, DMSO-$d_6$) δ ppm 1.85-2.09 (m, 1H) 2.51-2.62 (m, 1H) 2.68-3.01 (m, 2H) 5.33 (q, J=7.91 Hz, 1H) 6.98-7.11 (m, 2H) 7.27 (dd, J=8.48, 5.09 Hz, 1H) 7.53-7.63 (m, 2H) 7.74 (dd, J=7.97, 1.53 Hz, 1H) 7.92 (dd, J=8.14, 1.36 Hz, 1H).

Example 136

N-[4,5-difluoro-2-(pyridin-2-yloxy)benzyl]-1-[2-fluoro-3-(trifluoromethyl)phenyl]-1H-tetraazol-5-amine

Example 136A 2-(2-bromo-4,5-difluorophenoxy)pyridine

To a solution of 2-bromo-4,5-difluoro-phenol (1 g, 4.78 mmol) in N,N-dimethylformamide were added $K_2CO_3$ and 2-fluoropyridine (0.46 g, 4.78 mmol) and heated at 120° C. for overnight. One more equivalent of 2-fluoropyridine was added and heated at 150° C. for 12 h. The reaction mixture was dissolved in ethyl acetate, washed with 1M $NaHCO_3$, concentrated and purified by flash column chromatography using 0%, 5% and 10% of ethyl acetate in hexanes to yield 0.8 g (59%) of product. MS ($ESI^+$) m/z 286 $(M+H)^+$.

Example 136B 4,5-difluoro-2-(pyridin-2-yloxy)benzonitrile

To a solution of product of Example 136A (0.8 g, 2.76 mmol) in N,N-dimethylformamide (10 ml) were added $Zn(CN)_2$ (0.18 g, 1.52 mmol) and $Pd(Ph_3)_4$ (0.32 g, 0.28 mmol) and stirred at 120° C. for overnight. The crude product was purified by flash column chromatography using 0%, 5% and 10% of ethylacetate in hexanes to yield 0.28 g (44%) of product. MS ($ESI^+$) m/z 233 $(M+H)^+$;

Example 136C

1-[4,5-difluoro-2-(pyridin-2-yloxy)phenyl]methanamine

The product of Example 136B and Raney/nickel were processed according to the method of Example 131C to provide the product. MS ($ESI^+$) m/z 237 $(M+H)^+$;

Example 136D

N-[4,5-difluoro-2-(pyridin-2-yloxy)benzyl]-1-[2-fluoro-3-(trifluoromethyl)phenyl]-1H-tetraazol-5-amine The product of Example 136C was treated with 2,3-dichlorophenylisothiocyanate according to the method of Example 78C to provide the title compound. MS ($ESI^+$) m/z 467 $(M+H)^+$; $^1H$ NMR (300 MHz, DMSO-$d_6$) δ ppm 4.38 (d, J=5.76 Hz, 2H) 7.04-7.10 (m, 1H) 7.12-7.19 (m, 1H) 7.33-7.51 (m, 2H) 7.65 (t, J=7.97 Hz, 1H) 7.78 (t, J=5.59 Hz, 1H) 7.83-7.93 (m, 1H) 7.94-8.10 (m, 2H) 8.10-8.14 (m, 1H).

Example 137

N-[1-(2,3-dichlorophenyl)-1H-tetraazol-5-yl]-2,3-dihydrospiro[indene-1,4'-piperidin]-3-amine

Example 137A tert-butyl (3Z)-3-(methoxyimino)-2,3-dihydro-1'H-spiro[indene-1,4'-piperidine]-1'-carboxylate N-boc-1-[4-spiro-piperidine]-3-indanone and the HCl salt of methoxylamine were processed according to the method of Example 135A to provide the product. MS ($ESI^+$) m/z 331 $(M+H)^+$.

Example 137B tert-butyl 3-amino-2,3-dihydro-1'H-spiro[indene-1,4'-piperidine]-1'-carboxylate The product of Example 137A and Raney/nickel were processed according to the method of Example 131C to provide the product. MS ($ESI^+$) m/z 303 $(M+H)^+$.

Example 137C tert-butyl 3-{[1-(2,3-dichlorophenyl)-1H-tetraazol-5-yl]amino}-2,3-dihydro-1'H-spiro[indene-1,4'-piperidine]-1'-carboxylate The product of Example 137B was treated with 2,3-dichlorophenylisothiocyanate according to the method of Example 78C to provide the product. MS ($ESI^+$) m/z 515 $(M+H)^+$.

Example 137D

N-[1-(2,3-dichlorophenyl)-1H-tetraazol-5-yl]-2,3-dihydrospiro[indene-1,4'-piperidin]-3-amine The product of Example 136C (0.2 g, 0.38 mmole) was treated with ice-cold trifluoroacetic acid (10 ml) in an ice bath, stirred for 10 min at the same temperature and then for 20 min at room temperature. The product was purified by preparative HPLC on a waters Symmetry C8 column (40 mm×100 mm, 7 μm particle size) using a gradient of 10% to 100% acetonitrile: ammonium acetate (10 mM) over 15 min at a flow rate of 70 mL/min to yield 0.02 g (13%) of product. MS ($ESI^+$) m/z 415 $(M+H)^+$; $^1H$ NMR (300 MHz, DMSO-$d_6$) δ ppm 1.32-1.56 (m, 4H) 1.63-1.78 (m, 1H) 1.91-2.10 (m, 1H) 2.53-2.68 (m, 1H) 2.68-2.83 (m, 2H) 2.94 (q, 2H) 5.38 (q, J=8.14 Hz, 1H) 7.16-7.34 (m, 3H) 7.51-7.62 (m, 2H) 7.69-7.74 (m, 1H) 7.91 (dd, J=8.14, 1.36 Hz, 1H).

Example 138

N-[1-(2,3-dichlorophenyl)-1H-tetraazol-5-yl]-1'-methyl-2,3-dihydrospiro[indene-1,4'-piperidin]-3-amine

Example 138A spiro[indene-1,4'-piperidin]-3(2H)-one

N-boc-1-[4-spiro-piperidine]-3-indanone and trifluoroacetic acid were processed according to the method of Example 137D to provide the product. No purification was required. MS (ESI$^+$) m/z 202 (M+H)$^+$.

Example 138B

1'-methylspiro[indene-1,4'-piperidin]-3(2H)-one

To the product of Example 138A were added formic acid (88% sol, 0.64 g) and formaldehyde (36% sol, 0.45 g) and stirred at 120° C. overnight. The crude product was used in the next step.

Example 138C

1'-methylspiro[indene-1,4'-piperidin]-3(2H)-one O-methyloxime

The product of Example 138B and the HCl salt of methoxylamine were processed according to the method of Example 135A to provide the product. MS (ESI$^+$) m/z 245 (M+H)$^+$.

Example 138D

1'-methyl-2,3-dihydrospiro[indene-1,4'-piperidin]-3-amine

The product of Example 138C and Raney/nickel were processed according to the method of Example 131C to provide the product. MS (ESI$^+$) m/z 217 (M+H)$^+$.

Example 138E

N-[1-(2,3-dichlorophenyl)-1H-tetraazol-5-yl]-1'-methyl-2,3-dihydrospiro[indene-1,4'-piperidin]-3-amine The Example 138D was treated with 2,3-dichlorophenylisothiocyanate according to the method of Example 78C to provide the title compound. MS (ESI$^+$) m/z 429 (M+H)$^+$; $^1$H NMR (300 MHz, DMSO-d$_6$) δ ppm 1.34-1.50 (m, 2H) 1.54-1.74 (m, 2H) 1.92-2.18 (m, 3H) 2.19 (s, 3H) 2.58-2.80 (m, 3H) 5.37 (q, J=8.25 Hz, 1H) 7.12-7.38 (m, 3H) 7.48-7.64 (m, 2H) 7.71 (dd, J=7.97, 1.19 Hz, 1H) 7.91 (dd, J=7.97, 1.19 Hz, 1H).

Example 139

1-(2,3-dichloro-4-fluorophenyl)-N-{[2-(pyridin-3-yloxy)pyridin-3-yl]methyl}-1H-tetraazol-5-amine

Example 139A

2-(pyridin-3-yloxy)nicotinonitrile

Pyridin-3-ol was treated with 2-chloronicotinonitrile and processed according to the method of Example 128B to provide the product. MS (ESI$^+$) m/z 198 (M+H)$^+$.

Example 139B

[2-(pyridin-3-yloxy)pyridin-3-yl]methylamine

The product of Example 139A and Raney/nickel were processed according to the method of Example 131C to provide the product. MS (ESI$^+$) m/z 202 (M+H)$^+$;

Example 139C

1-(2,3-dichloro-4-fluorophenyl)-N-{[2-(pyridin-3-yloxy)pyridin-3-yl]methyl}-1H-tetraazol-5-amine The product of Example 139B was treated with the product of Example 192D according to the method of Example 78C to provide the title compound. MS (ESI$^+$) m/z 432 (M+H)$^+$; $^1$H NMR (300 MHz, DMSO-d$_6$) δ ppm 4.62 (d, J=5.49 Hz, 2H) 7.16 (dd, J=7.32, 4.88 Hz, 1H) 7.48 (dd, J=8.09, 4.42 Hz, 1H) 7.62 (dq, J=8.24, 1.53, 1.37 Hz, 1H) 7.71-7.78 (m, 2H) 7.81 (dd, J=7.32, 1.83 Hz, 1H) 7.89 (dd, J=9.00, 5.34 Hz, 1H) 8.02 (dd, J=4.88, 1.83 Hz, 1H) 8.35-8.48 (m, 2H).

Example 140

1-(2,3-dichloro-4-fluorophenyl)-N-[2-(pyridin-2-yloxy)benzyl]-1H-tetraazol-5-amine The product of Example 192D was treated with 2-(pyridin-2-yloxy)benzylamine hydrochloride according to the method of Example 78C to provide the title compound. MS (ESI$^+$) m/z 431 (M+H)$^+$; $^1$H NMR (300 MHz, DMSO-d$_6$) δ ppm 4.41 (d, J=5.80 Hz, 2H) 7.01 (d, J=8.24 Hz, 1H) 7.08 (dd, J=7.93, 0.92 Hz, 1H) 7.12 (qd, 1H) 7.21 (td, J=7.55, 1.07 Hz, 1H) 7.32 (td, J=7.78, 1.53 Hz, 1H) 7.40 (dd, J=7.48, 1.37 Hz, 1H) 7.54 (t, J=5.80 Hz, 1H) 7.67-7.79 (m, 2H) 7.82-7.91 (m, 1H) 8.06-8.20 (m, 1H).

Example 141

N-[(2-chloropyridin-3-yl)methyl]-1-(2,3-dichlorophenyl)-1H-tetraazol-5-amine

Example 141A

(2-chloropyridin-3-yl)methylamine hydrochloride

To an oven-dried, N$_2$-purged, 250-mL, round-bottomed flask containing a magnetic stir bar were added 2-chloro-3-methylpyridine (1.07 mL, 1.28 g, 10.0 mmol), N-bromosuccinimide (1.96 g, 11.0 mmol), and carbon tetrachloride (50 mL). A reflux condenser with N$_2$-inlet was attached and a heating mantle was applied. The pale yellow slurry was heated to reflux and stirred for 16 h. After cooling to room temperature, the solids were removed by vacuum filtration through a glass frit. The mother liquor was concentrated by rotary evaporator to one-half the original volume and the solids again were removed by vacuum filtration. The liquor was concentrated to a golden oil and used for the next step without further purification.

To an oven-dried, $N_2$-purged, 250-mL, round-bottomed flask containing a magnetic stir bar were added the crude 3-bromomethyl-2-chloropyridine from above, hexamethylenetetraazene (1.54 g, 11.0 mmol), and chloroform (30 mL). A reflux condenser with $N_2$-inlet was attached and a heating mantle was applied. The pale yellow solution was heated to reflux and stirred for 4 hours. A white precipitate formed after 5 minutes at reflux. After cooling to room temperature, the white solid was collected by vacuum filtration on a glass frit. The solid was washed with hexanes and dried under house vacuum to give 2.50 g of a fine white powder. The crude product was used for the next step without further purification.

To a 100-mL, round-bottomed flask containing a magnetic stir bar were added the crude solid product from above, 97% ethanol (15 mL), and concentrated hydrochloric acid (3.5 mL). A reflux condenser was attached and a heating mantle was applied. The mixture was heated to reflux and stirred for 16 hours. After 1 hour at reflux, the precipitate dissolved to form a yellow solution. Gradually, a crystalline precipitate reformed in the reaction. After cooling to room temperature, the solids were removed by vacuum filtration on a glass frit. The mother liquor was concentrated to one-half the original volume and the solids were again removed by vacuum filtration. The product was crystallized from the golden liquor by dropwise addition of anhydrous ether. The fine white powder was collected by vacuum filtration on a glass frit, washed with hexanes, and dried under vacuum to give 649 mg (42%) of the title compound-as the hydrochloride salt. MS (ESI+) m/z 143.0 $(M-35)^+$; $^1$H NMR (DMSO-$d_6$) δ 4.14 (q, J=5.8 Hz, 3H), 7.54 (dd, J=7.6, 4.9 Hz, 1H), 8.12 (dd, J=7.8, 1.7 Hz, 1H), 8.43 (dd, J=4.9, 1.9 Hz, 1H), 8.75 (br s, 3H).

Example 141B

N-[(2-chloropyridin-3-yl)methyl]-N'-(2,3-dichlorophenyl)thiourea

To an oven-dried, $N_2$-purged, 25-mL, round-bottomed flask containing a magnetic stir bar were added the product of Example 141A, anhydrous tetrahydrofuran (5 mL), and diisopropylethylamine (646 mg, 0.886 mL, 5.00 mmol). The flask was sealed with a septum and neat dichlorophenylisothiocyanate (306 mg, 0.213 mL, 1.50 mmol) was added via syringe. The reaction mixture was stirred at room temperature overnight. Water (10 mL) was added, and the reaction was transferred to a separatory funnel. The mixture was extracted with dichloromethane (3×10 mL). The combined organic extracts were dried over magnesium sulfate, filtered, and concentrated by rotary evaporator to give a brown solid. The product was recrystallized from ethyl acetate/hexanes to give 197 mg (47%) of the title compound as a white powder. MS (ESI$^-$) m/z 345.9 $(M+H)^+$; $^1$H NMR (DMSO-$d_6$) δ 4.75 (d, J=5.1 Hz, 2H), 7.37 (dd, J=8.0, 8.0 Hz, 1H), 7.46 (dd, J=7.5, 4.7 Hz, 1H), 7.55 (d, J=8.1 Hz, 1H), 7.61 (d, J=7.8 Hz, 1H), 7.76 (dd, J=7.6, 1.5 Hz, 1H), 8.32 (dd, J=4.7, 1.7 Hz, 1H), 8.44 (br s, 1H), 9.68 (br s, 1H).

Example 141C

N-[(2-chloropyridin-3-yl)methyl]-1-(2,3-dichlorophenyl)-1H-tetraazol-5-amine

To an oven-dried, $N_2$-purged, 25-mL, round-bottomed flask containing a magnetic stir bar was added the product of Example 141B. The flask was sealed with a septum. Anhydrous tetrahydrofuran (3 mL), neat triethylamine (75.8 mg, 105 μL, 0.75 mmol), and azidotrimethylsilane (28.8 mg, 32.9 mL, 0.250 mmol) were added via syringe. Solid mercury(II) chloride (59.7 mg, 0.220 mmol) was added, and a white precipitate formed immediately. The mixture was stirred at room temperature for 4 hours. Ethyl acetate (10 mL) was added and the solids were removed by vacuum filtration through a glass frit. The liquor was washed with water (10 mL). The organic phase was dried over magnesium sulfate, filtered, and concentrated by rotary evaporator to give a white solid. The product was recrystallized from ethyl acetate/hexanes to give 23.9 mg (34%) of the title compound as a white powder. MS (ESI+) m/z 355.0 $(M+H)^+$; $^1$H NMR (DMSO-$d_6$) δ 5.75 (s, 2H), 7.44 (dd, J=7.5, 4.7 Hz, 1H), 7.64 (dd, J=8.1, 8.0 Hz, 1H), 7.76-7.85 (m, 3H), 7.97 (dd, J=8.1, 1.7 Hz, 1H), 8.33 (dd, J=4.7, 1.7 Hz, 1H).

Example 142

N-[(2-bromopyridin-3-yl)methyl]-1-(2,3-dichlorophenyl)-1H-tetraazol-5-amine

Example 142A (2-bromopyridin-3-yl)methylamine hydrochloride

Prepared in 33% yield from 2-bromo-3-methylpyridine according to the procedure described for Example 141A. MS (ESI+) m/z 188.8 $(M-35)^+$; $^1$H NMR (DMSO-$d_6$) δ 4.13 (q, J=5.8 Hz, 2H), 7.57 (dd, J=7.5, 4.7 Hz, 1H), 8.05 (dd, J=7.6, 1.9 Hz, 1H), 8.40 (dd, J=4.7, 2.0 Hz, 1H), 8.68 (br s, 3H).

Example 142B

N-[(2-bromopyridin-3-yl)methyl]-N'-(2,3-dichlorophenyl)thiourea

Prepared in 55% yield by treatment of the product of Example 142A with 2,3-dichlorophenylisothiocyanate according to the procedure described for Example 141B. MS (ESI$^-$) m/z 389.9 $(M+H)^+$; $^1$H NMR (DMSO-$d_6$) δ 4.71 (d, J=4.4 Hz, 2H), 7.37 (dd, J=8.0, 8.0 Hz, 1H), 7.48 (dd, J=7.5, 4.7 Hz, 1H), 7.55 (dd, J=8.1, 1.7 Hz, 1H), 7.58-7.63 (m, 1H), 7.69 (dd, J=7.6, 1.9 Hz, 1H), 8.29 (dd, J=4.7, 2.0 Hz, 1H), 8.44 (br s, 1H), 9.70 (br s, 1H).

Example 142C

N-[(2-bromopyridin-3-yl)methyl]-1-(2,3-dichlorophenyl)-1H-tetraazol-5-amine

Prepared in 34% yield by treatment of Example 142B with mercury(II) chloride and trimethylsilyl azide according to the procedure described for Example 141C. MS (ESI+) m/z 400.8 $(M+H)^+$; $^1$H NMR (DMSO-$d_6$) δ 4.50 (d, J=5.8 Hz, 2H), 7.46 (dd, J=7.6, 4.6 Hz, 1H), 7.64 (dd, J=8.1, 8.0 Hz, 1H), 7.73-7.80 (m, 2H), 7.83 (dd, J=5.8, 5.8 Hz, 1H), 7.97 (dd, J=8.1, 1.4 Hz, 1H), 8.31 (4.7, 1.7 Hz, 1H).

Example 143

1-(2,3-dichlorophenyl)-N-[(2-fluoropyridin-4-yl)methyl]-1H-tetraazol-5-amine

Example 143A (2-fluoropyridin-4-yl)methylamine hydrochloride

Prepared in 50% yield from 2-fluoro-4-methylpyridine according to the procedure described for Example 141A.

Example 143B 1-(2,3-dichloro-phenyl)-3-(2-fluoro-pyridin-4-ylmethyl)-thiourea Prepared in 53% yield from the product of Example 143A and 2,3-dichlorophenylisothiocyanate according to the procedure described for Example 141B. MS (ESI+) m/z 329.9 (M+H)$^+$; $^1$H NMR (DMSO-d$_6$) δ 4.79 (d, J=5.8 Hz, 2H), 7.02 (br s, 1H), 7.26 (d, J=5.1 Hz, 1H), 7.39 (d, J=8.1 Hz, 1H), 7.48-7.61 (m, 2H), 8.18 (d, J=5.1 Hz, 1H), 8.43 (br s, 1H), 9.69 (br s, 1H).

Example 143C 1-(2,3-dichlorophenyl)-N-[(2-fluoropyridin-4-yl)methyl]-1H-tetraazol-5-amine Prepared in 26% yield from the product of Example 143B according to the procedure described for Example 141C. MS (ESI+) m/z 338.9 (M+H)$^+$; $^1$H NMR (DMSO-d$_6$) δ 4.57 (d, J=5.8 Hz, 2H), 7.08 (brs, 1H), 7.27-7.31 (m, 1H), 7.65 (dd, J=8.1, 8.0 Hz, 1H), 7.81 (dd, J=8.1, 1.7 Hz, 1H), 7.85 (dd, J=6.0, 5.9 Hz, 1H), 7.98 (dd, J=8.1, 1.7 Hz, 1H), 8.19 (d, J=5.1 Hz, 1H).

Example 144

N-[(2-bromopyridin-4-yl)methyl]-1-(2,3-dichlorophenyl)-1H-tetraazol-5-amine

Example 144A

C-(2-bromo-pyridin-4-yl)-methylamine hydrochloride

Prepared in 40% yield from 2-bromo-4-methylpyridine according to the procedure described for Example 141A. MS (ESI+) m/z 186.9 (M-35)$^+$; $^1$H NMR (DMSO-d$_6$) δ 4.09 (q, J=6.0 Hz, 2H), 7.58 (dd, J=5.1, 1.4 Hz, 1H), 7.84 (s, 1H), 8.43 (d, J=5.1 Hz, 1H), 8.71 (br s, 3H).

Example 144B

N-[(2-bromopyridin-4-yl)methyl]-N'-(2,3-dichlorophenyl)thiourea

Prepared in 84% yield from the product of Example 144A and 2,3-dichlorophenylisothiocyanate according to the procedure described for Example 141B and 141C.

MS (ESI+) m/z 391.7 (M+H)$^+$; $^1$H NMR (DMSO-d$_6$) δ 4.79 (d, J=5.8 Hz, 2H), 7.02 (br s, 1H), 7.26 (d, J=5.1 Hz, 1H).

Example 145

1-(2,3-dichlorophenyl)-N-[(2-pyrrolidin-1-ylpyridin-4-yl)methyl]-1H-tetraazol-5-amine To an oven-dried N$_2$-purged, 20-mL scintillation vial containing a magnetic stir bar was added the product of Example 143C (34 mg, 0.10 mmol) and anhydrous tetrahydrofuran (1 mL). Neat pyrrolidine (160 mL, 140 mg, 2.0 mmol) was added via syringe, and the vial was sealed. The reaction mixture was heated to 60° C. and the vial was shaken for 48 hours. After cooling to room temperature, the solvent/volatiles were removed by rotary evaporator to give a brown oil. The product was purified by flash chromatography (silica gel: 25% ethyl acetate, 75% hexanes—product R$_f$~0.2) to give 5.6 mg (14%) of the title compound as a white powder. MS (ESI+) m/z 390.1 (M+H)$^+$; $^1$H NMR (DMSO-d$_6$) δ 1.54 (br s, 4H), 3.46 (br s, 4H), 4.61 (d, J=6.1 Hz, 2H), 6.37 (br s, 1H), 6.46-6.48 (m, 1H), 7.39-7.47 (m, 2H), 7.72 (dd, J=7.6, 2.2 Hz, 1H), 8.08 (d, J=5.1 Hz, J=5.1 Hz, 1H).

Example 146

1-(2,3-dichlorophenyl)-N-[(2-phenylpyridin-3-yl)methyl]-1H-tetraazol-5-amine

To a 100-mL, round-bottomed flask containing a magnetic stir bar were added Example 142C (800 mg, 2.00 mmol), phenylboronic acid (305 mg, 2.50 mmol), and dichlorobis(triphenylphosphine)palladium(II) (140 mg, 0.20 mol). Isopropyl alcohol (10 mL) and 2M sodium carbonate solution (10 mL) were added. The flask was stoppered and immersed in an oil bath. The mixture was heated to 50-60° C. and stirred for 8 hours during which a black emulsion formed. After cooling to room temperature, the mixture was transferred to a separatory funnel and extracted with ethyl acetate (3×25 mL). The combined organic extracts were dried over magnesium sulfate, filtered, and concentrated by rotary evaporator to a brown oil. The product was purified by flash chromatography (silica gel: 75% ethyl acetate, 25% hexanes—product R$_f$~0.2) to give 58.3 mg (7%) of the title compound as a white powder. MS (ESI+) m/z 396.9 (M+H)$^+$; $^1$H NMR (DMSO-d$_6$) δ 4.52 (d, J=5.4 Hz, 2H), 7.39 (dd, J=8.0, 4.6 Hz, 1H), 7.44-7.51 (m, 3H), 7.56-7.73 (m, 5H), 7.84 (dd, J=7.8, 1.7 Hz, 1H), 7.94 (dd, J=7.8, 1.7 Hz, 1H), 8.56 (dd, J=4.7, 1.7 Hz, 1H).

Example 147

1-(2,3-dichlorophenyl)-N-{[2-(4-ethoxyphenyl)pyridin-3-yl]methyl}-1H-tetraazol-5-amine Prepared in 6% yield from (2-bromo-pyridin-3-ylmethyl)-[1-(2,3-dichloro-phenyl)-1H-tetrazol-5-yl]-amine from Example 142C and 4-ethoxyphenylboronic acid according to the procedure described for Example 146. MS (ESI+) m/z 441.0 (M+H)$^+$; $^1$H NMR (DMSO-d$_6$) δ 1.36 (t, J=6.9 Hz, 3H), 4.09 (q, J=6.9 Hz, 2H), 4.53 (d, J=5.4 Hz, 2H), 7.01 (d, J=8.8 Hz, 2H), 7.34 (dd, J=7.8, 4.7 Hz, 1H), 7.51 (d, J=8.8 Hz, 2H), 7.61 (dd, J=8.1, 8.0 Hz, 1H), 7.67-7.74 (m, 2H), 7.81 (dd, J=7.8, 1.7 Hz, 1H), 7.94 (dd, J=8.1, 1.7 Hz, 1H), 8.53 (dd, J=4.6, 1.5 Hz, 1H).

Example 148

1-(2,3-dichlorophenyl)-N-{[2-(4-fluorophenyl)pyridin-3-yl]methyl}-1H-tetraazol-5-amine Prepared in 9% yield from Example 142C and 4-fluorophenylboronic acid according to the procedure described for Example 146. MS (ESI+) m/z 414.9 (M+H)$^+$;
$^1$H NMR (DMSO-d$_6$) δ 4.51 (d, J=5.8 Hz, 2H), 7.28-7.34 (m, 2H), 7.40 (dd, J=7.8, 4.7 Hz, 1H), 7.58-7.73 (m, 5H), 7.85 (dd, J=7.8, 1.4 Hz, 1H), 7.94 (dd, J=8.1, 1.7 Hz, 1H), 8.55 (dd, J=4.7, 1.7 Hz, 1H).

Example 149

1-(2,3-dichlorophenyl)-N-{[2-(4-methylphenyl)pyridin-3-yl]methyl}-1H-tetraazol-5-amine Prepared in 13% yield from Example 142C and 4-methylphenylboronic acid according to the procedure described for Example 146. MS (ESI+) m/z 411.0 (M+H)$^+$; $^1$H NMR (DMSO-d$_6$) δ 2.38 (s, 3H), 4.51 (d, J=5.4 Hz, 2H), 7.28 (d, J=7.8 Hz, 2H), 7.36 (dd, J=7.8, 4.7 Hz, 1H), 7.46 (d, J=8.1 Hz, 2H), 7.60 (dd, J=8.1, 8.0 Hz, 1H), 7.67-7.72 (m, 2H), 7.82 (dd, J=7.8, 1.7 Hz, 1H), 7.94 (dd, J=7.8, 1.7 Hz, 1H), 8.54 (dd, J=4.7, 1.7 Hz, 1H).

Example 150

N-{[2-(4-chlorophenyl)pyridin-3-yl]methyl}-1-(2,3-dichlorophenyl)-1H-tetraazol-5-amine Prepared in 31% yield from Example 142C and 4-chlorophenylboronic acid according to the procedure described for Example 146. MS (ESI+) m/z 430.3 (M+H)$^+$; $^1$H NMR (DMSO-d$_6$) δ 4.51 (d, J=5.4 Hz, 2H), 7.41 (dd, J=7.8, 4.7 Hz, 1H), 7.52-7.73 (m, 7H), 7.86 (dd, J=8.0, 1.5 Hz, 1H), 7.94 (dd, J=7.8, 1.7 Hz, 1H), 8.57 (dd, J=4.6, 1.5 Hz, 1H).

Example 151

N-{[2-(3-chlorophenyl)pyridin-3-yl]methyl}-1-(2,3-dichlorophenyl)-1H-tetraazol-5-amine Prepared in 23% yield from Example 142C and 3-chlorophenylboronic acid according to the procedure described for Example 146. MS (ESI+) m/z 432.9 (M+H)$^+$; $^1$H NMR (DMSO-d$_6$) δ 4.52 (d, J=5.5 Hz, 2H), 7.43 (dd, J=8.0, 4.9 Hz, 1H), 7.52-7.67 (m, 7H), 7.87 (dd, J=8.0, 1.5 Hz, 1H), 7.94 (dd, J=8.0, 1.9 Hz, 1H), 8.57 (dd, J=4.6, 1.5 Hz, 1H).

Example 152

1-(2,3-dichlorophenyl)-N-{[2-(3-methylphenyl)pyridin-3-yl]methyl}-1H-tetraazol-5-amine Prepared in 38% yield from Example 142C and 3-methylphenylboronic acid according to the procedure described for Example 146. MS (LC-MS, ESI+) m/z 410.8 (M+H)$^+$; $^1$H NMR (DMSO-d$_6$) δ 2.37 (s, 3H), 4.52 (J=5.4 Hz, 2H), 7.24-7.27 (m, 1H), 7.35-7.40 (m, 4H), 7.60 (dd, J=8.1, 8.0 Hz, 1H), 7.65-7.70 (m, 2H), 7.83 (dd, J=8.0, 1.5 Hz, 1H), 7.94 (dd, J=7.8, 1.7 Hz, 1H), 8.55 (dd, J=4.7, 1.7 Hz, 1H).

Example 153

1-(2,3-dichlorophenyl)-N-{[2-(2-methoxyphenyl)pyridin-3-yl]methyl}-1H-tetraazol-5-amine

Example 153A 2-(2-methoxy-phenylnicotinonitrile

To a 250-mL, round-bottomed flask containing a large magnetic stir bar were added 2-chloro-3-cyanopyridine (1.39 g, 10.0 mmol), 2-methoxyphenylboronic acid (1.82 g, 12.0 mmol), and dichlorobis(triphenylphosphine)palladium(II) (351 mg, 0.50 mmol). Isopropyl alcohol (50 mL) and 2M sodium carbonate solution (50 mL) were added. The flask was stoppered and immersed in an oil bath heated to 80-90° C. The biphasic mixture was stirred vigorously and heated for 8 hours. After cooling to room temperature, ethyl acetate (50 mL) was added and the black mixture was transferred to a separatory funnel. The aqueous layer was removed and subsequently extracted with ethyl acetate (3×20 mL). The combined ethyl acetate layers were dried over magnesium sulfate, filtered, and concentrated by rotary evaporator to give a brown oil. The product was crystallized from ethyl acetate/hexanes to give 1.38 g (66%) of the title compound as a tan powder.

Example 153B 1-(2,3-dichloro-phenyl)-3-[2-(2-methoxy-phenyl)-pyridin-3-ylmethyl]-thiourea To an argon-purged, thick-walled pressure vessel was added wet Raney nickel (~5 g). A solution of ammonia-saturated methanol (100 mL) was added. The product of Example 153A (1.05 g, 5.00 mmol) was added as a solid. The vessel was inserted into a Parr shaker and was charged with 60 psi of H$_2$ gas. The mixture was shaken at room temperature under static H$_2$ pressure for 2 hours. The H$_2$ gas was vented and the vessel was purged with argon. The solids were removed by vacuum filtration through a glass frit covered with a nylon filter. The solvent/volatiles were removed by rotary evaporator to give a pale green oil that was used without further purification.

To an oven-dried, N$_2$-purged, 25-mL, round-bottomed flask containing a magnetic stir bar was added the crude C-[2-(2-methoxy-phenyl)-pyridin-3-yl]-methylamine (430 mg, 2.0 mmol) from above. The flask was sealed with a septum and purged with N$_2$ atmosphere. Anhydrous tetrahydrofuran (10 mL) was added via syringe. Neat 2,3-dichlorophenylisothiocyanate (510 mg, 356 μL, 2.50 mmol) was added via syringe. The pale green solution was stirred at room temperature overnight. Saturated aqueous sodium bicarbonate (10 mL) was added to quench. The mixture was transferred to a separatory funnel and extracted with dichloromethane (3×10 mL). The combined organic extracts were dried over magnesium sulfate, filtered, and concentrated by rotary evaporator to give a tan solid. The product was recrystallized from ethyl acetate/hexanes to give a 712 mg (85%) of the title compound as a white powder. MS (LC-MS, ESI+) m/z 417.0 (M+H)$^+$; $^1$H NMR (DMSO-d$_6$) δ 3.74 (s, 3H), 4.35 (br s, 1H), 4.66 (br s, 1H), 7.03-7.13 (m, 2H), 7.22 (dd, J=7.5, 1.7 Hz, 1H), 7.31-7.60 (m, 6H), 7.74 (dd, J=7.1, 1.0 Hz, 1H), 8.23 (br s, 1H), 8.51 (dd, J=4.9, 1.5 Hz, 1H), 9.46 (br s, 1H).

Example 153C 1-(2,3-dichlorophenyl)-N-{[2-(2-methoxyphenyl)pyridin-3-yl]methyl}-1H-tetraazol-5-amine To an oven-dried, 100-mL, round-bottomed flask containing a magnetic stir bar were added the product of Example 153B (628 mg, 1.50 mmol), sodium azide (293 mg, 4.50 mmol), and anhydrous tetrahydrofuran (15 mL). Neat triethylamine (455 mg, 627 µL, 4.50 mmol) was added via syringe. Solid mercury(II) chloride (448 mg, 1.65 mmol) was added in one portion. A thick, white precipitate formed upon addition of the mercury salt. The mixture was stirred at room temperature overnight during which the solids darkened to black. Ethyl acetate (10 mL) was added and the solids were removed by vacuum filtration through a glass frit. The liquor was washed with water (10 mL). The organic phase was dried over magnesium sulfate, filtered, and concentrated by rotary evaporator to give a tan solid. The product was recrystallized from ethyl acetate/hexanes to give 389 mg (61%) of the title compound as a white powder. MS (ESI+) m/z 427.0 (M+H)$^+$; $^1$H NMR (DMSO-d$_6$) δ 3.74 (s, 3H), 4.16 (br s, 1H), 4.42 (br s, 1H), 7.04-7.09 (m, 1H), 7.12 (d, J=8.5 Hz, 1H), 7.24 (dd, J=7.5, 1.7 Hz, 1H), 7.36 (dd, J=7.8, 4.7 Hz, 1H), 7.40-7.46 (m, 1H), 7.52-7.68 (m, 3H), 7.73 (dd, J=7.8, 1.7 Hz, 1H), 7.94 (dd, J=8.0, 1.9 Hz, 1H), 8.50 (dd, J=4.7, 1.7 Hz, 1H).

Example 154

1-(2,3-dichlorophenyl)-N-{[2-(3,4-difluorophenyl)pyridin-3-yl]methyl}-1H-tetraazol-5-amine

Example 154A 2-(3,4-difluorophenlynicotinonitrile

Prepared in 77% yield from 2-chloro-3-cyanopyridine and 3,4-difluorophenylboronic acid according to the procedure described for Example 153A. $^1$H NMR (DMSO-d$_6$) δ 7.62-7.71 (m, 2H), 7.74-7.79 (m, 1H), 7.95 (ddd, J=11.7, 7.8, 2.2 Hz, 1H), 8.46 (dd, J=7.8, 1.7 Hz, 1H) 8.94 (dd, J=5.1, 1.7 Hz, 1H).

Example 154B 1-(2,3-dichloro-phenyl)-3-[2-(3,4-difluoro-phenyl)-pyridin-3-ylmethyl]-thiourea Prepared in 77% yield from Example 154A according to the procedure described for Example 153B. MS (ESI+) m/z 423.9 (M+H)$^+$; $^1$H NMR (DMSO-d$_6$) δ 4.73 (s, 2H), 7.32-7.64 (m, 7H), 7.84 (dd, J=7.8, 1.4 Hz, 1H), 8.35 (s, 1H), 8.56 (dd, J=4.6, 1.5 Hz, 1H), 9.48 (s, 1H).

Example 154C 1-(2,3-dichlorophenyl)-N-{[2-(3,4-difluorophenylpyridin-3-yl]methyl}-1H-tetraazol-5-amine Prepared in 60% yield from Example 154B according to the procedure described for Example 153C. MS (ESI+) m/z 432.9 (M+H)$^+$; $^1$H NMR (DMSO-d$_6$) δ 4.52 (d, J=5.8 Hz, 1H), 7.41-7.46 (m, 2H), 7.50-7.73 (m, 5H), 7.87 (dd, J=7.8, 1.7 Hz, 1H), 7.95 (dd, J=7.8, 1.7 Hz, 1H), 8.56 (dd, J=4.7, 1.7 Hz, 1H).

Example 155

1-(2,3-dichlorophenyl)-N-{[2-(2-fluorophenyl)pyridin-3-yl]methyl}-1H-tetraazol-5-amine

Example 155A 2-(2-fluoro-phenyl)-nicotinonitrile

Prepared in 74% yield from 2-chloro-3-cyanopyridine and 2-fluorophenylboronic acid according to the procedure described for Example 153A. MS (ESI+) m/z 199.0 (M+H)$^+$; $^1$H NMR (CDCl$_3$) δ 7.22-7.34 (m, 2H), 7.42-7.55 (m, 2H), 7.57-7.63 (m, 1H), 8.09 (dd, J=7.8, 1.7 Hz, 1H), 8.91 (dd, J=4.7, 1.7 Hz, 1H).

Example 155B 1-(2,3-Dichloro-phenyl)-3-[2-(2-fluoro-phenyl)-pyridin-3-ylmethyl]-thiourea Prepared in 99% yield from Example 155A according to the procedure described for Example 153B. MS (ESI+) m/z 406.0 (M+H)$^+$; $^1$H NMR (CDCl$_3$) δ 4.85 (d, J=5.4 Hz, 2H), 6.46 (br s, 1H), 7.06-7.26 (m, 3H), 7.35-7.46 (m, 5H), 7.64 (Br s, 1H), 8.02 (d, J=7.8 Hz, 1H), 8.67 (br s, 1H).

Example 155C 1-(2,3-dichlorophenyl)-N-{[2-(2-fluorophenyl)pyridin-3-yl]methyl}-1H-tetraazol-5-amine Prepared in 37% yield from Example 155B according to the procedure described for Example 153C. MS (ESI+) m/z 414.9 (M+H)$^+$; $^1$H NMR (DMSO-d$_6$) δ 4.36 (d, J=5.8 Hz, 2H), 7.30-7.36 (m, 2H), 7.43-7.53 (m, 3H), 7.61-7.68 (m, 3H), 7.84 (dd, J=8.0, 1.5 Hz, 1H), 7.94 (dd, J=7.8, 1.7 Hz, 1H), 8.57 (dd, J=4.7, 1.7 Hz, 1H).

Example 156

1-(2,3-dichlorophenyl)-N-({2-[3-(trifluoromethoxy)phenyl]pyridin-3-yl}methyl)-1H-tetraazol-5-amine

Example 156A 2-(3-trifluoromethoxyphenyl)-nicotinonitrile

Prepared in 91% yield from 2-chloro-3-cyanopyridine and 3-trifluoromethoxyphenylboronic acid according to the procedure described for Example 153A. MS (ESI−) m/z 264.9 (M+H)$^+$; $^1$H NMR (CDCl$_3$) δ 7.37-7.45 (m, 2H), 7.57 (dd, J=8.0, 8.0 Hz, 1H), 7.82 (br s, 1H), 7.91 (d, J=7.8 Hz, 1H), 8.11 (dd, J=7.8, 1.7 Hz, 1H), 8.90 (dd, J=4.7, 1.7 Hz, 1H).

Example 156B 1-(2,3-Dichloro-phenyl)-3-[2-(3-trifluoromethoxy-phenyl)-pyridin-3-ylmethyl]-thiourea Prepared in 66% yield from Example 156A according to the procedure described for Example 153B. MS (ESI+) m/z 471.9 (M+H)$^+$; $^1$H NMR (CDCl$_3$) δ 4.97 (d, J=5.8, 2H), 6.28

(br s, 1H), 7.19-7.27 (m, 4H), 7.36-7.49 (m, 5H), 7.63 (br s, 1H), 7.98 (d, J=7.8 Hz, 1H), 8.63 (br s, 1H).

Example 156C 1-(2,3-dichlorophenyl)-N-({2-[3-(trifluoromethoxy)phenyl]pyridin-3-yl}methyl)-1H-tetraazol-5-amine Prepared in 61% yield from the product of Example 156B according to the procedure described for Example 153C. MS (ESI+) m/z 480.9 (M+H)$^+$; $^1$H NMR (CDCl$_3$) δ 4.74 (d, J=6.1 Hz, 1H), 7.25-7.49 (m, 8H), 7.70 (dd, J=8.1, 1.7 Hz, 1H), 7.92 (dd, J=7.8, 1.7 Hz, 1H), 8.64 (dd, J=4.7, 1.7 Hz, 1H).

Example 157

1-(2,3-dichlorophenyl)-N-{[2-(2-methylphenyl)pyridin-3-yl]methyl}-1H-tetraazol-5-amine

Example 157A 2-o-olyl-nicotinonitrile

Prepared in 76% yield from 2-chloro-3-cyanopyridine and 2-methylphenylboronic acid according to the procedure described for Example 153A. MS (ESI−) m/z 195.0 (M+H)$^+$; $^1$H NMR (CDCl$_3$) δ 2.27 (s, 3H), 7.29-7.44 (m, 5H), 8.08 (dd, J−7.8, 1.7 Hz, 1H), 8.88 (dd, J=4.7, 1.7 Hz, 1H).

Example 157B 1-(2,3-dichloro-phenyl)-3-(2-o-tolyl-pyridin-3-ylmethyl)thiourea Prepared in 70% yield from the product of Example 157A according to the procedure described for Example 153B. MS (ESI+) m/z 401.9 (M+H)$^+$; $^1$H NMR (CDCl$_3$) δ 2.04 (s, 3H), 4.66 (br s, 2H), 6.05 (Br s, 1H), 7.04-7.24 (m, 8H), 7.28-7.42 (m, 3H), 7.63 (br s, 1H), 7.93 (dd, J=7.8, 1.7 Hz, 1H), 8.54 (dd, J=4.9, 1.5 Hz, 1H).

Example 157C 1-(2,3-dichlorophenyl)-N-{[2-(2-methylphenyl)pyridin-3-yl]methyl}-1H-tetraazol-5-amine Prepared in 16% yield from the product of Example 157B according to the procedure described for Example 153C. MS (ESI+) m/z 411.0 (M+H)$^+$; $^1$H NMR (CDCl$_3$) δ 2.01 (s, 3H), 4.03 (t, J=5.9 Hz, 1H), 4.51 (br s, 2H), 7.08-7.31 (m, 6H), 7.42 (dd, J=8.0, 8.0 Hz, 1H), 7.72 (dd, J=8.1, 1.4 Hz, 1H), 7.89 (dd, J=7.8, 1.7 Hz, 1H), 8.61 (dd, J=4.9, 1.5 Hz, 1H).

Example 158

1-(2,3-dichlorophenyl)-N-{[2-(3-fluorophenyl)pyridin-3-yl]methyl}-1H-tetraazol-5-amine

Example 158A 2-(3-fluorophenyl)nicotinonitrile

Prepared in 91% yield from 2-chloro-3-cyanopyridine and 3-fluorophenylboronic acid according to the procedure described for Example 153A. MS (ESI−) m/z 264.9 (M+H)$^+$; $^1$H NMR (CDCl$_3$) δ 7.19-7.26 (m, 1H), 7.42 (dd, J=8.0, 4.9 Hz, 1H), 7.47-7.54 (m, 1H), 7.65 (ddd, J=9.7, 2.2, 2.0 Hz, 1H), 7.75 (d, J=7.8 Hz, 1H), 8.10 (dd, J=8.1, 1.9 Hz, 1H), 8.89 (dd, J=4.7, 1.7 Hz, 1H).

Example 158B 1-(2,3-Dichloro-phenyl)-3-[2-(3-fluoro-phenyl)-pyridin-3-ylmethyl]-thiourea Prepared in 66% yield from the product of Example 158A according to the procedure described for Example 153B. MS (ESI+) m/z 406.0 (M+H)$^+$; $^1$H NMR (CDCl$_3$) δ 4.95 (d, J=5.1 Hz, 2H), 6.13 (br s, 1H), 7.06-7.26 (m, 5H), 7.31-7.41 (m, 3H), 7.59 (br s, 1H), 7.93 (d, J=7.8 Hz, 1H), 8.60 (d, J=4.4 Hz, 1H).

Example 158C 1-(2,3-dichlorophenyl)-N-{[2-(3-fluorophenyl)pyridin-3-yl]methyl}-1H-tetraazol-5-amine Prepared in 64% yield from the product of Example 158B according to the procedure described for Example 153C. MS (ESI+) m/z 414.9 (M+H)$^+$; $^1$H NMR (CDCl$_3$) δ 4.24 (t, J=5.9 Hz, 1H), 4.75 (d, J=5.8 Hz, 2H), 7.06-7.12 (m, 1H), 7.14-7.18 (m, 1H), 7.22-7.25 (m, 1H), 7.25-7.26 (m, 1H), 7.31 (dd, J=7.8, 4.7 Hz, 1H), 7.36-7.43 (m, 2H), 7.69 (dd, J=8.1, 1.7 Hz, 1H), 7.88 (dd, J=7.8, 1.7 Hz, 1H), 8.61 (dd, J=4.7, 1.7 Hz, 1H).

Example 159

1-(2,3-dichlorophenyl)-N-({2-[4-(trifluoromethoxy)phenyl]pyridin-3-yl}methyl)-1H-tetraazol-5-amine

Example 159A 2-(4-Trifluoromethoxy-phenyl)-nicotinonitrile

Prepared in 70% yield from 2-chloro-3-cyanopyridine and 4-trifluoromethoxyphenylboronic acid according to the procedure described for Example 153A. MS (ESI−) m/z 265.0 (M+H)$^+$; $^1$H NMR (CDCl$_3$) δ 7.37-7.44 (m, 3H), 7.98-8.03 (m, 2H), 8.10 (dd, J=8.0, 1.9 Hz, 1H), 8.89 (dd, J=4.7, 1.7 Hz, 1H).

Example 159B 1-(2,3-Dichloro-phenyl-3-[2-(4-trifluoromethoxy-phenyl)-pyridin-3-ylmethyl]-thiourea Prepared in 63% yield from the product of Example 159A according to the procedure described for Example 153B. MS (ESI+) m/z 471.9 (M+H)$^+$; $^1$H NMR (DMSO-d$_6$) δ 4.73 (d, J=4.7 Hz, 2H), 7.35 (dd, J=8.1, 8.0 Hz, 1H), 7.45-7.55 (m, 5H), 7.67 (d, J=8.5 Hz, 1H), 7.84 (dd, J=7.8, 1.7 Hz, 1H), 8.35 (br s, 1H), 8.57 (dd, J=4.7, 1.7 Hz, 1H), 9.51 (br s, 1H).

Example 159C 1-(2,3-dichlorophenyl)-N-({2-[4-(trifluoromethoxy)phenyl]pyridin-3-yl}methyl)-1H-tetraazol-5-amine Prepared in 48% yield from the product of Example 159B according to the procedure described for Example 153C. MS (ESI+) m/z 481.0 (M+H)$^+$; $^1$H NMR (CDCl$_3$) δ 4.23 (t, J=5.8 Hz, 1H), 4.77 (d, J=6.1 Hz, 2H), 7.26-7.30 (m, 2H), 7.33 (dd, J=7.8, 4.7 Hz, 1H), 7.40 (dd, J=8.1, 8.1 Hz, 1H), 7.53 (J=8.8 Hz, 2H), 7.70 (dd, J=8.1, 1.7 Hz, 1H), 7.90 (dd, J=7.8, 1.4 Hz, 1H), 8.63 (dd, J=4.7, 1.4 Hz, 1H).

Example 160

1-(2,3-dichlorophenyl)-N-({2-[2-(trifluoromethoxy)phenyl]pyridin-3-yl}methyl)-1H-tetraazol-5-amine

Example 160A 2-(4-Trifluoromethoxy-phenyl-nicotinonitrile

Prepared in 71% yield from 2-chloro-3-cyanopyridine and 2-trifluoromethoxyphenylboronic acid according to the procedure described for Example 153A. MS (ESI−) m/z 264.8 (M+H)$^+$; $^1$H NMR (CDCl$_3$) δ 7.41-7.48 (m, 3H), 7.54-7.60 (m, 2H), 8.09 (dd, J=7.8, 1.7 Hz, 1H), 8.91 (dd, J=5.1, 1.7 Hz, 1H).

Example 160B 1-(2,3-Dichloro-phenyl)-3-[2-(2-trifluoromethoxy-phenyl)-pyridin-3-ylmethyl]-thiourea Prepared in 63% yield from the product of Example 160A according to the procedure described for Example 153B. MS (ESI+) m/z 471.8 (M+H)$^+$; $^1$H NMR (CDCl$_3$) δ 4.63 (br s, 1H), 4.88 (br s, 1H), 6.41 (d, J=5.1 Hz, 1H), 7.16-7.26 (m, 2H), 7.29-7.49 (m, 6H), 7.68 (br s, 1H), 8.04 (d, J=7.8 Hz, 1H), 8.62 (d, J=3.7 Hz, 1H).

Example 160C 1-(2,3-dichlorophenyl)-N-({2-[2-(trifluoromethoxy)phenyl]pyridin-3-yl}methyl)-1H-tetraazol-5-amine Prepared in 61% yield from the product of Example 160B according to the procedure described for Example 153C. MS (ESI+) m/z 481.1 (M+H)$^+$; $^1$H NMR (DMSO-d$_6$) δ 4.29 (d, J=4.4 Hz, 2H), 7.43-7.69 (m, 8H), 7.85 (dd, J=8.0, 1.5 Hz, 1H), 7.95 (dd, J=8.0, 1.9 Hz, 1H), 8.57 (dd, J=4.6, 1.5 Hz, 1H).

Example 161

N-{[2-(2-chlorophenyl)pyridin-3-yl]methyl}-1-(2,3-dichlorophenyl)-1H-tetraazol-5-amine

Example 161A 2-(2-chlorophenyl)nicotinonitrile

Prepared in 18% yield from 2-chloro-3-cyanopyridine and 2-chlorophenylboronic acid according to the procedure described for Example 153A. MS (ESI−) m/z 215.0 (M+H)$^+$; $^1$H NMR (CDCl$_3$) δ 7.41-7.49 (m, 4H), 7.53-7.56 (m, 1H), 8.09 (dd, J=7.8, 1.7 Hz, 1H), 8.90 (dd, J=5.1, 1.7 Hz, 1H).

Example 161B

1-[2-(2-Chloro-phenyl)-pyridin-3-ylmethyl]-3-(2,3-dichloro-phenyl)-thiourea

Prepared in 51% yield from the product of Example 161A according to the procedure described for Example 153B. MS (ESI+) m/z 421.8 (M+H)$^+$; $^1$H NMR (CDCl$_3$) δ 4.55-4.62 (m, 1H), 4.85-4.97 (m, 1H), 6.18 (br s, 1H), 7.18-7.42 (m, 8H), 7.56 (br s, 1H), 7.98 (dd, J=7.8, 1.4 Hz, 1H), 8.62 (dd, J=4.7, 1.4 Hz, 1H).

Example 161C

N-{[2-(2-chlorophenyl)pyridin-3-yl]methyl}-1-(2,3-dichlorophenyl)-1H-tetraazol-5-amine Prepared in 48% yield from the product of Example 161B according to the procedure described for Example 153C. MS (ESI+) m/z 432.9 (M+H)$^+$; $^1$H NMR (CDCl$_3$) δ 4.20-4.24 (m, 1H), 4.48-4.59 (m, 2H), 7.31-7.44 (m, 8H), 7.93 (dd, J=7.8, 1.4 Hz, 1H), 8.64 (dd, J=4.7, 1.4 Hz, 1H).

Example 162

1-(2,3-dichlorophenyl)-N-{[2-(2-phenoxyphenyl)pyridin-3-yl]methyl}-1H-tetraazol-5-amine

Example 162A 2-(2-phenoxy-phenyl)nicotinonitrile

Prepared in 50% yield from 2-chloro-3-cyanopyridine and 2-phenoxyphenylboronic acid according to the procedure described for Example 153A. MS (ESI−) m/z 273.0 (M+H)$^+$; $^1$H NMR (CDCl$_3$) δ 6.94 (d, J=7.1 Hz, 1H), 7.06-7.11 (m, 3H), 7.20-7.44 (m, 5H), 7.54 (dd, J=7.5, 1.7 Hz, 1H), 8.00 (dd, J=8.1, 2.0 Hz, 1H), 8.86 (dd, J=5.1, 1.7 Hz, 1H).

Example 162B 1-(2,3-dichlorophenyl)-3-[2-(2-phenoxyphenyl)-pyridin-3-ylmethyl]thiourea Prepared in 95% yield from the product of Example 162A according to the procedure described for Example 153B. MS (ESI+) m/z 479.9 (M+H)$^+$.

Example 162C 1-(2,3-dichlorophenyl)-N-{[2-(2-phenoxyphenyl)pyridin-3-yl]methyl}-1H-tetraazol-5-amine Prepared in 46% yield from the product of Example 162B according to the procedure described for Example 153C. MS (ESI+) m/z 489.9 (M+H)$^+$; $^1$H NMR (CDCl$_3$) δ 4.63 (t, J=5.6 Hz, 1H), 4.70 (br s, 2H), 6.61-6.65 (m, 2H), 6.87 (J=8.3, 1.0 Hz, 1H), 6.96-7.01 (m, 1H), 7.12-7.37 (m, 7H), 7.42 (dd, J=7.5, 1.7 Hz, 1H), 7.62 (dd, J=8.1, 1.7 Hz, 1H), 7.93 (dd, J=7.8, 1.7 Hz, 1H), 8.59 (dd, J=4.7, 1.7 Hz, 1H).

Example 163

1-(2,3-dichlorophenyl)-N-({2-[2-(trifluoromethyl)phenyl]pyridin-3-yl}methyl)-1H-tetraazol-5-amine

Example 163A 2-(2-Trifluoromethyl-phenyl)-nicotinonitrile

Prepared in 30% yield from 2-chloro-3-cyanopyridine and 2-trifluoromethylphenylboronic acid according to the procedure described for Example 153A. MS (ESI−) m/z 249.0

(M+H)⁺; ¹H NMR (CDCl₃) δ 7.45-7.50 (m, 2H), 7.62-7.72 (m, 2H), 7.83-7.86 (m, 1H), 8.09 (dd, J=7.8, 1.7 Hz, 1H), 8.87 (dd, J=5.7, 1.7 Hz, 1H).

Example 163B 1-(2,3-Dichloro-phenyl)-3-[2-(2-trifluoromethyl-phenyl)-pyridin-3-ylmethyl]-thiourea Prepared in 95% yield from the product of Example 163A according to the procedure described for Example 153B. MS (ESI+) m/z 455.6 (M+H)⁺; ¹H NMR (CDCl₃) δ 4.38-4.44 (m, 1H), 4.85-4.90 (m, 1H), 6.12 (br s, 1H), 7.16-7.43 (m, 5H), 7.50-7.59 (m, 2H), 7.64 (br s, 1H), 7.72-7.75 (m, 1H), 7.92 (dd, J=8.0, 1.5 Hz, 1H), 8.58 (dd, J=4.7, 1.7 Hz, 1H).

Example 163C 1-(2,3-dichlorophenyl)-N-({2-[2-(trifluoromethyl)phenyl]pyridin-3-yl}methyl)-1H-tetraazol-5-amine Prepared in 58% yield from the product of Example 163B according to the procedure described for Example 153C. MS (ESI+) m/z 464.7 (M+H)⁺; ¹H NMR (CDCl₃) δ 4.12 (t, J=5.4 Hz, 1H), 4.37-4.47 (m, 1H), 4.50-4.57 (m, 1H), 7.29-7.45 (m, 4H), 7.52-7.62 (m, 2H), 7.70-7.77 (m, 2H), 7.90 (dd, J=8.0, 1.5 Hz, 1H), 8.60 (dd, J=4.9, 1.5 Hz, 1H).

Example 164

1-(2,3-dichlorophenyl)-N-[(2-thien-2-ylpyridin-3-yl)methyl]-1H-tetraazol-5-amine Example 164A 2-thiophen-2-ylnicotinonitrile To an oven-dried, N₂-purged, 50-mL, round-bottomed flask containing a magnetic stir bar were added cesium fluoride (1.34 g, 8.80 mmol), bis(tri-t-butylphosphine)palladium (66.0 mg, 0.13 mmol), and 2-chloro-3-cyanopyridine (559 mg, 4.00 mmol). The flask was sealed with a septum and purged with dry N₂ atmosphere. Anhydrous dioxane (4 mL) was added via syringe. Neat 2-(tri-n-butylstannyl)thiophene (2.38 g, 2.02 mL, 6.38 mmol) was added via syringe. The reaction mixture was heated to ~90° C. in an oil bath for 18 hours. After cooling to room temperature, ethyl acetate (15 mL) was added and the mixture was filtered through a pad of silica. The filtrate was concentrated by rotary evaporator to give a brown oil. The product was purified by flash chromatography (silica gel: 25% ethyl acetate, 75% hexanes=product R_f~0.4) to give ~750 mg of the title compound as a beige solid that was used without further purification for the next step. MS (ESI–) m/z 186.7 (M+H)⁺; ¹H NMR (CDCl₃) δ 7.19 (dd, J=5.1, 4.0 Hz, 1H), 7.23-7.27 (m, 1H), 7.56 (dd, J=5.1, 1.0 Hz, 1H), 8.00 (dd, J=8.1, 2.0 Hz, 1H), 8.27 (d, J=4.1 Hz, 1H), 8.74 (dd, J=4.7, 1.7 Hz, 1H).

Example 164B 1-(2,3-Dichlorophenyl)-3-(2-thiophen-2-ylpyridin-3-ylmethyl)thiourea Prepared in 95% yield from the product of Example 164A according to the procedure described for Example 153B. MS (ESI+) m/z 393.6 (M+H)⁺; ¹H NMR (CDCl₃) δ 5.12 (d; J=5.1 Hz, 2H), 6.43 (br s, 1H), 7.09-7.18 (m, 3H), 7.20-7.24 (m, 1H), 7.33-7.38 (m, 1H), 7.43 (dd, J=5.1, 1.0 hz, 1H), 7.70 (br s, 1H), 7.80 (d, J=7.8 Hz, 1H), 8.58 (br s, 1H).

Example 164C 1-(2,3-dichlorophenyl)-N-[(2-thien-2-ylpyridin-3-yl)methyl]-1H-tetraazol-5-amine Prepared in 29% yield from the product of Example 164B according to the procedure described for Example 153C. MS (ESI+) m/z 402.6 (M+H)⁺; ¹H NMR (CDCl₃) δ 4.35 (t, J=5.6 Hz, 1H), 4.94 (d, J=5.8 Hz, 2H), 7.09 (dd, J=5.1, 3.7 Hz, 1H), 7.22 (dd, J=7.2, 4.7 Hz, 1H), 7.26-7.29 (m, 1H), 7.34-7.41 (m, 2H), 7.43 (dd, J=5.0, 1.0 Hz, 1H), 7.67 (dd, J=8.0, 1.5 Hz, 1H), 7.81 (dd, J=7.8, 1.7 Hz, 1H), 8.58 (dd, J=4.7, 1.7 Hz, 1H).

Example 165

1-(2,3-dichlorophenyl)-N-[(2-thien-3-ylpyridin-3-yl)methyl]-1H-tetraazol-5-amine Example 165A 2-thiophen-3-ylnicotinonitrile To an oven-dried, N₂-purged, 50 mL, round-bottomed flask containing a magnetic stir bar were added potassium fluoride (767 mg, 13.2 mmol), bis(tri-t-butylphosphine)palladium (51.0 mg, 0.10 mmol), tris(dibenzylideneacetone)dipalladium 46 mg, 0.05 mmol), 2-chloro-3-cyanopyridine (559 mg, 4.00 mmol), and 3-thiopheneboronic acid (819 mg, 6.4 mmol). The flask was sealed with a septum and purged with dry N₂ atmosphere. Anhydrous dioxane (4 mL) was added via syringe. The reaction mixture was heated to ~90° C. in an oil bath for 18 hours. After cooling to room temperature, ethyl acetate (15 mL) was added and the mixture was filtered through a pad of silica. The filtrate was concentrated by rotary evaporator to give a brown oil. The product was purified by recrystallization from ethyl acetate/hexanes to give 417 mg (56%) of the title compound as a beige solid. MS (ESI–) m/z 186.9 (M+H)⁺; ¹H NMR (CDCl₃) δ 7.30 (7.8, 4.7 Hz, 1H), 7.44 (dd, J=5.3, 2.9 Hz, 1H), 7.88 (dd, J=5.1, 1.4 Hz, 1H), 8.03 (dd, J=8.0, 1.9 Hz, 1H), 8.29 (dd, J=3.0, 1.4 Hz, 1H), 8.82 (dd, J=4.7, 1.7 Hz, 1H).

Example 165B 1-(2,3-Dichloro-phenyl)-3-(2-thiophen-3-yl-pyridin-3-ylmethyl)-thiourea Prepared in 95% yield from the product of Example 165A according to the procedure described for Example 153B. MS (ESI+) m/z 393.8 (M+H)⁺; ¹H NMR (CDCl₃) δ 5.04 (d, J=5.4 Hz, 2H), 6.38 (br s, 1H), 7.10-7.20 (m, 2H), 7.28-7.34 (m, 1H), 7.35-7.39 (m, 3H), 7.57 (br s, 1H), 7.67 (br s, 1H), 7.90 (d, J=7.1 Hz, 1H), 8.59 (br s, 1H).

Example 165C 1-(2,3-dichlorophenyl)-N-[(2-thien-3-ylpyridin-3-yl)methyl]-1H-tetraazol-5-amine Prepared in 85% yield from the product of Example 165B according to the procedure described for Example 153C. MS (ESI+) m/z 402.9 (M+H)⁺; ¹H NMR (CDCl₃) δ 4.23 (t, J=5.6 Hz, 1H), 4.84 (d, J=6.1 Hz, 2H), 7.24-7.28 (m, 2H), 7.33 (dd, J=5.1, 1.9 Hz, 1H), 7.37-7.42 (m, 2H), 7.51 (dd, J=3.0, 1.4 Hz, 1H), 7.69 (dd, J=8.1, 1.7 Hz, 1H), 7.83 (dd, J=7.8, 1.7 Hz, 1H), 8.60 (dd, J=4.9, 1.5 Hz, 1H).

Example 166

N-(2,3'-bipyridin-3-ylmethyl)-1-(2,3-dichlorophenyl)-1H-tetraazol-5-amine

Example 166A

[2,3']Bipyridinyl-3-carbonitrile

Prepared in 84% yield from 2-chloro-3-cyanopyridine and 3-(tributylstannyl)pyridine according to the procedure described for Example 164A. MS (ESI+) m/z 182.0 (M+H)$^+$; $^1$H NMR (CDCl$_3$) δ 7.44-7.51 (m, 2H), 8.13 (dd, J=7.8, 1.7 Hz, 1H), 8.27-8.31 (m, 1H), 8.77 (d, J=4.7 Hz, 1H), 8.93 (dd, J=8.9, 1.9 Hz, 1H), 9.19 (br s, 1H).

Example 166B

1-[2,3']Bipyridinyl-3-ylmethyl-3-(2,3-dichloro-phenyl)-thiourea

Prepared in 95% yield from the product of Example 166A according to the procedure described for Example 153B. MS (ESI+) m/z 388.9 (M+H)$^+$; $^1$H NMR (CDCl$_3$) δ 4.95 (d, J=5.4 Hz, 2H), 6.57 (br s, 1H), 7.19 (dd, J=8.1, 1.0 Hz, 1H), 7.25-7.28 (m, 1H), 7.33-7.38 (m, 2H), 7.45 (dd, J=7.6, 4.9 Hz, 1H), 7.83 (br s, 1H), 7.90-7.95 (m, 2H), 8.62-8.64 (m, 2H), 8.76 (br s, 1H).

Example 166C

N-(2,3'-bipyridin-3-ylmethyl)-1-(2,3-dichlorophenyl)-1H-tetraazol-5-amine

Prepared in 54% yield from the product of Example 166B according to the procedure described for Example 153C. MS (ESI+) m/z 397.9 (M+H)$^+$; $^1$H NMR (DMSO-d$_6$) δ 4.61 (br s, 1H), 4.75 (D, J=5.8 Hz, 2H), 7.31-7.39 (m, 2H), 7.42 (dd, J=8.0, 8.0 Hz, 1H), 7.50 (br s, 1H), 7.69 (dd, J=8.1, 1.7 Hz, 1H), 7.98 (d, J=7.8 Hz, 1H), 8.04 (d, J=7.8 Hz, 1H), 8.65 (br s, 1H), 8.67 (dd, J=4.7, 1.4 Hz, 1H), 8.77 (Br s, 1H).

Example 167

N-(2,4'-bipyridin-3-ylmethyl)-1-(2,3-dichlorophenyl)-1H-tetraazol-5-amine

Example 167A

[2,4']Bipyridinyl-3-carbonitrile

Prepared in 39% yield from 2-chloro-3-cyanopyridine and 4-(tributylstannyl)pyridine according to the procedure described for Example 164A. MS (ESI+) m/z 181.9 (M+H)$^+$; $^1$H NMR (CDCl$_3$) δ 7.50 (dd, J=8.1, 4.7 Hz, 1H), 7.88 (d, J=6.4 Hz, 2H), 8.14 (dd, J=8.0, 1.9 Hz, 1H), 8.83 (d, J=4.4 Hz, 2H), 8.94 (dd, J=4.9, 1.9 Hz, 1H).

Example 167B

1-[2,4']Bipyridinyl-3-ylmethyl-3-(2,3-dichlorophenyl)thiourea

Prepared in 95% yield from the product of Example 167A according to the procedure described for Example 153B. MS (ESI+) m/z 388.9 (M+H)$^+$;

Example 167C

N-(2,4'-bipyridin-3-ylmethyl)-1-(2,3-dichlorophenyl)-1H-tetraazol-5-amine

Prepared in 15% yield from the product of Example 167B according to the procedure described for Example 153C. MS (ESI+) m/z (M+H)$^+$; $^1$H NMR (DMSO-d$_6$) δ 4.54 (d, J=5.4 Hz, 2H), 7.48 (dd, J=7.8, 4.7 Hz, 1H), 7.59-7.68 (m, 4H), 7.73 (dd, J=5.6 Hz, 1H), 7.89-7.96 (m, 2H), 8.61 (dd, J=4.7, 1.7 Hz, 1H), 8.68-8.70 (m, 2H).

Example 168

1-(2,3-dichlorophenyl)-N-{[2-(1,3-thiazol-2-yl)pyridin-3-yl]methyl}-1H-tetraazol-5-amine

Example 168A

2-Thiazol-2-yl-nicotinonitrile

Prepared in 39% yield from 2-chloro-3-cyanopyridine and 2-(tributylstannyl)thiazole according to the procedure described for Example 164A. MS (ESI+) m/z 187.9 (M+H)$^+$; $^1$H NMR (CDCl$_3$) δ 7.44 (dd, J=7.8, 4.7 Hz, 1H), 7.57 (d, J=3.0 Hz, 1H), 8.10-8.14 (m, 2H), 8.80 (d, J=3.4 Hz, 1H).

Example 168B 1-(2,3-dichloro-phenyl)-3-(2-thiazol-2-ylpyridin-3-ylmethyl)thiourea Prepared in 57% yield from the product of Example 168A according to the procedure described for Example 153B. MS (ESI+) m/z 395.0 (M+H)$^+$; $^1$H NMR (DMSO-d$_6$) δ 5.23 (d, J=5.8 Hz, 2H), 7.35 (dd, J=8.0, 8.0 Hz, 1H), 7.43 (dd, J=8.0, 8.0 Hz, 1H), 7.48-7.58 (m, 2H), 7.66 (dd, J=8.1, 1.9 Hz, 1H), 7.88-7.96 (m, 2H), 8.42 (br s, 1H), 8.57 (dd, J=4.7, 1.4 Hz, 1H), 9.74 (br s, 1H).

Example 168C 1-(2,3-dichlorophenyl)-N-{[2-(1,3-thiazol-2-yl)pyridin-3-yl]methyl}-1H-tetraazol-5-amine Prepared in 51% yield from the product of Example 168B according to the procedure described for Example 153C. MS (ESI+) m/z 403.9 (M+H)$^+$; $^1$H NMR (DMSO-d$_6$) δ 5.09 (d, J=6.1 Hz, 2H), 7.49 (dd, J=8.0, 4.6 Hz, 1H), 7.63 (dd, J=8.0, 8.0 Hz, 1H), 1.74-7.82 (m, 2H), 7.89-7.92 (m, 2H), 7.96 (dd, J=8.1, 3.5 Hz, 1H), 8.01 (d, J=3.0 Hz, 1H), 8.57 (dd, J=4.6, 1.5 Hz, 1H).

Example 169

1-(2,3-dichlorophenyl)-N-{[5-fluoro-2-(4-fluorophenyl)pyridin-3-yl]methyl}-1H-tetraazol-5-amine

Example 169A 2-chloro-5-fluoro-nicotinonitrile

To an oven-dried, 250-mL, round-bottomed flask containing a magnetic stir bar were added 2-chloro-5-fluoro-nicotinic acid (4.39 g, 25.0 mmol) and anhydrous toluene (50 mL). Thionyl chloride (5.95 g, 3.65 mL, 50 mmol) was added, and a reflux condenser with $N_2$-inlet was attached. A heating mantle was applied and the solution was heated to reflux for 2 hours. After cooling to room temperature, the solvent/volatiles were removed by rotary evaporator to give a golden oil. The crude acid chloride was added to a cold (0° C.) solution of ammonium hydroxide, and a white precipitate formed. The precipitate was collected by vacuum filtration on a glass frit and air dried.

To an oven-dried, 250 mL, round-bottomed flask were added the crude 2-chloro-5-fluoronicotinamide (1.05 g, 6.00 mmol) from above, anhydrous dichloromethane (25 mL), and triethylamine (2.12 g, 2.92 mL, 21.0 mmol). The flask was sealed with a septum and cooled to 0° C. in an ice bath. Neat trifluoroacetic anhydride (1.89 g, 1.25 mL, 9.00 mmol) was added slowly via syringe and the resulting solution was stirred at 0° C. for 30 minutes then allowed to warm to room temperature over 1 hour. Water (20 mL) was added, and the mixture was transferred to a separatory funnel. The mixture was extracted with dichloromethane (3×20 mL). The combined organic extracts were dried over magnesium sulfate, filtered, and concentrated by rotary evaporator to give a golden oil. The product was purified by flash chromatography (silica gel: 10% ethyl acetate, 90% hexanes—product Rf~0.3) to give 862 mg (92%) of the title compound as a pale yellow solid. $^1$H NMR (CDCl$_3$) δ 8.66 (dd, J=7.8, 3.0 Hz, 1H), 8.82 (d, J=2.7 Hz, 1H).

Example 169B 5-fluoro-2-(4-fluorophenyl)nicotinonitrile

Prepared in 68% yield from the product of Example 169A and 4-fluorophenylboronic acid according to the procedure described for Example 153A. $^1$H NMR (DMSO-d$_6$) δ 7.39-7.45 (m, 2H), 7.87-7.92 (m, 2H), 8.58 (dd, J=8.6, 2.9 Hz, 1H), 8.99 (d, J=3.0 Hz, 1H).

Example 169C 1-(2,3-Dichloro-phenyl)-3-[5-fluoro-2-(4-fluorophenyl)-pyridin-3-ylmethyl]-thiourea Prepared in 71% yield from the product of Example 169B according to the procedure described for Example 153B. MS (ESI+) m/z 423.9 (M+H)$^+$; $^1$H NMR (DMSO-d$_6$) δ 4.72 (d, J=5.1 HZ, 2H), 7.28-7.39 (m, 3H), 7.51-7.59 (m, 4H), 7.65 (dd, J=9.8, 3.0 Hz, 1H), 8.35 (br s, 1H), 8.56 (d, J=2.7 Hz, 1H), 9.61 (br s, 1H).

Example 169D 1-(2,3-dichlorophenyl)-N-{[5-fluoro-2-(4-fluorophenyl)pyridin-3-yl]methyl}-1H-tetraazol-5-amine Prepared in 86% yield from the product of Example 169B according to the procedure described for Example 153C. MS (ESI+) m/z 432.9 (M+H)$^+$; $^1$H NMR (DMSO-d$_6$) δ 4.52 (d, J=5.4 Hz, 2H), 7.29-7.35 (m, 2H), 7.59-7.65 (m, 3H), 7.71-7.77 (m, 3H), 7.96 (dd, J=8.1, 1.4 Hz, 1H), 8.57 (d, J=3.0 Hz, 1H).

Example 170

1-(2,3-dichlorophenyl)-N-{[2-(2-methoxyphenyl)-6-(trifluoromethyl)pyridin-3-yl]methyl}-1H-tetraazol-5-amine

Example 170A 2-(2-Methoxy-phenyl)-6-trifluoromethyl-nicotinonitrile

Prepared in 91% yield from 2-chloro-6-trifluoromethylnicotinonitrile and 2-methoxyphenylboronic acid according to the procedure described for Example 153A. MS (ESI−) m/z 279.0 (M+H)$^+$; $^1$H NMR (CDCl$_3$) δ 3.83 (s, 3H), 7.15 (dd, J=7.5, 7.5 Hz, 1H), 7.25 (d, J=7.8 Hz, 1H), 7.43 (dd, J=7.4, 1.7 Hz, 1H), 7.55-7.63 (m, 2H), 8.12 (d, J=8.1 Hz, 1H), 8.71 (d, J=7.5 Hz, 1H).

Example 170B 1-(2,3-Dichloro-phenyl)-3-[2-(2-methoxy-phenyl)-6-trifluoromethyl-pyridin-3-ylmethyl]-thiourea Prepared in 53% yield from the product of Example 170A according to the procedure described for Example 153B. MS (ESI+) m/z 485.9 (M+H)$^+$; $^1$H NMR (DMSO-d$_6$) δ 3.77 (s, 3H), 4.37 (br s, 1H), 4.76 (br s, 1H), 7.10 (dd, J=7.8, 7, 8 Hz, 1H), 7.17 (d, J=8.1 Hz, 1H), 7.25 (d, J=8.8 Hz, 1H), 7.35 (dd, J=8.3, 8.1 Hz, 1H), 7.47-7.55 (m, 3H), 7.91-7.98 (m, 2H), 8.28 (br s, 1H), 9.62 (br s, 1H).

Example 170C 1-(2,3-dichlorophenyl)-N-{[2-(2-methoxyphenyl)-6-(trifluoromethyl)pyridin-3-yl]methyl}-1H-tetraazol-5-amine Prepared in 56% yield from the product of Example 170B according to the procedure described for Example 153C. MS (ESI+) m/z 494.9 (M+H)$^+$; $^1$H NMR (DMSO-d$_6$) δ 3.77 (s, 3H), 4.23 (br s, 1H), 4.48 (br s, 1H), 7.11 (d, J=7.5, 7.5 Hz, 1H), 7.17 (d, J=7.8 Hz, 1H), 7.29 (dd, J=7.5, 1.7 Hz, 1H), 7.47-7.53 (m, 1H), 7.61 (dd, J=8.1, 9.0 Hz, 1H), 7.76-7.70 (m, 2H), 7.95 (dd, J=8.1, 1.7 Hz, 1H), 8.01 (d, J=7.8 Hz, 1H).

Example 171

1-(2,3-dichlorophenyl)-N-{[2-(5-fluoro-2-methoxyphenyl)pyridin-3-yl]methyl}-1H-tetraazol-5-amine

Example 171A 2-(5-Fluoro-2-methoxy-phenyl)-nicotinonitrile

Prepared in 89% yield from 2-chloronicotinonitrile and 5-fluoro-2-methoxyphenylboronic acid according to the procedure described for Example 153A. MS (ESI−) m/z 228.9 (M+H)⁺; ¹H NMR (CDCl₃) δ 3.86 (s, 3H), 6.98 (dd, J=8.8, 4.0 Hz, 1H), 7.13-7.22 (m, 2H), 7.40 (dd, J=8.0, 4.9 Hz, 1H), 8.04 (dd, J=8.1, 1.7 Hz, 1H), 8.88 (dd, J=5.1, 1.7 Hz, 1H).

Example 171B 1-(2,3-Dichloro-phenyl)-3-[2-(5-fluoro-2-methoxy-phenyl)-pyridin-3-ylmethyl]-thiourea Prepared in 95% yield from the product of Example 171A according to the procedure described for Example 153B. MS (ESI+) m/z 435.9 (M+H)⁺; ¹H NMR (DMSO-d₆) δ 3.54 (s, 3H), 4.79 (br s, 2H), 6.76 (br s, 1H), 6.89 (dd, J=9.2, 4.4 Hz, 1H), 7.03-7.12 (m, 2H), 7.17-7.26 (m, 2H), 7.29-7.44 (m, 2H), 7.73 (br s, 1H), 8.11 (d, J=7.1 Hz, 1H), 8.59 (br s, 1H).

Example 171C 1-(2,3-dichlorophenyl)-N-{[2-(5-fluoro-2-methoxyphenyl)pyridin-3-yl]methyl}-1H-tetraazol-5-amine Prepared in 30% yield from the product of Example 171B according to the procedure described for Example 153C. MS (ESI+) m/z 444.9 (M+H)⁺; ¹H NMR (DMSO-d₆) δ 3.73 (s, 3H), 4.21 (br s, 1H), 4.40 (br s, 1H), 7.05-7.14 (m, 2H), 7.23-7.30 (m, 1H), 7.39 (dd, J=8.1, 4.7 Hz, 1H), 7.52-7.56 (m, 1H), 7.57-7.67 (m, 2H), 7.77 (dd, J=8.0, 1.5 Hz, 1H), 7.94 (dd, J=7.8, 1.7 Hz, 1H), 8.51 (dd, J=4.7, 1.7 Hz, 1H).

Example 172

1-(2,3-dichlorophenyl)-N-{[2-(4-fluoro-2-methoxyphenyl)pyridin-3-yl]methyl}-1H-tetraazol-5-amine Example 172A 2-(4-fluoro-2-methoxy-phenyl)nicotinonitrile Prepared in 85% yield from 2-chloronicotinonitrile and 4-fluoro-2-methoxyphenylboronic acid according to the procedure described for Example 153A. MS (ESI−) m/z 228.9 (M+H)⁺; ¹H NMR (CDCl₃) δ 6.75-6.84 (m, 2H), 7.37 (dd, J=8.0, 4.9 Hz, 1H), 7.44 (dd, J=8.5, 6.8 Hz, 1H), 8.02 (dd, J=7.8, 1.7 Hz, 1H), 8.86 (dd, J=4.9, 1.9 Hz, 1H).

Example 172B 1-(2,3-Dichloro-phenyl)-3-[2-(4-fluoro-2-methoxy-phenyl)-pyridin-3-ylmethyl]-thiourea Prepared in 95% yield from the product of Example 172A according to the procedure described for Example 153B. MS (ESI+) m/z 435.8 (M+H)⁺ ¹H NMR (CDCl₃) δ 3.59 (s, 3H), 4.76 (d, J=5.1 Hz, 1H), 6.50 (br s, 1H), 6.63-6.74 (m, 2H), 7.16-7.30 (m, 3H), 7.35-7.41 (m, 3H), 7.68 (br s, 1H), 8.03 (d, J=7.5 Hz, 1H), 8.58 (d, J=5.1 Hz, 1H).

Example 172C 1-(2,3-dichlorophenyl)-N-{[2-(4-fluoro-2-methoxyphenyl)pyridin-3-yl]methyl}-1H-tetraazol-5-amine Prepared in 9% yield from the product of Example 172B according to the procedure described for Example 153C. MS (ESI+) m/z 444.9 (M+H)⁺; ¹H NMR (DMSO-d₆) δ 3.76 (s, 3H), 4.20 (br s, 1H), 4.39 (br s, 1H), 6.85-6.92 (m, 1H), 7.03 (dd, J=11.5, 2.4 Hz, 1H), 7.27 (dd, J=8.5, 7.1 Hz, 1H), 7.37 (dd, J=8.0, 4.9 Hz, 1H), 7.55 (dd, J=5.8 Hz, 1H), 7.58-7.66 (m, 2H), 7.75 (dd, J=8.0, 1.5 Hz, 1H), 7.94 (dd, J=8.0, 1.9 Hz, 1H), 8.50 (dd, J=4.7, 1.7 Hz, 1H).

Example 173

1-(2,3-dichlorophenyl)-N-{[2-(2-fluoro-6-methoxyphenyl)pyridin-3-yl]methyl}-1H-tetraazol-5-amine Example 173A 2-(4-fluoro-2-methoxyphenyl)nicotinonitrile Prepared in 85% yield from 2-chloronicotinonitrile and 2-fluoro-6-methoxyphenylboronic acid according to the procedure described for Example 153A. MS (ESI−) m/z 228.9 (M+H)⁺; ¹H NMR (CDCl₃) δ 6.82-6.88 (m, 2H), 7.38-7.46 (m, 2H), 8.07 (dd, J=7.8, 1.7 Hz, 1H), 8.91 (dd, J=4.9, 1.9 Hz, 1H).

Example 173B 1-(2,3-dichlorophenyl)-3-[2-(2-fluoro-6-methoxyphenyl)-pyridin-3-ylmethyl]-thiourea Prepared in 95% yield from the product of Example 153A according to the procedure described for Example 153B. MS (ESI+) m/z 436.0 (M+H)⁺; ¹H NMR (CDCl₃) δ 3.65 (s, 3H), 4.64-4.71 (m, 1H), 4.78-4.85 (m, 1H), 6.73-6.78 (m, 2H), 7.18-7.24 (m, 2H), 7.33-7.38 (m, 3H), 7.45 (dd, J=7.5, 4.7 Hz, 1H), 7.86 (br s, 1H), 8.14 (d, J=7.8 Hz, 1H), 8.62 (d, J=4.7 Hz, 1H).

Example 173C 1-(2,3-dichlorophenyl)-N-{[2-(2-fluoro-6-methoxyphenyl)pyridin-3-yl]methyl}-1H-tetraazol-5-amine Prepared in 37% yield from the product of Example 173B according to the procedure described for Example 153C. MS (ESI+) m/z 445.1 (M+H)⁺; ¹H NMR (DMSO-d₆) δ 3.74 (s, 3H), 4.17-4.25 (m, 1H), 4.28-4.36 (m, 1H), 6.92 (dd, J=8.8 Hz, 1H), 6.99 (d, J=8.5 Hz, 1H), 7.38-7.49 (m, 2H), 7.56-7.60 (m, 1H), 7.61-7.69 (m, 2H), 7.77 (dd, J=8.0, 1.5 Hz, 1H), 7.94 (dd, J=8.0, 1.9 Hz, 1H), 8.53 (dd, J=4.7, 1.7 Hz, 1H).

Example 174

1-(2,3-dichlorophenyl)-N-{[2-(2,4-difluorophenyl)pyridin-3-yl]methyl}-1H-tetraazol-5-amine Example 174A 2-(2,4-difluoro-phenyl)-nicotinonitrile Prepared in 78% yield from 2-chloronicotinonitrile and 2,4-difluorophenylboronic acid according to the procedure described for Example 153A. MS (ESI−) m/z 216.9 (M+H)⁺;

¹H NMR (CDCl₃) δ 6.97-7.09 (m, 2H), 7.45 (dd, J=8.0, 4.9 Hz, 1H), 7.57-7.64 (m, 1H), 8.09 (dd, J=8.0, 1.9 Hz, 1H), 8.90 (dd, J=5.1, 1.7 Hz, 1H).

Example 174B 1-(2,3-Dichloro-phenyl)-3-[2-(2,4-difluoro-phenyl)-pyridin-3-ylmethyl]thiourea Prepared in 95% yield from the product of Example 174A according to the procedure described for Example 153B. MS (ESI+) m/z 423.8 (M+H)⁺.

Example 174C 1-(2,3-dichlorophenyl)-N-{[2-(2,4-difluorophenyl)pyridin-3-yl]methyl}-1H-tetraazol-5-amine Prepared in 25% yield from the product of Example 174B according to the procedure described for Example 153C. MS (ESI+) m/z 432.8 (M+H)⁺; ¹H NMR (DMSO-d₆) δ 4.36 (d, J=5.4 Hz, 2H), 7.19-7.25 (m, 1H), 7.34-7.41 (m, 1H), 7.46 (dd, J=7.8, 4.7 Hz, 1H), 7.50-7.58 (m, 1H), 7.58-7.69 (m, 3H), 7.86 (dd, J=8.0, 1.5 Hz, 1H), 7.94 (dd, J=7.8, 1.7 Hz, 1H), 8.57 (dd, J=4.7, 1.7 Hz, 1H).

Example 175

1-(2,3-dichlorophenyl)-N-{[2-(2,3-difluorophenyl)pyridin-3-yl]methyl}-1H-tetraazol-5-amine

Example 175A 2-(2,3-difluoro-phenyl)-nicotinonitrile

Prepared in 91% yield from 2-chloronicotinonitrile and 2,3-difluorophenylboronic acid according to the procedure described for Example 153A. MS (ESI−) m/z 216.9 (M+H)⁺; ¹H NMR (CDCl₃) δ 7.21-7.29 (m, 1H), 7.30-7.39 (m, 2H), 7.49 (dd, J=8.0, 4.9 Hz, 1H), 8.12 (dd, J=7.8, 1.7 Hz, 1H), 8.92 (dd, J=4.9, 1.9 Hz, 1H).

Example 175B 1-(2,3-Dichloro-phenyl)-3-[2-(2,3-difluoro-phenyl)-pyridin-3-ylmethyl]-thiourea Prepared in 56% yield from the product of Example 175A according to the procedure described for Example 153B. MS (ESI+) m/z 423.8 (M+H)⁺; ¹H NMR (DMSO-d₆) δ 4.84 (d, J=5.4 Hz, 2H), 6.37 (br s, 1H), 7.123-7.27 (m, 5H), 7.35-7.43 (m, 2H), 7.65 (br s, 1H), 8.03 (d, J=7.8 Hz, 1H), 8.66 (br s, 1H).

Example 175C 1-(2,3-dichlorophenyl)-N-{[2-(2,3-difluorophenyl)pyridin-3-yl]methyl}-1H-tetraazol-5-amine Prepared in 59% yield from the product of Example 175B according to the procedure described for Example 153C. MS (ESI+) m/z 433.1 (M+H)⁺; ¹H NMR (DMSO-d₆) δ 4.39 (d, J=5.4 Hz, 2H), 7.28-7.35 (m, 2H), 7.47-7.58 (m, 2H), 7.60-7.66 (m, 3H), 7.89 (dd, J=7.8, 1.4 Hz, 1H), 7.94 (dd, J=7.5, 2.0 Hz, 1H), 8.59 (dd, J=4.6, 1.5 Hz, 1H).

Example 176

1-(2,3-dichlorophenyl)-N-{[2-(2,5-difluorophenyl)pyridin-3-yl]methyl}-1H-tetraazol-5-amine

Example 176A 2-(2,5-Difluoro-phenyl)-nicotinonitrile

Prepared in 66% yield from 2-chloronicotinonitrile and 2,5-difluorophenylboronic acid according to the procedure described for Example 153A. ¹H NMR (CDCl₃) δ 7.19-7.23 (m, 2H), 7.29-7.34 (m, 1H), 7.48 (dd, J=8.0, 4.9 Hz, 1H), 8.10 (dd, J=8.0, 1.9 Hz, 1H), 8.92 (dd, J=5.1, 1.7 Hz, 1H).

Example 176B 1-(2,3-Dichloro-phenyl)-3-[2-(2,5-difluoro-phenyl)-pyridin-3-ylmethyl]-thiourea Prepared in 95% yield from the product of Example 176A according to the procedure described for Example 153B. MS (ESI+) m/z 423.8 (M+H)⁺; ¹H NMR (DMSO-d₆) δ 4.86 (d, J=5.4 Hz, 2H), 6.53 (br s, 1H), 7.08-7.23 (m, 4H), 7.29-7.46 (m, 3H), 7.70 (br s, 1H), 8.10 (d, J=7.8 Hz, 1H), 8.65 (br s, 1H).

Example 176C 1-(2,3-dichlorophenyl)-N-{[2-(2,5-difluorophenyl)pyridin-3-yl]methyl}-1H-tetraazol-5-amine Prepared in 89% yield from the product of Example 176B according to the procedure described for Example 153C. MS (ESI+) m/z 433.1 (M+H)⁺; ¹H NMR (DMSO-d₆) δ 4.39 (d, J=5.4 Hz, 2H), 7.32-7.41 (m, 3H), 7.48 (dd, J=8.1, 4.7 Hz, 1H), 7.58-7.69 (m, 4H), 7.88 (dd, J=7.8, 1.7 Hz, 1H), 7.94 (dd, J=7.8, 2.0 Hz, 1H), 8.58 (dd, J=4.7, 1.7 Hz, 1H).

Example 177

1-(2,3-dichlorophenyl)-N-{[2-(2,4,6-trifluorophenyl)pyridin-3-yl]methyl}-1H-tetraazol-5-amine

Example 177A 2-(2,4,6-trifluorophenylnicotinonitrile

Prepared in 82% yield from 2-chloronicotinonitrile and 2,4,6-trifluorophenylboronic acid according to the procedure described for Example 153A. MS (ESI+) m/z 235.0 (M+H)⁺; ¹H NMR (CDCl₃) δ 6.83-6.88 m, 2H), 7.51 (dd, J=8.0, 4.9 Hz, 1H), 8.12 (dd, J=8.1, 1.7 Hz, 1H), 8.94 (dd, J=5.1, 1.7 Hz, 1H).

Example 177B 1-(2,4,6-trichlorophenyl)-3-[2-(2,5-difluorophenyl)pyridin-3-ylmethyl]thiourea Prepared in 87% yield from the product of Example 177A according to the procedure described for Example 153B. MS (ESI+) m/z 442.0 (M+H)⁺ ¹H NMR (CDCl₃) δ 4.78 (d, J=5.8H, 2H), 6.22 (br s, 1H), 6.74-6.79 (m, 2H), 7.15-7.23 (m, 2H), 7.29-7.44 (m, 2H), 7.63 (br s, 1H), 8.02 (d, J=6.8 Hz, 1H), 8.67 (dd, J=4.9, 1.5 Hz, 1H).

Example 177C 1-(2,3-dichlorophenyl)-N-{[2-(2,4,6-trifluorophenyl) pyridin-3-yl]methyl}-1H-tetraazol-5-amine Prepared in 23% yield from the product of Example 177B according to the procedure described for Example 153C. MS (ESI+) m/z 451.1 (M+H)+; $^1$H NMR (DMSO-d$_6$) δ 4.34 (d, J=5.8 Hz, 1H), 7.34-7.37 (m, 2H), 7.51 (dd, J=8.0, 4.9 Hz, 1H), 7.59-7.66 (m, 3H), 7.89 (dd, J=7.8, 1.7 Hz, 1H), 7.94 (dd, J=7.1, 2.7 Hz, 1H), 8.60 (dd, J=4.7, 1.7 Hz, 1H).

Example 178

1-(2,3-dichlorophenyl)-N-[(2-pyrrolidin-1-ylpyridin-3-yl)methyl]-1H-tetraazol-5-amine

Example 178A 2-pyrrolidin-1-yl-nicotinonitrile

To an oven-dried, N$_2$-purged, 50-mL flask containing a magnetic stir bar were added 2-fluoronicotinonitrile (1.22 g, 10.0 mmol), anhydrous tetrahydrofuran (5 mL), and triethylamine (3.04 g, 4.19 mL, 30.0 mmol). The flask was sealed with a septum and cooled to 0° C. in an ice bath. Neat pyrrolidine (1.04 g, 1.24 mmol, 15.0 mmol) was added via syringe. The mixture was stirred at 0° C. for 30 minutes and then allowed to warm to room temperature overnight. Water (10 mL) was added and the mixture was transferred to a separatory funnel. The mixture was extracted with dichloromethane (3×10 mL). The combined organic extracts were dried over magnesium sulfate, filtered, and concentrated by rotary evaporator to a brown oil. The product was recrystallized from ethyl acetate/hexanes to give 1.29 g (75%) of the title compound as a tan powder. MS (ESI+) m/z 174.0 (M+H)+; $^1$H NMR (DMSO-d$_6$) δ 1.91-1.95 (m, 4H), 3.63-3.68 (m, 4H), 6.68 (dd, J=7.6, 4.6 Hz, 1H), 7.91 (dd, J=7.6, 1.9 Hz, 1H), 8.31 (dd, J=4.7, 2.0 Hz, 1H).

Example 178B 1-(2,3-Dichloro-phenyl)-3-(2-pyrrolidin-1-yl-pyridin-3-ylmethyl)-thiourea To a thick-walled pressure bottle were added Raney nickel (~5 g, wet) and ammonia-saturated methanol (100 mL). The product of Example 178A (866 mg, 5.00 mmol) was added, and the bottle was inserted into a Parr shaker. The bottle was charged with 60 psi of H$_2$ gas, and the grey mixture was shaken under static hydrogen pressure at room temperature for 2 hours. After venting, the solids were removed by vacuum filtration through a glass frit covered with a nylon filter. The solvent/volatiles were removed by rotary evaporator to give ~900 mg a pale green oil containing C-(2-pyrrolidin-1-yl-pyridin-3-yl)-methylamine that was used without further purification for the next step.

To an oven-dried, 100-mL, round-bottomed flask containing a magnetic stir bar was added the C-(2-pyrrolidin-1-yl-pyridin-3-yl)-methylamine (~0.71 g, 4.0 mmol) from above. Anhydrous tetrahydrofuran (20 mL) and 2-3-dichlorophenyl-isothiocyanate (1.02 g, 0.71 mL, 5.00 mmol) were added via syringe. The flask was sealed with a septum. The mixture was stirred at room temperature overnight. Water (20 mL) was added, and the reaction was transferred to a separatory funnel. The mixture was extracted with dichloromethane (3×15 mL). The combined organic extracts were dried over magnesium sulfate, filtered, and concentrated by rotary evaporator to give a brown solid. The product was recrystallized from ethyl acetate/hexanes to give 1.31 g (86%) of the title compound as a white powder. MS (ESI+) m/z 380.9 (M+H)+; $^1$H NMR (DMSO-d$_6$) δ 1.84-1.88 (m, 4H), 3.43-3.48 (m, 4H), 4.69 (br s, 2H), 6.72 (dd, J=7.5 4.7 HZ, 1H), 7.35 (dd, J=8.1, 8.0 Hz, 1H), 7.47-7.51 (m, 2H), 7.67 (d, J=7.1 Hz, 1H), 8.03 (dd, J=4.7, 1.7 Hz, 1H), 8.31 (br s, 1H), 9.39 (br s, 1H).

Example 178C 1-(2,3-dichlorophenyl)-N-[(2-pyrrolidin-1-ylpyridin-3-yl)methyl]-1H-tetraazol-5-amine To an oven-dried, 100-mL, round-bottomed flask containing a magnetic stir bar were added the product of Example 178B (1.14 g, 3.00 mmol), sodium azide (585 mg, 9.00 mmol), and anhydrous tetrahydrofuran (30 mL). Neat triethylamine (911 mg, 1.25 mL, 9.00 mmol) was added via syringe. Solid mercury (II) chloride (896 mg, 3.30 mmol) was added in one portion. A thick, white precipitate formed upon addition of the mercury salt. The mixture was stirred at room temperature overnight during which the solids darkened to black. Ethyl acetate (20 mL) was added and the solids were removed by vacuum filtration through a glass frit. The liquor was washed with water (20 mL). The organic phase was dried over magnesium sulfate, filtered, and concentrated by rotary evaporator to give a tan solid. The product was recrystallized from ethyl acetate/hexanes to give 912 mg (78%) of the title compound as a white powder. MS (ESI+) m/z 390.0 (M+H)+; $^1$H NMR (DMSO-d$_6$) δ 1.82-1.88 (m, 4H), 3.43-3.48 (m, 4H), 4.49 (d, J=5.4 Hz, 2H), 6.67 (dd, J=7.3, 4.9 Hz, 1H), 7.46 (dd, J=7.3, 1.9 Hz, 1H), 7.57-7.63 (m, 2H), 7.93 (dd, J=8.1, 1.7 Hz, 1H), 8.00 (dd, J=4.7, 2.0 Hz, 1H).

Example 179

1-(2,3-dichlorophenyl)-N-[(2-piperidin-1-ylpyridin-3-yl)methyl]-1H-tetraazol-5-amine Prepared by the same methods as 178A-C substituting piperidine for pyrrolidine. MS (ESI+) m/z 404.0 (M+H)+; $^1$H NMR (DMSO-d$_6$) δ 1.55-1.63 (m, 6H), 2.97-3.00 (m, 4H), 4.48 (d, J=5.8 Hz, 2H), 6.98 (dd, J=7.6, 4.9 Hz, 1H), 7.57-7.67 (m, 3H), 7.73 (J=8.0, 1.7 Hz, 1H), 7.94 (dd, J=8.1, 1.7 Hz, 1H), 8.16 (dd, J=4.7, 1.7 Hz, 1H).

Example 180

N-[(2-azetidin-1-ylpyridin-3-yl)methyl]-1-(2,3-dichlorophenyl)-1H-tetraazol-5-amine

Example 180A 2-azetidin-1-yl-nicotinonitrile

Prepared in 82% yield from 3-cyano-2-fluoropyridine and azetidine hydrochloride according to the procedure described for Example 178A. MS (ESI+) m/z 160.0 (M+H)+; $^1$H NMR (DMSO-d$_6$) δ 2.28-2.38 (m, 2H), 4.19-4.25 (m, 4H), 6.73 (Dd, J=7.6, 4.9 HZ, 1H), 7.92 (dd, J=7.7, 1.8 Hz, 1H), 8.30 (dd, J=4.9, 1.9 Hz, 1H).

Example 180B 1-(2-azetidin-1-yl-pyridin-3-ylmethyl)-3-(2,3-dichloro-phenyl)-thiourea Prepared in 84% yield from the product of Example 180A according to the procedure described for Example 178B. MS (ESI+) m/z 367.0 (M+H)⁺; ¹H NMR (DMSO-d$_6$) δ 2.20-2.30 (m, 2H), 4.02-4.07 (m, 4H), 4.54 (br s, 2H), 6.73 (dd, 7.3, 4.9 Hz, 1H), J=7.32-7.43 (m, 2H), 7.50 (dd, J=8.1, 1.4 Hz, 1H), 7.70 (d, J=6.4 Hz, 1H), 8.04 (dd, J=4.7, 1.7 Hz, 1H), 8.32 (br s, 1H), 9.42 (br s, 1H).

Example 180C

N-[(2-azetidin-1-ylpyridin-3-yl)methyl]-1-(2,3-dichlorophenyl)-1H-tetraazol-5-amine Prepared in 30% yield from the product of Example 180B according to the procedure described for Example 178C. MS (ESI+) m/z 375.9 (M+H)⁺; ¹H NMR (DMSO-d$_6$) δ 2.18-2.28 (m, 2H), 4.01-4.06 (m, 4H), 4.34 (d, J=5.4 Hz, 1H), 6.69 (dd, J=7.5 Hz, 4.7 Hz, 1H), 7.39 (dd, J=7.5, 1.7 Hz, 1H), 7.55-7.64 (m, 2H), 7.73 (dd, J=7.8 1.9 Hz, 1H), 7.95 (dd, J=8.1, 1.4 Hz, 1H), 8.01 (dd, J=4.9, 1.9 Hz, 1H).

Example 181

1-(2,3-dichlorophenyl)-N-[(3-pyrrolidin-1-ylpyridin-4-yl)methyl]-1H-tetraazol-5-amine

Example 181A 2-chloro-3-pyrrolidin-1-ylisonicotinonitrile

Prepared in 94% yield from 2-chloro-4-cyano-3-fluoropyridine and pyrrolidine according to the procedure described for Example 178A. MS (ESI+) m/z 207.9 (M+H)⁺; ¹H NMR (DMSO-d$_6$) δ 1.91-1.95 (m, 4H), 3.62-3.67 (m, 4H), 7.63 (d, J=4.7 Hz, 1H), 7.98 (d, J=4.7 HZ, 1H).

Example 181B 1-(2,3-dichloro-phenyl)-3-(3-pyrrolidin-1-yl-pyridin-4-ylmethyl)-thiourea Prepared in 89% yield from the product of Example 181A according to the procedure described for Example 178B with the modification that the Raney Nickel reduction of the nitrile was conducted for 4 hours. MS (ESI+) m/z 381.0 (M+H)⁺; ¹H NMR (DMSO-d$_6$) δ 1.88-1.91 (m, 4H), 3.20-3.25 (m, 4H), 4.74 (d, J=4.4 Hz, 2H), 7.13 (d, J=4.7 Hz, 1H), 7.33-7.39 (m, 1H), 7.52-7.57 (m, 1H), 7.66 (dd, J=8.1, 1.7 Hz, 1H), 8.06 (d, J=4.7 Hz, 1H), 8.14 (s, 1H), 8.33 (br s, 1H), 9.55 (br s, 1H).

Example 181C 1-(2,3-dichlorophenyl)-N-[(3-pyrrolidin-1-ylpyridin-4-yl)methyl]-1H-tetraazol-5-amine Prepared in 44% yield from the product of Example 181B according to the procedure described for Example 178C. MS (ESI+) m/z 390.0 (M+H)⁺; ¹H NMR (DMSO-d$_6$) δ 1.87-1.91 (m, 4H), 3.20-3.25 (m, 4H), 4.49 (D, J=5.8 Hz, 2H), 7.14 (D, J=5.1 HZ, 1H), 7.62 (dd, J=8.1, 8.0 Hz, 1H), 7.69-7.71 (m, 1H), 7.75 (dd, J=8.1, 1.7 Hz, 1H), 7.96 (dd, J=8.1, 1.7 HZ, 1H), 8.02 (d, J=5.1 HZ, 1H), 8.14 (br s, 1H).

Example 182

1-(2,3-dichlorophenyl)-N-[(5-fluoro-2-pyrrolidin-1-ylpyridin-3-yl)methyl]-1H-tetraazol-5-amine

Example 182A

5-Fluoro-2-pyrrolidin-1-yl-nicotinonitrile

Prepared in 90% yield from the product of Example 169A and pyrrolidine according to the procedure described for Example 178A. MS (ESI+) m/z 192.0 (M+H)⁺; ¹H NMR (DMSO-d$_6$) δ 1.90-1.96 (m, 4H), 3.61-3.65 (m, 4H), 8.05 (dd, J=8.5, 3.0 Hz, 1H), 8.38 (d, J=3.0 Hz, 1H).

Example 182B 1-(2,3-Dichloro-phenyl)-3-(5-fluoro-2-pyrrolidin-1-yl-pyridin-3-ylmethyl)-thiourea Prepared in 82% yield from the product of Example 182A according to the procedure described for Example 178B. MS (ESI+) m/z 399.0 (M+H)⁺; ¹H NMR (DMSO-d$_6$) δ 1.85-1.88 (m, 4H), 3.37-3.42 (m, 4H), 4.71 (d, J=3.7 Hz, 2H), 7.34-7.39 (m, 2H), 7.53 (dd, J=8.1, 1.4 Hz, 1H), 7.61 (d, J=8.5 Hz, 1H), 8.01 (d, J=3.0 Hz, 1H), 8.33 (br s, 1H), 9.55 (br s, 1H).

Example 182C 1-(2,3-dichlorophenyl)-N-[(5-fluoro-2-pyrrolidin-1-ylpyridin-3-yl)methyl]-1H-tetraazol-5-amine Prepared in 59% yield from the product of Example 182B according to the procedure described for Example 178C. MS (ESI+) m/z 407.9 (M+H)⁺; ¹H NMR (DMSO-d$_6$) δ 1.82-1.87 (m, 4H), 3.38-3.42 (m, 4H), 4.49 (d, J=5.4 Hz, 2H), 7.40 (dd, J=9.5, 3.0 Hz, 1H), 7.63 (dd, J=8.1, 8.0 Hz, 1H), 7.69 (dd, J=5.6, 5.6 Hz, 1H), 7.77 (dd, J=7.8, 1.9 Hz, 1H), 7.96 (dd, J=8.1, 1.4 Hz, 1H), 8.00 (d, J=3.0 Hz, 1H).

Example 183

N-benzyl-3-({[1-(2,3-dichlorophenyl)-1H-tetraazol-5-yl]amino}methyl)pyridin-2-amine

Example 183A 2-benzylaminonicotinonitrile

Prepared in 66% yield from 2-fluoronicotinonitrile and benzylamine according to the procedure described for Example 178A. MS (ESI+) m/z 210.0 (M+H)⁺; ¹H NMR (DMSO-d$_6$) δ 4.59 (d, J=6.1 Hz, 2H), 6.64 (dd, J=7.6, 4.9 HZ, 1H), 7.16-7.24 (m, 1H), 7.26-7.32 (m, 5H), 7.71 (dd, J=5.9, 5.9 Hz, 1H), 7.91 (dd, J=7.6, 1.9 Hz, 1H), 8.23 (dd, J=4.9, 1.9 Hz, 1H).

Example 183B 1-(2-Benzylamino-pyridin-3-ylmethyl)-3-(2,3-dichloro-phenyl)thiourea Prepared in 67% yield from the product of Example 183A according to the procedure described for from Example 178B. MS (ESI+) m/z 416.9 (M+H)+; 1H NMR (DMSO-$d_6$) δ 4.60 (d, J=5.8 Hz, 2H), 4.65 (d, J=4.4 Hz, 1H), 6.53 (dd, J=7.1, 5.1 Hz, 1H), 6.71 (dd, J=5.9, 5.9 Hz, 1H), 7.16-7.20 (m, 1H), 7.24-7.37 (m, 6H), 7.53 (d, J=8.5 Hz, 2H), 7.90 (dd, J=4.9, 1.9 Hz, 1H), 8.30 (br s, 1H), 9.51 (br s, 1H).

Example 183C

N-benzyl-3-({[1-(2,3-dichlorophenyl)-1H-tetraazol-5-yl]amino}methyl)pyridin-2-amine Prepared in 14% yield from the product of Example 183B according to the procedure described for Example 178C. MS (ESI+) m/z 425.7 (M+H)+; 1H NMR (DMSO-$d_6$) δ 4.36 (d, J=5.8 Hz, 2H), 4.59 (d, J=5.8 Hz, 2H), 6.50-6.55 (m, 2H), 7.16-7.21 (m, 1H), 7.27-7.28 (m, 4H), 7.36 (dd, J=7.3, 1.9 Hz, 1H), 7.54 (dd, J=5.4, 5.4 Hz, 1H), 7.61 (dd, J=8.0, 8.0 Hz, 1H), 7.74 (dd, J=7.8, 1.7 Hz, 1H), 7.89 (dd, J=4.9, 1.9 Hz, 1H), J=7.95 (dd, J=8.1, 1.7 Hz, 1H).

Example 184

1-(2,3-dichlorophenyl)-N-{[2-(3,3-difluoroazetidin-1-yl)pyridin-3-yl]methyl}-1H-tetraazol-5-amine

Example 184A 2-(3,3-difluoro-azetidin-1-yl)-nicotinonitrile

Prepared in 84% yield from 2-fluoronicotinonitrile and 3,3-difluoroazetidine hydrochloride according to the procedure described for Example 178A. 1H NMR (DMSO-$d_6$) δ 4.65 (t, J=12.4 Hz, 4H), 6.94 (dd, J=7.6, 4.9 Hz, 1H). 8.08 (dd, J=7.8, 1.7 Hz, 1H), 8.40 (dd, J=4.9, 1.9 Hz, 1H).

Example 184B 1-(2,3-Dichloro-phenyl)-3-[2-(3,3-difluoro-azetidin-1-yl-pyridin-3-ylmethyl]-thiourea Prepared in 65% yield from the product of Example 184A according to the procedure described for Example 178B. MS (ESI+) m/z 402.6 (M+H)+; 1H NMR (DMSO-$d_6$) δ 4.48 (t, J=12.7 Hz, 4H), 4.57 (dd, J=3.7 Hz, 2H), 6.92 (dd, J=7.3, 4.9 Hz, 1H), 7.36 (dd, J=8.0, 8.0 Hz, 1H), 7.51-7.56 (m, 2H), 7.63 (d, J=9.5 Hz, 1H), 8.12 (dd, J=5.1, 1.7 Hz, 1H), 8.35 (br s, 1H), 9.46 (br s, 1H).

Example 184C 1-(2,3-dichlorophenyl)-N-{[2-(3,3-difluoroazetidin-1-yl)pyridin-3-yl]methyl}-1H-tetraazol-5-amine Prepared in 66% yield from the product of Example 184B according to the procedure described for Example 178C. MS (ESI+) m/z 411.6 (M+H)+; 1H NMR (DMSO-$d_6$) δ 4.36 (d, J=5.8 Hz, 2H), 4.49 (t, J=12.9 Hz, 4H), 6.88 (dd, J=7.5, 4.7 Hz, 1H), 7.53 (dd, J=7.5, 1.7 Hz, 1H), 7.59-7.66 (m, 2H), 7.75 (dd, J=8.0, 1.5 Hz, 1H), 7.95 (dd, J=8.1, 1.4 Hz, 1H), 8.10 (dd, J=5.1, 1.7 Hz, 1H).

Example 185

N-[(2-chloro-3-pyrrolidin-1-ylpyridin-4-yl)methyl]-1-(2,3-dichlorophenyl)-1H-tetraazol-5-amine

Example 185A 1-(2-Chloro-3-pyrrolidin-1-yl-pyridin-4-ylmethyl)-3-(2,3-dichloro-phenyl)-thiourea Prepared in 89% yield from the product of Example 181A according to the procedure described for Example 178B with the modification that the Raney Nickel reduction of the nitrile was conducted for 45 minutes. MS (ESI+) m/z 414.5 (M+H)+; 1H NMR (DMSO-$d_6$) δ 1.94-1.99 (m, 4H), 3.17-3.21 (m, 4H), 4.81 (d, J=5.8 Hz, 2H), 7.24 (d, J=5.1 Hz, 1H), 7.37 (dd, J=8.0, 8.0 Hz, 1H), 7.53-7.59 (m, 2H), 8.19 (d, J=4.7 Hz, 1H), 8.32 (br s, 1H), 9.65 (br s, 1H).

Example 185B

N-[(2-chloro-3-pyrrolidin-1-ylpyridin-4-yl)methyl]-1-(2,3-dichlorophenyl)-1H-tetraazol-5-amine Prepared in 34% yield from the product of Example 185A according to the procedure described for Example 178C. MS (ESI+) m/z 423.9 (M+H)+; 1H NMR (DMSO-$d_6$) δ 1.94-1.99 (m, 4H), 3.18-3.22 (m, 4H), 4.59 (d, J=5.8 Hz, 1H), 7.28 (d, J=5.1 Hz, 1H), 7.64 (dd, J=8.0, 8.0 Hz, 1H), 7.72-7.78 (m, 2H), 7.97 (dd, J=8.1, 1.7 Hz, 1H), 8.17 (d, J=4.7 Hz, 1H).

Example 186

N-[(2-azetidin-1-yl-5-fluoropyridin-3-yl)methyl]-1-(2,3-dichlorophenyl)-1H-tetraazol-5-amine

Example 186A

2-Azetidin-1-yl-5-fluoro-nicotinonitrile

Prepared in 78% yield from the product of Example 169A and azetidine hydrochloride according to the procedure described for Example 178A. MS (ESI+) m/z 177.8 (M+H)+; 1H NMR (DMSO-$d_6$) δ 2.28-2.38 (m, 2H), 4.17-4.22 (m, 4H), 8.07 (dd, J=8.3, 2.9 Hz, 1H), 8.66 (dd, J=8.1, 3.0 Hz, 1H).

Example 186B 1-(2-Azetidin-1-yl-5-fluoro-pyridin-3-ylmethyl)-3-(2,3-dichloro-phenyl)-thiourea Prepared in 36% yield from the product of Example 186A according to the procedure described for Example 178B.

Example 186C

N-[(2-azetidin-1-yl-5-fluoropyridin-3-yl)methyl]-1-(2,3-dichlorophenyl)-1H-tetraazol-5-amine Prepared in 12% yield from the product of Example 186B according to the procedure described for Example 178C. MS (ESI+) m/z 393.9 (M+H)+; 1H NMR (DMSO-$d_6$) δ 2.19-2.29 (m, 2H), 4.01 (t, J=7.5 Hz, 4H), 4.34 (d, J=5.8 Hz, 2H), 7.33 (dd, J=9.3, 2.9 Hz, 1H), 7.61-7.66 (m, 2H), 7.79 (dd, J=8.0, 1.5 Hz, 1H), 7.97 (dd, J=8.1, 1.4 Hz, 1H), 8.01 (d, J=2.7 Hz, 1H).

Example 187

1-(2,3-dichlorophenyl)-N-[(2,5-difluoro-6-pyrrolidin-1-ylpyridin-3-ylmethyl]-1H-tetraazol-5-amine

Example 187A 2,5-Difluoro-6-pyrrolidin-1-yl-nicotinonitrile

Prepared in 57% yield from 2,5,6-Trifluoro-nicotinonitrile and pyrrolidine according to the procedure described for Example 178A. ¹H NMR (DMSO-d₆) δ 1.85-1.93 (m, 4H), 3.55-3.62 (m, 4H), 8.01 (dd, J=12.2, 6.8 Hz, 1H).

Example 187B 1-(2,3-Dichloro-phenyl)-3-(2,5-difluoro-6-pyrrolidin-1-yl-pyridin-3-ylmethyl)-thiourea Prepared in 32% yield from the product of Example 187A according to the procedure described for Example 178B. MS (ESI+) m/z 416.7 (M+H)⁺; ¹H NMR (DMSO-d₆) δ 1.86-1.90 (m, 4H), 3.49-3.53 (m, 4H), 4.52 (d, J=3.4 Hz, 2H), 7.35 (dd, J=8.1, 8.0 Hz, 1H), 7.50-7.56 (m, 2H), 7.60 (d, J=7.1 Hz, 1H), 8.36 (br s, 1H), 9.42 (br s, 1H).

Example 187C 1-(2,3-dichlorophenyl)-N-[(2,5-difluoro-6-pyrrolidin-1-ylpyridin-3-yl)methyl]-1H-tetraazol-5-amine Prepared in 45% yield from the product of Example 187B according to the procedure described for Example 178C. MS (ESI⁺) m/z 425.9 (M+H)⁺; ¹H NMR (DMSO-d₆) δ 1.85-1.89 (m, 4H), 3.47-3.52 (m, 4H), 4.30 (d, J=5.8 Hz, 2H), 7.50 (dd, J=12.6, 7.5 Hz, 1H), 7.56-7.63 (m, 2H), 7.70 (dd, J=7.8, 1.7 Hz, 1H), 7.95 (dd, J=8.1, 1.7 Hz, 1H).

Example 188

1-(2,3-dichlorophenyl)-N-[(2-phenyl-3-pyrrolidin-1-ylpyridin-4-yl)methyl]-1H-tetraazol-5-amine

Example 188A

2-Phenyl-3-pyrrolidin-1-yl-isonicotinonitrile

Prepared in 66% yield from the product of Example 181A and phenylboronic acid according to the procedure described for Example 153A. MS (ESI+) m/z 249.8 (M+H)⁺; ¹H NMR (DMSO-d₆) δ 1.72-1.77 (m, 4H), 3.17-3.21 (m, 4H), 7.38-7.52 (m, 6H), 8.14 (d, J=4.7 Hz, 1H).

Example 188B 1-(2,3-Dichloro-phenyl)-3-(2-phenyl-3-pyrrolidin-1-yl-pyridin-4-ylmethyl)-thiourea Prepared in 72% yield from the product of Example 188A according to the procedure described for Example 178B.

Example 188C 1-(2,3-dichlorophenyl)-N-[(2-phenyl-3-pyrrolidin-1-ylpyridin-4-yl)methyl]-1H-tetraazol-5-amine Prepared in 64% yield from the product of Example 188B according to the procedure described for Example 178C. MS (ESI+) m/z 466.0 (M+H)⁺; ¹H NMR (DMSO-d₆) δ 1.70-1.74 (m, 4H), 2.92-2.96 (m, 4H), 4.52 (d, J=6.1 Hz, 1H), 7.25 (d, J=4.7 Hz, 1H), 7.39-7.48 (m, 5H), 6.64 (dd, J=8.0, 8.0 Hz, 1H), 7.76-7.80 (m, 2H), 7.98 (dd, J=8.1, 1.4 Hz, 1H), 8.33 (d, J=4.7 Hz, 1H).

Example 189

N-[(2-azepan-1-ylpyridin-3-yl)methyl]-1-(2,3-dichlorophenyl)-1H-tetraazol-5-amine

Example 189A 2-azepan-1-yl-nicotinonitrile

Prepared in 67% yield from 2-fluoronicotinonitrile and hexamethyleneimine according to the procedure described for Example 178A.

Example 189B 1-(2-Azepan-1-yl-pyridin-3-ylmethyl)-3-(2,3-dichloro-phenyl)-thiourea Prepared in 64% yield from the product of Example 189A according to the procedure described for Example 178B. MS (ESI+) m/z 408.9 (M+H)⁺; ¹H NMR (DMSO-d₆) δ 1.56-1.58 (m, 4H), 1.74-1.76 (m, 4H), 3.35-3.39 (m, 4H), 4.66 (br s, 2H), 6.86 (dd, J=7.3, 4.9 Hz, 1H), 7.35 (dd, J=8.0, 8.0 Hz, 1H), 7.50-7.53 (m, 2H), 7.64 (d, J=5.8 Hz, 1H), 8.09 (dd, J=4.7, 1.7 Hz, 1H), 8.28 (br s, 1H), 9.47 (br s, 1H).

Example 189C

N-[(2-azepan-1-ylpyridin-3-yl)methyl]-1-(2,3-dichlorophenyl)-1H-tetraazol-5-amine Prepared in 70% yield from the product of Example 189B according to the procedure described for Example 178C. MS (ESI⁺) m/z 418.0 (M+H)⁺; ¹H NMR (DMSO-d₆) δ 1.59-1.62 (m, 4H) 1.73-1.74 (m, 4H), 3.34-3.38 (m, 4H), 4.45 (d, J=5.4 Hz, 2H), 6.82 (dd, J=7.5, 4.7 Hz, 1H), 7.52 (dd, J=7.5, 1.7 Hz, 1H), 7.58-7.63 (m, 2H), 7.72 (dd, J=7.8, 1.7 Hz, 1H), 7.94 (dd, J=8.1, 1.7 Hz, 1H), 8.07 (dd, J=4.7, 1.7 Hz, 1H).

Example 190

1-(2,3-dichlorophenyl)-N-{[2-pyrrolidin-1-yl-6-(trifluoromethyl)pyridin-3-yl]methyl}-1H-tetraazol-5-amine

Example 190A

2-Pyrrolidin-1-yl-6-trifluoromethyl-nicotinonitrile

Prepared in 67% yield from 2-chloro-6-trifluoromethyl-nicotinonitrile and pyrrolidine according to the procedure described for Example 178A. MS (ESI+) m/z 242.9 (M+H)⁺; ¹H NMR (DMSO-d₆) δ 1.92-1.97 (m, 4H), 3.67-3.72 (m, 4H), 7.07 (d, J=7.8 Hz, 1H), 8.22 (d, J=7.8 Hz, 1H).

Example 190B 1-(2,3-Dichloro-phenyl)-3-(2-pyrrolidin-1-yl-6-trifluoromethyl-pyridin-3-ylmethyl)-thiourea Prepared in 85% yield from the product of Example 190A according to the procedure described for Example 178B. MS (ESI+) m/z 448.9 (M+H)⁺; ¹H NMR (DMSO-d₆) δ 1.87-1.91

(m, 4H), 3.50-3.55 (m, 4H), 4.79 (s, 2H), 7.13 (d, J=7.8 Hz, 1H), 7.36 (dd, J=8.1, 8.0 Hz, 1H), 7.52 (dd, J=8.1, 1.4 Hz, 1H), 7.63 (d, J=7.1 Hz, 1H), 8.36 (br s, 1H), 9.49 (br s, 1H).

Example 190C 1-(2,3-dichlorophenyl)-N-{[2-pyrrolidin-1-yl-6-(trifluoromethyl)pyridin-3-yl]methyl}-1H-tetraazol-5-amine Prepared in 59% yield from the product of Example 190B according to the procedure described for Example 178C. MS (ESI+) m/z 457.9 (M+H)$^+$; $^1$H NMR (DMSO-d$_6$) δ 1.85-1.89 (m, 4H), 3.51-3.55 (m, 4H), 4.58 (d, J=5.1 Hz, 1H), 7.07 (d, J=7.8 Hz, 1H), 7.58-7.70 (m, 3H), 7.73 (J=7.8, 1.9 Hz, 1H), 7.95 (dd, J=8.1, 1.4 Hz, 1H).

Example 191

N-benzyl-3-({[1-(2,3-dichlorophenyl)-1H-tetraazol-5-yl]amino}methyl)-N-methylpyridin-2-amine

Example 191A 2-(benzylmethylamino)nicotinonitrile

Prepared in 62% yield from 2-fluoronicotinonitrile and N-methylbenzylamine according to the procedure described for Example 178A. MS (ESI+) m/z 224.0 (M+H)$^+$; $^1$H NMR (DMSO-d$_6$) δ 3.21 (s, 3H), 4.92 (s, 2H), 6.80 (dd, J=7.8, 4.8 Hz, 1H), 7.23-7.28 (m, 3H), 7.32-7.37 (m, 2H), 8.00 (dd, J=7.8, 2.0 Hz, 1H), 8.36 (dd, J=4.6, 1.9 Hz, 1H).

Example 191B

1-[2-(benzylmethylamino)-pyridin-3-ylmethyl]-3-(2,3-dichloro-phenyl)thiourea

Prepared in 76% yield from the product of Example 191A according to the procedure described for Example 178B. MS (ESI+) m/z 430.9 (M+H)$^+$; $^1$H NMR (DMSO-d$_6$) δ2.69 (s, 3H), 4.29 (br s, 2H), 4.79 (br s, 2H), 7.02 (dd, J=7.5, 4.7 Hz, 1H), 7.22-7.38 (, 6H), 7.53 (d, J=8.1 Hz, 1H), 7.60 (d, J=6.1 Hz, 1H), 8.16 (dd, J=4.7, 1.7 Hz, 1H), 8.37 (br s, 1H), 9.54 (br s, 1H).

Example 191C

N-benzyl-3-({[1-(2,3-dichlorophenyl)-1H-tetraazol-5-yl]amino}methyl)-N-methylpyridin-2-amine Prepared in 86% yield from the product of Example 191B according to the procedure described for Example 178C. MS (ESI+) m/z 439.9 (M+H)$^+$; $^1$H NMR (DMSO-d$_6$) δ 2.70 (s, 3H), 4.31 (s, 2H), 4.56 (d, J=5.8 Hz, 2H), 6.98 (dd, J=7.5, 4.7 Hz, 1H), 7.22-7.27 (m, 1H), 7.30-7.38 (m, 4H), 7.59-7.64 (m, 2H), 7.70-7.74 (m, 2H), 7.95 (dd, J=8.1, 1.7 Hz, 1H), 8.15 (dd, J=4.9, 1.9 Hz, 1H).

Example 192

1-(2,3-dichloro-4-fluorophenyl)-N-[(6'-fluoro-2,3'-bipyridin-3-yl)methyl]-1H-tetraazol-5-amine

Example 192A 2,3-dichloro-4-fluorobenzoic acid

To an oven-dried, N$_2$-purged 1-L, round-bottomed flask containing a large magnetic stir bar were added via syringe anhydrous tetrahydrofuran (200 mL) and tetramethylethylenediamine (11.3 mL, 8.72 g, 75.0 mmol). The flask was cooled to −85° C. (dry ice/anhydrous ether slurry) and the sec-butyllithium/cyclohexane solution (53.6 mL of 1.4 M solution, 75.0 mmol) was added via syringe. A solution of commercially available 3-chloro-4-fluorobenzoic acid (5.24 g, 30 mmol) in anhydrous tetrahydrofuran (10 mL) was added dropwise to the reaction via syringe. The resulting orange/brown slurry was stirred at −85° C. for 2 hours. A solution of hexachloroethane (28.4 g, 120 mmol) in anhydrous tetrahydrofuran (30 mL) was added dropwise to the reaction mixture. The mixture was stirred at −85° C. for 1 hour and then allowed to warm to room temperature over 4 hours. The solvents/volatiles were removed by rotary evaporator to give a brown semi-solid. Water (150 mL) was added. The mixture was transferred to a separatory funnel and washed with ether (2×100 mL). Hydrochloric acid (1 N) was added via pipet to adjust the pH to ~1. The mixture was extracted with ethyl acetate (4×100 mL). The combined organic extracts were dried over magnesium sulfate, filtered, and concentrated by rotary evaporator to give a tan solid. The product was recrystallized from ethyl acetate/hexanes to give 4.36 g (70%) of the title compound as a fine white powder. MS (ESI−) m/z 206.9 (M−H); $^1$H NMR (DMSO-d$_6$) δ 7.54 (dd, J=8.8, 8.8 Hz, 1H), 7.85 (dd, J=8.8, 5.8 Hz, 1H), 13.72 (br s, 1H).

Example 192B (2,3-dichloro-4-fluoro-phenyl)-carbamic acid t-butyl ester

To an oven-dried, N$_2$-purged, 250-mL, round-bottomed flask containing a magnetic stir bar was added the product of Example 192A (3.14 g, 15.0 mmol). Anhydrous t-butanol (50 mL) was added via syringe. Triethylamine (2.62 mL, 1.90 g, 18.75 mmol) was added via syringe. Diphenylphosphorylazide (3.45 mL, 4.40 g, 16.5 mmol) was added via syringe. A reflux condenser with N$_2$-inlet was attached and a heating mantle was applied. The golden solution was heated to reflux and stirred for 8 hours. After cooling to room temperature, the solvent/volatiles were removed by rotary evaporator to give a thick golden oil. The product was purified by flash chromatography (silica gel: 10% ethyl acetate, 90% hexanes—product R$_f$~0.6) to give a 3.57 g (85%) of the title compound as a white powder. MS (ESI−) m/z 278.0 (M−H); $^1$H NMR (DMSO-d$_6$) δ 1.45 (s, 9H), 7.42 (dd, J=9.0, 9.0 Hz, 1H), 7.54 (dd, J=9.2, 5.8 Hz, 1H), 8.95 (br s, 1H).

Example 192C 2,3-dichloro-4-fluoroaniline

To an oven-dried, N$_2$-purged, 100-mL, round-bottomed flask containing a magnetic stir bar were added the product of Example 192B (3.08 g, 11.0 mmol) and dichloromethane (25 mL). The flask was sealed with a septum and cooled to 0° C. in an ice bath. Trifluoroacetic acid (18 mL) was added dropwise via syringe. The brown solution was stirred at 0° C. for 30 minutes and then allowed to warm to room temperature for 2 hours. The mixture was transferred to a large Erlenmeyer flask and the acid was neutralized by the careful addition of saturated aqueous sodium bicarbonate. The mixture was transferred to a separatory funnel and extracted with dichloromethane (3×25 mL). The combined organic extracts were dried over magnesium sulfate, filtered, and concentrated by rotary evaporator to give a brown semi-solid. The product was purified by flash chromatography (silica gel: 20% ethyl acetate, 80% hexanes, product $R_f$~0.3) to give 1.49 g (81%) of the title compound as a pink solid. MS (ESI–) m/z 178.0 (M–H); $^1$H NMR (DMSO-$d_6$) δ 5.53 (br s, 2H), 6.77 (dd, J=9.2, 5.1 Hz, 1H), 7.13 (dd, J=9.2, 9.2 Hz, 1H).

Example 192D 2,3-dichloro-1-fluorophenylisothiocyanate

To an oven-dried, $N_2$-purged, 100-mL, round-bottomed flask containing a large magnetic stir bar were added the product of Example 192C (756 mg, 4.20 mmol), dichloromethane (40 mL), and potassium carbonate powder (2.90 g, 21.0 mmol). The flask was sealed with a septum and purged with $N_2$ atmosphere. Thiophosgene (483 µL, 724 mg, 6.30 mmol) was added via syringe to form an orange/yellow slurry with white precipitate. The mixture was stirred vigorously at room temperature for 24 hours. The solids were removed by vacuum filtration through a glass frit, and the filtrate was washed with dichloromethane and hexanes. The liquor was concentrated by rotary evaporator to give a golden/brown oil. The product was purified by flash chromatography (silica gel: 100% hexanes, product Rf~0.5) to give the title compound as a colorless oil.

Example 192E

6'-fluoro-[2,3']bipyridinyl-3-carbonitrile

To an oven-dried, $N_2$-purged, 250-mL, round-bottomed flask containing a magnetic stir bar were added the commercially available 2-chloro-3-cyanopyridine (1.25 g, 9.00 mmol), the commercially available 2-fluoropyridine-5-boronic acid (845 mg, 6.00 mmol), and dichlorobis(triphenylphosphine)pallalium(II) (211 mg, 0.300 mmol). The flask was sealed with a septum and purged with $N_2$ atmosphere. Anhydrous dioxane (45 mL) and a $N_2$-purged solution of cesium carbonate (5.86 g, 18.0 mmol) in water (45 mL) were added via syringe. The reaction mixture was heated to ~90° C. in an oil bath and stirred for 2 hours. The reaction was monitored by LC-MS. After cooling to room temperature, the solvent/volatiles were removed by rotary evaporator to give a thick brown oil. Water (75 mL) was added and the mixture was transferred to a separatory funnel. The mixture was extracted with ethyl acetate (4×30 mL). The combined organic extracts were dried over magnesium sulfate, filtered, and concentrated by rotary evaporator to give a brown solid. The product was recrystallized from ethyl acetate/hexanes to give 1.01 g (84%) of the title compound as a tan powder. MS (ESI$^+$) m/z 200.0 (M+H)$^+$; $^1$H NMR (DMSO-$d_6$) δ 7.43 (dd, J=8.6, 2.9 Hz, 1H), 7.70 (dd, J=8.1, 5.1 Hz, 1H), 8.49 (d, J=1.7 Hz, 1H), 8.51 (d, J=1.7 Hz, 1H), 8.74 (d, J=2.7 Hz, 1H), 8.98 (dd, J=4.7, 1.7 Hz, 1H).

Example 192F

C-(6'-fluoro-[2,3']bipyridinyl-3-yl)-methylamine

To an argon-purged, thick-walled pressure vessel was added wet Raney nickel (~250 mg). A solution of ammonia-saturated methanol (20 mL) was added. The product of Example 192E (150 mg, 0.750 mmol) was added as a solid. The vessel was inserted into a Parr shaker and was charged with 60 psi of $H_2$ gas. The mixture was shaken at room temperature under static $H_2$ pressure for 1 hour. The $H_2$ gas was vented and the vessel was purged with argon. The solids were removed by vacuum filtration through a glass frit covered with a nylon filter. The solvent/volatiles were removed by rotary evaporator to give the title compound as a pale green oil that was used without further purification.

Example 192G 1-(2,3-dichloro-4-fluoro-phenyl)-3-(6'-fluoro-[2,3'] bipyridinyl-3-ylmethyl)-thiourea To an oven-dried, $N_2$-purged, 25-mL, round-bottomed flask containing a magnetic stir bar were added the product of Example 192D (111 mg, 0.500 mmol) and anhydrous tetrahydrofuran (5 mL). The flask was sealed with a septum and purged with $N_2$ atmosphere. A solution of the crude product of Example 192F (122 mg, 0.600 mmol) in anhydrous tetrahydrofuran (1 mL) was added via syringe. The pale green solution was stirred at room temperature overnight. Saturated aqueous sodium bicarbonate (10 mL) was added to quench. The mixture was transferred to a separatory funnel and extracted with dichloromethane (3×10 mL). The combined organic extracts were dried over magnesium sulfate, filtered, and concentrated by rotary evaporator to give a tan solid. The product was recrystallized from ethyl acetate/hexanes to give a 198 mg (93%) of the title compound as a white powder. MS (ESI$^+$) m/z 425.0 (M+H)$^+$; $^1$H NMR (DMSO-$d_6$) δ 4.72 (d, J=4.7 Hz, 2H), 7.31 (dd, J=8.3, 2.9 Hz, 1H), 7.42-7.50 (m, 3H), 7.85 (dd, J=7.8, 1.4 Hz, 1H), 8.14-8.20 (m, 1H), 8.31 (br s, 1H), 8.40 (d, J=2.4 Hz, 1H), 8.59 (dd, J=4.7, 1.4 Hz, 1H), 9.51 (br s, 1H).

Example 192H 1-(2,3-dichloro-4-fluorophenyl)-N-[(6'-fluoro-2,3'-bipyridin-3-yl)methyl]-1H-tetraazol-5-amine To an oven-dried, $N_2$-purged, 25-mL, round-bottomed flask containing a magnetic stir bar were added the product of Example 192G (170 mg, 0.400 mmol), and sodium azide (78.0 mg, 1.20 mmol). The flask was sealed with a septum and purged with $N_2$ atmosphere. Anhydrous tetrahydrofuran (5 mL) was added via syringe. Triethylamine (209 µL, 152 mg, 1.50 mmol) was added via syringe. The solid mercury (II) chloride (136 mg, 0.500 mmol) was added in one portion and the flask was resealed. A thick, white precipitate formed immediately upon addition of the mercury salt. The mixture was stirred at room temperature overnight and monitored by LC-MS. Ethyl acetate (10 mL) was added, and the solids were removed by vacuum filtration through a glass frit. The solids were washed with ethyl acetate. The liquor was transferred to a separatory funnel and washed with water (10 mL). The organic phase was dried over magnesium sulfate, filtered, and concentrated by rotary evaporator to give an off-white solid. The product was recrystallized from ethyl acetate/hexanes to give 121 mg (70%) of the title compound as a white powder. MS (ESI$^+$) m/z 434.0 (M+H)$^+$; $^1$H NMR (DMSO-$d_6$) δ 4.53 (d, J=5.4 Hz, 2H), 7.31 (dd, J=8.5, 2.7 Hz, 1H), 7.46 (dd, J=7.8, 4.7 Hz, 1H), 7.67-7.84 (m, 3H), 7.90 (d, J=7.8 Hz, 1H), 8.19-8.25 (m, 1H), 8.44 (br s, 1H), 8.60-8.61 (m, 1H).

Example 193

1-[2-chloro-4-fluoro-3-(trifluoromethyl)phenyl]-N-[(2-fluoropyridin-3-yl)methyl]-1H-tetraazol-5-amine

Example 193A 2-chloro-4-fluoro-1-nitro-3-(trifluoromethyl)benzene

To a 100-mL, round-bottomed flask containing a magnetic stir bar and cooled to 0° C. in an ice bath were added fuming nitric acid (12.6 mL) and fuming sulfuric acid (12.6 mL). Neat 1-chloro-3-fluoro-2-trifluoromethyl-benzene (5.36 g, 26.5 mmol) was added dropwise while stirring. The mixture was stirred at 0° C. for 10 min and then allowed to warm to room temperature for 30 min. The mixture was poured into a beaker containing ice (50 g) and then transferred to a separatory funnel. The mixture was extracted with dichloromethane (3×30 mL). The combined organic extracts were dried over sodium sulfate, filtered, and concentrated by rotary evaporator to give a brown oil. The product—an inseparable mixture of ~4.5:1 2-chloro-4-fluoro-1-nitro-3-trifluoromethyl-benzene:1-chloro-3-fluoro-4-nitro-2-trifluoro-methylbenzene was flash chromatographed (silica gel/10% ethyl acetate in hexanes, product $R_f$=0.5) to give 6.41 g (99%) of the mixture of nitration products in the aforementioned ratio as a yellow oil. $^1$H NMR (CDCl$_3$) major regioisomer: δ7.97 (dd, 1H), 7.33 (dd, 1H); $^1$H NMR (CDCl$_3$) minor regioisomer δ 8.18 (dd, 1H), 7.53 (d, 1H).

Example 193B 2-chloro-4-fluoro-3-trifluoromethylphenylamine

To a 100-mL, round-bottomed flask containing a large magnetic stir bar were added absolute ethanol (10 mL) and glacial acetic acid (20 mL) and the mixture from Example 193A (1.46 g, 6.00 mmol). Fine mesh iron powder (1.73 g, 30.0 mmol) was added in portions. A reflux condenser was attached and a heating mantle was applied. The gray slurry was heated to reflux and stirred for 30 min. After cooling to room temperature, the gray solids were removed by vacuum filtration through a glass frit and the solids were washed with dichloromethane and methanol. The solution was concentrated to a brown oil by rotary evaporator and then dissolved in 10% methanol in dichloromethane (25 mL). The solution was transferred to a 125 mL separatory funnel and washed with saturated sodium bicarbonate solution. Solids precipitated so the mixture was again filtered through a glass frit and then separated. The organic layer was dried over sodium sulfate, filtered, and concentrated by rotary evaporator to give a brown oil. Flash chromatography (silica gel/20% ethyl acetate in hexanes) afforded 1.11 g (87%) of a pale yellow oil that contained mixture of ~4.5:1 2-chloro-4-fluoro-3-trifluoromethylaniline:4-chloro-2-fluoro-3-trifluoromethylaniline. The regioisomers could be separated by careful flash chromatography using a large excess of silica gel and 10% ethyl acetate/90% hexanes. 2-Chloro-4-fluoro-3-trifluoromethylenylamine (major regioisomer): MS (ESI$^+$) m/z 211.9 (M−H)$^+$, $^1$H NMR (DMSO-d$_6$): δ 7.18 (dd, 1H), 7.10 (dd, 1H). 4-Chloro-2-fluoro-3-trifluoromethylphenylamine (minor regioisomer): δ 7.18 (d, 1H), 7.01 (d, 1H).

Example 193C

C-(2-fluoro-pyridin-3-yl)methylamine

Prepared in 29% yield from 2-fluoro-3-methylpyridine according to the procedure described for Example 141A.

Example 193D 1-(2-chloro-4-fluoro-3-trifluoromethyl-phenyl)-3-(2-fluoro-pyridin-3-ylmethyl)-thiourea Prepared in 32% yield from 2-chloro-4-fluoro-3-trifluoromethylphenylamine of Example 193B and the product of Example 193C according to the procedures described for Example 192D and Example 192G. MS (ESI+) m/z 381.6 (M+H)$^+$; $^1$H NMR (DMSO-d$_6$) δ 4.73 (br s, 2H), 7.33-7.39 (m, 1H), 7.51 (dd, J=10.8, 9.1 Hz, 1H), 7.84-7.86 (m, 2H), 7.98-8.09 (m, 1H), 8.14 (d, J=5.1 Hz, 1H), 8.50 (br s, 1H).

Example 193E

1-[2-chloro-4-fluoro-3-(trifluoromethyl)phenyl]-N-[(2-fluoropyridin-3-yl)methyl]-1H-tetraazol-5-amine Prepared in 10% yield from the product of Example 193D according to the procedure described for Example 192H. MS (ESI+) m/z 391.0 (M+H)$^+$; $^1$H NMR (DMSO-d$_6$) δ 4.52 (d, J=5.4 Hz, 1H), 7.33-7.37 (m, 1H), 7.79-7.86 (m, 2H), 7.88-7.94 (m, 1H), 8.15 (d, J=4.7 Hz, 1H), 8.21 (dd, J=9.0, 5.3 Hz, 1H).

Example 194

1-[4-chloro-2-fluoro-3-(trifluoromethyl)phenyl]-N-[(2-fluoropyridin-3-ylmethyl]-1H-tetraazol-5-amine Example 194A 1-(4-Chloro-2-fluoro-3-trifluoromethyl-phenyl)-3-(2-fluoro-pyridin-3-ylmethyl)thiourea Prepared in 44% yield from 4-chloro-2-fluoro-3-trifluoromethylphenylamine and the product of Example 193C according to the procedures described for Example 192D and Example 192G. MS (ESI+) m/z 381.9 (M+H)$^+$; $^1$H NMR (DMSO-d$_6$) δ 4.74 (d, J=5.4 Hz, 2H), 7.34-7.40 (m, 1H), 7.56 (d, J=9.5 Hz, 1H), 7.83-7.88 (m, 1H), 8.02-8.06 (m, 1H), 8.15 (d, J=4.7 Hz, 1H), 8.66 (br s, 1H), 9.66 (br s, 1H).

Example 194B

1-[4-chloro-2-fluoro-3-(trifluoromethyl)phenyl]-N-[(2-fluoropyridin-3-ylmethyl]-1H-tetraazol-5-amine Prepared in 71% yield from the product of Example 194A according to the procedure described for Example 192H. MS (ESI+) m/z 391.0 (M+H)$^+$; $^1$H NMR (DMSO-d$_6$) δ 4.54 (d, J=5.4 Hz, 2H), 7.35 (ddd, J=7.3, 5.1, 1.9 Hz, 1H), 7.85-7.96 (m, 3H), 8.10 (d, J=8.5 Hz, 1H), 8.14-8.16 (m, 1H).

Example 195

N-[(2-fluoropyridin-3-yl)methyl]-1-(2,3,4-trichlorophenyl)-1H-tetraazol-5-amine

Example 195A 1-(2-fluoro-pyridin-3-ylmethyl)-3-(2,3,4-trichlorophenyl)-thiourea

Prepared in 58% yield from the product of Example 193C and 2,3,4-trichloroaniline according to the procedures described for Example 192D and Example 192G. MS (ESI+) m/z 363.8 (M+H)$^+$; $^1$H NMR (DMSO-d$_6$) δ 4.72 (d, J=5.1 Hz, 2H), 7.36 (ddd, J=7.2, 5.0, 1.7 Hz, 1H), 7.63-7.68 (m, 2H), 7.84-7.90 (m, 1H), 8.14 (d, J=5.1 Hz, 1H), 8.51 (br s, 1H), 9.66 (br s, 1H).

Example 195B

N-[(2-fluoropyridin-3-ylmethyl]-1-(2,3,4-trichlorophenyl)-1H-tetraazol-5-amine

Prepared in 52% yield from the product of Example 195A according to the procedures described for Example 192H. MS (ESI+) m/z 374.9 (M+H)$^+$; $^1$H NMR (DMSO-d$_6$) δ 4.51 (d, J=5.4 Hz, 2H), 7.35 (ddd, J=7.3, 5.1, 1.9 Hz, 1H), 7.76-7.83 (m, 2H), 7.88-7.96 (m, 2H), 8.14-8.16 (m, 1H).

Example 196

N-[(2-fluoropyridin-3-yl)methyl]-1-(2,3,5-trichlorophenyl)-1H-tetraazol-5-amine

Example 196A 1-(2-fluoro-pyridin-3-ylmethyl)-3-(2,3,5-trichlorophenyl)-thiourea Prepared in 55% yield from the product of Example 193C and 2,3,5-trichloroaniline according to the procedures described for Example 192D and Example 192G. MS (ESI+) m/z 363.8 (M+H)$^+$; $^1$H NMR (DMSO-d$_6$) δ 4.73 (br s, 2H), 7.37 (ddd, J=7.1, 5.1, 2.0 Hz, 1H), 7.72 (d, J=2.0 Hz, 1H), 7.83-7.84 (m, 1H), 7.89 (ddd, J=10.0, 7.6, 2.0 Hz, 1H), 8.15 (d, J=5.1 Hz, 1H), 8.65 (br s, 1H), 9.60 (br s, 1H).

Example 196B

N-[(2-fluoropyridin-3-yl)methyl]-1-(2,3,5-trichlorophenyl)-1H-tetraazol-5-amine

Prepared in 60% yield from the product of Example 196A according to the procedures described for Example 192H. MS (ESI+) m/z 372.9 (M+H)$^+$; $^1$H NMR (DMSO-d$_6$) δ 4.52 (d, J=5.8 Hz, 2H), 7.35 (ddd, J=7.2, 5.0, 1.7 Hz, 1H), 7.85 (dd, J=5.8 Hz, 1H), 7.92 (ddd, J=9.7, 7.5, 2.0 Hz, 1H), 8.07 (d, J=2.4 Hz, 1H), 8.14-8.16 (m, 1H), 8.22 (d, J=2.7 Hz, 1H).

Example 197

1-[2,3-bis(trifluoromethyl)phenyl]-N-[(2-fluoropyridin-3-yl)methyl]-1H-tetraazol-5-amine

Example 197A 2,3-Bis(trifluoromethyl)phenylamine

Prepared from 1-nitro-2,3-bis(trifluoromethyl)benzene according to the method of Example 193B. MS (ESI−) m/z 228.0 (M−H)$^+$; $^1$H NMR (DMSO-d$_6$) δ 6.11 (br s, 2H), 7.03 (d, J=7.5 Hz, 1H), 7.15 (d, J=8.1 Hz, 1H), 7.41 (dd, J=8.0 Hz, 1H).

Example 197B 1-(2,3-bis(trifluoromethyl)phenyl)-3-(2-fluoropyridin-3-ylmethyl)thiourea Prepared in 90% yield from the product of Example 197A and the product of Example 193C according to the procedure described for the product of Example 192D and Example 192G.

Example 197C

1-[2,3-bis(trifluoromethyl)phenyl]-N-[(2-fluoropyridin-3-yl)methyl]-1H-tetraazol-5-amine Prepared in 42% yield from the product of Example 197B according to the procedures described for Example 192H. MS (ESI+) m/z 407.0 (M+H)$^+$; $^1$H NMR (DMSO-d$_6$) δ 4.52 (d, J=5.8 Hz, 2H), 7.35 (ddd, J=7.2, 5.0, 1.7 Hz, 1H), 7.83-7.93 (m, 2H), 8.10-8.20 (m, 3H), 8.37 (d, J=7.8 Hz, 1H).

Example 198

1-(2,3-dichloro-4-fluorophenyl)-N-[(2-fluoropyridin-3-yl)methyl]-1H-tetraazol-5-amine

Example 198A 1-(2,3-Dichloro-4-fluoro-phenyl)-3-(2-fluoro-pyridin-3-ylmethyl)-thiourea Prepared in 84% yield from Example 192D and Example 193C according to the procedure described for Example 192G. MS (ESI+) m/z 347.8 (M+H)$^+$; $^1$H NMR (DMSO-d$_6$) δ 4.71 (d, J=5.4 HZ, 2H), 7.34-7.38 (m, 1H), 7.47 (dd, J=8.8, 8.8 Hz, 1H), 7.55-7.60 (m, 1H), 7.83-7.89 (m, 1H), 8.13 (d, J=4.4 Hz, 1H), 8.36 (br s, 1H), 9.60 (br s, 1H).

Example 198B 1-(2,3-dichloro-4-fluorophenyl)-N-[(2-fluoropyridin-3-yl)methyl]-1H-tetraazol-5-amine Prepared in 52% yield from the product of Example 198A according to the procedure described for Example 192H. MS (ESI+) m/z 357.0 (M+H)$^+$; $^1$H NMR (DMSO-d$_6$) δ 4.51 (d, J=5.4 Hz, 2H), 7.35 (ddd, J=7.2, 5.0, 2.0 Hz, 1H), 7.72-7.78 (m, 2H), 7.86-7.94 (m, 2H), 8.15 (d, J=4.4 Hz, 1H).

Example 199

1-(2,3-dichloro-4-fluorophenyl)-N-[(2-thien-3-ylpyridin-3-yl)methyl]-1H-tetraazol-5-amine

Example 199A 1-(2,3-Dichloro-4-fluoro-phenyl)-3-(2-thiophen-3-yl-pyridin-3-ylmethyl)-thiourea Prepared in 50% yield from the product of Example 192D and 2-thiophen-3-ylnicotinonitrile (Example 165A) according to the 2-step nitrile reduction and amine-isothiocyanate coupling procedures described for Example 153B. MS (ESI+) m/z 412.0 (M+H)+.

Example 199B 1-(2,3-dichloro-4-fluorophenyl)-N-[(2-thien-3-ylpyridin-3-yl)methyl]-1H-tetraazol-5-amine Prepared in 46% yield from the product of Example 199A according to the procedure described for Example 192H. MS (ESI+) m/z 421.0 (M+H)+; $^1$H NMR (DMSO-$d_6$) δ 4.63 (d, J=5.4 Hz, 2 h) 7.34 (dd, J=8.0 4.6 Hz, 1H), 7.49 (dd, J=5.1, 1.9 Hz, 1H), 7.65 (dd, J=4.9, 2.9 Hz, 1H), 7.70-7.73 (m, 1H), 7.75 (d, J=8.8 Hz, 1H), 7.81 (dd, J=8.1, 1.7 Hz, 1H), 7.83-7.88 (m, 2H), 8.53 (dd, J=4.7, 1.7 Hz, 1H).

Example 200

N-[(2-azetidin-1-yl-5-fluoropyridin-3-yl)methyl]-1-(2,3-dichloro-4-fluorophenyl)-1H-tetraazol-5-amine Example 200A 1-(2-Azetidin-1-yl-5-fluoro-pyridin-3-ylmethyl)-3-(2,3-dichloro-4-fluoro-phenyl)thiourea Prepared in 43% yield from the product of Example 192D and the product of Example 186A according to the 2-step nitrile reduction and amine-isothiocyanate coupling procedures described for Example 186B. MS (ESI+) m/z 403.0 (M+H)+; $^1$H NMR (DMSO-$d_6$) δ 2.19-2.27 (m, 2H), 3.98-4.03 (m, 4H), 4.54 (br s, 2H), 7.28 (dd, J=9.3, 2.9 Hz, 1H), 7.48 (dd, J=8.8, 8.8 Hz, 1H), 7.58 (br s, 1H), 8.02 (d, J=2.7 Hz, 1H), 8.27 (br s, 1H).

Example 200B

N-[(2-azetidin-1-yl-5-fluoropyridin-3-yl)methyl]-1-(2,3-dichloro-4-fluorophenyl)-1H-tetraazol-5-amine Prepared in 5% yield from the product of Example 200A according to the procedure described for Example 192H. MS (ESI+) m/z 412.0 (M+H)+; $^1$H NMR (DMSO-$d_6$) δ 2.19-2.28 (m, 2H), 3.99-4.03 (m, 4H), 4.34 (d, J=5.4 Hz, 2H), 7.34 (dd, J=9.3, 2.9 Hz, 1H), 7.60 (dd, J=5.6 Hz, 1H), 7.76 (dd, J=8.8, 8.8 Hz, 1H), 7.93 (dd, J=8.8, 5.1 Hz, 1H), 8.01 (d, J=2.7 Hz, 1H).

Example 201

1-(2,3-dichloro-4-fluorophenyl)-N-{[2-(4-methyl-1,4-diazepan-1-yl)pyridin-3-yl]methyl}-1H-tetraazol-5-amine Example 201A 1-(2,3-Dichloro-4-fluoro-phenyl)-3-[2-(4-methyl-[1,4]diazepan-1-yl)-pyridin-3-ylmethyl]-thiourea Prepared in 86% yield from the product of Example 192D and the product of Example 261B according to the procedure for Example 192G. MS (ESI+) m/z 442.1 (M+H)+.

Example 201B 1-(2,3-dichloro-4-fluorophenyl)-N-{[2-(4-methyl-1,4-diazepan-1-yl)pyridin-3-yl]methyl}-1H-tetraazol-5-amine Prepared in 58% yield from the product of Example 201A according to the procedure described for Example 192H. MS (ESI+) m/z 451.1 (M+H)+; $^1$H NMR (DMSO-$d_6$) δ 1.84-1.88 (m, 2H), 2.57-2.67 (m, 4H), 3.38-4.45 (m, 4H), 4.44 (dd, J=5.8 Hz, 2H), 6.84 (dd, J=7.5, 4.7 Hz, 1H), 7.53 (dd, J=7.5, 2.0 Hz, 1H), 7.59 (dd, J=5.6, 5.6 Hz, 1H), 7.74 (dd. J=8.5, 8.5 Hz, 1H), 7.86 (dd, J=9.0, 5.3 Hz, 1H), 8.07 (dd, J=4.7, 1.7 Hz, 1H).

Example 202

N-(2,3'-bipyridin-3-ylmethyl)-1-(2,3-dichloro-4-fluorophenyl)-1H-tetraazol-5-amine Example 202A 1-[2,3']Bipyridinyl-3-ylmethyl-3-(2,3-dichloro-4-fluoro-phenyl)-thiourea Prepared in 56% yield from the product of Example 192D and [2,3']bipyridinyl-3-carbonitrile (Example 166A) according to the 2-step nitrile reduction and amine-isothiocyanate coupling procedures described for Example 153B. MS (ESI+) m/z 407.1 (M+H)+; $^1$H NMR (DMSO-$d_6$) δ 4.73 (d, J=5.1 Hz, 2H), 7.42-7.54 (m, 4H), 7.85 (dd, J=7.8, 1.7 Hz, 1H), 7.94-7.98 (m, 1H), 8.30 (br s, 1H), 8.60 (dd, J=4.6, 1.5 Hz, 1H), 8.65 (dd, J=4.7, 1.4 Hz, 1H), 8.73 (d, J=1.7 Hz, 1H), 9.53 (br s, 1H).

Example 202B

N-(2,3'-bipyridin-3-ylmethyl)-1-(2,3-dichloro-4-fluorophenyl)-1H-tetraazol-5-amine Prepared in 31% yield from the product of Example 202A according to the procedure described for Example 192H. MS (ESI+) m/z 416.0 (M+H)+; $^1$H NMR (DMSO-$d_6$) δ 4.53 (d, J=5.8 Hz, 2H), 7.46 (dd, J=7.8, 4.7 Hz, 1H), 7.52 (ddd, J=7.8, 4.9, 0.8 Hz, 1H), 7.68-7.71 (m, 1H), 7.74-7.83 (m, 2H), 7.89 (dd, J=8.0, 1.5 Hz, 1H), 7.99-6.03 (m, 1H), 8.61 (dd, J=4.7, 8.7 Hz, 1H), 8.65 (dd, J=4.7, 1.7 Hz, 1H), 8.77 (d, J=2.4 Hz, 1H).

Example 203

1-(2,3-dichlorophenyl)-N-{[2-(trifluoromethyl)pyridin-3-yl]methyl}-1H-tetraazol-5-amine Example 203A 2-trifluoromethylnicotinonitrile To an oven-dried, $N_2$-purged, 100-mL, round-bottomed flask containing a magnetic stir bar were added copper(I) iodide (1.26 g, 6.6 mmol) and potassium fluoride (383 mg, 6.6 mmol). The flask was heated to 120° C. for 1 hour under vacuum. After cooling to room temperature, 2-iodonicotinonitrile (1.38 g, 6.00 mmol) was added followed by the addition via syringe of anhydrous dimethylformamide (6 mL) and anhydrous N-methylpyrrolidinone (6 mL). A solution of (trifluoromethyl)trimethylsilane (12 mL of 0.5 M, 6.00 mmol) in tetrahydrofuran was added via syringe and the reaction mixture was stirred at room temperature overnight. Water (20 mL) was added. The mixture was transferred to a separatory funnel and extracted with ether (3×30 mL). The combined organic extracts were washed with ammonium hydroxide (30 mL), 1N hydrochloric acid (30 mL), and saturated sodium bicarbonate (30 mL). The ether solution was dried over magnesium sulfate and concentrated by rotary evaporator. The product was purified by flash chromatography (silica gel: 35% ethyl acetate, 65% hexanes, product Rf~0.3) to give 800 mg (77%) of the title compound as a white powder. $^1$H NMR (CDCl$_3$) δ 7.69 (dd, J=8.0, 4.9 Hz, 1H), 8.21 (dd, J=8.0, 1.5 HZ, 1H), 8.92 (dd, J=4.7, 9.4 Hz, 1H).

Example 203B 1-(2,3-dichlorophenyl)-3-(2-trifluoromethyl-pyridin-3-ylmethyl)thiourea Prepared in 95% yield from 2,3-dichlorophenylisothiocyanate and the product of Example 203A according to the procedure described for Example 153B. MS (ESI+) m/z 379.9 (M+H)$^+$; $^1$H NMR (CDCl$_3$) δ 5.11 (d, J=5.4 Hz, 2H), 6.38 (br s, 1H), 7.15-7.28 (m, 1H), 7.29 (d, J=7.8 Hz, 1H), 7.34-7.38 (m, 1H), 7.44 (d, J=7.8, 1.7 Hz, 1H), 7.51 (dd, J=5.1, 4.7 Hz, 1H), 7.65 (br s, 1H), 8.18 (d, J=7.5 Hz, 1H), 8.63 (d, J=4.7 Hz, 1H).

Example 203C 1-(2,3-dichlorophenyl)-N-{[2-(trifluoromethyl)pyridin-3-yl]methyl}-1H-tetraazol-5-amine Prepared in 34% yield from the product of Example 203B according to the procedure described for Example 153C. MS (ESI+) m/z 389.0 (M+H)$^+$; $^1$H NMR (DMSO-d$_6$) δ 4.70 (d, J=5.4 Hz, 2H), 7.64 (dd, J=8.1, 8.1 Hz, 1H), 7.73 (dd, J=8.0, 4.6 Hz, 1H), 7.78 (dd, J=8.0, 1.5 Hz, 1H), 7.88 (dd, J=5.8, 5.8 Hz, 1H), 7.97 (dd, J=8.1, 1.4 Hz, 1H), 8.01 (d, J=7.5 Hz, 1H), 8.64 (d, J=4.4 Hz, 1H).

Example 204

1-(2,3-dichlorophenyl)-N-{[1-(4-methoxyphenyl)-3-methyl-1H-pyrazol-5-yl]methyl}-1H-tetraazol-5-amine

Example 204A 2-(4-Methoxy-phenyl)-5-methyl-2H-pyrazole-3-carbonitrile

Prepared in 45% yield from 2-(4-methoxy-phenyl)-5-methyl-2H-pyrazole-3-carboxylic acid according to the procedure described for Example 169A. MS (ESI+) m/z 214.0 (M+H)$^+$; $^1$H NMR (DMSO-d$_6$) δ 2.29 (s, 3H), 3.83 (s, 3H), 6.95 (s, 1H), 7.10 (d, J=9.0 Hz, 2H), 7.49 (d, J=9.1 Hz, 2H).

Example 204B 1-(2,3-Dichloro-phenyl)-3-[2-(4-methoxy-phenyl)-5-methyl-2H-pyrazol-3-ylmethyl]-thiourea Prepared in 76% yield from 2,3-dichlorophenylisothiocyanate and the product of Example 204A according to the procedure described for Example 153B. MS (ESI+) m/z 421.1 (M+H)$^+$; $^1$H NMR (DMSO-d$_6$) δ 2.26 (s, 3H), 3.81 (s, 3H), 4.65 (s, 2H), 6.25 (s, 1H), 7.05 (d, J=9.0 Hz, 2H), 7.34 (dd, J=8.1, 8.0 Hz, 1H), 7.41 (d, J=8.8 Hz, 2H), 7.46-7.50 (m, 1H), 7.71 (d, J=7.5 Hz, 1H), 8.43 (br s, 1H), 9.41 (br s, 1H).

Example 204C 1-(2,3-dichlorophenyl)-N-{[1-(4-methoxyphenyl)-3-methyl-1H-pyrazol-5-yl]methyl}-1H-tetraazol-5-amine Prepared in 34% yield from the product of Example 204B according to the procedure described for Example 153C. MS (ESI+) m/z 430.1 (M+H)$^+$; $^1$H NMR (DMSO-d$_6$) δ 2.23 (s, 3H), 3.80 (s, 3H), 4.43 (d, J=5.8 Hz, 2H), 6.16 (s, 1H), 7.03 (d, J=9.2 Hz, 2H), 7.37 (d, J=9.2 Hz, 2H), 7.57-7.70 (m, 3H), 7.93 (dd, J=8.0, 1.5 Hz, 1H).

Example 205

N-{[1-(4-chlorophenyl)-3-methyl-1H-pyrazol-5-yl]methyl}-1-(2,3-dichlorophenyl)-1H-tetraazol-5-amine

Example 205A 2-(4-chlorophenyl)-5-methyl-2H-pyrazole-3-carbonitrile

Prepared in 41% yield from 2-(4-chlorophenyl)-5-methyl-2H-pyrazole-3-carboxylic acid according to the procedure described for Example 169A. MS (ESI+) m/z 217.9 (M+H)$^+$; $^1$H NMR (DMSO-d$_6$) δ 2.34 (s, 3H), 7.00 (s, 1H), 7.65 (s, 4H).

Example 205B 1-(2,3-Dichloro-phenyl)-3-[2-(4-chlorophenyl)-5-methyl-2H-pyrazol-3-ylmethyl]-thiourea Prepared in 56% yield from 2,3-dichlorophenylisothiocyanate and the product of Example 205A according to the procedure described for Example 153B.

Example 205C

N-{[1-(4-chlorophenyl)-3-methyl-1H-pyrazol-5-yl]methyl}-1-(2,3-dichlorophenyl)-1H-tetraazol-5-amine Prepared in 68% yield from the product of Example 205B according to the procedure described for Example 153C. MS (ESI+) m/z 434.0 (M+H)$^+$; $^1$H NMR (DMSO-d$_6$) δ 2.31 (s, 3H), 4.44 (d, J=5.8 Hz, 2H), 6.22 (s, 1H), 7.51-7.58 (m, 4H), 7.61 (d, J=8.1H), 7.64-7.66 (m, 1H), 7.69 (dd, J=7.9, 1.9 Hz, 1H), 7.93 (dd, J=8.0, 1.5 Hz, 1H).

Example 206

1-(2,3-dichlorophenyl)-N-{[1-phenyl-3-(trifluoromethyl)-1H-pyrazol-5-yl]methyl}-1H-tetraazol-5-amine

Example 206A

2-Phenyl-5-trifluoromethyl-2H-pyrazole-3-carbonitrile

Prepared according to the method described in: *J. Med. Chem.* 2000, 43, 2975-2981.

Example 206B 1-(2,3-Dichloro-phenyl)-3-(2-phenyl-5-trifluoromethyl-2H-pyrazol-3-ylmethyl)-thiourea Prepared in 61% yield from 2,3-dichlorophenylisothiocyanate and the product of Example 206A according to the procedure described for Example 153B. MS (ESI+) m/z 445.1 (M+H)$^+$; $^1$H NMR (DMSO-d$_6$) δ 4.78 (d, J=5.4 Hz, 2H), 6.82 (s, 1H), 7.35 (dd, J=7.8, 7.8 Hz, 1H), 7.40-7.67 (m, 7H), 8.39 (br s, 1H), 9.55 (s, 1H).

Example 206C 1-(2,3-dichlorophenyl)-N-{[1-phenyl-3-(trifluoromethyl)-1H-pyrazol-5-yl]methyl}-1H-tetraazol-5-amine Prepared in 85% yield from the product of Example 206B according to the procedure described for Example 153C. MS (ESI+) m/z 454.0 (M+H)$^+$; $^1$H NMR (DMSO-d$_6$) δ 4.60 (d, J=5.4 Hz, 2H), 6.86 (s, 1H), 7.54-7.65 (m, 7H), 7.75 (dd, J=5.4, 5.4 Hz, 1H), 7.95 (dd, J=6.8, 2.7 Hz, 1H).

Example 207

1-(2,3-dichlorophenyl)-5-(2-phenylpyrrolidin-1-yl)-1H-tetraazole

The product of Example 75B (0.1 g) was reacted with 2-phenylpyrrolidine (0.1 g) according to the method of Example 75C to provide 0.029 g of the title compound as a white solid. MS (ESI/NH$_3$) m/z 359 (M+H)$^+$. $^1$H NMR (DMSO-d$_6$) δ 1.78-1.9 (m, 4H), 3.3-3.6 (m, 2H), 4.8-5.0 (m, 1H) 6.8-6.9 (m, 1H), 7.0-7.2 (m, 5H), 7.59-7.65 (t, 1H), 7.79-7.85 (d, 1H), 7.95-7.99 (d, 1H).

Example 208

5-[2-(4-chlorophenyl)pyrrolidin-1-yl]-1-(2,3-dichlorophenyl)-1H-tetraazole

The compound from Example 75B (0.1 g) was reacted with 2-(4-Chloro-phenyl)-pyrrolidine (0.1 g) according to the method of Example 75C to provide 0.016 g of the title compound as a white solid. MS (ESI/NH$_3$) m/z 395 (M+H)$^+$; $^1$H NMR (δ, DMSO-d$_6$) 1.78-1.9 (m, 4H), 3.3-3.6 (m, 2H), 4.8-5.0 (m, 1H) 6.8-6.9 (m, 1H), 7.05-7.19 (m, 4H), 7.60-7.65 (t, 1H), 7.79-7.85 (d, 1H), 7.99-8.1 (d, 1H).

Example 209

N-(cyclohexylmethyl)-1-(2,3-dichlorophenyl)-1H-tetraazol-5-amine

To a solution of 2,3 dichlorophenylisocyanate (0.1 g, 0.49 mmol) in 5 mL anhydrous tetrahydrofuran was added cyclohexylmethylamine (0.1 g). The solution was stirred at room temperature for 2 h when mercury (II) acetate (0.13 g, 0.49 mmol), sodium azide (0.095 g, 1.47 mmol) and triethylamine (0.148 g, 1.47 mmol) were added. The resulting suspension was stirred at room temperature for 12 hours, at which time the precipitate was filtered through Celite and the organics concentrated in vacuo. The crude residue was purified by column chromatography (gradient elution; 25% ethyl acetate/hexanes to 35%) to give 0.09 g of the title compound as a sticky foam. MS (ESI/NH$_3$) m/z 325 (M+H)$^+$ $^1$H NMR (δ, DMSO-d$_6$) 0.8-0.95 (m, 2H), 1.05-1.3 (m, 3H), 1.5-1.8 (m, 7H), 3.05-3.12 (t, 2H), 7.05-7.17 (t, 1H), 7.58-7.65 (m, 2H), 7.90-7.95 (d, 1H).

Example 210

1-(2,3-dichlorophenyl)-N-(2,3,6-trifluorobenzyl)-1H-tetraazol-5-amine

Using the procedure as described in Example 209, substituting 2,3,6-trifluorobenzylamine (0.079 g) for cyclohexylmethylamine, to give 0.040 g of the title compound. MS (ESI/NH$_3$) m/z 374 (M+H)$^+$ $^1$H NMR (δ, DMSO-d$_6$) 4.59-4.60 (d, 2H), 7.05-7.15 (m, 1H), 7.38-7.49 (m 1H), 7.56-7.65 (m, 3H), 7.92-7.95 (d, 1H).

Example 211

N-(2-chloro-3,6-difluorobenzyl)-1-(2,3-dichlorophenyl)-1H-tetraazol-5-amine

Using the procedure as described in Example 209, substituting 2-chloro-3,6-difluorobenzylamine (0.087 g) for cyclohexylmethylamine, to give 0.07 g of the title compound. MS (ESI/NH$_3$) m/z 390 (M+H)$^+$ $^1$HNMR (δ, DMSO-d$_6$) 4.6-4.67 (d, 2H), 7.25-7.38 (m, 1H), 7.4-7.65 (m, 4H), 7.95-7.98 (d, 1H).

Example 212

1-(2,3-dichlorophenyl)-N-(3-methoxy-2-methylbenzyl)-1H-tetraazol-5-amine

Using the procedure as described in Example 209, substituting 2-methyl-3-methoxybenzylamine (0.37 g) for cyclohexylmethylamine, to give 0.24 g of the title compound. MS (ESI/NH$_3$) m/z 363 (M+H)$^+$ $^1$H NMR (δ, DMSO-d$_6$) 2.08 (s, 3H), 3.79 (s, 3H), 4.41-4.5 (d, 2H), 6.82-6.89 (m, 2H), 7.02-7.12 (t, 1H), 7.5-7.7 (m, 3H), 7.9-7.94 (d, 1H).

Example 213

1-(2,3-dichlorophenyl)-N-(5-fluoro-2-methoxybenzyl)-1H-tetraazol-5-amine

Using the procedure as described in Example 209, substituting 2-methoxy-5-fluorobenzylamine (0.5 g) for cyclohexylmethylamine, to give 0.575 g of the title compound. MS (ESI/NH$_3$) m/z 367 (M+H)$^+$ $^1$H NMR (δ, DMSO-d$_6$) 3.8 (s, 3H), 4.41-4.43 (d, 2H), 6.92-7.02 (m, 3H), 7.59-7.65 (m, 2H), 7.75-7.8 (d, 1H), 7.90-7.95 (d, 1H).

Example 214

1-(2,3-dichlorophenyl)-N-(2,3-dimethylbenzyl)-1H-tetraazol-5-amine

Using the procedure as described in Example 209, substituting 2,3-dimethylbenzylamine (0.2 g) for cyclohexylmethylamine, to give 0.13 g of the title compound. MS (ESI/

NH$_3$) m/z 347 (M+H)$^+$; $^1$H NMR (δ, DMSO-d$_6$) 2.19 (s, 3H), 2.22 (s, 3H), 4.42-4.45 (d, 2H), 6.98-7.15 (m, 3H), 7.55-7.72 (m, 3H), 7.90-7.95 (d, 2H).

Example 215

1-(2,3-dichlorophenyl)-N-(2,3-dihydro-1,4-benzodioxin-5-ylmethyl)-1H-tetraazol-5-amine Using the procedure as described in Example 209, substituting C-(2,3-dihydro-benzo[1,4]dioxin-5-yl)-methylamine (0.3 g) for cyclohexylmethylamine, to give 0.065 g of the title compound. MS (ESI/NH$_3$) m/z 378 (M+H)$^+$; $^1$H NMR (δ, DMSO-d$_6$) 4.21-4.36 (m, 4H) 4.42-4.45 (d, 2H), 6.78-6.82 (m, 3H), 7.55-7.72 (m, 3H), 7.90-7.95 (d, 2H).

Example 216

N-(1,3-benzodioxol-4-ylmethyl)-1-(2,3-dichlorophenyl)-1H-tetraazol-5-amine

Using the procedure as described in Example 209, substituting C-benzo[1,3]dioxol-4-yl-methylamine (0.25 g) for cyclohexylmethylamine, to give 0.070 g of the title compound. MS (ESI/NH$_3$) m/z 363 (M+H)$^+$; $^1$H NMR (δ, DMSO-d$_6$) 4.42-4.45 (d, 2H), 6.0 (s, 2H), 6.78-6.82 (m, 3H), 7.61-7.72 (m, 3H), 7.90-7.95 (d, 2H).

Example 217

1-(2,3-dichlorophenyl)-N-(2,3-dihydro-1,4-benzodioxin-6-ylmethyl)-1H-tetraazol-5-amine Using the procedure as described in Example 209, substituting C-benzo[1,3]dioxol-6-yl-methylamine (0.08 g) for cyclohexylmethylamine, to give 0.050 g of the title compound. MS (ESI/NH$_3$) m/z 378 (M+H)$^+$; $^1$H NMR (δ, DMSO-d$_6$) 4.21-4.36 (m, 4H) 4.42-4.45 (d, 2H), 6.78-6.82 (m, 3H), 7.58-7.68 (t, 2), 7.69-7.71 (d, 1H), 7.93-7.96 (d, 1H).

Example 218

N-(1,3-benzodioxol-5-ylmethyl)-1-(2,3-dichlorophenyl)-1H-tetraazol-5-amine

Using the procedure as described in Example 209, substituting C-benzo[1,3]dioxol-5-yl-methylamine (0.07 g) for cyclohexylmethylamine, to give 0.070 g of the title compound. MS (ESI/NH$_3$) m/z 363 (M+H)$^+$; $^1$H NMR (δ, DMSO-d$_6$) 4.42-4.45 (d, 2H), 6.0 (s, 2H), 6.79-6.88 (m, 3H), 7.58-7.71 (m, 3H), 7.93-7.96 (d, 1H).

Example 219

1-(2,3-dichlorophenyl)-N-(2,3-dimethoxybenzyl)-1H-tetraazol-5-amine

Using the procedure as described in Example 209, substituting 2,3-dimethoxybenzylamine (0.82 g) for cyclohexylmethylamine, to give 10 g of the title compound. MS (ESI/NH$_3$) m/z 378 (M+H)$^+$; $^1$H NMR (δ, DMSO-d$_6$) 3.75 (s, 3H), 3.8 (s, 3H), 4.44-4.52 (d, 2H), 6.8-7.03 (m, 3H), 7.55-7.61 (m, 2H), 7.68-7.73 (t, 1H), 7.95-7.99 (d, 1H).

Example 220

1-(2,3-dichlorophenyl)-N-(3,5-dimethoxybenzyl)-1H-tetraazol-5-amine

Using the procedure as described in Example 209, substituting 3,5-dimethoxybenzylamine (0.082 g) for cyclohexylmethylamine, to give 0.015 g of the title compound. MS (ESI/NH$_3$) m/z 380 (M+H)$^+$; $^1$H NMR (δ, DMSO-d$_6$) 3.7 (s, 6H) 4.4-4.45 (d, 2H), 6.83-6.98 (m, 2H), 6.38 (s, 1H), 6.5 (s, 2H), 7.57-7.75 (m, 3H), 7.95-7.99 (d, 1H).

Example 221

1-(2,3-dichlorophenyl)-N-(2,4-dimethoxybenzyl)-1H-tetraazol-5-amine

Using the procedure as described in Example 209, substituting 2,4-dimethoxybenzylamine (0.082 g) for cyclohexylmethylamine, to give 0.050 g of the title compound. MS (ESI/NH$_3$) m/z 380 (M+H)$^+$; $^1$H NMR (δ, DMSO-d$_6$) 3.7 (s, 3H), 3.8 (s, 3H), 4.35-4.40 (d, 2H), 6.42-6.5 (m, 1H), 6.59 (s, 1H), 7.05-7.12 (d, 1H), 7.4-7.43 (t, 1H), 7.58-7.61 (t, 1H), 7.62-7.68 (d, 1H), 7.95-7.99 (d, 1H).

Example 222

1-(2,3-dichlorophenyl)-N-(2,5-dimethylbenzyl)-1H-tetraazol-5-amine

Using the procedure as described in Example 209, substituting 2,5-dimethylbenzylamine (0.082 g) for cyclohexylmethylamine, to give 0.050 g of the title compound. MS (ESI/NH$_3$) m/z 348 (M+H)$^+$; $^1$H NMR (δ, DMSO-d$_6$) 2.2 (s, 6H), 4.39-4.42 (d, 2H), 6.97-7.1 (m, 3H), 7.45-7.77 (m, 3H), 7.95-7.99 (d, 1H).

Example 223

N-(3-chloro-2-methylbenzyl)-1-(2,3-dichlorophenyl)-1H-tetraazol-5-amine

Using the procedure as described in Example 209, substituting 2-methyl-3-chlorobenzylamine (0.076 g) for cyclohexylmethylamine, to give 0.080 g of the title compound. MS (ESI/NH$_3$) m/z 367 (M+H)$^+$; $^1$H NMR (δ, DMSO-d$_6$) 2.37 (s, 3H), 4.41-4.45 (d, 2H), 7.16-7.20 (t, 1H), 7.22-7.25 (d, 1H), 7.31-7.35 (d, 1H), 7.58-7.65 (m, 2H), 7.71-7.78 (d, 1H), 7.96-7.99 (d, 1H).

Example 224

N-(5-chloro-2-methylbenzyl)-1-(2,3-dichlorophenyl)-1H-tetraazol-5-amine

Using the procedure as described in Example 209, substituting 2-methyl-5-chlorobenzylamine (0.076 g) for cyclohexylmethylamine to give 0.060 g of the title compound. MS (ESI/NH$_3$) m/z 367 (M+H)$^+$; $^1$H NMR (δ, DMSO-d$_6$) 2.37 (s, 3H), 4.41-4.45 (d, 2H), 7.16-7.20 (m, 2H), 7.22-7.25 (s, 1H), 7.58-7.65 (m, 2H), 7.71-7.78 (d, 1H), 7.96-7.99 (d, 1H).

Example 225

1-(2,3-dichlorophenyl)-N-(2,5-difluorobenzyl)-1H-tetraazol-5-amine

Using the procedure as described in Example 209, substituting 2,5-difluorobenzylamine (0.08 g) for cyclohexylmethylamine, to give 0.035 g of the title compound. MS (ESI/NH$_3$) m/z 355 (M+H)$^+$; $^1$H NMR (δ, DMSO-d$_6$) 4.41-4.45 (d, 2H), 7.05-7.3 (m, 3H), 7.58-7.61 (t, 1H), 7.7-7.79 (m, 2H), 7.95-7.99 (d, 1H).

Example 226

N-(5-chloro-2-fluorobenzyl)-1-(2,3-dichlorophenyl)-1H-tetraazol-5-amine

Using the procedure as described in Example 209, substituting 2-fluoro-5-chlorobenzylamine (0.078 g) for cyclohexylmethylamine, to give 0.028 g of the title compound. MS (ESI/NH$_3$) m/z 373 (M+H)$^+$; $^1$H NMR (δ, DMSO-d$_6$) 4.48-4.51 (d, 2H), 7.2-7.26 (t, 1H), 7.3-7.41 (m, 2H), 7.6-7.64 (t, 1H), 7.65-7.79 (m, 2H), 7.95-7.99 (d, 1H).

Example 227

N-[2-chloro-5-(trifluoromethyl)benzyl]-1-(2,3-dichlorophenyl)-1H-tetraazol-5-amine Using the procedure as described in Example 209, substituting 2-fluoro-5-chlorobenzylamine (0.102 g) for cyclohexylmethylamine, to give 0.040 g of the title compound. MS (ESI/NH$_3$) m/z 422 (M+H)$^+$; $^1$H NMR (δ, DMSO-d$_6$) 4.61-4.65 (d, 2H), 7.6-7.78 (m, 5H), 7.81-7.88 (t, 1H), 7.96-8.0 (d, 1H).

Example 228

1-(2,3-dichlorophenyl)-N-(2,5-dimethoxybenzyl)-1H-tetraazol-5-amine

Using the procedure as described in Example 209, substituting 2,5-dimethoxybenzylamine (0.082 g) for cyclohexylmethylamine, to give 0.040 g of the title compound. MS (ESI/NH$_3$) m/z 380 (M+H)$^+$; $^1$H NMR (δ, DMSO-d$_6$) 3.65 (s, 3H), 3.78 (s, 3H), 4.40-4.43 (d, 2H), 6.78-6.82 (m, 2H), 6.93-6.97 (m, 1H), 7.51-7.56 (t, 1H), 7.59-7.61 (d, 1H), 7.69-7.72 (d, 1H), 7.95-7.99 (d, 1H).

Example 229

N-(2-chloro-6-methylbenzyl)-1-(2,3-dichlorophenyl)-1H-tetraazol-5-amine

Using the procedure as described in Example 209, substituting 2-chloro-6-methylbenzylamine (0.076 g) for cyclohexylmethylamine, to give 0.07 g of the title compound. MS (ESI/NH$_3$) m/z 369 (M+H)$^+$; $^1$H NMR (δ, DMSO-d$_6$) 2.39 (s, 3H), 4.59-4.61 (d, 2H), 7.15-7.35 (m, 4H), 7.42-7.5 (t, 1H), 7.58-7.61 (d, 1H), 7.92-7.96 (d, 2H).

Example 230

1-(2,3-dichlorophenyl)-N-(2,3-difluorobenzyl)-1H-tetraazol-5-amine

Using the procedure as described in Example 209, substituting 2,3-difluorobenzylamine (0.07 g) for cyclohexylmethylamine, to give 0.025 g of the title compound. MS (ESI/NH$_3$) m/z 356 (M+H)$^+$; $^1$H NMR (δ, DMSO-d$_6$) 4.5-4.59 (d, 2H), 7.15-7.4 (m, 3H), 7.58-7.62 (t, 1H), 7.65-7.8 (m, 2H), 7.95-7.98 (d, 1H).

Example 231

1-(2,3-dichlorophenyl)-N-(3-isobutylbenzyl)-1H-tetraazol-5-amine

Using the procedure as described in Example 209, substituting 3-isobutylbenzylamine (0.125 g) for cyclohexylmethylamine, to give 0.09 g of the title compound. MS (ESI/NH$_3$) m/z 376 (M+H)$^+$; $^1$H NMR (δ, DMSO-d$_6$) 0.81-0.85 (d, 6H), 1.7-1.81 (m, 1H), 2.38-2.41 (d, 1H), 4.41-4.44 (d, 2H), 6.98-7.01 (d, 1H), 7.09-7.12 (m, 2H), 7.19-7.22 (t, 1H), 7.58-7.7 (m, 3H), 7.95-7.99 (d, 1H).

Example 232

N-(2-chlorobenzyl)-1-(2,3-dichlorophenyl)-1H-tetraazol-5-amine

Using the procedure as described in Example 209, substituting 2-chlorobenzylamine (0.073 g) for cyclohexylmethylamine, to give 0.06 g of the title compound. MS (ESI/NH$_3$) m/z 354 (M+H)$^+$; $^1$H NMR (δ, DMSO-d$_6$) 4.51-4.59 (d, 2H), 7.25-7.39 (m, 4H), 7.59-7.62 (t, 1H), 7.7-7.8 (m, 2H), 7.95-7.99 (d, 2H).

Example 233

N-(3-chlorobenzyl)-1-(2,3-dichlorophenyl)-1H-tetraazol-5-amine

Using the procedure as described in Example 209, substituting 3-chlorobenzylamine (0.073 g) for cyclohexylmethylamine, to give 0.06 g of the title compound. MS (ESI/NH$_3$) m/z 354 (M+H)$^+$; $^1$H NMR (δ, DMSO-d$_6$) 4.41-4.44 (d, 2H), 7.25-7.39 (m, 4H), 7.59-7.62 (t, 1H), 7.7-7.8 (m, 2H), 7.95-7.99 (d, 2H).

Example 234

N-(4-chlorobenzyl)-1-(2,3-dichlorophenyl)-1H-tetraazol-5-amine

Using the procedure as described in Example 209, substituting 4-chlorobenzylamine (0.069 g) for cyclohexylmethylamine, to give 0.06 g of the title compound. MS (ESI/NH$_3$)

m/z 354 (M+H)⁺; ¹H NMR (δ, DMSO-d₆) 4.41-4.44 (d, 2H), 7.25-7.39 (m, 4H), 7.59-7.62 (t, 1H), 7.7-7.8 (m, 2H), 7.95-7.99 (d, 2H).

Example 235

1-(2,3-dichlorophenyl)-N-(2-fluorobenzyl)-1H-tetraazol-5-amine

Using the procedure as described in Example 209, substituting 2-fluorobenzylamine (0.61 g) for cyclohexylmethylamine, to give 0.78 g of the title compound. MS (ESI/NH₃) m/z 338 (M+H)⁺; ¹H NMR (δ, DMSO-d₆) 4.44-4.52 (d, 2H), 7.15-7.2 (m, 2H), 7.28-7.4 (m, 2H), 7.59-7.61 (t, 1H), 7.67-7.78 (m, 2H), 7.95-7.99 (d, 1H).

Example 236

1-(2,3-dichlorophenyl)-N-(3-fluorobenzyl)-1H-tetraazol-5-amine

Using the procedure as described in Example 209, substituting 3-fluorobenzylamine (0.61 g) for cyclohexylmethylamine, to give 0.96 g of the title compound. MS (ESI/NH₃) m/z 338 (M+H)⁺; ¹H NMR (δ, DMSO-d₆) 4.44-4.52 (d, 2H), 7.05-7.2 (m, 3H), 7.31-7.42 (m, 1H), 7.59-7.61 (t, 1H), 7.67-7.78 (m, 2H), 7.95-7.99 (d, 1H).

Example 237

1-(2,3-dichlorophenyl)-N-(4-fluorobenzyl)-1H-tetraazol-5-amine

Using the procedure as described in Example 209, substituting 4-fluorobenzylamine (0.61 g) for cyclohexylmethylamine, to give 0.05 g of the title compound. MS (ESI/NH₃) m/z 338 (M+H)⁺; ¹H NMR (δ, DMSO-d₆) 4.44-4.52 (d, 2H), 7.05-7.18 (m, 2H), 7.31-7.42 (m, 2H), 7.59-7.65 (t, 1H), 7.67-7.78 (m, 2H), 7.95-7.99 (d, 1H).

Example 238

1-(2,3-dichlorophenyl)-N-(2-methoxybenzyl)-1H-tetraazol-5-amine

Using the procedure as described in Example 209, substituting 2-methoxybenzylamine (0.06 g) for cyclohexylmethylamine, to give 0.075 g of the title compound. MS (ESI/NH₃) m/z 350 (M+H)⁺; ¹H NMR (δ, DMSO-d₆) 3.8 (s, 3H) 4.4-4.45 (d, 2H), 6.83-6.98 (m, 2H), 7.18-7.22 (m, 2H), 7.5-7.55 (t, 1H), 7.58-7.60 (t, 1H), 7365-7.71 (d, 1H), 7.95-7.98 (d, 1H).

Example 239

1-(2,3-dichlorophenyl)-N-(3-methoxybenzyl)-1H-tetraazol-5-amine

Using the procedure as described in Example 209, substituting 3-methoxybenzylamine (0.067 g) for cyclohexylmethylamine, to give 0.06 g of the title compound. MS (ESI/NH₃) m/z 350 (M+H)⁺; ¹H NMR (δ, DMSO-d₆) 3.79 (s, 3H), 4.49-4.52 (d, 2H), 6.8-6.92 (m, 3H), 7.2-7.3 (m, 1H), 7.6-7.72 (m, 3H), 7.98-8.0 (d, 1H).

Example 240

1-(2,3-dichlorophenyl)-N-[2-(trifluoromethyl)benzyl]-1H-tetraazol-5-amine

Using the procedure as described in Example 209, substituting 2-trifluoromethylbenzylamine (0.1 g) for cyclohexylmethylamine, to give 0.055 g of the title compound. MS (ESI/NH₃) m/z 387 (M+H)⁺; ¹H NMR (δ, DMSO-d₆) 4.60-4.62 (d, 2H), 7.4-7.8 (m, 7H), 7.95-7.99 (d, 1H)

Example 241

1-(2,3-dichlorophenyl)-N-[3-(trifluoromethyl)benzyl]-1H-tetraazol-5-amine

Using the procedure as described in Example 209, substituting 3-trifluoromethylbenzylamine (0.086 g) for cyclohexylmethylamine, to give 0.070 g of the title compound. MS (ESI/NH₃) m/z 387 (M+H)⁺

¹H NMR (δ, DMSO-d₆) 4.58-4.62 (d, 2H), 7.4-7.82 (m, 7H), 7.95-7.99 (d, 1H).

Example 242

1-(2,3-dichlorophenyl)-N-[4-(trifluoromethyl)benzyl]-1H-tetraazol-5-amine

Using the procedure as described in Example 209, substituting 4-trifluoromethylbenzylamine (0.086 g) for cyclohexylmethylamine, to give 0.080 g of the title compound. MS (ESI/NH₃) m/z 387 (M+H)⁺

¹H NMR (δ, DMSO-d₆) 4.58-4.62 (d, 2H), 7.4-7.82 (m, 7H), 7.95-7.99 (d, 1H).

Example 243

1-(2,3-dichlorophenyl)-N-[2-(difluoromethoxy)benzyl]-1H-tetraazol-5-amine

Using the procedure as described in Example 209, substituting 2-difluoromethoxybenzylamine (0.77 g) for cyclohexylmethylamine, to give 1.0 g of the title compound. MS (ESI/NH₃) m/z 386 (M+H)⁺

¹H NMR (δ, DMSO-d₆) 4.55-4.6 (d, 2H), 7.18-7.25 (m, 2H), 7.31-7.41 (m, 2H), 7.59-7.75 (m, 3H), 7.96-7.99 (d, 1H).

Example 244

1-(2,3-dichlorophenyl)-N-[2-(trifluoromethoxy)benzyl]-1H-tetraazol-5-amine

Using the procedure as described in Example 209, substituting 2-trifluoromethoxybenzylamine (0.094 g) for cyclohexylmethylamine, to give 0.08 g of the title compound. MS (ESI/NH₃) m/z 404 (M+H)⁺

¹H NMR (δ, DMSO-d₆) 4.55-4.63 (d, 2H), 7.3-7.5 (m, 3H), 7.59-7.63 (t, 1H), 7.65-7.75 (m, 2H), 7.95-7.99 (d, 1H)

Example 245

1-(2,3-dichlorophenyl)-N-[3-(trifluoromethoxy)benzyl]-1H-tetraazol-5-amine

Using the procedure as described in Example 209, substituting 3-trifluoromethoxybenzylamine (0.094 g) for cyclohexylmethylamine, to give 0.07 g of the title compound. MS (ESI/NH$_3$) m/z 404 (M+H)$^+$
$^1$H NMR (δ, DMSO-d$_6$) 4.53-4.59 (d, 2H), 7.2-7.25 (m, 2H), 7.29-7.36 (d, 1H), 7.41-7.46 (t, 1H), 7.59-7.62 (t, 1H), 7.69-7.8 (m, 2H), 7.95-7.99 (d, 1H).

Example 246

1-(2,3-dichlorophenyl)-N-[4-(trifluoromethoxy)benzyl]-1H-tetraazol-5-amine

Using the procedure as described in Example 209, substituting 4-trifluoromethoxybenzylamine (0.094 g) for cyclohexylmethylamine, to give 0.07 g of the title compound. MS (ESI/NH$_3$) m/z 404 (M+H)$^+$
$^1$H NMR (δ, DMSO-d$_6$) 4.49-4.56 (d, 2H), 7.2-7.25 (d, 2H), 7.4-7.46 (m, 2H), 7.59-7.62 (t, 1H), 7.62-7.72 (m, 2H), 7.94-7.98 (d, 1H).

Example 247

N-[2-(benzyloxy)benzyl]-1-(2,3-dichlorophenyl)-1H-tetraazol-5-amine

Using the procedure as described in Example 209, substituting 2-benzyloxybenzylamine (0.5 g) for cyclohexylmethylamine, to give 0.35 g of the title compound. MS (ESI/NH$_3$) m/z 426 (M+H)$^+$
$^1$H NMR (δ, DMSO-d$_6$) 4.49-4.56 (d, 2H), 5.19 (s, 2H), 6.85-6.95 (t, 1H), 7.0-7.09 (d, 1H), 7.19-7.23 (t, 2H), 7.3-7.7 (m, 10H), 7.95-7.99 (d, 1H).

Example 248

1-(2,3-dichlorophenyl)-N-[2-(methylsulfonyl)benzyl]-1H-tetraazol-5-amine

The product of Example 20 (0.14 g, 0.39 mmol) was dissolved in 10 mL acetone and treated with OXONE (0.94 g, 1.54 mmol) for 24 h. The resulting slurry was taken up in 100 mL ethyl acetate and washed with water (3×50 mL), brine (1×500 mL), dried (MgSO$_4$) and concentrated. Flash chromatography (gradient elution; 25% ethyl acetate/hexanes to 50%) gave 0.08 g of the title compound as a white solid. MS (ESI/NH$_3$) m/z 397 (M+H)$^+$
$^1$H NMR (δ, DMSO-d$_6$); 3.38, (s, 3H), 4.85-4.9 (d, 2H), 7.28-7.78 (m, 4H), 7.79-7.81 (m, 3H).

Example 249

N-{[2-(3-azabicyclo[3.2.2]non-3-ylpyridin-3-yl]methyl}-1-(2,3-dichlorophenyl)-1H-tetraazol-5-amine

Example 249A 2-(3-azabicyclo[3.2.2]non-3-yl)nicotinonitrile

To a solution of 2-fluoro-3-cyanopyridine (0.4 g, 3.27 mmol) in 30 mL tetrahydrofuran was added triethylamine (0.66 g, 6.5 mmol) and 3-aza-bicyclo[3.2.2]nonane (0.5 g, 3.9 mmol). The reaction was held at 50° C. for 12 hours, cooled and diluted with 100 mL ethyl acetate. The organics were washed with water (2×50 mL), brine (1×50 mL), dried (MgSO$_4$) and concentrated. Column chromatography (20% ethyl acetate/hexanes) gave the title compound as a solid. MS (ESI/NH$_3$) m/z 126 (M+H)$^+$

Example 249B

[2-(3-azabicyclo[3.2.2]non-3-ylpyridin-3-yl]methylamine

A solution of the product of Example 249A (0.52 g, 2 mmol), in 40 mL saturated NH$_3$/methanol solution was placed in a PAAR hydrogenation pressure vessel and was treated with Raney-Nickel 2300 (0.5 g). A pressure of 60 pounds per square inch of hydrogen gas was applied to the sealed system, and the reaction was allowed to shake for 5 hours. The pressure was vented and the suspension filtered through a nylon membrane, washing with methanol. The corresponding solution was concentrated to give 0.5 g of the title compound as a crude oil, which was used without further purification or characterization. MS (ESI/NH$_3$) m/z 130 (M+H)$^+$.

Example 249C

N-{[2-(3-azabicyclo[3.2.2]non-3-ylpyridin-3-yl]methyl}-1-(2,3-dichlorophenyl)-1H-tetraazol-5-amine Using the procedure as described in Example 209, substituting product of Example 249B (0.5 g) for cyclohexylmethylamine, gave 0.14 g of the title compound. MS (ESI/NH$_3$) m/z 444 (M+H)$^+$; $^1$H NMR (δ, DMSO-d$_6$) 1.58-1.7 (m, 3H), 1.71-1.9 (m, 3H), 2.01-2.1 (m 2H), 3.12-3.3 (m, 2H), 4.59-4.61 (d, 2H), 6.95-7.01 (m, 1H), 7.58-7.75 (m, 4H), 7.95-7.99 (d, 1H), 8.14-8.19 (m, 1H).

Example 250

1-(2,3-dichlorophenyl)-N-{[2-(3,3-difluoropiperidin-1-yl)pyridin-3-yl]methyl}-1H-tetraazol-5-amine

Example 250A 2-(3,3-difluoropiperidin-1-yl)nicotinonitrile

Using the procedure as described in Example 249A, substituting 3,3-difluoropiperizine (0.81 g) for 3-aza-bicyclo [3.2.2]nonane gave 0.8 g of the title compound. MS (ESI/NH$_3$) m/z 224 (M+H)$^+$.

Example 250B

[2-(3,3-difluoropiperidin-1-yl)pyridin-3-yl]methylamine

The compound from Example 250A (0.8 g) was subjected to reduction conditions according to the method of Example 249B to provide 0.59 g of the title compound as an oil. MS (ESI/NH$_3$) m/z 228 (M+H)$^+$

Example 250C 1-(2,3-dichlorophenyl)-N-{[2-(3,3-difluoropiperidin-1-yl)pyridin-3-yl]methyl}-1H-tetraazol-5-amine The compound from Example 250B (0.59 g) was subjected to reaction conditions according to the method of Example 209 to provide 0.04 g of the title compound. MS (ESI/NH$_3$) m/z 439 (M+H)$^+$; $^1$H NMR (δ, DMSO-d$_6$) 1.78-1.85 (m, 2H), 1.96-2.1 (m, 2H), 2.95-3.05 (m, 2H), 3.21-3.4 (m, 2H), 4.42-4.5 (d, 2H), 7.05-7.12 (m, 1H), 7.59-7.78 (m, 3H), 7.95-7.99 (d, 1H), 8.2 (s, 1H).

Example 251

1-(2,3-dichlorophenyl)-N-{[2-(4,4-difluoropiperidin-1-yl)pyridin-3-yl]methyl}-1H-tetraazol-5-amine

Example 251A 2-(4,4-difluoropiperidin-1-yl)nicotinonitrile

The procedure from Example 249A was followed, substituting 4,4-difluoropiperidine (0.77 g) for 3-aza-bicyclo[3.2.2]nonane to give 0.86 g of the title compound. MS (ESI/NH$_3$) m/z 224 (M+H)$^+$

Example 251B

[2-(4,4-difluoropiperidin-1-yl)pyridin-3-yl]methylamine

The compound from Example 251A (0.85 g) was subjected to reduction conditions according to the method of Example 249B to provide 0.84 g of the title compound as an oil. MS (ESI/NH$_3$) m/z 228 (M+H)$^+$.

Example 251C 1-(2,3-dichlorophenyl)-N-{[2-(4,4-difluoropiperidin-1-yl)pyridin-3-yl]methyl}-1H-tetraazol-5-amine The compound from Example 251B (0.3 g) was subjected to reaction conditions according to the method of Example 209 to provide 0.29 g of the title compound. MS (ESI/NH$_3$) m/z 439 (M+H)$^+$; $^1$H NMR (δ, DMSO-d$_6$) 1.96-2.2 (m, 4H), 2.95-3.4 (m, 4H), 4.42-4.5 (d, 2H), 7.05-7.12 (m, 1H), 7.59-7.78 (m, 4H), 7.95-7.99 (d, 1H), 8.2 (m, 1H).

Example 252

1-(2,3-dichlorophenyl)-N-({2-[4-(trifluoromethyl)piperidin-1-yl]pyridin-3-yl}methyl)-1H-tetraazol-5-amine

Example 252A

2-[4-(trifluoromethyl)piperidin-1-yl]nicotinonitrile

The procedure from Example 249A was followed, substituting 4-trifluoromethylpiperidine (0.92 g) for 3-aza-bicyclo[3.2.2]nonane to give 0.95 g of the title compound. MS (ESI/NH$_3$) m/z 256 (M+H)$^+$.

Example 252B

{2-[4-(trifluoromethyl)piperidin-1-yl]pyridin-3-yl}methylamine

The compound from Example 252A (0.95 g) was subjected to reduction conditions according to the method of Example 249B to provide 0.9 g of the title compound as an oil. MS (ESI/NH$_3$) m/z 260 (M+H)$^+$.

Example 252C 1-(2,3-dichlorophenyl)-N-({2-[4-(trifluoromethyl)piperidin-1-yl]pyridin-3-yl}methyl)-1H-tetraazol-5-amine The compound from Example 252B (0.3 g) was subjected to reaction conditions according to the method of Example 209 to provide 0.1 g of the title compound. MS (ESI/NH$_3$) m/z 471 (M+H)$^+$; $^1$H NMR (δ, DMSO-d$_6$) 1.57-1.69 (m, 2H), 1.8-1.9 (m, 2H), 2.75-2.83 (t, 2H), 3.41-3.5 (m, 2H), 4.42-4.5 (d, 2H), 6.98-7.07 (m, 1H), 7.59-7.78 (m, 4H), 7.95-7.99 (d, 1H), 8.2 (m, 1H).

Example 253

1-(2,3-dichlorophenyl)-N-{[2-(3-fluoropiperidin-1-yl)pyridin-3-yl]methyl}-1H-tetraazol-5-amine

Example 253A 2-(3-fluoropiperidin-1-yl)nicotinonitrile

The procedure from Example 249A was followed, substituting 3-fluoropiperidine (0.73 g) for 3-aza-bicyclo[3.2.2]nonane to give 0.8 g of the title compound. MS (ESI/NH$_3$) m/z 205 (M+H)$^+$.

Example 253B

[2-(3-fluoropiperidin-1-yl)pyridin-3-yl]methylamine

The compound from Example 253A (0.8 g) was subjected to reduction conditions according to the method of Example 249B to provide 0.87 g of the title compound as an oil. MS (ESI/NH$_3$) m/z 209 (M+H)$^+$

Example 253C 1-(2,3-dichlorophenyl)-N-{[2-(3-fluoropiperidin-1-yl)pyridin-3-yl]methyl}-1H-tetraazol-5-amine The compound from Example 253B (0.3 g) was subjected to reaction conditions according to the method of Example 209 to provide 0.15 g of the title compound. MS (ESI/NH$_3$) m/z 421 (M+H)$^+$; $^1$H NMR (δ, DMSO-d$_6$) 1.7-2.0 (m, 4H), 2.90-2.99 (t, 2H), 3.05-3.15 (m, 1H), 4.42-4.5 (d, 2H), 4.65-

4.72 (m, 1H), 4.82-4.9 (m, 1H), 6.98-7.07 (m, 1H), 7.59-7.78 (m, 4H), 7.95-7.99 (d, 1H), 8.2 (m, 1H).

Example 254

1-(2,3-dichlorophenyl)-N-{[2-(4-fluoropiperidin-1-yl)pyridin-3-yl]methyl}-1H-tetraazol-5-amine

Example 254A 2-(4-fluoropiperidin-1-yl)nicotinonitrile

The procedure from Example 249A was followed, substituting 4-fluoropiperidine (0.73 g) for 3-aza-bicyclo[3.2.2]nonane to give 0.75 g of the title compound. MS (ESI/NH$_3$) m/z 205 (M+H)$^+$.

Example 254B

[2-(4-fluoropiperidin-1-yl)pyridin-3-yl]methylamine

The compound from Example 254A (0.74 g) was subjected to reduction conditions according to the method of Example 249B to provide 0.75 g of the title compound as an oil. MS (ESI/NH$_3$) m/z 209 (M+H)$^+$

Example 254C 1-(2,3-dichlorophenyl)-N-{[2-(4-fluoropiperidin-1-yl)pyridin-3-yl]methyl}-1H-tetraazol-5-amine The compound from Example 254B (0.3 g) was subjected to reaction conditions according to the method of Example 209 to provide 0.15 g of the title compound. MS (ESI/NH$_3$) m/z 421 (M+H)$^+$; $^1$H NMR (δ, DMSO-d$_6$) 1.87-2.1 (m, 4H), 2.90-2.99 (t, 2H), 3.05-3.25 (m, 3H), 4.42-4.5 (d, 2H), 4.75-4.82 (m, 1H), 4.89-4.98 (m, 1H), 6.98-7.07 (m, 1H), 7.59-7.78 (m, 4H), 7.95-7.99 (d, 1H), 8.2 (m, 1H).

Example 255

1-(2,3-dichlorophenyl)-N-({2-[3-(trifluoromethyl)pyrrolidin-1-yl]pyridin-3-yl}methyl)-1H-tetraazol-5-amine

Example 255A

2-[3-(trifluoromethyl)pyrrolidin-1-yl]nicotinonitrile

The procedure from Example 249A was followed, substituting 3-trifluoromethylpyrrolidine (0.2 g) for 3-aza-bicyclo[3.2.2]nonane to give 0.25 g of the title compound. MS (ESI/NH$_3$) m/z 242 (M+H)$^+$.

Example 255B

{2-[3-(trifluoromethyl)pyrrolidin-1-yl]pyridin-3-yl}methylamine

The compound from Example 255A (0.25 g) was subjected to reduction conditions according to the method of Example 249B to provide 0.2 g of the title compound as an oil. MS (ESI/NH$_3$) m/z 246 (M+H)$^+$

Example 255C 1-(2,3-dichlorophenyl)-N-({2-[3-(trifluoromethyl)pyrrolidin-1-yl]pyridin-3-yl}methyl)-1H-tetraazol-5-amine The compound from Example 255B (0.2 g) was subjected to reaction conditions according to the method of Example 209 to provide 0.10 g of the title compound. MS (ESI/NH$_3$) m/z 458 (M+H)$^+$; $^1$H NMR (δ, DMSO-d$_6$) 1.94-2.01 (m, 1H), 2.15-2.2 (m, 1H), 3.2-3.4 (m, 2H), 3.43-3.7 (m, 3H), 6.78-6.82 (m, 1H), 7.5-7.75 (m, 4H), 7.95-7.99 (d, 1H), 8.02-8.1 (d, 1H).

Example 256

1-[3-({[1-(2,3-dichlorophenyl)-1H-tetraazol-5-yl]amino}methylpyridin-2-yl]pyrrolidin-3-ol

Example 256A 2-(3-hydroxypyrrolidin-1-yl)nicotinonitrile

The procedure from Example 249A was followed, substituting 3-hydroxypyrrolidine (0.5 g) for 3-aza-bicyclo[3.2.2]nonane to give 0.16 g of the title compound. MS (ESI/NH$_3$) m/z 189 (M+H)$^+$

Example 256B

1-[3-(aminomethyl)pyridin-2-yl]pyrrolidin-3-ol

The compound from Example 256A (0.15 g) was subjected to reduction conditions according to the method of Example 249B to provide 0.145 g of the title compound as an oil. MS (ESI/NH$_3$) m/z 193 (M+H)$^+$.

Example 256C

1-[3-({[1-(2,3-dichlorophenyl)-1H-tetraazol-5-yl]amino}methyl)pyridin-2-yl]pyrrolidin-3-ol The compound from Example 256B (0.2 g) was subjected to reaction conditions according to the method of Example 209 to provide 0.11 g of the title compound. MS (ESI/NH$_3$) m/z 406 (M+H)$^+$; $^1$H NMR (δ, DMSO-d$_6$) 1.84-2.01 (m, 2H), 3.2-3.4 (m, 1H), 3.43-3.7 (m, 3H), 4.25-4.6 (m, 2H), 4.90-4.96 (d, 2H), 6.68-6.72 (m, 1H), 7.41-7.45 (d, 1H), 7.56-7.62 (m, 2H), 7.69-7.72 (d, 1H), 7.95-8.01 (m, 2H).

Example 257

1-(2,3-dichlorophenyl)-N-{[2-(3,3-difluoropyrrolidin-1-yl)pyridin-3-yl]methyl}-1H-tetraazol-5-amine

Example 257A 2-(3,3-difluoropyrrolidin-1-yl)nicotinonitrile

The procedure from Example 249A was followed, substituting 3,3-difluoropyrrolidine (0.5 g) for 3-aza-bicyclo[3.2.2]nonane to give 0.58 g of the title compound. MS (ESI/NH$_3$) m/z 209 (M+H)$^+$

Example 257B

[2-(3,3-difluoropyrrolidin-1-yl)pyridin-3-yl]methylamine

The compound from Example 257A (0.58 g) was subjected to reduction conditions according to the method of Example 249B to provide 0.55 g of the title compound as an oil. MS (ESI/NH$_3$) m/z 213 (M+H)$^+$.

Example 257C 1-(2,3-dichlorophenyl)-N-{[2-(3,3-difluoropyrrolidin-1-yl)pyridin-3-yl]methyl}-1H-tetraazol-5-amine The compound from Example 257B (0.23 g) was subjected to reaction conditions according to the method of Example 209 to provide 0.07 g of the title compound. MS (ESI/NH$_3$) m/z 425 (M+H)$^+$; $^1$H NMR (δ, DMSO-d$_6$) 2.35-2.43 (m, 2H), 3.6-3.7 (t, 2H), 3.7-3.85 (t, 2H), 4.45-4.52 (d, 2H), 6.81-6.9 (m, 1H), 7.56-7.75 (m, 4H), 7.95-7.99 (d, 1H), 8.05-8.1 (m, 1H).

Example 258

1-(2,3-dichlorophenyl)-N-{[2-(2-methylpyrrolidin-1-yl)pyridin-3-yl]methyl}-1H-tetraazol-5-amine

Example 258A 2-(2-methylpyrrolidin-1-yl)nicotinonitrile

The procedure from Example 249A was followed, substituting 2-methylpyrrolidine (0.5 g) for 3-aza-bicyclo[3.2.2]nonane to give 0.57 g of the title compound. MS (ESI/NH$_3$) m/z 187 (M+H)$^+$.

Example 258B

[2-(2-methylpyrrolidin-1-ylpyridin-3-yl]methylamine

The compound from Example 258A (0.57 g) was subjected to reduction conditions according to the method of Example 249B to provide 0.56 g of the title compound as an oil. MS (ESI/NH$_3$) m/z 191 (M+H)$^+$.

Example 258C 1-(2,3-dichlorophenyl)-N-{[2-(2-methylpyrrolidin-1-yl)pyridin-3-yl]methyl}-1H-tetraazol-5-amine The compound from Example 258B (0.56 g) was subjected to reaction conditions according to the method of Example 209 to provide 0.135 g of the title compound. MS (ESI/NH$_3$) m/z 404 (M+H)$^+$; $^1$H NMR (δ, DMSO-d$_6$) 1.05-1.09 (d, 3H), 1.4-1.6 (m, 1H), 1.6-1.8 (m, 1H), 1.8-2.0 (m, 1H), 2.05-2.19 (m, 1H), 3.1-3.2 (m, 1H), 3.48-3.55 (m, 1H), 3.95-4.02 (m, 1H), 4.15-4.23 (m, 1H), 4.38-4.6 (m, 2H), 6.70-6.8 (m, 1H), 7.42-7.8 (m, 3H), 7.95-7.99 (d, 1H), 8.03-8.08 (m, 1H).

Example 259

1-(2,3-dichlorophenyl)-N-{[2-(2,5-dimethylpyrrolidin-1-yl)pyridin-3-yl]methyl}-1H-tetraazol-5-amine

Example 259A 2-(2,5-dimethylpyrrolidin-1-yl)nicotinonitrile

The procedure from Example 259A was followed, substituting racemic 2,5-dimethylpyrrolidine (0.5 g) for 3-aza-bicyclo[3.2.2]nonane to give the title compound. MS (ESI/NH$_3$) m/z 201 (M+H)$^+$.

Example 259B

[2-(2,5-dimethylpyrrolidin-1-yl)pyridin-3-yl]methylamine

The compound from Example 259A (0.76 g) was subjected to reduction conditions according to the method of Example 249B to provide 0.6 g of the title compound as an oil. MS (ESI/NH$_3$) m/z 205 (M+H)$^+$.

Example 259C 1-(2,3-dichlorophenyl)-N-{[2-(2,5-dimethylpyrrolidin-1-yl)pyridin-3-yl]methyl}-1H-tetraazol-5-amine The compound from Example 259B (0.6 g) was subjected to reaction conditions according to the method of Example 209 to provide 0.085 g of the title compound. MS (ESI/NH$_3$) m/z 404 (M+H)$^+$.

Example 260

1-(2,3-dichlorophenyl)-N-{[2-(1,4-oxazepan-4-yl)pyridin-3-yl]methyl}-1H-tetraazol-5-amine

Example 260A 2-(1,4-oxazepan-4-yl)nicotinonitrile

The procedure from Example 249A was followed, substituting homomorpholine (0.7 g) for 3-aza-bicyclo[3.2.2]nonane to give 0.73 g of the title compound. MS (ESI/NH$_3$) m/z 203 (M+H)$^+$.

Example 260B

[2-(1,4-oxazepan-4-yl)pyridin-3-yl]methylamine

The compound from Example 260A (0.73 g) was subjected to reduction conditions according to the method of Example 249B to provide 0.7 g of the title compound as an oil. MS (ESI/NH$_3$) m/z 207 (M+H)$^+$.

Example 260C 1-(2,3-dichlorophenyl)-N-{[2-(1,4-oxazepan-4-yl)pyridin-3-yl]methyl}-1H-tetraazol-5-amine The compound from Example 260B (0.7 g) was subjected to reaction conditions according to the method of Example 209 to provide 0.12 g of the title compound. MS (ESI/NH$_3$) m/z 420 (M+H)$^+$; $^1$H NMR (δ, DMSO-d$_6$) 1.75-1.9 (m, 2H), 3.38-3.42 (m, 4H), 3.68-3.8 (m, 4H), 4.41-4.5 (d, 2H), 6.82-6.9 (m, 1H), 7.58-7.78 (m, 4H), 7.95-7.99 (d, 1H), 8.07-8.12 (d, 1H).

Example 261

1-(2,3-dichlorophenyl)-N-{[2-(4-methyl-1,4-diazepan-1-yl)pyridin-3-yl]methyl}-1H-tetraazol-5-amine

Example 261A 2-(4-methyl-1,4-diazepan-1-yl)nicotinonitrile

The procedure from Example 249A was followed, substituting N-methylhomopiperizine (0.75 g) for 3-aza-bicyclo[3.2.2]nonane to give 1.1 g of the title compound. MS (ESI/NH$_3$) m/z 217 (M+H)$^+$.

Example 261B

[2-(4-methyl-1,4-diazepan-1-yl)pyridin-3-yl]methylamine

The compound from Example 261A (1.1 g) was subjected to reduction conditions according to the method of Example 249B to provide 1.0 g of the title compound as an oil. MS (ESI/NH$_3$) m/z 221 (M+H)$^+$.

Example 261C 1-(2,3-dichlorophenyl)-N-{[2-(4-methyl-1,4-diazepan-1-yl)pyridin-3-yl]methyl}-1H-tetraazol-5-amine The compound from Example 261B (0.67 g) was subjected to reaction conditions according to the method of Example 209 to provide 0.08 g of the title compound. MS (ESI/NH$_3$) m/z 433 (M+H)$^+$; $^1$H NMR (δ, DMSO-d$_6$) 1.8-1.9 (t, 1H), 2.23 (s, 3H), 2.56-2.65 (m, 2H), 3.4-3.5 (m, 4H), 4.42-4.45 (d, 2H), 6.8-6.85 (m, 1H), 7.5-7.6 (d, 1H), 7.61-7.63 (m, 2H), 7.69-7.72 (d, 1H), 7.95-7.99 (d, 1H), 8.05-8.12 (d, 1H).

Example 262 tert-butyl 4-[3-({[1-(2,3-dichlorophenyl)-1H-tetraazol-5-yl]amino}methyl)pyridin-2-yl]-1,4-diazepane-1-carboxylate

Example 262A tert-butyl 4-(3-cyanopyridin-2-yl)-1,4-diazepane-1-carboxylate

The procedure from Example 249A was followed, substituting N-tert-butyloxyhomopiperizine (0.75 g) for 3-aza-bicyclo[3.2.2]nonane to give 1.8 g of the title compound. MS (ESI/NH$_3$) m/z 303 (M+H)$^+$.

Example 262B tert-butyl 4-[3-(aminomethyl)pyridin-2-yl]-1,4-diazepane-1-carboxylate The compound from Example 262A (1.8 g) was subjected to reduction conditions according to the method of Example 249B to provide 1.8 g of the title compound as an oil. MS (ESI/NH$_3$) m/z 307 (M+H)$^+$.

Example 262C tert-butyl 4-[3-({[1-(2,3-dichlorophenyl)-1H-tetraazol-5-yl]amino}methylpyridin-2-yl]-1,4-diazepane-1-carboxylate The compound from Example 262B (0.67 g) was subjected to reaction conditions according to the method of Example 209 to provide 0.76 g of the title compound. MS (ESI/NH$_3$) m/z 519 (M+H)$^+$; $^1$H NMR (δ, DMSO-d$_6$) 123-1.4 (d, 9H), 1.76-1.82 (m, 1H), 3.2-3.6 (m, 8H), 4.4-4.46 (d, 2H), 6.8-6.85 (m, 1H), 7.5-7.6 (d, 1H), 7.61-7.63 (m, 2H), 7.69-7.72 (d, 1H), 7.95-7.99 (d, 1H), 8.05-8.12 (d, 1H).

Example 263

N-{[2-(1,4-diazepan-1-yl)pyridin-3-yl]methyl}-1-(2,3-dichlorophenyl)-1H-tetraazol-5-amine The compound from Example 262C (0.76 g) was subjected to reaction conditions according to the method of Example 289 to provide 0.195 g of the title compound. MS (ESI/NH$_3$) m/z 419 (M+H)$^+$; $^1$H NMR (δ, DMSO-d$_6$) 3.2-3.6 (m, 9H), 4.4-4.46 (d, 2H), 6.8-6.85 (m, 1H), 7.5-7.6 (d, 1H), 7.61-7.63 (m, 2H), 7.69-7.72 (d, 1H), 7.95-7.99 (d, 1H), 8.05-8.12 (d, 1H).

Example 264 tert-butyl 3-[3-({[1-(2,3-dichlorophenyl)-1H-tetraazol-5-yl]amino}methyl)pyridin-2-yl]-3,6-diazabicyclo[3.2.0]heptane-6-carboxylate

Example 264A tert-butyl 3-(3-cyanopyridin-2-yl)-3,6-diazabicyclo[3.2.0]heptane-6-carboxylate The procedure from Example 249A was followed, substituting 3,6-diaza-bicyclo[3.2.0]heptane-6-carboxylic acid tert-butyl ester WO 2001081347 (0.5 g) for 3-aza-bicyclo[3.2.2]nonane to give 0.5 g of the title compound. MS (ESI/NH$_3$) m/z 301 (M+H)$^+$.

Example 264B tert-butyl 3-[3-(aminomethyl)pyridin-2-yl]-3,6-diazabicyclo[3.2.0]heptane-6-carboxylate The compound from Example 264A (0.5 g) was subjected to reduction conditions according to the method of Example 249B to provide 0.5 g of the title compound as an oil. MS (ESI/NH$_3$) m/z 305 (M+H)$^+$.

Example 264C tert-butyl 3-[3-({[1-(2,3-dichlorophenyl)-1H-tetraazol-5-yl]amino}methylpyridin-2-yl]-3,6-diazabicyclo[3.2.0]heptane-6-carboxylate The compound from Example 264B (0.37 g) was subjected to reaction conditions according to the method of Example 209 to provide 0.45 g of the title compound. MS (ESI/NH$_3$) m/z 515 (M+H)$^+$; $^1$H NMR (δ, DMSO-d$_6$) 1.35-1.39 (m, 9H), 2.72-2.94 (dd, 1H), 3.0-3.15 (m, 2H), 3.5-3.7 (m, 2H), 3.8-4.0

(m, 2H), 4.4-4.56 (m, 2H), 4.61-4.69 (d, 2H), 6.91-6.99 (m, 1H), 7.56-7.77 (4H), 7-95-7.99 (d, 1H), 8.1-8.15 (d, 1H).

Example 265

N-{[2-(3,6-diazabicyclo[3.2.0]hept-3-yl)pyridin-3-yl]methyl}-1-(2,3-dichlorophenyl)-1H-tetraazol-5-amine The compound from Example 264C (0.45 g) was subjected to reaction conditions according to the method of Example 289 to provide 0.13 g of the title compound. MS (ESI/NH$_3$) m/z 417 (M+H)$^+$; $^1$H NMR (δ, DMSO-d$_6$) 2.9-3.1 (m, 4H), 3.58-3.8 (4H), 4.5-4.7 (m, 4H), 6.91-6.99 (m, 1H), 7.56-7.77 (4H), 7-95-7.99 (d, 1H), 8.1-8.15 (d, 1H).

Example 266 benzyl (1S,5S)-6-[3-({[1-(2,3-dichlorophenyl)-1H-tetraazol-5-yl]amino}methyl)pyridin-2-yl]-3,6-diazabicyclo[3.2.0]heptane-3-carboxylate Example 266A benzyl (1S,5S)-6-(3-cyanopyridin-2-yl)-3,6-diazabicyclo[3.2.0]heptane-3-carboxylate The procedure from Example 249A was followed, substituting 3S,6R-Diaza-bicyclo[3.2.0]heptane-3-carboxylic acid benzyl ester WO2001081347 (0.18 g) for 3-aza-bicyclo[3.2.2]nonane to give 0.35 g of the title compound. MS (ESI/NH$_3$) m/z 335 (M+H)$^+$ Example 266B benzyl (1S,5S)-6-[3-(aminomethyl)pyridin-2-yl]-3,6-diazabicyclo[3.2.0]heptane-3-carboxylate The compound from Example 266A (0.35 g) was subjected to reduction conditions according to the method of Example 249B to provide 0.35 g of the title compound as an oil. MS (ESI/NH$_3$) m/z 339 (M+H)$^+$.

Example 266C benzyl (1S,5S)-6-[3-({[1-(2,3-dichlorophenyl)-1H-tetraazol-5-yl]amino}methylpyridin-2-yl]-3,6-diazabicyclo[3.2.0]heptane-3-carboxylate The compound from Example 266B (0.37 g) was subjected to reaction conditions according to the method of Example 209 to provide 0.45 g of the title compound. MS (ESI/NH$_3$) m/z 551 (M+H)$^+$; $^1$H NMR (δ, DMSO-d$_6$) 3.1-3.4 (m, 1H), 3.7-4.15 (m, 7H), 4.9-5.1 (m, 3H), 6.67-6.72 (m 1H), 7.2-7.5 (7H), 7.5-7.61 (m, 2H), 7.7-7.76 (d, 1H), 7.96-7.99 (d, 1H), 8.02-8.05 (d, 1H).

Example 267

N-({2-[(1R,5S)-3,6-diazabicyclo[3.2.0]hept-6-yl]pyridin-3-yl}methyl)-1-(2,3-dichlorophenyl)-1H-tetraazol-5-amine The compound from Example 266C (0.45 g) was added to a solution of 10% Pd/C (50 mg) in 25 mL anhydrous methanol. Hydrogen gas was introduced to the system via vacuum cycle (3×) and was held at room temperature for 3 d. The catalyst filtered off and the residue purified by preparative HPLC on a Waters Symmetry C8 column (40 mm×100 mm, 7 um particle size) using a gradient of 10% to 100% acetonitrile:0.1% aqueous trifluoroacetic acid over 12 min (15 min run time) at a flow rate of 70 mL/min to give 0.085 g of the title compound as the trifluoroacetic acid salt. MS (ESI/NH$_3$) m/z 418 (M+H)$^+$; $^1$H NMR (δ, DMSO-d$_6$) 3.1-3.4 (m, 1H), 3.7-4.15 (m, 5H), 4.9-5.1 (m, 3H), 6.67-6.72 (m 1H), 7.5-7.61 (m, 2H), 7.7-7.76 (d, 1H), 7.96-7.99 (d, 1H), 8.02-8.05 (d, 1H), 9.2-9.4 (bs, 1H), 10.1 (bs, 1H).

Example 268 benzyl (1R,5R)-6-[3-({[1-(2,3-dichlorophenyl)-1H-tetraazol-5-yl]amino}methyl)pyridin-2-yl]-3,6-diazabicyclo[3.2.0]heptane-3-carboxylate Example 268A benzyl (1R,5R)-6-(3-cyanopyridin-2-yl)-3,6-diazabicyclo[3.2.0]heptane-3-carboxylate The procedure from Example 249A was followed, substituting 3R,6S-Diaza-bicyclo[3.2.0]heptane-3-carboxylic acid benzyl ester WO2001081347 (0.18 g) for 3-aza-bicyclo[3.2.2]nonane to give 0.35 g of the title compound. MS (ESI/NH$_3$) m/z 335 (M+H)$^+$.

Example 268B benzyl (1R,5R)-6-[3-(aminomethyl)pyridin-2-yl]-3,6-diazabicyclo[3.2.0]heptane-3-carboxylate The compound from Example 268A (0.35 g) was subjected to reduction conditions according to the method of Example 249B to provide 0.35 g of the title compound as an oil. MS (ESI/NH$_3$) m/z 339 (M+H)$^+$.

Example 268C benzyl (1R,5R)-6-[3-({[1-(2,3-dichlorophenyl)-1H-tetraazol-5-yl]amino}methyl)pyridin 2-yl]-3,6-diazabicyclo[3.2.0]heptane-3-carboxylate The compound from Example 268B (0.37 g) was subjected to reaction conditions according to the method of Example 209 to provide 0.45 g of the title compound. MS (ESI/NH$_3$) m/z 551 (M+H)$^+$; $^1$H NMR (δ, DMSO-d$_6$) 3.1-3.4 (m, 1H), 3.61-3.69 (m, 2H), 3.8-4.08 (m 2H), 4.1-4.18 (t, 1H), 4.25-4.29 (d, 2H), 4.95-5.15 (m, 4H), 6.67-6.72 (m 1H), 7.2-7.5 (7H), 7.5-7.61 (m, 2H), 7.7-7.76 (d, 1H), 7.96-7.99 (d, 1H), 8.02-8.05 (d, 1H).

Example 269

N-({2-[(1S,5R)-3,6-diazabicyclo[3.2.0]hept-6-yl]pyridin-3-yl}methyl)-1-(2,3-dichlorophenyl)-1H-tetraazol-5-amine The compound from Example 268C (0.45 g) was added to a solution of 10% Pd/C (50 mg) in 25 mL anhydrous methanol. Hydrogen gas was introduced to the system via vacuum cycle (3×) and was held at room temperature for 3 d. The catalyst filtered off and the residue purified by preparative HPLC on a Waters Symmetry C8 column (40 mm×100 mm, 7 um particle size) using a gradient of 10% to 100% acetonitrile:0.1% aqueous trifluoroacetic acid over 12 min (15 min run time) at a flow rate of 70 mL/min to give 0.075 g of the title compound as the trifluoroacetic acid salt. MS (ESI/NH$_3$) m/z 418 (M+H)$^+$; $^1$H NMR (δ, DMSO-d$_6$) 3.1-3.4 (m, 1H), 3.61-3.69 (m, 2H), 3.8-4.08 (m2H), 4.1-4.18 (t, 1H), 4.25-4.29 (d, 2H), 5.1-5.2 (d, 2H), 6.67-6.72 (m 1H), 7.2-7.5 (7H), 7.5-7.61 (m, 2H), 7.7-7.76 (d, 1H), 7.96-7.99 (d, 1H), 8.02-8.05 (d, 1H).

Example 270

1-(2,3-dichlorophenyl)-N-({2-[(3aR,7aS)-octahydro-2H-4,7-epoxyisoindol-2-yl]pyridin-3-yl}methyl)-1H-tetraazol-5-amine Example 270A 2-[(3aR,7aS)-octahydro-2H-4,7-epoxyisoindol-2-yl]nicotinonitrile The procedure from Example 249A was followed, substituting 10-Oxa-4-aza-tricyclo[5.2.1.02,6]decane WO2004092134 (0.73 g) for 3-aza-bicyclo[3.2.2]nonane to give 0.2 g of the title compound. MS (ESI/NH$_3$) m/z 242 (M+H)$^+$.

Example 270B

{2-[(3aR,7aS)-octahydro-2H-4,7-epoxyisoindol-2-yl]pyridin-3-yl}methylamine

The compound from Example 270A (0.7 g) was subjected to reduction conditions according to the method of Example 249B to provide 0.56 g of the title compound as an oil. MS (ESI/NH$_3$) m/z 246 (M+H)$^+$.

Example 270C 1-(2,3-dichlorophenyl)-N-({2-[(3aR,7aS)-octahydro-2H-4,7-epoxyisoindol-2-yl]pyridin-3-yl}methyl)-1H-tetraazol-5-amine The compound from Example 270B (0.19 g) was subjected to reaction conditions according to the method of Example 209 to provide 0.15 g of the title compound. MS (ESI/NH$_3$) m/z 455 (M+H)$^+$; $^1$H NMR (δ, DMSO-d$_6$) 1.4-1.6 (m, 4H), 2.4-2.55 (m, 2H), 2.81-2.9 (m, 2H), 4.23-4.3 (d, 2H), 4.42-4.5 (m, 2H), 6.8-6.85 (m, 1H), 7.43-7.49 (d, 1H), 7.55-7.61 (t, 2), 7.7-7.76 (d, 1H), 7.95-7.99 (d, 1H), 8.05-8.1 (d, 1H).

Example 271

1-(2,3-dichlorophenyl)-N-(7,8-dimethoxy-1,2,3,4-tetrahydro-1,4-methanonaphthalen-2-yl)-1H-tetraazol-5-amine The procedure from Example 209 was followed, substituting 7,8-dimethoxy-1,2,3,4-tetrahydro-1,4-methano-naphthalen-2-ylamine (0.19 g) (prepared using the procedure as described in Journal of Medicinal Chemistry, (1982), 25(4), 363-8) for cyclohexylmethylamine, to give 0.1 g of the title compound as a solid. MS (ESI/NH$_3$) m/z 432 (M+H)$^+$; $^1$H NMR (δ, DMSO-d$_6$) 1.62-1.84 (m, 4H), 3.2-3.24 (m, 1H), 3.6 (s, 1H), 3.62-3.65 (, 1H), 3.7 (s, 3H), 3.85 (s, 3H), 6.65-6.7 (d, 1H), 6.81-6.86 (d, 1H), 7.17-7.23 (d, 1H), 7.58-7.65 (t, 1H), 7.69-7.73 (d, 1H), 7.95-7.99 (d, 1H).

Example 272

1-(2,3-dichlorophenyl)-N-[(5-methoxy-2,3-dihydro-1H-inden-1-yl)methyl]-1H-tetraazol-5-amine The procedure from Example 209 was followed, substituting C-(5-methoxy-indan-1-yl)-methylamine (prepared using the procedure as described in Journal of Pharmacology and Experimental Therapeutics (2004), 308(2), 679-687) (0.16 g) for cyclohexylmethylamine, to give 0.12 g of the title compound as a solid. MS (ESI/NH$_3$) m/z 389 (M+H)$^+$; $^1$H NMR (δ, DMSO-d$_6$) 1.7-1.82 (m, 1H), 2.07-2.2 (m, 1H), 2.63-2.85 (m, 2H), 3.12-3.3 (m, 1H), 3.3-3.41 (m, 1H), 3.45-3.59 (m, 1H), 3.65 (s, 3H), 3.62-3.66 (d, 1H), 6.8 (s, 1H), 7.04-7.13 (d, 1H), 7.26-7.34 (t, 1H), 7.58-7.7 (m, 2H), 7.95-7.99 (d, 1H).

Example 273

1-({[1-(2,3-dichlorophenyl)-1H-tetraazol-5-yl]amino}methyl)indan-4-ol

The procedure from Example 209 was followed, substituting 1-aminomethyl-indan-4-ol (0.088 g) (prepared according to method as described in Journal of Medicinal Chemistry, (1985), 28(10), 1398-404) for cyclohexylmethylamine, to give 0.07 g of the title compound as a solid. MS (ESI/NH$_3$) m/z 375 (M+H)$^+$; $^1$H NMR (δ, DMSO-d$_6$) 1.7-1.82 (m, 1H), 2.07-2.2 (m, 1H), 2.63-2.85 (m, 2H), 3.12-3.3 (m, 1H), 3.3-3.41 (m, 1H), 3.45-3.59 (m, 1H), 3.62-3.66 (d, 1H), 6.5-6.6 (d, 1H), 6.9-6.99 (t, 1H), 7.26-7.34 (t, 1H), 7.58-7.7 (m, 2H), 7.95-7.99 (d, 1H), 9.16 (s, 1H).

Example 274

1-(2,3-dichlorophenyl)-N-[(6,7-dimethoxy-2,3-dihydro-1H-inden-1-yl)methyl]-1H-tetraazol-5-amine The procedure from Example 209 was followed, substituting C-(6,7-dimethoxy-indan-1-yl)-methylamine (0.188 g) (prepared according to method as described in Journal of Medicinal Chemistry, (1985), 28(10), 1398-404) for cyclohexylmethylamine, to give 0.15 g of the title compound as a solid. MS (ESI/NH$_3$) m/z 419 (M+H)$^+$; $^1$H NMR (δ, DMSO-d$_6$) 1.7-1.82 (m, 1H), 2.07-2.2 (m, 1H), 2.63-2.85 (m, 2H), 3.12-3.3 (m, 1H), 3.3-3.41 (m, 1H), 3.45-3.59 (m, 1H), 3.65 (s, 3H), 3.71 (s, 3H), 3.62-3.66 (d, 1H), 6.71-6.8 (d, 2H), 6.82-6.88 (d, 2H), 7.26-7.34 (t, 1H), 7.58-7.7 (m, 2H), 7.95-7.99 (d, 1H).

Example 275

1-(2,3-dichlorophenyl)-N-[(4-methoxy-2,3-dihydro-1H-inden-1-yl)methyl]-1H-tetraazol-5-amine The procedure from Example 209 was followed, substituting C-(4-methoxy-indan-1-yl)-methylamine (0.16 g) (prepared according to the method as described in Journal of Medicinal Chemistry, (1985), 28(10), 1398-404) for cyclohexylmethylamine, to give 0.086 g of the title compound as a solid. MS (ESI/NH$_3$) m/z 389 (M+H)$^+$; $^1$H NMR (δ, DMSO-d$_6$) 1.7-1.82 (m, 1H), 2.07-2.2 (m, 1H), 2.63-2.85 (m, 2H), 3.12-3.3 (m, 1H), 3.3-3.41 (m, 1H), 3.45-3.59 (m, 1H), 3.65 (s, 3H), 3.71 (s, 3H), 3.62-3.66 (d, 1H), 6.71-6.8 (d, 2H), 6.82-6.88 (d, 2H), 7.02-7.12 (t, 1H), 7.26-7.34 (t, 1H), 7.58-7.7 (m, 2H), 7.95-7.99 (d, 1H).

Example 276

1-(2,3-dichlorophenyl)-N-[4-(3-fluoropiperidin-1-yl)-2,3-dihydro-1H-inden-1-yl]-1H-tetraazol-5-amine The procedure from Example 209 was followed, substituting 4-(3-fluoro-piperidin-1-yl)-indan-1-ylamine, to give 0.115 g of the title compound as a solid. MS (ESI/NH$_3$) m/z 446 (M+H)$^+$; $^1$H NMR (δ, DMSO-d$_6$) 1.5-1.99 (m, 6H), 2.6-3.1 (m, 6H), 4.59-4.85 (m, 1H), 5.2-5.39 (q, 1H), 6.71-6.8 (d, 2H), 6.82-6.88 (d, 2H), 7.02-7.12 (t, 1H), 7.4-7.48 (d, 1H), 7.53-7.6 (t, 1H), 7.68-7.72 (d, 1H), 7.93-7.97 (d, 1H).

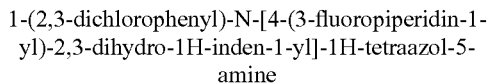

To an oven-dried, N$_2$-purged, 25-mL, round-bottomed flask containing a magnetic stir bar was added the isothiocyanate (1.0 eq) and anhydrous tetrahydrofuran (15 mL). The flask was sealed with a septum and purged with nitrogen. A solution of amine (2.0 eq) in anhydrous tetrahydrofuran (4 mL) was added via syringe. The solution was stirred at room temperature overnight. Saturated aqueous sodium bicarbonate (30 nL) was added to quench. The mixture was transferred to a separatory funnel and extracted with dichloromethane (3×30 mL). The combined organic extracts were dried over anhydrous magnesium sulfate, filtered, and concentrated by rotary evaporator to give a tan solid. The product was recrystallized from ethyl acetate/heptane to give the thiourea.

General Procedure 2: Tetrazole Formation

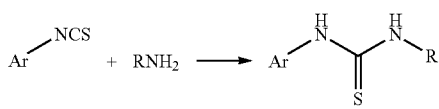

To an oven-dried, N$_2$-purged, 25-mL, round-bottomed flask containing a magnetic stir bar were added the thiourea (1.0 eq) and sodium azide (3.0 eq). The flask was sealed with a septum and purged with a nitrogen atmosphere. Anhydrous tetrahydrofuran (15 mL) was added via syringe. Triethylamine (3.4 eq) was added via syringe. The solid mercury(II) chloride (1.25 eq) was added in one portion and the flask was resealed. A thick, white precipitate formed immediately upon addition of the mercury salt. The mixture was stirred at room temperature overnight and monitored by LC-MS. Ethyl acetate (20 mL) was added, and the solids were removed by vacuum filtration through a glass frit. The solids were washed with ethyl acetate. The liquor was transferred to a separatory funnel and washed with water (30 mL). The organic phase was dried over magnesium sulfate, filtered, and concentrated in vacuo to give an off-white solid. The crude solid was purified by flash column chromatography (ISCO Combiflash) on a 40 g silica gel cartridge using 30% isocratic for one minutes, then 30%-100% ethyl acetate over 6 min, 40 mL/minute. The solvent was removed in vacuo to give the tetrazole.

General Procedure 3: Suzuki Coupling

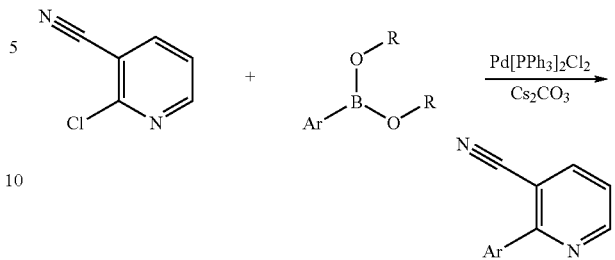

To an oven-dried, N$_2$-purged, 250-mL, round-bottomed flask containing a magnetic stir bar were added the commercially available 2-chloro-3-cyanopyridine (1.5 eq), the arylboronic acid or ester (1.0 eq), and dichlorobis(triphenylphosphine)palladium(II) (0.05 eq). The flask was sealed with a septum and purged with N$_2$ atmosphere. Anhydrous dioxane (15 mL) and a N$_2$-sparged solution of cesium carbonate (3.0 eq) in water (15 mL) were added via syringe. The reaction mixture was heated to ~90° C. in an oil bath and stirred for 2 hours. The reaction was monitored by LC-MS. After cooling to room temperature, the solvent/volatiles were removed in vacuo to give a thick brown oil. Water (25 mL) was added and the mixture was transferred to a separatory funnel. The mixture was extracted with ethyl acetate (4×10 mL). The combined organic extracts were dried over magnesium sulfate, filtered, and concentrated by rotary evaporator to give a brown solid. The crude solid was purified by flash column chromatography (ISCO Combiflash) on a 120 g silica gel cartridge using 30% isocratic for one minutes, then 30%-100% ethyl acetate over 6 min, 50 mL/minute. The solvent was removed in vacuo to give the 2-aryl-nicotinonitrile.

General Procedure 4: Thiourea Formation.

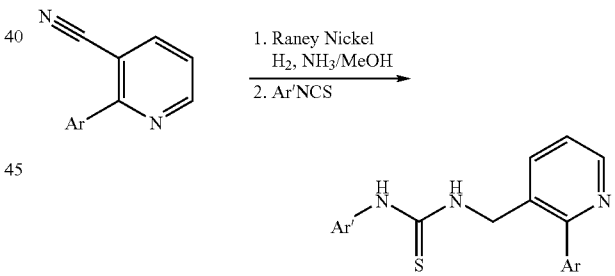

To an argon-purged, thick-walled pressure vessel was added wet Raney nickel (~500 mg). A solution of ammonia-saturated methanol (30 mL) was added, followed by the 2-aryl-nicotinonitrile (150 mmol) The vessel was inserted into a Parr shaker and was charged with 60 psi of H$_2$ gas. The mixture was shaken at room temperature under static H$_2$ pressure for 3 hours. The H$_2$ gas was vented and the vessel was purged with argon. The solids were removed by vacuum filtration through Celite® 545. The solvent/volatiles were removed by rotary evaporator to give the crude amine.

To an oven-dried, N$_2$-purged, 25-mL, round-bottomed flask containing a magnetic stir bar was added the arylisothiocyanate (1.0 eq) and anhydrous tetrahydrofuran (10 mL). The flask was sealed with a septum and purged with N$_2$ atmosphere. A solution of the crude amine (1.2 eq) in anhydrous tetrahydrofuran (2 mL) was added via syringe. The solution was stirred at room temperature overnight. Saturated aqueous sodium bicarbonate (10 mL) was added to quench. The mixture was transferred to a separatory funnel and extracted with dichloromethane (3×10 mL). The combined organic extracts were dried over magnesium sulfate, filtered, and concentrated by rotary evaporator to give a tan solid. The product was purified by recrystallization from ethyl acetate/heptane, trituration with dichloromethane or flash column chromatography to give the thio urea.

General Procedure 5: Tetrazole Formation.

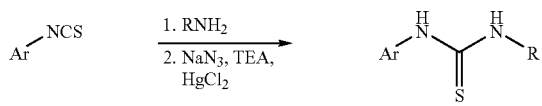

To a scintillation vial was added a solution of 0.16 M C-(6'-fluoro-[2,3']bipyridinyl-3-yl)-methylamine in tetrahydrofuran (3 mL, 0.492 mmol) and arylisothiocyanate (0.117 g, 0.492 mmol). The vial was shaken 1 hour at room temperature. Sodium azide (0.096 g, 1.48 mmol) and triethylamine (0.26 mL, 1.85 mmol) were added, followed by a solution of 0.62 M mercury (II) chloride in tetrahydrofuran (1 mL, 0.625 mmol). A thick, white precipitate formed immediately upon addition of the mercury salt. The mixture was stirred at room temperature overnight and monitored by LC-MS. Ethyl acetate (5 mL) was added, and the solids were removed by vacuum filtration through a glass frit. The solvent was removed in vacuo and the residue was purified by flash column chromatography (ISCO Combiflash) on a 12 g silica gel cartridge using 10% isocratic for one minutes, then 10%-100% ethyl acetate over 6 min, 25 mL/minute. The solvent was removed in vacuo to give the tetrazole.

General Procedure 6: Suzuki Coupling

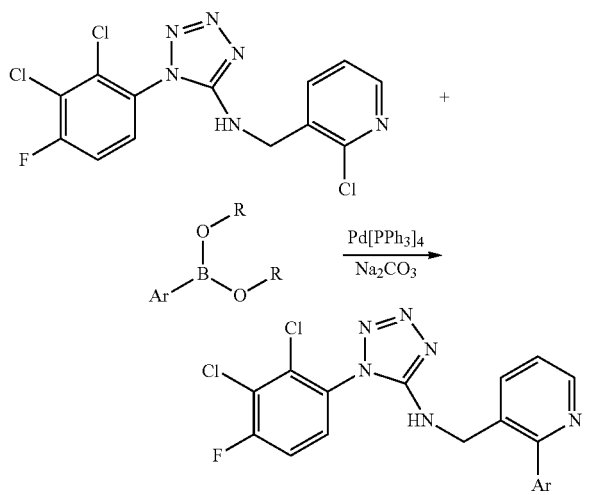

A mixture of (2-Chloro-pyridin-3-ylmethyl)-[1-(2,3-dichloro-4-fluoro-phenyl)-1H-tetrazol-5-yl]-amine (100 mg, 0.267 mmol), aryl boronic acid or ester (0.267 mmol), tetrakis(triphenylphosphine)palladium(0) (31 mg, 0.027 mmol) and sodium carbonate (71 mg, 0.669 mmol) in dioxane (4 mL) and water (1 mL) was microwaved at 120° C. for 45 minutes. The solid was removed by filtration and the filtrate was concentrated. The residue was purified by flash column chromatography on silica using ethyl acetate/dichloromethane (50:50) mixture as the mobile phase to give the coupled product.

Example 277

[1-(2,3-Dichloro-phenyl)-1H-tetrazol-5-yl]-(6'-fluoro-[2,3']bipyridinyl-3-ylmethyl)-amine Example 277A 1-(2,3-Dichloro-phenyl)-3-(6'-fluoro-[2,3']bipyridinyl-3-ylmethyl)-thiourea The title compound was synthesized by general procedure 1 using 2,3-dichlorophenylisothiocyanate and C-(6'-fluoro-[2,3']bipyridinyl-3-yl)-methylamine (Example 192F) to give 0.974 g (72%) of 1-(2,3-dichloro-phenyl)-3-(6'-fluoro-[2,3']bipyridinyl-3-ylmethyl)-thiourea as a white powder. $^1$H NMR (DMSO-$d_6$, 400 MHz) δ 4.74 (d, J=4.1 Hz, 2H), 7.31 (dd, J=2.5, J=8.2 Hz, 1H), 7.35 (t, J=8.2 Hz, 1H), 7.49 (dd, J=4.7 Hz, J=7.9 Hz, 1H), 7.53 (d, J=8.3 Hz, 1H), 7.87 (dd, J=1.5 Hz, J=7.9 Hz, 1H), 8.17 (dt, J=2.5 Hz, J=8.2 Hz, 1H), 8.39 (bs, 1H), 8.41 (d, J=2.5 Hz, 1H) 8.60 (dd, J=1.6 Hz, J=4.7 Hz, 1H), 9.49 (bs, 1H); RP-HPLC (Hypersil® HS C18, 5 μm, 100 Å, 25 cm; 5%-100% acetonitrile −0.1M ammonium acetate over 10 min, 1 mL/min), then 100% acetonitrile isocratic 2 minutes, $R_t$ 10.30 min. (94.3%); MS: M+H$^+$ 407.

Example 277B

[1-(2,3-Dichloro-phenyl)-1H-tetrazol-5-yl]-(6'-fluoro-[2,3']bipyridinyl-3-ylmethyl)-amine The title compound was prepared from the product of Example 277A using General Procedure 2. $^1$H NMR (DMSO-$d_6$, 400 MHz) δ 4.53 (d, J=5.3 Hz, 2H), 7.32 (dd, J=2.7 Hz, J=8.5 Hz, 1H), 7.47 (dd, J=4.8 Hz, J=7.8 Hz, 1H), 7.61 (t, J=7.7 Hz, 1H), 7.68 (dd, J=1.4 Hz, J=7.9 Hz, 1H), 7.75 (t, J=5.4 Hz, 1H), 7.91 (d, J=7.9 Hz, 1H), 7.95 (d, J=8.0 Hz, 1H), 8.23 (dt, J=2.4 Hz, J=8.2 Hz, 1H), 8.45 (d, J=2.4 Hz, 1H), 8.60 (t, J=4.8 Hz, 1H); RP-HPLC (Hypersil® HS C18, 5 μm, 100 Å, 25 cm; 5%-100% acetonitrile −0.1M ammonium acetate over 10 min, 1 mL/min), then 100% acetonitrile isocratic 2 minutes, $R_t$ 9.95 min. (>99.5%); MS: M+H$^+$ 415, 417.

Example 278

[1-(2,3-Dichloro-4-fluorophenyl)-1H-tetrazol-5-yl] (2'-fluoro-[2,4']bipyridinyl-3-ylmethyl)amine Example 278A 2-(1H-Pyrazol-4-yl)-nicotinonitrile The title compound was synthesized from 2-fluoropyridine-4-boronic acid using General Procedure 3. $^1$H NMR (DMSO-$d_6$, 400 MHz) 7.66 (m, 1H), 7.77 (dd, J=4.9 Hz, J=8.0 Hz, 1H), 7.84 (ddd, J=1.4 Hz, J=2.0 Hz, J=5.2 Hz, 1H), 8.49 (td, J=0.7 Hz, J=5.2 Hz, 1H), 8.55 (dd, J=1.7 Hz, J=8.0 Hz, 1H), 9.02 (dd, J=1.7 Hz, J=4.9 Hz, 1H); RP-HPLC (Hypersil® HS C18, 5 μm, 100 Å, 25 cm; 5%-100% acetonitrile −0.1M ammonium acetate over 10 min, 1 mL/min), then 100% acetonitrile isocratic 2 minutes, $R_t$ 9.10 min. (96.6%).

Example 278B 1-(2,3-Dichloro-4-fluorophenyl)-3-(2'-fluoro-[2,4'] bipyridinyl-3-ylmethyl)thiourea The title compound was prepared from the product of Example 278A and 2,3-dichloro-4-fluorophenylisothiocyanate using General Procedure 4. ¹H NMR (DMSO-d$_6$, 400 MHz) δ 4.74 (m, 2H), 7.31-7.38 (m, 1H), 7.39-7.59 (m, 4H), 7.88 (d, J=6.8 Hz, 1H), 8.19-8.39 (m, 1H), 8.36 (d, J=4.1 Hz, 1H), 8.55-8.73 (m, 1H), 9.44-9.64 (bs, 1H); RP-HPLC (Hypersil® HS C18, 5 μm, 100 Å, 25 cm; 5%-100% acetonitrile −0.1M ammonium acetate over 10 min, 1 mL/min), then 100% acetonitrile isocratic 2 minutes, R$_t$ 10.40 min. (95.3%); MS: MH$^+$ 424.

Example 278C

[1-(2,3-Dichloro-4-fluorophenyl)-1H-tetrazol-5-yl] (2'-fluoro-[2,4']bipyridinyl-3-ylmethyl)amine The title compound was prepared using General Procedure 2 from the product of Example 278B. ¹H NMR (DMSO-d$_6$, 400 MHz) δ 1H-NMR (400 MHz) δ 4.55 (d, J=5.5 Hz, 2H), 7.39-7.42 (m, 1H), 7.51 (dd, J=4.7 Hz, J=7.9 Hz, 1H), 7.57 (ddd, J=1.4 Hz, J=2.1 Hz, J=5.1 Hz, 1H), 7.68 (t, J=5.6 Hz, 1H), 7.74 (t, J=8.8 Hz, 1H), 7.80 (dd, J=5.4 Hz, J=9.0 Hz, 1H), 7.93 (dd, J=1.6 Hz, J=7.9 Hz, 1H), 8.36 (d, J=5.1 Hz, 1H), 8.62 (dd, J=1.6 Hz, J=4.7 Hz, 1H); RP-HPLC (Hypersil® HS C18, 5 μm, 100 Å, 25 cm; 50%-100% acetonitrile −0.1M ammonium acetate over 10 min, 1 mL/min), then 100% acetonitrile isocratic 2 minutes, R$_t$ 5.50 min. (99.6%), MS: MH$^+$ 434.

Example 279

[2-(1-Benzyl-1H-pyrazol-4-yl)pyridin-3-ylmethyl]-[1-(2,3-dichloro-4-fluorophenyl)-1H-tetrazol-5-yl]amine

Example 279A 2-(1-Benzyl-1H-pyrazol-4-yl)-nicotinonitrile

The title compound was prepared from 1-benzyl-4-(4,4,5,5-tetramethyl-1,3,2-dioxaborolan-2-yl)-1H-pyrazole using General Procedure 3. ¹H NMR (DMSO-d$_6$, 400 MHz) δ 5.46 (s, 2H), 7.30-7.38 (m, 5H), 7.41 (dd, J=4.9 Hz, J=7.9 Hz, 1H), 8.21 (s, 1H), 8.30 (dd, J=1.8 Hz, J=7.9 Hz, 1H), 8.62 (s, 1H), 8.80 (dd, J=1.7 Hz, J=4.8 Hz, 1H); RP-HPLC (Hypersil® HS C18, 5 μm, 100 Å, 25 cm; 50%-100% acetonitrile −0.1M ammonium acetate over 10 min, 1 mL/min), then 100% acetonitrile isocratic 2 minutes, R$_t$ 5.95 min. (99.0%), MS: M+H$^+$ 261.

Example 279B

1-[2-(1-Benzyl-1H-pyrazol-4-yl)-pyridin-3-ylmethyl]-3-(2,3-dichloro-4-fluorophenyl)thiourea The title compound was prepared from the product of Example 279A using General Procedure 4. ¹H NMR (DMSO-d$_6$, 400 MHz) δ 4.90 (d, J=3.5 Hz, 2H), 5.46 (s, 2H), 7.29-7.45 (m, 6H), 7.52 (t, J=8.9 Hz, 1H), 7.60-7.68 (m, 1H), 7.75 (dd, J=1.6 Hz, J=7.8 Hz, 1H), 8.01 (s, 1H), 8.37-8.45 (m, 2H), 8.53 (s, 1H), 9.62 (s, 1H); RP-HPLC (Hypersil® HS C18, 5 μm, 100 Å, 25 cm; 50%-100% acetonitrile −0.1M ammonium acetate over 10 min, 1 mL/min), then 100% acetonitrile isocratic 2 minutes, R$_t$ 7.01 min. (99.4%); MS: M+H$^+$ 487.

Example 279C

[2-(1-Benzyl-1H-pyrazol-4-yl)pyridin-3-ylmethyl]-[1-(2,3-dichloro-4-fluorophenyl)-1H-tetrazol-5-yl]amine The title compound was prepared from the product of Example 279B using General Procedure 4. ¹H NMR (DMSO-d$_6$, 400 MHz) δ 4.64 (d, J=5.2 Hz, 2H), 5.39 (s, 1H), 7.23 (s, 1H), 7.27-7.39 (m, 5H), 7.69-7.77 (m, 3H), 7.86 (dd, J=5.3 Hz, J=9.0 Hz, 1H), 7.94 (d, J=0.7 Hz, 1H), 8.32 (d, J=0.7 Hz, 1H), 8.47 (dd, J=1.7 Hz, J=4.7 Hz, 1H); RP-HPLC (Hypersil® HS C18, 5 μm, 100 Å, 25 cm; 50%-100% acetonitrile −0.1M ammonium acetate over 10 min, 1 mL/min), then 100% acetonitrile isocratic 2 minutes, R$_t$ 6.54 min. (99.5%), MS: M+H$^+$ 496.

Example 280

[1-(2,3-Dichloro-4-fluorophenyl)-1H-tetrazol-5-yl] (2-methylpyridin-3-ylmethyl)amine

Example 280A 1-(2,3-Dichloro-4-fluorophenyl)-3-(2-methylpyridin-3-ylmethyl)thiourea The title compound was prepared from 2,3-dichloro-4-fluorophenylisothiocyanate and C-(2-methylpyridin-3-yl)methylamine using General Procedure 1. ¹H NMR (DMSO-d$_6$, 400 MHz) δ 2.47 (s, 3H), 4.69 (m, 2H), 7.21 (dd, 1H, J=4.9 Hz, J=7.6 Hz), 7.46 (t, 1H, J=8.9 Hz), 7.54-7.67 (bs, 1H), 7.58 (dd, 1H, J=1.4 Hz, J=7.7 Hz), 8.26-8.42 (bs, 1H), 8.33 (dd, 1H, J=1.7 Hz, J=4.8 Hz), 9.49 (s, 1H); RP-HPLC (Hypersil®-100 C18, 5 μm, 100 Å, 10 cm; 5%-100% acetonitrile −0.1M ammonium acetate over 5 min, 2 mL/min), then 100% acetonitrile isocratic 1 minutes, R$_t$ 3.69 min. (90.8%); MS: M+H$^-$ 342.

Example 280B

[1-(2,3-Dichloro-4-fluorophenyl)-1H-tetrazol-5-yl] (2-methylpyridin-3-ylmethyl)amine The title compound was prepared from the product of Example 280A using General Procedure 2. ¹H NMR (DMSO-d$_6$, 400 MHz) δ 2.49 (s, 3H), 4.49 (d, J=5.5 Hz, 2H), 7.19 (dd, J=4.8 Hz, J=7.7 Hz, 1H), 7.58-7.65 (m, 2H), 7.75 (t, J=8.8 Hz, 1H), 7.89 (dd, J=5.3 Hz, J=9.0 Hz, 1H), 8.34 (dd, J=1.7 Hz, J=4.8 Hz, 1H); RP-HPLC (Hypersil®-100 C18, 5 μm, 100 Å, 10 cm; 5%-100% acetonitrile −0.1M ammonium acetate over 5 min, 2 mL/min), then 100% acetonitrile isocratic 1 minutes, R$_t$ 3.62 min. (95.1%); MS: M+H$^+$ 353.

Example 281

[1-(2,3-Dichloro-4-fluorophenyl)-1H-tetrazol-5-yl]-(5,6,7,8-tetrahydroquinolin-5-yl)amine

Example 281A 1-(2,3-Dichloro-4-fluorophenyl)-3-(5,6,7,8-tetrahydroquinolin-5-yl)thiourea The title compound was prepared from 2,3-dichloro-4-fluorophenylisothiocyanate and 5,6,7,8-tetrahydroquinolin-5-ylamine using General Procedure 1. ¹H NMR (DMSO-d$_6$, 400 MHz) δ 1.77-1.93 (m, 2H), 1.93-2.12 (m, 2H), 2.81-2.97 (m, 2H), 5.70-5.83 (m, 1H), 7.28 (dd, 1H, J=4.7 Hz, J=7.8 Hz), 7.51 (t, 1H, J=8.9 Hz), 7.62-7.78 (m, 2H), 8.37 (d, 1H, J=8.5 Hz), 8.43 (dd, 1H, J=1.4 Hz, J=4.5 Hz), 9.39 (s, 1H); RP-HPLC (Hypersil®-100 C18, 5 μm, 100 Å, 10 cm; 5%-100% acetonitrile −0.1M ammonium acetate over 5 min, 2 mL/min), then 100% acetonitrile isocratic 1 minutes, $R_t$ min. (98.9%); MS: M+H$^+$ 370.

Example 281B

[1-(2,3-Dichloro-4-fluorophenyl)-1H-tetrazol-5-yl]-(5,6,7,8-tetrahydroquinolin-5-yl)amine The title compound was prepared from the product of Example 281A using General Procedure 2. $^1$H NMR (DMSO-d$_6$, 400 MHz) δ 1.74-2.08 (m, 4H), 2.74-2.89 (m, 2H), 4.96-5.07 (m, 1H), 7.19 (dd, J=4.7 Hz, J=7.8 Hz. 1H), 7.49 (d, J=8.4 Hz, 1H), 7.65 (d, J=7.0 Hz, 1H), 7.70 (t, J=8.8 Hz, 1H), 7.85 (dd, J=5.3 Hz, J=9.0 Hz, 1H), 8.37 (dd, J=1.3 Hz, J=4.7 Hz, 1H); RP-HPLC (Hypersil®-100 C18, 5 μm, 100 Å, 10 cm; 5%-100% acetonitrile −0.1M ammonium acetate over 5 min, 2 mL/min), then 100% acetonitrile isocratic 1 minutes, $R_t$ 3.84 min. (98.3%); MS: M+H$^+$ 379.

Example 282

[1-(4-Chloro-3-trifluoromethylphenyl)-1H-tetrazol-5-yl](6'-fluoro-[2,3']bipyridinyl-3-ylmethyl)amine The title compound was synthesized from 4-chloro-3-(trifluoromethyl)phenyl isothiocyanate using General procedure 5. $^1$H NMR (DMSO-d$_6$, 400 MHz) δ 4.90 (s, 2H), 7.31 (dt, J=2.7 Hz, J=8.2 Hz, 1H), 7.38 (d, J=2.6 Hz, 1H), 7.53 (dd, J=4.7 Hz, J=7.8 Hz, 1H), 7.65 (d, J=8.6 Hz, 1H), 8.08 (dd, J=1.7 Hz, J=7.8 Hz, 1H), 8.21 (m, 1H), 8.45 (d, J=2.6 Hz, 1H), 8.67 (dd, J=1.7 Hz, J=4.8 Hz, 1H); RP-HPLC (Hypersil®-100 C18, 5 μm, 100 Å, 10 cm; 5%-100% acetonitrile −0.1M ammonium acetate over 5 min, 2 mL/min), then 100% acetonitrile isocratic 1 minutes, $R_t$ 5.30 min. (97.5%); MS: M+H$^+$ 448, 450.

Example 283

3-{5-[(6'-Fluoro-[2,3']bipyridinyl-3-ylmethyl)amino]tetrazol-1-yl}benzonitrile

The title compound was prepared from 5 3-cyanophenyl isothiocyanate using General Procedure. $^1$HNMR (DMSO-d$_6$, 400 MHz) δ 4.89 (s, 1H), 7.29-7.36 (m, 2H), 7.48-7.55 (m, 3H), 7.58-7.62 (m, 1H), 8.09 (dd, J=1.6 Hz, J=7.8 Hz, 1H), 8.20 (dd, J=2.6 Hz, J=8.1 Hz, 1H), 8.44-8.46 (m, 1H), 8.67 (dd, 1H, J=1.7 Hz, J=4.7 Hz); RP-HPLC (Hypersil®-100 C18, 5 μm, 100 Å, 10 cm; 5%-100% acetonitrile −0.1M ammonium acetate over 5 min, 2 mL/min), then 100% acetonitrile isocratic 1 minutes, $R_t$ 4.28 min. (98.5%); MS: M+H$^+$ 371, 373.

Example 284

1'-Benzyl-3-{[1-(2,3-dichloro-4-fluoro-phenyl)-1H-tetrazol-5-ylamino]-methyl}-1'H-[2,4']bipyridinyl-2'-one Example 284A 1'-Benzyl-2'-oxo-1',2'-dihydro-[2,4']bipyridinyl-3-carbonitrile The title compound was prepared from 1-Benzyl-4-(4,4,5,5-tetramethyl-[1,3,2]dioxaborolan-2-yl)-1H-pyridin-2-one using General Procedure 3. $^1$H-NMR (400 MHz DMSO-d$_6$) δ 5.18 (s, 2H), 6.65 (dd, J=2.1 Hz, J=7.1 Hz, 1H), 6.91 (d, J=1.6 Hz, 1H), 7.36 (m, 5H), 7.70 (dd, J=4.9 Hz, J=8.0 Hz, 1H), 8.00 (dd, J=0.5 Hz, J=7.1 Hz, 1H), 8.48 (dd, J=1.7 Hz, J=7.9 Hz, 1H), 8.95 (dd, J=1.7 Hz, J=4.9 Hz, 1H).

Example 284B 1-(1'-Benzyl-2'-oxo-1',2'-dihydro-[2,4']bipyridinyl-3-ylmethyl)-3-(2,3-dichloro-4-fluoro-phenyl)-thiourea The title compound was prepared from 1'-benzyl-2'-oxo-1',2'-dihydro-[2,4']bipyridinyl-3-carbonitrile using General Procedure 4. MS (ESI+) m/z 513.3 (M+H)$^+$; $R_t$=1.91 min. $^1$H-NMR (400 MHz DMSO-d$_6$) δ 4.75 (s, 2H), 5.17 (s, 2H), 6.41 (dd, J=1.5 Hz, J=6.9 Hz, 1H), 6.51 (s, 1H), 7.34 (m, 4H), 7.46 (m, 2H), 7.54 (m, 1H), 7.89 (d, J=7.0 Hz, 1H), 7.81 (d, J=7.9 Hz, 1H), 8.31 (s, 1H), 8.55 (d, J=4.0 Hz, 1H), 9.57 (s, 1H).

Example 284C

1'-Benzyl-3-{[1-(2,3-dichloro-4-fluoro-phenyl)-1H-tetrazol-5-ylamino]-methyl}-1'H-[2,4']bipyridinyl-2'-one The title compound was prepared by from the product of Example 284B using General Procedure 2. MS (ESI+) m/z 521.9 (M+H)$^+$; Rt=1.91 min; $^1$H-NMR (400 MHz, DMSO-d$_6$) δ 4.55 (d, J=5.43 Hz, 2H), 5.15 (s, 2H), 5.57 (d, J=1.7 Hz, 1H), 6.44 (dd, J=1.9 Hz, J=7.0 Hz, 1H), 7.36 (m, 5H), 7.45 (dd, J=4.7 Hz, J=7.9 Hz, 1H), 7.69 (m, 1H), 7.72 (m, 1H), 7.80 (dd, 1H, J=5.35 Hz, J=8.99 Hz), 7.87 (m, 2H), 8.56 (dd, J=1.6 Hz, J=4.7 Hz, 1H).

Example 285

(2-Chloro-pyridin-3-ylmethyl)-[1-(2,3-dichloro-4-fluoro-phenyl)-1H-tetrazol-5-yl]-amine Example 285A 1-(2-Chloropyridin-3-ylmethyl)-3-(2,3-dichloro-4-fluorophenyl)thiourea The title compound was prepared from 2,3-dichloro-1-fluorophenylisothiocyanate and C-(2-Chloro-pyridin-3-yl)-methylamine using General Procedure 1. MS (ESI+) m/z 364.1 (M+H)$^+$; $R_t$=2.08 min. $^1$H-NMR (400 MHz DMSO-d$_6$) δ 4.74 (s, 2H), 7.48 (m, 2H), 7.74 (dd, J=1.75, 7.62 Hz, 1H), 8.32 (dd, J=1.89, 4.72 Hz, 1H), 8.37 (s, 1H), 9.70 (s, 1H).

Example 285B (2-Chloro-pyridin-3-ylmethyl)-[1-(2,3-dichloro-4-fluoro-phenyl)-1H-tetrazol-5-yl]-amine The title compound was prepared from the product of Example 285B using General Procedure 2. MS (ESI+) m/z 373.2 (M+H)$^+$; $R_t$=1.96 min. $^1$H-NMR (400 MHz, DMSO-d$_6$) δ 4.55 (d, J=5.6 Hz, 1H), 7.44 (dd, J=4.7 Hz, J=7.6 Hz, 1H), 7.80 (m, 3H), 7.92 (dd, J=5.3 Hz, J=9.0 Hz, 1H), 8.34 (dd, J=1.9 Hz, J=4.7 Hz, 1H).

Example 286

[1-(2,3-Dichloro-4-fluoro-phenyl)-1H-tetrazol-5-yl]-(2'-fluoro-[2,3']bipyridinyl-3-ylmethyl)-amine The title compound was prepared from 2-fluoropyridine-3-boronic acid and the product of Example 285B using General Procedure 6. MS (ESI$^+$) m/z 434.2 (M+H)$^+$; R$_t$=1.87 min. $^1$H-NMR (400 MHz, DMSO-d$_6$) δ 5.56 (s, 2H), 7.46 (m, 2H), 7.55 (m, 2H), 7.73 (dd, J=1.5 Hz, J=7.9 Hz, 1H), 7.98 (ddd, J=2.0 Hz, J=7.4 Hz, J=9.6 Hz, 1H), 8.31 (d, J=4.8 Hz, 1H), 8.68 (dd, J=1.6 Hz, J=4.7 Hz, 1H), 8.99 (s, 1H).

Example 287

[1-(2,3-Dichloro-4-fluoro-phenyl)-1H-tetrazol-5-yl](2-pyrimidin-5-yl-pyridin-3-ylmethyl)amine The title compound was prepared from pyrimidine-5-boronic acid and the product of Example 285B using General Procedure 6. MS (ESI$^+$) m/z 417.2 (M+H)$^+$; R$_t$=1.50 min. $^1$H-NMR (400 MHz DMSO-d$_6$) δ 5.80 (s, 2H), 7.45 (t, J=8.9 Hz, 1H), 7.54 (m, 2H), 7.63 (m, 1H), 8.71 (dd, J=2.6 Hz, J=3.8 Hz, 1H), 9.02 (s, 3H), 9.27 (s, 1H).

Example 288

4-(3-{[1-(2,3-Dichloro-4-fluorophenyl)-1H-tetrazol-5-ylamino]methyl}pyridin-2-yl)-[1,4]diazepane-1-carboxylic acid tert-butyl ester

Example 288A 4-(2-Cyano-phenyl)-[1,4]diazepane-1-carboxylic acid tert-butyl ester 2-Chloro-nicotinonitrile (1.0 g, 7.215 mmol) was added to a mixture of [1,4]Diazepane-1-carboxylic acid tert-butyl ester and potassium hydrogencarbonate (0.87 g, 8.66 mmol) in N,N-dimethylformamide (20 mL). The mixture was heated at 90° C. overnight. The reaction mixture was poured onto ice and extracted with dichloromethane. The organic layer was washed with water and brine then dried over magnesium sulfate and filtered. The solvent was removed and the residue was purified by flash column chromatography on silica using ethyl acetate/heptane (50:50) mixture as the mobile phase to give 4-(2-Cyano-phenyl)-[1,4]diazepane-1-carboxylic acid tert-butyl ester. $^1$H-NMR (400 MHz, DMSO-d$_6$) δ 1.25 (d, 27 Hz, 9H), 1.81 (m, 1H), 1.87 (m, 1H), 3.31 (m, 2H), 3.55 (m, 1H), 3.60 (m, 1H), 3.84 (m, 2H), 3.94 (m, 2H), 6.75 (m, 2H), 8.34 (m, 1H).

Example 288B

4-{3-[3-(2,3-Dichloro-4-fluoro-phenyl)-thioureidomethyl]-pyridin-2-yl}-[1,4]diazepane-1-carboxylic acid tert-butyl ester The title compound was prepared from the product of Example 288A, and 2,3-dichloro-4-fluorophenylisothiocyanate using General Procedure 4. MS (ESI$^+$) m/z 512.9 (M+H)$^+$; R$_t$=1.96. $^1$H NMR (DMSO-d$_6$) δ 1.38 (d, J=15.0 Hz, 9H), 1.85 (m, 2H), 3.29 (m, 2H), 3.39 (m, 4H), 3.52 (m, 2H), 4.66 (s, 2H), 6.93 (dd, J=4.9 Hz, J=7.2 Hz, 1H), 7.54 (d, 1H, J=6.8 Hz, 7.46 (t, J=8.9 Hz, 1H), 7.58 (m, 1H), 8.11 (dd, J=1.7 Hz, J=4.7 Hz, 1H), 8.23 (s, 1H), 9.51 (s, 1H).

Example 288C 4-(3-{[1-(2,3-Dichloro-4-fluorophenyl)-1H-tetrazol-5-ylamino]methyl}pyridin-2-yl)-[1,4]diazepane-1-carboxylic acid tert-butyl ester The title compound was prepared from 4-{3-[3-(2,3-Dichloro-4-fluoro-phenyl)-thioureidomethyl]-pyridin-2-yl}-[1,4]diazepane-1-carboxylic acid tert-butyl using General Procedure 2. MS (ESI$^+$) m/z 536.9 (M+H)$^+$; R$_t$=2.35 min. $^1$H-NMR (400 MHz, DMSO-d$_6$) δ 1.37 (d, J=14.4 Hz, 9H), 1.84 (m, 2H), 3.29 (m, 2H), 3.38 (m, 4H), 3.52 (m 2H), 4.45 (d, J=4.7 Hz, 1H), 6.91 (dd, J=4.8 Hz, J=7.5 Hz, 1H), 7.56 (dd, J=1.8 Hz, J=7.5 Hz, 1H), 7.61 (m, 1H), 7.74 (t, J=8.8 Hz, 1H), 7.87 (dd, J=5.3 Hz, J=9.0 Hz, 1H), 8.11 (dd, J=1.9 Hz, J=4.8 Hz, 1H).

Example 289

(2-[1,4]Diazepan-1-yl-pyridin-3-ylmethyl)-[1-(2,3-dichloro-4-fluoro-phenyl)-1H-tetrazol-5-yl]-amine, diacetate salt Trifluoroacetic acid (3 mL) was added to a solution of the product of Example 288C (0.40 g, 0.744 mmol) in dichloromethane (15 mL) at 0° C. 5 minutes later, the ice bath was removed and the reaction mixture was stirred at room temperature for 16 hours. The solvent was removed and the residue was purified by preparative HPLC on a Thermoquest, hyperprep HS C18 column (250×21.2 mm., 8 µm particle size) using a gradient of 5% to 75% acetonitrile to ammonium acetate (10 mM) over 20 minutes at a flow rate of 21 mL/min to provide the title compound. MS (ESI$^+$) m/z 437.3 (M+H)$^+$; R$_t$=1.41 min. $^1$H-NMR (400 MHz, DMSO-d$_6$) δ 1.78 (m, 2H), 1.98 (s, 6H), 2.84 (m, 2H), 2.90 (m, 2H), 3.38 (m, 4H), 4.46 (d, J=5.1 Hz, 2H), 6.85 (dd, J=4.8 Hz, J=7.5 Hz, 1H), 7.53 (dd, J=1.9 Hz, J=7.5 Hz, 1H), 7.61 (t, J=5.6 Hz, 1H), 7.74 (t, J=8.8 Hz, 1H), 7.86 (dd, J=5.3 Hz, J=9.0 Hz, 1H), 8.08 (dd, J=1.9 Hz, J=4.8 Hz, 1H).

Example 290

[1-(2,3-Dichloro-4-fluoro-phenyl)-1H-tetrazol-5-yl]-[2-(4-isopropyl-[1,4]diazepan-1-yl)-pyridin-3-ylmethyl]-amine, diacetate salt Acetone (0.5 mL) was added to a mixture of the product of Example 289 (80 mg, 0.183 mmol) and sodium triacetoxyborohydride (77 mg, 0.366 mmol) in 1,2-dichloroethane (5 mL). The reaction mixture was stirred at room temperature overnight. The mixture was filtered and washed with dichloromethane. The filtrate was concentrated under reduced pressure and purified by preparative HPLC on a Thermoquest, hyperprep HS C18 column (250×21.2 mm., 8 µm particle size) using a gradient of 5% to 75% acetonitrile to ammonium acetate (10 mM) over 20 minutes at a flow rate of 21 mL/min to provide the title compound. MS (ESI$^+$) m/z 479.3 (M+H)$^+$; R$_t$=1.63 min. $^1$H-NMR (400 MHz, DMSO-d$_6$) δ 0.96 (d, J=6.6 Hz, 1H), 1.80 (m, 2H), 1.90 (s, 2H), 2.65 (m, 2H), 2.70 (m, 2H), 2.86 (m, 1H), 3.38 (m, 4H), 4.44 (d, J=5.3 Hz, 1H), 5.75 (s, 1H), 6.84 (dd, J=4.8 Hz, J=7.5 Hz, 1H), 7.52 (dd, J=1.9 Hz, J=7.5 Hz, 1H), 7.58 (t, J=50.5 Hz, 1H), 7.73 (t, J=8.8 Hz, 1H), 7.86 (dd, J=5.3 Hz, J=9.0 Hz, 1H), 8.07 (dd, J=1.9 Hz, J=4.7 Hz, 1H).

Examples 291-298 in Table 1 were prepared from the appropriate aldehydes or ketones using the procedure as described in Example 290.

TABLE 1

| Name | | MH+ | Rt |
|---|---|---|---|
| Example 291 | [1-(2,3-Dichloro-4-fluoro-phenyl)-1H-tetrazol-5-yl]-[2-(4-isobutyl-[1,4]diazepan-1-yl)-pyridin-3-ylmethyl]-amine | 493.3 | 1.77 |
| Example 292 | [2-(4-Cyclopropylmethyl-[1,4]diazepan-1-yl)-pyridin-3-ylmethyl]-[1-(2,3-dichloro-4-fluoro-phenyl)-1H-tetrazol-5-yl]-amine | 491.4 | 1.59 |
| Example 293 | [1-(2,3-Dichloro-4-fluoro-phenyl)-1H-tetrazol-5-yl]-{2-[4-(2,2-dimethyl-propyl)-[1,4]diazepan-1-yl]-pyridin-3-ylmethyl}-amine | 507.4 | 1.89 |
| Example 294 | [1-(2,3-Dichloro-4-fluoro-phenyl)-1H-tetrazol-5-yl]-[2-(4-propyl-[1,4]diazepan-1-yl)-pyridin-3-ylmethyl]-amine | 479.3 | 1.63 |
| Example 295 | [1-(2,3-Dichloro-4-fluoro-phenyl)-1H-tetrazol-5-yl]-{2-[4-(3,3,3-trifluoro-propyl)-[1,4]diazepan-1-yl]-pyridin-3-ylmethyl}-amine | 533.3 | 1.75 |
| Example 296 | [1-(2,3-Dichloro-4-fluoro-phenyl)-1H-tetrazol-5-yl]-{2-[4-(tetrahydro-pyran-4-ylmethyl)-[1,4]diazepan-1-yl]-pyridin-3-ylmethyl}-amine | 535.4 | 1.48 |
| Example 297 | [2-(4-Cyclopentyl-[1,4]diazepan-1-yl)-pyridin-3-ylmethyl]-[1-(2,3-dichloro-4-fluoro-phenyl)-1H-tetrazol-5-yl]-amine | 505.4 | 1.73 |
| Example 298 | [1-(2,3-Dichloro-4-fluoro-phenyl)-1H-tetrazol-5-yl]-{2-[4-(tetrahydro-pyran-4-yl)-[1,4]diazepan-1-yl]-pyridin-3-ylmethyl}-amine | 521.4 | 1.49 |

Example 299

1-(2,3-dichlorophenyl)-N-[(2,4-dimethylpyridin-3-yl)methyl]-1H-tetraazol-5-amine C-(2,4-dimethyl-pyridin-3-yl)-methylamine (Lu et al *Bioorg. Med. Chem. Lett.* Vol. 13, page 1821-1824, 2003),) was reacted with 2,3-dichlorophenylisothiocyanate according to the method of Example 78C to provide the title compound. MS (ESI+) m/z 349 (M+H)+; $^1$H NMR (400 MHz, DMSO-$d_6$) δ ppm 2.33 (s, 3H) 2.51 (s, 3H) 4.51 (d, J=4.60 Hz, 2H) 7.05 (d, J=4.91 Hz, 1H) 7.28 (t, J=4.76 Hz, 1H) 7.57 (t, J=7.98 Hz, 1H) 7.67 (dd, J=8.00, 1.53 Hz, 1H) 7.90 (dd, J=8.13, 1.38 Hz, 1H)

Example 300

1-(2,3-dichlorophenyl)-N-(quinolin-8-ylmethyl-1H-tetraazol-5-amine

C-quinolin-8-yl-methylamine (WO 2001070229) was reacted with 2,3-dichlorophenylisothiocyanate according to the method of Example 78C to provide the title compound. MS (ESI+) m/z 372 (M+H)+; $^1$H NMR (400 MHz, DMSO-$d_6$) δ ppm 5.15 (d, J=5.83 Hz, 2H) 7.55-7.61 (m, 2H) 7.62 (t, J=8.29 Hz, 1H) 7.68 (dd, J=7.21, 1.38 Hz, 1H) 7.72-7.75 (m, 1H) 7.77 (dd, J=8.00, 1.53 Hz, 1H) 7.90 (dd, J=7.98, 1.23 Hz, 1H) 7.94 (dd, J=8.13, 1.38 Hz, 1H) 8.39 (dd, J=8.29, 1.84 Hz, 1H) 8.94 (dd, J=4.30, 1.84 Hz, 1H).

Example 301

1-(2,3-dichlorophenyl)-N-[2-(4-methylphenoxy)benzyl]-1H-tetraazol-5-amine 2-p-Tolyloxy-benzylamine (US 2002143003) was reacted with 2,3-dichlorophenylisothiocyanate according to the method of Example 78C to provide the title compound. MS (ESI+) m/z 426 (M+H)+; $^1$H NMR (300 MHz, DMSO-$d_6$) δ ppm 2.29 (s, 3H) 4.51 (d, J=5.76 Hz, 2H) 6.80 (dd, J=8.14, 1.02 Hz, 1H) 6.86 (d, J=8.48 Hz, 2H) 7.07-7.14 (m, 1H) 7.18 (d, J=8.14 Hz, 2H) 7.21-7.29 (m, 1H) 7.39 (dd, J=7.63, 1.53 Hz, 1H) 7.56-7.68 (m, 3H) 7.94 (dd, J=7.80, 2.03 Hz, 1H).

Example 302

1-(2,3-dichlorophenyl)-N-[(1R)-1-(3-methoxyphenyl)ethyl]-1H-tetraazol-5-amine (R)-1-(3-methoxyphenyl)ethylamine was reacted with 2,3-dichlorophenylisothiocyanate according to the method of Example 78C to provide the title compound. MS (ESI+) m/z 364 (M+H)+; $^1$H NMR (300 MHz, DMSO-$d_6$) δ ppm 1.43 (d, J=7.12 Hz, 3H) 3.73 (s, 3H) 4.82-4.93 (m, 1H) 6.76-6.81 (m, 1H) 6.89-6.95 (m, 2H) 7.22 (t, J=8.14 Hz, 1H) 7.56 (d, J=7.80 Hz, 1H) 7.62 (t, J=7.80 Hz, 1H) 7.67 (dd, J=6.00, 2.03 Hz, 1H) 7.96 (dd, J=7.97, 1.86 Hz, 1H).

Example 303

1-(2,3-dichlorophenyl)-N-[(1S)-1-(3-methoxyphenyl)ethyl]-1H-tetraazol-5-amine (S)-1-(3-methoxyphenyl)ethylamine was reacted with 2,3-dichlorophenylisothiocyanate according to the method of Example 78C to provide the title compound. MS (ESI+) m/z 364 (M+H)+; $^1$H NMR (300 MHz, DMSO-$d_6$) δ ppm 1.43 (d, J=7.12 Hz, 3H) 3.73 (s, 3H) 4.81-4.94 (m, 1H) 6.75-6.82 (m, 1H) 6.89-6.95 (m, 2H) 7.22 (t, J=8.14 Hz, 1H) 7.56 (d, J=8.14 Hz, 1H) 7.62 (t, J=7.80 Hz, 1H) 7.68 (dd, J=9.00, 2.03 Hz, 1H) 7.96 (dd, J=7.97, 1.86 Hz, 1H)

Example 304

1-(2,3-dichlorophenyl)-N-{2-[(1-methylpiperidin-3-yl)oxy]benzyl}-1H-tetraazol-5-amine

Example 304A

2-[(1-methylpiperidin-3-yl)oxy]benzonitrile

2-Fluoro-benzonitrile was reacted with 1-methyl-piperidin-3-ol according to the method of Example 85A to provide the title compound. MS (DCI/NH$_3$) m/z 217 (M+1)+.

Example 304B

1-{2-[(1-methylpiperidin-3-yl)oxy]phenyl}methanamine

The product from Example 304A according to the method of Example 78B provided the title compound. MS (DCI/NH$_3$) m/z 221 (M+1)+.

Example 304C 1-(2,3-dichlorophenyl)-N-{2-[(1-methylpiperidin-3-yl)oxy]benzyl}-1H-tetraazol-5-amine The product from Example 304B was reacted with 2,3-dichlorophenylisothiocyanate according to the method of Example 78C to provide the title compound. MS (DCI/NH$_3$) m/z 434 (M+1)+, $^1$HNMR (400 MHz, DMSO-$d_6$) δ ppm 0.99-1.10 (m, 1H) 1.37-1.49 (m, 1H) 1.53-1.62 (m, 1H) 1.70-1.84 (m, 3H) 2.02 (s, 3H) 2.39-2.47 (m, 1H) 2.62 (d, J=8.54 Hz, 1H) 4.31-4.39 (m, 1H) 5.48 (s, 2H) 6.95 (t, J=7.48 Hz, 1H) 7.06 (d, J=8.24 Hz, 1H) 7.25-7.33 (m, 2H) 7.34-7.37 (m, 2H) 7.70 (dd, J=6.26, 3.51 Hz, 1H) 8.58-9.26 (br. s, 1H).

Example 305

1-(2,3-dichloro-4-fluorophenyl)-N-[(2-{4-[(dimethylamino)acetyl]-1,4-diazepan-1-yl}pyridin-3-yl)methyl]-1H-tetraazol-5-amine diacetate Example 306

1-(2,3-dichloro-4-fluorophenyl)-N-{[2-(1H-pyrazol-4-yl)pyridin-3-yl]methyl}-1H-tetraazol-5-amine Example 307

4-[3-({[1-(2,3-dichloro-4-fluorophenyl)-1H-tetraazol-5-yl]amino}methylpyridin-2-yl]-N,N-dimethyl-1,4-diazepane-1-sulfonamide Example 308

1-(2,3-dichloro-4-fluorophenyl)-N-({2-[4-(methylsulfonyl)-1,4-diazepan-1-yl]pyridin-3-yl}methyl)-1H-tetraazol-5-amine Example 309 ethyl {4-[3-({[1-(2,3-dichloro-4-fluorophenyl)-1H-tetraazol-5-yl]amino}methyl)pyridin-2-yl]-1,4-diazepan-1-yl}acetate Example 310

N-{[2-(4-acetyl-1,4-diazepan-1-yl)pyridin-3-yl]methyl}-1-(2,3-dichloro-4-fluorophenyl)-1H-tetraazol-5-amine Example 311

2-{4-[3-({[1-(2,3-dichloro-4-fluorophenyl)-1H-tetraazol-5-yl]amino}methyl)pyridin-2-yl]-1,4-diazepan-1-yl}acetamide acetate The following compounds encompassed by the present invention may be prepared by one skilled in the art using known synthetic methodologies, the starting materials may be varied and additional steps may be employed. Alternatively they may be prepared by using synthetic methodology described in the scheme and examples contained herein, with readily apparent modifications:

1-(2,3-dichlorophenyl)-N-[(2'-fluoro-2,3'-bipyridin-3-yl)methyl]-1H-tetraazol-5-amine;
1-(2,3-dichlorophenyl)-N-[(2',6'-difluoro-2,3'-bipyridin-3-yl)methyl]-1H-tetraazol-5-amine;
1-(2,3-dichlorophenyl)-N-[(2',4',6'-trifluoro-2,3'-bipyridin-3-yl)methyl]-1H-tetraazol-5-amine;
1-(2,3-dichlorophenyl)-N-[(2',5'-difluoro-2,3'-bipyridin-3-yl)methyl]-1H-tetraazol-5-amine;
1-(2,3-dichlorophenyl)-N-[(5',6'-difluoro-2,3'-bipyridin-3-yl)methyl]-1H-tetraazol-5-amine;
1-(2,3-dichlorophenyl)-N-[(2',4'-difluoro-2,3'-bipyridin-3-yl)methyl]-1H-tetraazol-5-amine;
1-(2,3-dichlorophenyl)-N-[(2'-fluoro-2,4'-bipyridin-3-yl)methyl]-1H-tetraazol-5-amine;
1-(2,3-dichlorophenyl)-N-[(2',6'-difluoro-2,4'-bipyridin-3-yl)methyl]-1H-tetraazol-5-amine;
1-(2,3-dichlorophenyl)-N-[(2',5'-difluoro-2,4'-bipyridin-3-yl)methyl]-1H-tetraazol-5-amine;
1-(2,3-dichlorophenyl)-N-[(2',3'-difluoro-2,4'-bipyridin-3-yl)methyl]-1H-tetraazol-5-amine;
1-(2,3-dichlorophenyl)-N-({2-[(2,6-difluoropyridin-3-yl)oxy]pyridin-3-yl}methyl)-1H-tetraazol-5-amine;
1-(2,3-dichlorophenyl)-N-({2-[(6-fluoropyridin-3-yl)oxy]pyridin-3-yl}methyl)-1H-tetraazol-5-amine;
1-(2,3-dichlorophenyl)-N-({2-[(4,6-difluoropyridin-3-yl)oxy]pyridin-3-yl}methyl)-1H-tetraazol-5-amine;
1-(2,3-dichlorophenyl)-N-({2-[(2,5-difluoropyridin-3-yl)oxy]pyridin-3-yl}methyl)-1H-tetraazol-5-amine;
1-(2,3-dichlorophenyl)-N-{[2-(pyrimidin-5-yloxy)pyridin-3-yl]methyl}-1H-tetraazol-5-amine;
1-(2,3-dichlorophenyl)-N-{[2-(pyridazin-4-yloxy)pyridin-3-yl]methyl}-1H-tetraazol-5-amine;
1-(2,3-dichlorophenyl)-N-{[2-(pyrazin-2-yloxy)pyridin-3-yl]methyl}-1H-tetraazol-5-amine;
1-(2,3-dichlorophenyl)-N-[(2-pyridazin-4-ylpyridin-3-yl)methyl]-1H-tetraazol-5-amine;
1-(2,3-dichlorophenyl)-N-[(2-pyrimidin-5-ylpyridin-3-yl)methyl]-1H-tetraazol-5-amine;
1-(2,3-dichlorophenyl)-N-[(2-pyrazin-2-ylpyridin-3-yl)methyl]-1H-tetraazol-5-amine;
1-(2,3-dichlorophenyl)-N-{[2-(1,3-thiazol-5-yl)pyridin-3-yl]methyl}-1H-tetraazol-5-amine;
1-(2,3-dichlorophenyl)-N-{[2-(1,3,4-thiadiazol-2-yl)pyridin-3-yl]methyl}-1H-tetraazol-5-amine;
1-(2,3-dichlorophenyl)-N-{[2-(1,3-oxazol-5-yl)pyridin-3-yl]methyl}-1H-tetraazol-5-amine;
1-(2,3-dichlorophenyl)-N-{[2-(1,3,4-oxadiazol-2-yl)pyridin-3-yl]methyl}-1H-tetraazol-5-amine;
4-[3-({[1-(2,3-dichlorophenyl)-1H-tetraazol-5-yl]amino}methyl)pyridin-2-yl]-3H-pyrazol-3-one;
3-[3-({[1-(2,3-dichlorophenyl)-1H-tetraazol-5-yl]amino}methyl)pyridin-2-yl]-pyridine N-oxide;
4-[3-({[1-(2,3-dichlorophenyl)-1H-tetraazol-5-yl]amino}methyl)pyridin-2-yl]-pyridine N-oxide;
3'-({[1-(2,3-dichlorophenyl)-1H-tetraazol-5-yl]amino}methyl)-2H-1,2'-bipyridin-2-one;
1-[3-({[1-(2,3-dichlorophenyl)-1H-tetraazol-5-yl]amino}methyl)pyridin-2-yl]pyrimidin-2(1H)-one;
1-(2,3-dichlorophenyl)-N-{[2-(4H-1,2,4-triazol-4-yl)pyridin-3-yl]methyl}-1H-tetraazol-5-amine;
3-[3-({[1-(2,3-dichlorophenyl)-1H-tetraazol-5-yl]amino}methyl)pyridin-2-yl]-1,3,4-oxadiazol-2(3H)-one;
2-[3-({[1-(2,3-dichlorophenyl)-1H-tetraazol-5-yl]amino}methyl)pyridin-2-yl]-2,4-dihydro-3H-1,2,4-triazol-3-one;
1-(2,3-dichlorophenyl)-N-({2-[(6-fluoropyridin-3-yl)sulfonyl]pyridin-3-yl}methyl)-1H-tetraazol-5-amine;
1-(2,3-dichlorophenyl)-N-({2-[(5-fluoropyridin-3-yl)sulfonyl]pyridin-3-yl}methyl)-1H-tetraazol-5-amine;
1-(2,3-dichlorophenyl)-N-({2-[(4-fluoropyridin-3-yl)sulfonyl]pyridin-3-yl}methyl)-1H-tetraazol-5-amine;
1-(2,3-dichlorophenyl)-N-({2-[(2-fluoropyridin-3-yl)sulfonyl]pyridin-3-yl}methyl)-1H-tetraazol-5-amine;
1-(2,3-dichlorophenyl)-N-{[2-(pyrrolidin-3-yloxy)pyridin-3-yl]methyl}-1H-tetraazol-5-amine;
3-({[1-(2,3-dichlorophenyl)-1H-tetraazol-5-yl]amino}methyl)-N-pyrrolidin-3-ylpyridin-2-amine;
3-({[1-(2,3-dichlorophenyl)-1H-tetraazol-5-yl]amino}methyl)-N-tetrahydrofuran-3-ylpyridin-2-amine;
N-{[2-(3-aminopyrrolidin-1-yl)pyridin-3-yl]methyl}-1-(2,3-dichlorophenyl)-1H-tetraazol-5-amine;
1-(2,3-dichlorophenyl)-N-[(2-hexahydropyrrolo[3,2-b]pyrrol-1(2H)-ylpyridin-3-yl)methyl]-1H-tetraazol-5-amine;

1-(2,3-dichlorophenyl)-N-[(2-hexahydropyrrolo[3,4-b]pyrrol-1(2H)-ylpyridin-3-yl)methyl]-1H-tetraazol-5-amine;
1-(2,3-dichlorophenyl)-N-{[2-(hexahydro-1H-pyrrolizin-1-yloxy)pyridin-3-yl]methyl}-1H-tetraazol-5-amine;
1-(2,3-dichlorophenyl)-N-[(2-piperazin-1-ylpyridin-3-yl)methyl]-1H-tetraazol-5-amine;
N-{[2-(2,5-diazabicyclo[2.2.1]hept-2-yl)pyridin-3-yl]methyl}-1-(2,3-dichlorophenyl)-1H-tetraazol-5-amine;
N-{[2-(1,4-diazabicyclo[3.2.2]non-4-yl)pyridin-3-yl]methyl}-1-(2,3-dichlorophenyl)-1H-tetraazol-5-amine;
1-(2,3-dichlorophenyl)-N-[(3-ethylpyridin-4-yl)methyl]-1H-tetraazol-5-amine;
N-[(3-chloropyridin-4-yl)methyl]-1-(2,3-dichlorophenyl)-1H-tetraazol-5-amine;
1-(2,3-dichlorophenyl)-N-[(3-methoxypyridin-4-yl)methyl]-1H-tetraazol-5-amine;
1-(2,3-dichlorophenyl)-N-{[3-(trifluoromethyl)pyridin-4-yl]methyl}-1H-tetraazol-5-amine;
1-(2,3-dichlorophenyl)-N-[(3-isopropylpyridin-4-yl)methyl]-1H-tetraazol-5-amine;
1-(2,3-dichlorophenyl)-N-[(3-fluoropyridin-4-yl)methyl]-1H-tetraazol-5-amine;
1-(2,3-dichlorophenyl)-N-[(3-phenoxypyridin-4-yl)methyl]-1H-tetraazol-5-amine;
4-({[1-(2,3-dichlorophenyl)-1H-tetraazol-5-yl]amino}methyl)nicotinonitrile;
1-(2,3-dichlorophenyl)-N-[1-methyl-1-(3-methylpyridin-4-yl)ethyl]-1H-tetraazol-5-amine;
1-(2,3-dichlorophenyl)-N-[(3-morpholin-4-ylpyridin-4-yl)methyl]-1H-tetraazol-5-amine;
N-[1-(2,3-dichlorophenyl)-1H-tetraazol-5-yl]-5,6,7,8-tetrahydroisoquinolin-5-amine;
1-(2,3-dichlorophenyl)-N-[(2-ethylpyridin-3-yl)methyl]-1H-tetraazol-5-amine;
N-[(2-chloropyridin-3-yl)methyl]-1-(2,3-dichlorophenyl)-1H-tetraazol-5-amine;
1-(2,3-dichlorophenyl)-N-[(2-methoxypyridin-3-yl)methyl]-1H-tetraazol-5-amine;
1-(2,3-dichlorophenyl)-N-{[2-(trifluoromethyl)pyridin-3-yl]methyl}-1H-tetraazol-5-amine;
1-(2,3-dichlorophenyl)-N-[(2-isopropylpyridin-3-yl)methyl]-1H-tetraazol-5-amine;
1-(2,3-dichlorophenyl)-N-[(2-fluoropyridin-3-yl)methyl]-1H-tetraazol-5-amine;
1-(2,3-dichlorophenyl)-N-[(2-phenoxypyridin-3-yl)methyl]-1H-tetraazol-5-amine;
1-(2,3-dichlorophenyl)-N-[1-methyl-1-(2-methylpyridin-3-yl)ethyl]-1H-tetraazol-5-amine;
1-(2,3-dichlorophenyl)-N-[(2-morpholin-4-ylpyridin-3-yl)methyl]-1H-tetraazol-5-amine;
1-(2,3-dichlorophenyl)-N-[2-(2,6-dimethylmorpholin-4-yl)benzyl]-1H-tetraazol-5-amine;
1-(2,3-dichlorophenyl)-N-[2-(3,5-dimethylmorpholin-4-yl)benzyl]-1H-tetraazol-5-amine;
1-(2,3-dichlorophenyl)-N-(2-pyrrolidin-1-ylbenzyl)-1H-tetraazol-5-amine;
1-(2,3-dichlorophenyl)-N-(2-piperidin-1-ylbenzyl)-1H-tetraazol-5-amine;
N-(2-azetidin-1-ylbenzyl)-1-(2,3-dichlorophenyl)-1H-tetraazol-5-amine;
1-(2,3-dichlorophenyl)-N-(2-piperazin-1-ylbenzyl)-1H-tetraazol-5-amine;
1-(2,3-dichlorophenyl)-N-[2-(4-methylpiperazin-1-yl)benzyl]-1H-tetraazol-5-amine;
N-(2-anilinobenzyl)-1-(2,3-dichlorophenyl)-1H-tetraazol-5-amine;
1-(2,3-dichlorophenyl)-N-{2-[methyl(phenyl)amino]benzyl}-1H-tetraazol-5-amine;
1-(2,3-dichlorophenyl)-N-(2-pyridin-2-ylbenzyl)-1H-tetraazol-5-amine;
1-(2,3-dichlorophenyl)-N-(2-pyridin-3-ylbenzyl)-1H-tetraazol-5-amine;
1-(2,3-dichlorophenyl)-N-(2-pyridin-4-ylbenzyl)-1H-tetraazol-5-amine;
1-(2,3-dichlorophenyl)-N-[2-(4,5-dihydro-1H-imidazol-1-yl)benzyl]-1H-tetraazol-5-amine;
1-(2,3-dichlorophenyl)-N-[2-(1H-imidazol-1-yl)benzyl]-1H-tetraazol-5-amine;
1-(2,3-dichlorophenyl)-N-[2-(1,3-oxazol-2-yl)benzyl]-1H-tetraazol-5-amine;
1-(2,3-dichlorophenyl)-N-[2-(pyrazin-2-yloxy)benzyl]-1H-tetraazol-5-amine;
1-(2,3-dichlorophenyl)-N-[2-(pyridin-3-yloxy)benzyl]-1H-tetraazol-5-amine;
1-(2,3-dichlorophenyl)-N-(imidazo[1,2-a]pyridin-8-ylmethyl)-1H-tetraazol-5-amine;
1-(2,3-dichlorophenyl)-N-[(3-methylpyridazin-4-yl)methyl]-1H-tetraazol-5-amine;
1-(2,3-dichlorophenyl)-N-[(4-methylpyrimidin-5-yl)methyl]-1H-tetraazol-5-amine;
1-(2,3-dichlorophenyl)-N-[(3-methylpyrazin-2-yl)methyl]-1H-tetraazol-5-amine;
1-(2,3-dichlorophenyl)-N-[(5-methylpyrimidin-4-yl)methyl]-1H-tetraazol-5-amine;
1-(2,3-dichlorophenyl)-N-[(5-methylpyridazin-4-yl)methyl]-1H-tetraazol-5-amine;
1-(2,3-dichlorophenyl)-N-(1,5-naphthyridin-4-ylmethyl)-1H-tetraazol-5-amine;
N-[1-(2,3-dichlorophenyl)-1H-tetraazol-5-yl]-2-methylpyridin-3-amine;
N-[1-(2,3-dichlorophenyl)-1H-tetraazol-5-yl]-3-methylpyridin-4-amine;
1-[2-chloro-3-(trifluoromethyl)phenyl]-N-(2-methylphenyl)-1H-tetraazol-5-amine;
N-[1-(2,3-dichlorophenyl)-1H-tetraazol-5-yl]pyridin-3-amine;
N-[1-(2,3-dichlorophenyl)-1H-tetraazol-5-yl]pyridin-4-amine;
1-(2,3-dichloro-4-fluorophenyl)-N-(2-methylphenyl)-1H-tetraazol-5-amine;
1-[2-fluoro-3-(trifluoromethyl)phenyl]-N-(2-methylphenyl)-1H-tetraazol-5-amine;
1-(2,3-dichlorophenyl)-5-(2-phenylpyrrolidin-1-yl)-1H-tetraazole;
1-(2,3-dichlorophenyl)-N-{2-[2-(dimethylamino)ethoxy]benzyl}-1H-tetraazol-5-amine;
1-(2,3-dichlorophenyl)-N-{2-[(dimethylamino)methyl]benzyl}-1H-tetraazol-5-amine;
N-[5-chloro-2-(trifluoromethyl)benzyl]-1-(2,3-dichlorophenyl)-1H-tetraazol-5-amine;
N-(2-chloro-6-fluoro-3-methylbenzyl)-1-(2,3-dichlorophenyl)-1H-tetraazol-5-amine;
N-(2-chloro-3,6-difluorobenzyl)-1-(2,3-dichlorophenyl)-1H-tetraazol-5-amine;
1-(2,3-dichlorophenyl)-N-(2,3,6-trifluorobenzyl)-1H-tetraazol-5-amine;
N-(6-chloro-2-fluoro-3-methylbenzyl)-1-(2,3-dichlorophenyl)-1H-tetraazol-5-amine;
N-(5-chloro-2-fluorobenzyl)-1-(2,3-dichlorophenyl)-1H-tetraazol-5-amine;
1-(2,3-dichlorophenyl)-N-(5-fluoro-2-methylbenzyl)-1H-tetraazol-5-amine;

N-[2-chloro-5-(trifluoromethyl)benzyl]-1-(2,3-dichlorophenyl)-1H-tetraazol-5-amine;
1-(2,3-dichlorophenyl)-N-[5-fluoro-2-(trifluoromethyl)benzyl]-1H-tetraazol-5-amine;
N-(5-chloro-2-methylbenzyl)-1-(2,3-dichlorophenyl)-1H-tetraazol-5-amine;
1-(2,3-dichlorophenyl)-N-[2-(trifluoromethyl)benzyl]-1H-tetraazol-5-amine;
N-(3-chloro-2-fluorobenzyl)-1-(2,3-dichlorophenyl)-1H-tetraazol-5-amine;
1-(2,3-dichlorophenyl)-N-(2,5-difluorobenzyl)-1H-tetraazol-5-amine;
1-(2,3-dichlorophenyl)-N-[2-(difluoromethoxy)benzyl]-1H-tetraazol-5-amine;
N-(2,5-dichlorobenzyl)-1-(2,3-dichlorophenyl)-1H-tetraazol-5-amine;
N-(2,3-dichlorobenzyl)-1-(2,3-dichlorophenyl)-1H-tetraazol-5-amine;
1-(2,3-dichlorophenyl)-N-(2-tetrahydro-1H-furo[3,4-c]pyrrol-5(3H)-ylbenzyl)-1H-tetraazol-5-amine;
1-(2,3-dichlorophenyl)-N-[2-(8-oxa-3-azabicyclo[3.2.1]oct-3-yl)benzyl]-1H-tetraazol-5-amine;
1-(2,3-dichlorophenyl)-N-[2-(3-oxa-8-azabicyclo[3.2.1]oct-8-yl)benzyl]-1H-tetraazol-5-amine;
1-(2,3-dichlorophenyl)-N-(2-octahydro-2H-4,7-epoxyisoindol-2-ylbenzyl)-1H-tetraazol-5-amine;
1-(2,3-dichlorophenyl)-N-[2-(2-oxa-5-azabicyclo[2.2.2]oct-5-yl)benzyl]-1H-tetraazol-5-amine;
N-[2-(2-azabicyclo[2.2.1]hept-2-yl)benzyl]-1-(2,3-dichlorophenyl)-1H-tetraazol-5-amine;
1-(2,3-dichlorophenyl)-N-[2-(2-oxa-5-azabicyclo[2.2.1]hept-5-yl)benzyl]-1H-tetraazol-5-amine;
1-(2,3-dichlorophenyl)-N-[2-(5-methyl-2,5-diazabicyclo[2.2.1]hept-2-yl)benzyl]-1H-tetraazol-5-amine;
N-(3-chloro-2-morpholin-4-ylbenzyl)-1-(2,3-dichlorophenyl)-1H-tetraazol-5-amine;
N-(4-chloro-2-morpholin-4-ylbenzyl)-1-(2,3-dichlorophenyl)-1H-tetraazol-5-amine;
N-(5-chloro-2-morpholin-4-ylbenzyl)-1-(2,3-dichlorophenyl)-1H-tetraazol-5-amine;
N-(2-chloro-6-morpholin-4-ylbenzyl)-1-(2,3-dichlorophenyl)-1H-tetraazol-5-amine;
1-(2,3-dichlorophenyl)-N-(2-fluoro-6-morpholin-4-ylbenzyl)-1H-tetraazol-5-amine;
1-(2,3-dichlorophenyl)-N-(3-fluoro-2-morpholin-4-ylbenzyl)-1H-tetraazol-5-amine;
1-(2,3-dichlorophenyl)-N-(4-fluoro-2-morpholin-4-ylbenzyl)-1H-tetraazol-5-amine;
1-(2,3-dichlorophenyl)-N-(5-fluoro-2-morpholin-4-ylbenzyl)-1H-tetraazol-5-amine;
N-[(3-chloropyridin-4-yl)methyl]-1-[2-chloro-3-(trifluoromethyl)phenyl]-1H-tetraazol-5-amine;
N-[(3-chloropyridin-4-yl)methyl]-1-[2-fluoro-3-(trifluoromethyl)phenyl]-1H-tetraazol-5-amine;
1-[2-chloro-3-(trifluoromethyl)phenyl]-N-[(3-methylpyridin-4-yl)methyl]-1H-tetraazol-5-amine;
1-[2-fluoro-3-(trifluoromethyl)phenyl]-N-[(3-methylpyridin-4-yl)methyl]-1H-tetraazol-5-amine;
1-[2-chloro-3-(trifluoromethyl)phenyl]-N-[2-(pyridin-2-yloxy)benzyl]-1H-tetraazol-5-amine; and
1-[2-fluoro-3-(trifluoromethyl)phenyl]-N-[2-(pyridin-2-yloxy)benzyl]-1H-tetraazol-5-amine.

The foregoing detailed description and accompanying examples are merely illustrative and are not intended to limit the invention to the disclosed compounds. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope of the invention which are defined in the appended claim.

We claim:

1. A compound having Formula (I),

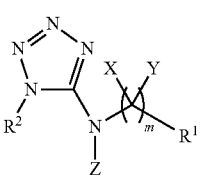

Formula (I)

or a therapeutically acceptable salt thereof, in which
$R^2$ is phenyl, in which each $R^2$ is substituted with one, two, three, four, or five substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;
$R^{2a}$ is —C$_2$-alkyl, —C$_3$-alkyl, —C$_4$-alkyl, —C$_5$-alkyl, —C$_6$-alkyl, or R$^{2b}$;
$R^{2b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{2c}$, —N(R$^{2c}$)$_2$, —CN, —SR$^{2c}$, and —SO$_2$R$^{2c}$;
$R^{2c}$ is —C$_1$-alkyl, —C$_2$-alkyl, —C$_3$-alkyl, —C$_4$-alkyl, —C$_5$-alkyl, or —C$_6$-alkyl;
m is 1;
X and Y are independently selected from the group consisting of —H, —C$_1$-alkyl, —C$_2$-alkyl, —C$_3$-alkyl, —C$_4$-alkyl, —C$_5$-alkyl, and C$_6$-alkyl; or
X and Y together with the carbon atom to which they are attached form a ring selected from the group consisting of cyclopropane, cyclobutane, cyclopentane, cyclohexane, tetrahydrofuran, tetrahydrothiophene, pyrrolidine, dioxolane, tetrahydropyran, piperidine, morpholine, thiomorpholine, and piperazine, each or which is unsubstituted or substituted with one, two, three, or four substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;
Z is —H, —C$_1$-alkyl, —C$_2$-alkyl, —C$_3$-alkyl, —C$_4$-alkyl, —C$_5$-alkyl, or —C$_6$-alkyl; or
Z and X together with the atoms to which they are attached form a ring selected from the group consisting of pyrrolidine, piperidine, morpholine, thiomorpholine, and piperazine;
$R^1$ is phenyl which is unfused or fused with
a ring selected from the group consisting of cyclopentane, cyclohexane, cyclopentene, cyclohexene, dioxane, dioxolane, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, pyrazolidine, pyran, piperidine, morpholine, thiomorpholine, oxazolidinone, morpholinone, and piperazine, wherein each ring contained in R$^1$, independently of each other, is unsubstituted or substituted with one, two, three, or four substituents independently selected from the group consisting of —Cl, —F, —Br, —I, —OH, —NH$_2$, —NO$_2$, R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H) (R$^{1a}$), —SO$_2$N(R$^{1a}$)$_2$, —C(O)R$^{1d}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$;

R$^{1a}$ is —C$_1$-alkyl, —C$_3$-alkyl, —C$_4$-alkyl, —C$_5$-alkyl, —C$_6$-alkyl, or —R$^{1b}$;

R$^{1b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —OR$^{1d}$, —C$_1$-alkyl, —C$_2$-alkyl, —C$_3$-alkyl, —C$_4$-alkyl, —C$_5$-alkyl, —C$_6$-alkyl, —R$^{1c}$, —N(R$^{1d}$)$_2$, and —NHR$^{1d}$;

R$^{1c}$ is cycloalkyl, cycloalkenyl, indanyl, indenyl, naphthyl, tetrahydronaphthyl, heteroaryl or heterocycle, in which each R$^{1c}$ is unsubstituted or substituted with one, two, three, or four substituents independently selected from the group consisting of =O, —Cl, —F, —Br, —I, —NO$_2$, —CN, —OH, —R$^{1aa}$, —NH$_2$, —OR$^{1aa}$, —NHR$^{1aa}$, —N(R$^{1aa}$)$_2$, —C(O)R$^{1aa}$, —S(O)$_2$R$^{1aa}$, —S(O)$_2$NH$_2$, —S(O)$_2$N(R$^{1aa}$)$_2$, —C(O)NH$_2$, —C(O)N(H)(R$^{1aa}$), —C(O)N(R$^{1aa}$)$_2$, —C(O)OH, —C(O)OR$^{1aa}$, —OR$^{1h}$, —N(H)R$^{1h}$), —N(R$^{1d}$)(R$^{1b}$) and —R$^{1h}$;

R$^{1aa}$ is —C$_1$-alkyl, —C$_2$-alkyl, —C$_3$-alkyl, —C$_4$-alkyl, —C$_5$-alkyl, —C$_6$-alkyl, or —R$^{1bb}$;

R$^{1bb}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), —S(O)$_2$N(R$^{1d}$)$_2$ and —R$^{1h}$;

R$^{1d}$ is —C$_1$-alkyl, —C$_2$-alkyl, —C$_3$-alkyl, —C$_4$-alkyl, —C$_5$-alkyl, or —C$_6$-alkyl;

R$^{1e}$ is a monocyclic or bicyclic ring selected from the group consisting of cycloalkyl, heterocycle, aryl and heteroaryl, wherein each ring is unsubstituted or substituted with one, two, three or four substituents independently selected from the group consisting of =O, —Cl, —F, —Br, —I, —NO$_2$, —CN, —OH, —R$^{1aa}$, —OR$^{1aa}$, —SR$^{1aa}$, —NH$_2$, —NHR$^{1aa}$, and —N(R$^{1aa}$)$_2$;

R$^{1f}$ is —C$_1$-alkyl, —C$_2$-alkyl, —C$_3$-alkyl, —C$_4$-alkyl, —C$_5$-alkyl, —C$_6$-alkyl, aryl, heteroaryl, —R$^{1h}$, or R$^{1g}$;

R$^{1g}$ is —C$_1$-alkyl, —C$_2$-alkyl, —C$_3$-alkyl, —C$_4$-alkyl, —C$_5$-alkyl, or —C$_6$-alkyl, each of which is substituted with one substituent selected from the group consisting —R$^{1h}$; and R$^{1h}$ is cycloalkyl, cycloalkenyl, aryl, heteroaryl or heterocycle, in which each R$^{1h}$ is unsubstituted or substituted with one or two or three or four or five substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H) (R$^{1d}$), —C(O)N(R$^{1d}$)$_2$, —S(O)$_2$NH$_2$, —S(O)$_2$N(H) (R$^{1d}$), and —S(O)$_2$N(R$^{1d}$)$_2$;

provided that when R$^1$ is phenyl fused with a pyrrole, thiophene, furan, pyrazole, isoxazole, or isothiazole ring, the pyrrole, thiophene, furan, pyrazole, isoxazole, or isothiazole ring is not substituted with —C$_1$-alkyl, —C$_2$-alkyl, —C$_3$-alkyl, —C$_4$-alkyl, —C$_5$-alkyl, —C$_6$-alkyl, pyrrolidinyl, piperidyl, tetrahydropyridyl, pyrrolinyl, —C$_1$-alkyl substituted with pyrrolidinyl or piperidyl, —C$_2$-alkyl substituted with —N(R$^{1d}$)$_2$, —NH$_2$, or —NHR$^{1d}$, —C$_3$-alkyl substituted with —N(R$^{1d}$)$_2$, —NH$_2$, or —NHR$^{1d}$, —C$_4$-alkyl substituted with —N(R$^{1d}$)$_2$, —NH$_2$, or —NHR$^{1d}$, —C$_5$-alkyl substituted with —N(R$^{1d}$)$_2$, —NH$_2$, or —NHR$^{1d}$, or —C$_6$-alkyl substituted with —N(R$^{1d}$)$_2$, —NH$_2$, or —NHR$^{1d}$; and with the proviso that the following compounds are excluded:

N-benzyl-1-(4-methoxyphenyl)-1H-tetraazol-5-amine.

2. A compound having Formula (I),

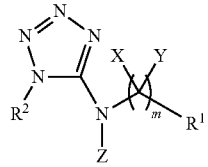

Formula (I)

or a therapeutically acceptable salt thereof, in which

R$^2$ is phenyl, wherein each R$^2$ is substituted with one, two, three, four, or five substituents independently selected from the group consisting of —Cl, —F, —Br, —I, —NH$_2$, —R$^{2a}$, —NHR$^{2a}$, —N(R$^{2a}$)$_2$, —CN, —SR$^{2a}$, and —SO$_2$R$^{2a}$;

R$^{2a}$ is —C$_2$-alkyl, —C$_3$-alkyl, —C$_4$-alkyl, —C$_5$-alkyl, —C$_6$-alkyl, or R$^{2b}$;

R$^{2b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{2c}$, —N(R$^{2c}$)$_2$, —CN, —SR$^{2c}$, and —SO$_2$R$^{2c}$;

R$^{2c}$ is —C$_1$-alkyl, —C$_2$-alkyl, —C$_3$-alkyl, —C$_4$-alkyl, —C$_5$-alkyl, or —C$_6$-alkyl;

m is 1;

X and Y are independently selected from the group consisting of —H, —C$_1$-alkyl, —C$_2$-alkyl, —C$_3$-alkyl, —C$_4$-alkyl, —C$_5$-alkyl, and C$_6$-alkyl; or X and Y together with the carbon atom to which they are attached form a ring selected from the group consisting of cyclopropane, cyclobutane, cyclopentane, cyclohexane, tetrahydrofuran, tetrahydrothiophene, pyrrolidine, dioxolane, tetrahydropyran, piperidine, morpholine, thiomorpholine, and piperazine, each or which is unsubstituted or substituted with one, two, three, or four substituents independently selected from the group consisting of —Cl, —F, —Br, —I, —NH$_2$, —R$^{2a}$, —OR$^{2a}$, —N(R$^{2a}$)$_2$, —CN, —SR$^{2a}$, and —SO$_2$R$^{2a}$;

Z is —H, —C$_1$-alkyl, —C$_2$-alkyl, —C$_3$-alkyl, —C$_4$-alkyl, —C$_5$-alkyl, or —C$_6$-alkyl; or Z and X together with the atoms to which they are attached form a ring selected from the group consisting of pyrrolidine, piperidine, morpholine, thiomorpholine, and piperazine;

$R^1$ is phenyl which is unfused or fused with
a ring selected from the group consisting of cyclopentane, cyclohexane, cyclopentene, cyclohexene, dioxane, dioxolane, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, pyrazolidine, pyran, piperidine, morpholine, thiomorpholine, oxazolidinone, morpholinone, and piperazine wherein each ring contained in $R^1$, independently of each other, is unsubstituted or substituted with one, two, three, or four substituents independently selected from the group consisting of —Cl, —F, —Br, —I, —OH, —NH$_2$, —NO$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1d}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)(R$^{1e}$), —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$;

$R^{1a}$ is —C$_1$-alkyl, —C$_2$-alkyl, —C$_3$-alkyl, —C$_4$-alkyl, —C$_5$-alkyl, —C$_6$-alkyl, or —R$^{1b}$;

$R^{1b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —OR$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, and —NHR$^{1d}$;

$R^{1c}$ is cyclopentyl, cyclohexyl, cyclopentenyl, cyclohexenyl, azetidinyl, naphthyl, quinolinyl, isoquinolinyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, each of which is unsubstituted or substituted with one, two, three, or four substituents independently selected from the group consisting of —Cl, —F, —Br, —I, =O, —NO$_2$, —CN, —OH, —R$^{1aa}$, —NH$_2$, —OR$^{1aa}$, —SR$^{1aa}$, —NHR$^{1aa}$, —N(R$^{1aa}$)$_2$, —C(O)R$^{1aa}$, S(O)$_2$R$^{1aa}$, S(O)$_2$NH$_2$, S(O)$_2$N(R$^{1aa}$)$_2$, —C(O)NH$_2$, —C(O)N(H)(R$^{1aa}$), —C(O)N(R$^{1aa}$)$_2$, —C(O)OH, —C(O)OR$^{1aa}$, —OR$^{1h}$, —N(H)R$^{1h}$), —N(R$^{1d}$)(R$^{1h}$) and —R$^{1h}$;

$R^{1aa}$ is —C$_1$-alkyl, —C$_2$-alkyl, —C$_3$-alkyl, —C$_4$-alkyl, —C$_5$-alkyl, —C$_6$-alkyl, or —R$^{1bb}$;

$R^{1bb}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), —S(O)$_2$N(R$^{1d}$)$_2$ and —R$^{1h}$;

$R^{1d}$ is —C$_1$-alkyl, —C$_2$-alkyl, —C$_3$-alkyl, —C$_4$-alkyl, —C$_5$-alkyl, or —C$_6$-alkyl;

$R^{1e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each $R^{1e}$ is unsubstituted or substituted with one, two, three or four substituents independently selected from the group consisting of =O, —Cl, —F, —Br, —I, —NO$_2$, —CN, —OH, —R$^{1aa}$, —OR$^{1aa}$, —SR$^{1aa}$, —NH$_2$, —NHR$^{1aa}$, and —N(R$^{1aa}$)$_2$;

$R^{1f}$ is —C$_1$-alkyl, —C$_2$-alkyl, —C$_3$-alkyl, —C$_4$-alkyl, —C$_5$-alkyl, —C$_6$-alkyl, aryl, heteroaryl, —R$^{1h}$, or R$^{1g}$;

$R^{1g}$ is —C$_1$-alkyl, —C$_2$-alkyl, —C$_3$-alkyl, —C$_4$-alkyl, —C$_5$-alkyl, or —C$_6$-alkyl, each of which is substituted with one substituent selected from the group consisting of R$^{1h}$; and $R^{1h}$ is cycloalkyl, cycloalkenyl, aryl, heteroaryl or heterocycle, in which each $R^{1h}$ is unsubstituted or substituted with one or two or three or four or five substituents independently selected from the group consisting of —F, —Cl, —Br, —I, —NO$_2$, —CN, haloalkyl, haloalkoxy, —NH$_2$, —OH, —OR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), and —S(O)$_2$N(R$^{1d}$)$_2$;

provided that when $R^1$ is phenyl fused with a pyrrole, thiophene, furan, pyrazole, isoxazole, or isothiazole ring, the pyrrole, thiophene, furan, pyrazole, isoxazole, or isothiazole ring is not substituted with —C$_1$-alkyl, —C$_2$-alkyl, —C$_3$-alkyl, —C$_4$-alkyl, —C$_5$-alkyl, —C$_6$-alkyl, pyrrolidinyl, piperidyl, —C$_1$-alkyl substituted with pyrrolidinyl or piperidyl, —C$_2$-alkyl substituted with —N(R$^{1d}$)$_2$, —NH$_2$, or —NHR$^{1d}$, —C$_3$-alkyl substituted with —N(R$^{1d}$)$_2$, —NH$_2$, or —NHR$^{1d}$, —C$_4$-alkyl substituted with —N(R$^{1d}$)$_2$, —NH$_2$, or —NHR$^{1d}$, —C$_5$-alkyl substituted with —N(R$^{1d}$)$_2$, —NH$_2$, or —NHR$^{1d}$, or —C$_6$-alkyl substituted with —N(R$^{1d}$)$_2$, —NH$_2$, or —NHR$^{1d}$; and with the proviso that the following compounds are excluded:

N-benzyl-1-(4-methoxyphenyl)-1H-tetraazol-5-amine.

3. The compound of claim 2, or a therapeutically acceptable salt thereof, in which $R^2$ is phenyl substituted with one, two, three, four, or five substituents independently selected from the group consisting of —Cl, —F, —Br, —I, —NH$_2$, —R$^{2a}$, —OR$^{2a}$, —NHR$^{2a}$, —N(R$^{2a}$)$_2$, —CN, —SR$^{2a}$, and —SO$_2$R$^{2a}$;

$R^{2a}$ is —C$_2$-alkyl, —C$_3$-alkyl, —C$_4$-alkyl, —C$_5$-alkyl, —C$_6$-alkyl, or R$^{2b}$;

$R^{2b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —Br, —I, —F, —Cl, —C$_1$-alkyl, —C$_2$-alkyl, —C$_3$-alkyl, —C$_4$-alkyl, —NH$_2$, —NHR$^{2c}$, —N(R$^{2c}$)$_2$, —CN, —SR$^{2c}$, and —SO$_2$R$^{2c}$;

R$^{2c}$ is —C$_1$-alkyl, —C$_2$-alkyl, —C$_3$-alkyl, —C$_4$-alkyl, —C$_5$-alkyl, or —C$_6$-alkyl;

R$^1$ is unfused phenyl, unsubstituted or substituted with one, two, three, or four substituents independently selected from the group consisting of —Cl, —F, —Br, —I, —OH, —NH$_2$, —NO$_2$, —R$^{1a}$, —OR$^{1a}$, —NHR$^{1a}$, —N(R$^{1a}$)$_2$, —CN, —SR$^{1a}$, —SO$_2$R$^{1a}$, —SO$_2$NH$_2$, —SO$_2$N(H)(R$^{1a}$), —SO$_2$N(R$^{1a}$)$_2$, —C(O)R$^{1a}$, —C(O)OH, —C(O)OR$^{1a}$, —C(O)NH$_2$, —C(O)N(H)(R$^{1a}$), —C(O)N(R$^{1a}$)$_2$, —OR$^{1e}$, —SR$^{1e}$, —SO$_2$R$^{1e}$, —SO$_2$N(H)R$^{1e}$, —SO$_2$N(R$^{1d}$)(R$^{1e}$), —NH(R$^{1e}$), —N(R$^{1d}$)(R$^{1e}$), —NHC(O)R$^{1f}$, —N(R$^{1d}$)C(O)R$^{1f}$, and —R$^{1c}$;

R$^{1a}$ is —C$_1$-alkyl, —C$_2$-alkyl, —C$_3$-alkyl, —C$_4$-alkyl, —C$_5$-alkyl, —C$_6$-alkyl, or —R$^{1b}$;

R$^{1b}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NH$_2$, —OH, —C$_1$-alkyl, —C$_2$-alkyl, —C$_3$-alkyl, —C$_4$-alkyl, —C$_5$-alkyl, —C$_6$-alkyl, —R$^{1c}$, —N(R$^{1d}$)$_2$, and —NHR$^{1d}$;

R$^{1c}$ is cyclopentyl, cyclohexyl, cyclopentenyl, cyclohexenyl, azetidinyl, naphthyl, quinolinyl, isoquinolinyl, furyl, imidazolyl, isothiazolyl, oxazolyl, oxazolinyl, isoxazolyl, pyrazinyl, pyrazolyl, pyridazinyl, pyridyl, pyrimidinyl, pyrrolyl, imidazolinyl, tetrahydrofuryl, tetrahydrothienyl thiazolyl, thienyl, pyrrolidinyl, dioxolanyl, pyrazolinyl, pyrazolidinyl, pyranyl, piperidyl, morpholinyl, thiomorpholinyl, piperazinyl, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, octahydropyrrolo[3,4-c]pyrrolyl, 3-azabicyclo[3.1.1]heptyl, 6-oxa-3-azabicyclo[3.1.1]heptyl, octahydro-1H-4,7-methanoisoindolyl, octahydro-1H-4,7-epoxyisoindolyl, 8-azabicyclo[3.2.1]octyl, 3-oxa-8-azabicyclo[3.2.1]octyl, 1,4-diazepanyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, each of which is unsubstituted or substituted with one, two, three, or four substituents independently selected from the group consisting of =O, —Cl, —F, —Br, —I, —NO$_2$, —CN, —OH, —R$^{1aa}$, —S$^{1aa}$, —NH$_2$, —OR$^{1aa}$, —NHR$^{1aa}$, —N(R$^{1aa}$)$_2$—C(O)R$^{1aa}$, —S(O)$_2$R$^{1aa}$, —S(O)$_2$NH$_2$, —S(O)$_2$N(R$^{1aa}$)$_2$, —C(O)NH$_2$, —C(O)N(H)(R$^{1aa}$), —C(O)N(R$^{1aa}$)$_2$, —C(O)OH, —C(O)OR$^{1aa}$, —OR$^{1h}$, —N(H)R$^{1h}$), —N(R$^{1d}$)(R$^{1h}$) and —R$^{1h}$;

R$^{1aa}$ is —C$_1$-alkyl, —C$_2$-alkyl, —C$_3$-alkyl, —C$_4$-alkyl, —C$_5$-alkyl, —C$_6$-alkyl, or —R$^{1bb}$;

R$^{1bb}$ is —C$_1$-alkyl, —C$_2$-alkyl, —C$_3$-alkyl, —C$_4$-alkyl, —C$_5$-alkyl, or —C$_6$-alkyl, each of which is substituted with one or two or three substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$—C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), —S(O)$_2$N(R$^{1d}$)$_2$ and —R$^{1h}$;

R$^{1d}$ is —C$_1$-alkyl, —C$_2$-alkyl, —C$_3$-alkyl, —C$_4$-alkyl, —C$_5$-alkyl, or —C$_6$-alkyl;

R$^{1e}$ is phenyl, cyclopropyl, cyclobutyl, cyclopentyl, cyclohexyl, cycloheptyl, pyridyl, pyrazinyl, pyrimidinyl, pyridazinyl, pyrrolyl, furyl, thienyl, imidazolyl, thiazolyl, pyrrolidinyl, piperidyl, azepinyl, tetrahydrofuryl, tetrahydropyranyl or oxazolyl; wherein each R$^{1e}$ is unsubstituted or substituted with one, two, three or four substituents independently selected from the group consisting of =O, —Cl, —F, —Br, —I, —NO$_2$, —CN, —OH, —R$^{1aa}$, —OR$^{1aa}$, —SR$^{1aa}$, —NH$_2$, —NHR$^{1aa}$, and —N(R$^{1aa}$)$_2$;

R$^{1f}$ is —C$_1$-alkyl, —C$_2$-alkyl, —C$_3$-alkyl, —C$_4$-alkyl, —C$_5$-alkyl, —C$_6$-alkyl, aryl, heteroaryl, —R$^{1h}$, or R$^{1g}$;

R$^{1g}$ is —C$_1$-alkyl, —C$_2$-alkyl, —C$_3$-alkyl, —C$_4$-alkyl, —C$_5$-alkyl, or —C$_6$-alkyl, each of which is substituted with one substituent selected from the group consisting of —R$^{1h}$; and R$^{1h}$ is cycloalkyl, cycloalkenyl, aryl, heteroaryl or heterocycle, in which each R$^{1h}$ is unsubstituted or substituted with one or two or three or four or five substituents independently selected from the group consisting of —F, —Cl, —Br, —I, —NO$_2$, —CN, haloalkyl, haloalkoxy, —NH$_2$, —OH, —OR$^{1d}$, —SR$^{1d}$, —S(O)$_2$R$^{1d}$, —C$_1$-alkyl, —C$_2$-alkyl, —C$_3$-alkyl, —C$_4$-alkyl, —C$_5$-alkyl, —C$_6$-alkyl, —N(R$^{1d}$)$_2$, —NHR$^{1d}$, —C(O)OH, —C(O)OR$^{1d}$, —C(O)NH$_2$, —C(O)N(H)(R$^{1d}$), —C(O)N(R$^{1d}$)$_2$, —S(O)$_2$NH$_2$, —S(O)$_2$N(H)(R$^{1d}$), and —S(O)$_2$N(R$^{1d}$)$_2$.

4. The compound of claim 2, or a therapeutically acceptable salt thereof, in which R$^2$ is phenyl substituted with two substituents independently selected from the group consisting of —Cl, —F, —Br, —I and R$^{2a}$;

R$^{2a}$ is —C$_2$-alkyl, —C$_3$-alkyl, —C$_4$-alkyl, —C$_5$-alkyl, or —C$_6$-alkyl;

m is 1;

X and Y are independently selected from the group consisting of —H, —C$_1$-alkyl, —C$_2$-alkyl, —C$_3$-alkyl, —C$_4$-alkyl, —C$_5$-alkyl, and —C$_6$-alkyl;

Z is —H, —C$_1$-alkyl, —C$_2$-alkyl, —C$_3$-alkyl, —C$_4$-alkyl, —C$_5$-alkyl, or —C$_6$-alkyl;

R$^1$ is unfused phenyl, unsubstituted or substituted with one substituent selected from the group consisting of —R$^{1a}$, —N(R$^{1a}$)$_2$, —SR$^{1a}$, —O(pyridyl), —O(phenyl), —O(pyrazinyl), pyrrolyl or morpholinyl; in which the phenyl moiety of O(phenyl) is unsubstituted or substituted with one substituent independently selected from the group consisting of —Cl, —F, —Br, and —I; and R$^{1a}$ is —C$_1$-alkyl, —C$_2$-alkyl, —C$_3$-alkyl, —C$_4$-alkyl, —C$_5$-alkyl or —C$_6$-alkyl.

5. The compound of claim 2, or a therapeutically acceptable salt thereof, in which R$^2$ is phenyl substituted with two substituents independently selected from the group consisting of —Cl and —C$_1$-alkyl;

m is 1;

X and Y are independently selected from the group consisting of —H and —C$_1$-alkyl;

Z is H or —C$_1$-alkyl; and

R¹ is
  unfused phenyl, unsubstituted or substituted with one substituent selected from the group consisting of —R$^{1a}$, —N(R$^{1a}$)$_2$, —SR$^{1a}$, —O(pyridyl), —O(phenyl), —O(pyrazinyl), pyrrolyl or morpholinyl; in which the phenyl moiety of O(phenyl) is unsubstituted or substituted with one substituent independently selected from the group consisting of —Cl, —F, —Br, and —I.

6. The compound of claim 2, or a therapeutically acceptable salt thereof, in which
  R² is 2,3-dichlorophenyl or 2-methylphenyl;
  m is 1;
  X and Y are independently selected from the group consisting of —H and methyl;
  Z is —H or methyl; and
  R¹ is 2-methylphenyl, 2-(morpholin-4-yl)phenyl, 2-(dimethylamino)phenyl, 2-(pyridine-2-yloxy)phenyl, phenyl, 3-(dimethylamino)phenyl, 2-(methylthio)phenyl, 2-(4-fluorophenoxy)phenyl, 3-(pyrazin-2-yloxy)phenyl, 2-(1H-pyrrol-1-yl)phenyl, 4-(pyridine-2-yloxy)phenyl, 3-(pyridine-2-yloxy)phenyl, or 4-(morpholin-4-yl)phenyl.

7. The compound of claim 2, or a therapeutically acceptable salt thereof, selected from the group consisting of:
  1-(2,3-dichlorophenyl)-N-[(2-methylphenyl)methyl]-1H-tetraazol-5-amine;
  1-(2,3-dichlorophenyl)-N-[(2-morpholin-4-ylphenyl)methyl]-1H-tetraazol-5-amine;
  1-(2,3-dichlorophenyl)-N-{[2-(dimethylamino)phenyl]methyl}-1H-tetraazol-5-amine;
  1-(2,3-dichlorophenyl)-N-{[2-(pyridin-2-yloxy)phenyl]methyl}-1H-tetraazol-5-amine;
  1-(2,3-dichlorophenyl)-N-(1-phenylethyl)-1H-tetraazol-5-amine;
  1-(2,3-dichlorophenyl)-N-[3-(dimethylamino)benzyl]-1H-tetraazol-5-amine;
  1-(2,3-dichlorophenyl)-N-[2-(4-fluorophenoxy)benzyl]-1H-tetraazol-5-amine;
  1-(2,3-dichlorophenyl)-N-[2-(methylthio)benzyl]-1H-tetraazol-5-amine;
  N-benzyl-1-(2,3-dichlorophenyl)-1H-tetraazol-5-amine;
  1-(2,3-dichlorophenyl)-N-[3-(pyrazin-2-yloxy)benzyl]-1H-tetraazol-5-amine;
  1-(2,3-dichlorophenyl)-N-[2-(1H-pyrrol-1-yl)benzyl]-1H-tetraazol-5-amine;
  1-(2,3-dichlorophenyl)-N-[4-(pyridin-2-yloxy)benzyl]-1H-tetraazol-5-amine;
  1-(2,3-dichlorophenyl)-N-[3-(pyridin-2-yloxy)benzyl]-1H-tetraazol-5-amine;
  1-(2,3-dichlorophenyl)-N-[(1R)-1-phenylethyl]-1H-tetraazol-5-amine;
  1-(2,3-dichlorophenyl)-N-methyl-N-[(1R)-1-phenylethyl]-1H-tetraazol-5-amine;
  1-(2,3-dichlorophenyl)-N-[(1S)-1-phenylethyl]-1H-tetraazol-5-amine;
  1-(2,3-dichlorophenyl)-N-(4-morpholin-4-ylbenzyl)-1H-tetraazol-5-amine;
  1-(2-methylphenyl)-N-[(1R)-1-phenylethyl]-1H-tetraazol-5-amine;
  1-(2,3-dichlorophenyl)-N-(2-ethoxybenzyl)-1H-tetraazol-5-amine;
  1-(2,3-dichlorophenyl)-N-(2-isopropoxybenzyl)-1H-tetraazol-5-amine;
  1-(2-fluorophenyl)-N-[2-(pyridin-2-yloxy)benzyl]-1H-tetraazol-5-amine;
  1-(2-chlorophenyl)-N-[2-(pyridin-2-yloxy)benzyl]-1H-tetraazol-5-amine;
  1-(2,3-dichlorophenyl)-N-[2-(2-methoxyphenoxy)benzyl]-1H-tetraazol-5-amine;
  1-(2,3-dichlorophenyl)-N-((2,3-dihydrobenzofuran-7-yl)methyl)-1H-tetraazol-5-amine
  1-(2,3-dichlorophenyl)-N-[2-(2-methylphenoxy)benzyl]-1H-tetraazol-5-amine;
  1-(2,3-dichlorophenyl)-N-[2-(pyrazin-2-yloxy)benzyl]-1H-tetraazol-5-amine;
  1-(2,3-dichlorophenyl)-N-(3-nitrobenzyl)-1H-tetraazol-5-amine;
  1-(2,3-dichlorophenyl)-N-[2-(4-methylpiperazin-1-yl)benzyl]-1H-tetraazol-5-amine;
  N-(5-chloro-2-methoxybenzyl)-1-(2,3-dichlorophenyl)-1H-tetraazol-5-amine;
  1-(2,3-dichlorophenyl)-N-[(6-fluoro-4H-1,3-benzodioxin-8-yl)methyl]-1H-tetraazol-5-amine;
  4-({[1-(2,3-dichlorophenyl)-1H-tetraazol-5-yl]amino}methyl)-3-methoxybenzonitrile;
  1-(2,3-dichlorophenyl)-N-(2-piperidin-1-ylbenzyl)-1H-tetraazol-5-amine;
  1-(2,3-dichlorophenyl)-N-(2,4-difluorobenzyl)-1H-tetraazol-5-amine;
  N-(2-chloro-4-fluorobenzyl)-1-(2,3-dichlorophenyl)-1H-tetraazol-5-amine;
  N-[3-({[1-(2,3-dichlorophenyl)-1H-tetraazol-5-yl]amino}methyl)phenyl]-N-methylacetamide;
  1-(2,3-dichlorophenyl)-N-[4-fluoro-2-(trifluoromethyl)benzyl]-1H-tetraazol-5-amine;
  1-(2,3-dichlorophenyl)-N-(5-fluoro-2-methylbenzyl)-1H-tetraazol-5-amine;
  1-(2,3-dichlorophenyl)-N-(2,4,5-trifluorobenzyl)-1H-tetraazol-5-amine;
  1-(2,3-difluorophenyl)-N-[2-(pyridin-2-yloxy)benzyl]-1H-tetraazol-5-amine;
  3-{[1-(2,3-Dichloro-phenyl)-1H-tetrazol-5-ylamino]-methyl}-phenol;
  [1-(2,3-Dichloro-phenyl)-1H-tetrazol-5-yl]-[3-(pyrimidin-2-yloxy)-benzyl]-amine;
  [1-(2,3-Dichloro-phenyl)-1H-tetrazol-5-yl]-[3-(5-methyl-pyridin-2-yloxy)-benzyl]-amine;
  [1-(2,3-Dichloro-phenyl)-1H-tetrazol-5-yl]-[3-(1-methyl-piperidin-4-yloxy)-benzyl]-amine;
  [1-(2,3-Dichloro-phenyl)-1H-tetrazol-5-yl]-[3-(5-nitro-pyridin-2-yloxy)-benzyl]-amine;
  [3-(5-Chloro-pyridin-2-yloxy)-benzyl]-[1-(2,3-dichloro-phenyl)-1H-tetrazol-5-yl]-amine;
  [1-(2,3-Dichloro-phenyl)-1H-tetrazol-5-yl]-[3-(3-methyl-pyridin-2-yloxy)-benzyl]-amine;
  [1-(2,3-Dichloro-phenyl)-1H-tetrazol-5-yl]-[3-(4-methyl-pyridin-2-yloxy)-benzyl]-amine;
  [1-(2,3-Dichloro-phenyl)-1H-tetrazol-5-yl]-[2-(1-methyl-piperidin-4-yloxy)-benzyl]-amine;
  [1-(2,3-Dichloro-phenyl)-1H-tetrazol-5-yl]-[2-methyl-3-(pyridin-2-yloxy)-benzyl]-amine;
  2-{[1-(2,3-Dichloro-phenyl)-1H-tetrazol-5-ylamino]-methyl}-benzonitrile;
  [1-(2,3-Dichloro-phenyl)-1H-tetrazol-5-yl]-[5-fluoro-2-(pyridin-2-yloxy)-benzyl]-amine;
  [1-(2,3-Dichloro-phenyl)-1H-tetrazol-5-yl]-[5-fluoro-2-(pyridin-3-yloxy)-benzyl]amine;
  [1-(2,3-Dichloro-phenyl)-1H-tetrazol-5-yl]-[5-fluoro-2-(2,2,2-trifluoro-ethoxy)-benzyl]-amine;
  [1-(2,3-Dichloro-phenyl)-1H-tetrazol-5-yl]-[4,5-difluoro-2-(pyridin-2-yloxy)-benzyl]-amine;

[1-(2,3-Dichloro-phenyl)-1H-tetrazol-5-yl]-[4-fluoro-2-(pyridin-2-yloxy)-benzyl]amine;
[1-(2,3-Dichloro-phenyl)-1H-tetrazol-5-yl]-(4-fluoro-2-pyridin-2-yl-benzyl)-amine;
[1-(2,3-Dichloro-phenyl)-1H-tetrazol-5-yl]-[4-fluoro-2-(3-fluoro-pyridin-2-yl)-benzyl]-amine;
[1-(2,3-Dichloro-phenyl)-1H-tetrazol-5-yl]-[4-fluoro-2-(6-fluoro-pyridin-3-yl)-benzyl]-amine;
[1-(2,3-Dichloro-phenyl)-1H-tetrazol-5-yl]-[2-(5,6-difluoro-pyridin-3-yl)-4-fluoro-benzyl]-amine;
[1-(2,3-Dichloro-phenyl)-1H-tetrazol-5-yl]-[4,5-difluoro-2-(2,2,2-trifluoro-ethoxy)-benzyl]-amine;
[1-(2,3-Dichloro-phenyl)-1H-tetrazol-5-yl]-[4-fluoro-2-(2,2,2-trifluoro-ethoxy)-benzyl]-amine;
1-(2,3-dichlorophenyl)-N-(quinolin-5-ylmethyl)-1H-tetraazol-5-amine;
1-[2-fluoro-3-(trifluoromethyl)phenyl]-N-[2-(pyridin-2-yloxy)benzyl]-1H-tetraazol-5-amine;
1-[2-chloro-3-(trifluoromethyl)phenyl]-N-[2-(pyridin-2-yloxy)benzyl]-1H-tetraazol-5-amine;
1-(2,3-dichlorophenyl)-N-[2-(pyridin-3-yloxy)benzyl]-1H-tetraazol-5-amine;
1-(2,3-dichlorophenyl)-N-(2-pyridin-3-ylbenzyl)-1H-tetraazol-5-amine;
1-(2,3-dichlorophenyl)-N-(2-pyridin-4-ylbenzyl)-1H-tetraazol-5-amine;
{1-[2-({[1-(2,3-dichlorophenyl)-1H-tetraazol-5-yl]amino}methyl)phenyl]piperidin-4-yl}methanol;
1-(2,3-dichlorophenyl)-N-{2-[2-(diethylamino)ethoxy]benzyl}-1H-tetraazol-5-amine;
1-(2,3-dichlorophenyl)-N-[4-fluoro-3-(pyrazin-2-yloxy)benzyl]-1H-tetraazol-5-amine;
1-(2,3-dichlorophenyl)-N-[(2,2-difluoro-1,3-benzodioxol-4-yl)methyl]-1H-tetraazol-5-amine;
N-[4,5-difluoro-2-(pyridin-2-yloxy)benzyl]-1-[2-fluoro-3-(trifluoromethyl)phenyl]-1H-tetraazol-5-amine;
1-(2,3-dichloro-4-fluorophenyl)-N-[2-(pyridin-2-yloxy)benzyl]-1H-tetraazol-5-amine;
1-(2,3-dichlorophenyl)-5-(2-phenylpyrrolidin-1-yl)-1H-tetraazole;
5-[2-(4-chlorophenyl)pyrrolidin-1-yl]-1-(2,3-dichlorophenyl)-1H-tetraazole;
1-(2,3-dichlorophenyl)-N-(2,3,6-trifluorobenzyl)-1H-tetraazol-5-amine;
N-(2-chloro-3,6-difluorobenzyl)-1-(2,3-dichlorophenyl)-1H-tetraazol-5-amine;
1-(2,3-dichlorophenyl)-N-(3-methoxy-2-methylbenzyl)-1H-tetraazol-5-amine;
1-(2,3-dichlorophenyl)-N-(5-fluoro-2-methoxybenzyl)-1H-tetraazol-5-amine;
1-(2,3-dichlorophenyl)-N-(2,3-dimethylbenzyl)-1H-tetraazol-5-amine;
1-(2,3-dichlorophenyl)-N-(2,3-dihydro-1,4-benzodioxin-5-ylmethyl)-1H-tetraazol-5-amine;
N-(1,3-benzodioxol-4-ylmethyl)-1-(2,3-dichlorophenyl)-1H-tetraazol-5-amine;
1-(2,3-dichlorophenyl)-N-(2,3-dihydro-1,4-benzodioxin-6-ylmethyl)-1H-tetraazol-5-amine;
N-(1,3-benzodioxol-5-ylmethyl)-1-(2,3-dichlorophenyl)-1H-tetraazol-5-amine;
1-(2,3-dichlorophenyl)-N-(2,3-dimethoxybenzyl)-1H-tetraazol-5-amine;
1-(2,3-dichlorophenyl)-N-(3,5-dimethoxybenzyl)-1H-tetraazol-5-amine;
1-(2,3-dichlorophenyl)-N-(2,4-dimethoxybenzyl)-1H-tetraazol-5-amine;
1-(2,3-dichlorophenyl)-N-(2,5-dimethylbenzyl)-1H-tetraazol-5-amine;
N-(3-chloro-2-methylbenzyl)-1-(2,3-dichlorophenyl)-1H-tetraazol-5-amine;
N-(5-chloro-2-methylbenzyl)-1-(2,3-dichlorophenyl)-1H-tetraazol-5-amine;
1-(2,3-dichlorophenyl)-N-(2,5-difluorobenzyl)-1H-tetraazol-5-amine;
N-(5-chloro-2-fluorobenzyl)-1-(2,3-dichlorophenyl)-1H-tetraazol-5-amine;
N-[2-chloro-5-(trifluoromethyl)benzyl]-1-(2,3-dichlorophenyl)-1H-tetraazol-5-amine;
1-(2,3-dichlorophenyl)-N-(2,5-dimethoxybenzyl)-1H-tetraazol-5-amine;
N-(2-chloro-6-methylbenzyl)-1-(2,3-dichlorophenyl)-1H-tetraazol-5-amine;
1-(2,3-dichlorophenyl)-N-(2,3-difluorobenzyl)-1H-tetraazol-5-amine;
1-(2,3-dichlorophenyl)-N-(3-isobutylbenzyl)-1H-tetraazol-5-amine;
N-(2-chlorobenzyl)-1-(2,3-dichlorophenyl)-1H-tetraazol-5-amine;
N-(3-chlorobenzyl)-1-(2,3-dichlorophenyl)-1H-tetraazol-5-amine;
N-(4-chlorobenzyl)-1-(2,3-dichlorophenyl)-1H-tetraazol-5-amine;
1-(2,3-dichlorophenyl)-N-(2-fluorobenzyl)-1H-tetraazol-5-amine;
1-(2,3-dichlorophenyl)-N-(3-fluorobenzyl)-1H-tetraazol-5-amine;
1-(2,3-dichlorophenyl)-N-(4-fluorobenzyl)-1H-tetraazol-5-amine;
1-(2,3-dichlorophenyl)-N-(2-methoxybenzyl)-1H-tetraazol-5-amine;
1-(2,3-dichlorophenyl)-N-(3-methoxybenzyl)-1H-tetraazol-5-amine;
1-(2,3-dichlorophenyl)-N-[2-(trifluoromethyl)benzyl]-1H-tetraazol-5-amine;
1-(2,3-dichlorophenyl)-N-[3-(trifluoromethyl)benzyl]-1H-tetraazol-5-amine;
1-(2,3-dichlorophenyl)-N-[4-(trifluoromethyl)benzyl]-1H-tetraazol-5-amine;
1-(2,3-dichlorophenyl)-N-[2-(difluoromethoxy)benzyl]-1H-tetraazol-5-amine;
1-(2,3-dichlorophenyl)-N-[2-(trifluoromethoxy)benzyl]-1H-tetraazol-5-amine;
1-(2,3-dichlorophenyl)-N-[3-(trifluoromethoxy)benzyl]-1H-tetraazol-5-amine;
1-(2,3-dichlorophenyl)-N-[4-(trifluoromethoxy)benzyl]-1H-tetraazol-5-amine;
N-[2-(benzyloxy)benzyl]-1-(2,3-dichlorophenyl)-1H-tetraazol-5-amine;
1-(2,3-dichlorophenyl)-N-[2-(methylsulfonyl)benzyl]-1H-tetraazol-5-amine;
1-(2,3-dichlorophenyl)-N-(quinolin-8-ylmethyl)-1H-tetraazol-5-amine;
1-(2,3-dichlorophenyl)-N-[2-(4-methylphenoxy)benzyl]-1H-tetraazol-5-amine;
1-(2,3-dichlorophenyl)-N-[(1R)-1-(3-methoxyphenyl)ethyl]-1H-tetraazol-5-amine;
1-(2,3-dichlorophenyl)-N-[(1S)-1-(3-methoxyphenyl)ethyl]-1H-tetraazol-5-amine; and
1-(2,3-dichlorophenyl)-N-{2-[(1-methylpiperidin-3-yl)oxy]benzyl}-1H-tetraazol-5-amine.

8. A pharmaceutical composition comprising a therapeutically effective amount of a compound of claim 1 or 2, or a therapeutically acceptable salt thereof, and a pharmaceutically acceptable carrier.

9. The compound of claim 2, wherein $R^2$ is phenyl substituted with two, three, four, or five substituents independently selected from the group consisting of —Cl, —F, —Br, —I, —$R^{2a}$, —$OR^{2a}$, —CN, and —$SR^{2a}$;

$R^{2a}$ is —$C_2$-alkyl, —$C_3$-alkyl, —$C_4$-alkyl, or $R^{2b}$;

$R^{2b}$ is —$C_1$-alkyl, —$C_2$-alkyl, —$C_3$-alkyl, or —$C_4$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —CN, and —$SR^{2c}$;

X and Y are independently selected from the group consisting of —H, —$C_1$-alkyl, —$C_2$-alkyl, —$C_3$-alkyl, —$C_4$-alkyl, —$C_5$-alkyl, and —$C_6$-alkyl;

Z is —H, —$C_1$-alkyl, —$C_2$-alkyl, —$C_3$-alkyl, or —$C_4$-alkyl; and $R^1$ is phenyl which is fused with a ring selected from the group consisting of cyclopentane, cyclohexane, cyclopentene, cyclohexene, dioxane, dioxolane, naphthalene, benzene, furan, imidazole, isothiazole, oxazole, isoxazole, pyrazine, pyrazole, pyridazine, pyridine, pyrimidine, pyrrole, tetrahydrofuran, tetrahydrothiophene, thiazole, thiophene, pyrrolidine, pyrazolidine, pyran, piperidine, morpholine, thiomorpholine, oxazolidinone, morpholidinone, or piperazine wherein each ring contained in $R^1$, independently of each other, is unsubstituted or substituted with one, two, three, or four substituents independently selected from the group consisting of —Cl, —F, —Br, —I, —$NO_2$, —OH, —$NH_2$, —$R^{1a}$, —$OR^{1a}$, —$NHR^{1a}$, —$N(R^{1a})_2$, —CN, —$SO_2R^{1a}$, —$SO_2NH_2$, —$SO_2N(H)(R^{1a})$, —$SO_2N(R^{1a})_2$, —C(O)$R^{1d}$, —C(O)OH, —C(O)$OR^{1a}$, —C(O)$NH_2$, —C(O)N(H)($R^{1a}$), —C(O)N($R^{1a}$)$_2$, —$OR^{1e}$, —$SR^{1e}$, —$SO_2R^{1e}$, —$SO_2N(H)(R^{1e})$, —$SO_2N(R^{1d})(R^{1e})$, —$NH(R^{1e})$, —$N(R^{1d})(R^{1e})$, —$NHC(O)R^{1f}$, —$N(R^{1d})C(O)R^{1f}$, and —$R^{1c}$.

10. The compound of 9, wherein $R^2$ is phenyl substituted with two or three, substituents independently selected from the group consisting of —Cl, —F, —Br, —I, and —$R^{2a}$;

$R^{2a}$ is $R^{2b}$;

$R^{2b}$ is —$C_1$-alkyl or —$C_2$-alkyl, each of which is substituted with one or two or three —F;

X and Y are independently selected from the group consisting of —H and —$C_1$-alkyl;

Z is —H or —$C_1$-alkyl;

$R^1$ is phenyl which is fused with dioxane, dioxolane, pyridine, or tetrahydrofuran, wherein each ring contained in $R^1$, independently of each other, is unsubstituted or substituted with one, two, three, or four substituents independently selected from the group consisting of —Cl, —F, —Br, —I, —$NO_2$, —OH, —$R^{1a}$, —$OR^{1a}$, —$N(R^{1a})_2$, —CN, —$SR^{1a}$, —$SO_2R^{1a}$, and —$N(R^{1d})C(O)R^{1f}$;

$R^{1a}$ is —$C_1$-alkyl, —$C_2$-alkyl, —$C_3$-alkyl, —$C_4$-alkyl, or —$R^{1b}$;

$R^{1b}$ is —$C_1$-alkyl or —$C_2$-alkyl, each of which is substituted with one or two or three substituents independently selected from the group consisting of —F, —Cl, —Br, or —I;

$R^{1d}$ is —$C_1$-alkyl or —$C_2$-alkyl; and $R^{1f}$ is —$C_1$-alkyl or —$C_2$-alkyl.

11. The compound of claim 3 wherein Z is —H, —$C_1$-alkyl, —$C_2$-alkyl, —$C_3$-alkyl, —$C_4$-alkyl, —$C_5$-alkyl, or —$C_6$-alkyl.

12. The compound of claim 11, wherein $R^2$ is phenyl substituted with two, three, four, or five substituents independently selected from the group consisting of —Cl, —F, —Br, —I, —$R^{2a}$, —$OR^{2a}$, —CN, and —$SR^{2a}$;

$R^{2a}$ is —$C_2$-alkyl, —$C_3$-alkyl, —$C_4$-alkyl, or $R^{2b}$;

$R^{2b}$ is —$C_1$-alkyl, —$C_2$-alkyl, —$C_3$-alkyl, or —$C_4$-alkyl, each of which is substituted with one or two or three substituents independently selected from the group consisting of —Br, —I, —F, —Cl, —$C_1$-alkyl, —$C_2$-alkyl, —$C_3$-alkyl, —$C_4$-alkyl, —CN, and —$S^{2c}$;

X and Y are independently selected from the group consisting of —H, —$C_1$-alkyl, —$C_2$-alkyl, —$C_3$-alkyl, —$C_4$-alkyl, —$C_5$-alkyl, and $C_6$-alkyl; and Z is —H, —$C_1$-alkyl, —$C_2$-alkyl, —$C_3$-alkyl, or —$C_4$-alkyl.

13. The compound of claim 12, wherein $R^2$ is phenyl substituted with two or three substituents independently selected from the group consisting of —Cl, —F, —Br, —I, and —$R^{2a}$;

$R^{2a}$ is $R^{2b}$;

$R^{2b}$ is —$C_1$-alkyl or —$C_2$-alkyl, each of which is substituted with one or two or three —F;

X and Y are independently selected from the group consisting of —H or —$C_1$-alkyl; Z is —H or —$C_1$-alkyl;

$R^1$ is unfused phenyl which is unsubstituted or substituted with one, two, three, or four substituents independently selected from the group consisting of —Cl, —F, —Br, —I, —$NO_2$, —OH, —$R^{1a}$, —$OR^{1a}$, —$N(R^{1a})_2$, —CN, —$SR^{1a}$, —$SO_2R^{1a}$, —$OR^{1e}$, —$N(R^{1d})C(O)R^{1f}$, and —$R^{1c}$;

$R^{1a}$ is —$C_1$-alkyl, —$C_2$-alkyl, —$C_3$-alkyl, —$C_4$-alkyl, or —$R^{1b}$;

$R^{1b}$ is —$C_1$-alkyl or —$C_2$-alkyl, each of which is substituted with one or two or three substituents independently selected from the group consisting of —F, —Cl, —Br, —I, —$R^{1c}$, and —$N(R^{1d})_2$;

$R^{1c}$ is pyridyl, pyrrolyl, pyrazolinyl, piperidyl, morpholinyl, or piperazinyl, each of which is unsubstituted or substituted with one, two, three, or four substituents independently selected from the group consisting of —Cl, —F, —Br, —I, and —$R^{1aa}$;

$R^{1aa}$ is —$C_1$-alkyl, —$C_2$-alkyl, or —$R^{1bb}$;

$R^{1bb}$ is —$C_1$-alkyl or —$C_2$-alkyl, each of which is substituted with one or two or three substituents independently selected from the group consisting of —F, —Cl, —Br, —I, and —OH;

$R^{1d}$ is —$C_1$-alkyl or —$C_2$-alkyl;

$R^{1e}$ is phenyl, pyridyl, pyrazinyl, pyrimidinyl or piperidyl, wherein each $R^{1e}$ is unsubstituted or substituted with one, two, three or four substituents independently selected from the group consisting of —Cl, —F, —Br, —I, —$NO_2$, —$R^{1aa}$, and —$OR^{1aa}$; and $R^{1f}$ is —$C_1$-alky or —$C_2$-alkyl.

* * * * *